(12) United States Patent
Dasseux et al.

(10) Patent No.: US 10,328,119 B2
(45) Date of Patent: Jun. 25, 2019

(54) LIPOPROTEIN COMPLEXES AND MANUFACTURING AND USES THEREOF

(71) Applicant: Cerenis Therapeutics Holding S.A., Labège (FR)

(72) Inventors: Jean-Louis Dasseux, Toulouse (FR); Rose Ackermann, Northville, MI (US); Daniela Carmen Oniciu, Toulouse (FR)

(73) Assignee: CERENIS THERAPEUTICS HOLDING S.A., Balma (FR)

( * ) Notice: Subject to any disclaimer, the term of this patent is extended or adjusted under 35 U.S.C. 154(b) by 0 days.

(21) Appl. No.: 14/334,519

(22) Filed: Jul. 17, 2014

(65) Prior Publication Data

US 2015/0152164 A1   Jun. 4, 2015

Related U.S. Application Data

(63) Continuation of application No. 13/367,237, filed on Feb. 6, 2012, now abandoned.

(60) Provisional application No. 61/487,263, filed on May 17, 2011, provisional application No. 61/452,630, filed on Mar. 14, 2011, provisional application No. 61/440,371, filed on Feb. 7, 2011.

(51) Int. Cl.

| | | |
|---|---|---|
| C07K 1/00 | (2006.01) | |
| C07K 14/00 | (2006.01) | |
| C07K 16/00 | (2006.01) | |
| C07K 17/00 | (2006.01) | |
| C09H 1/04 | (2006.01) | |
| A61K 38/00 | (2006.01) | |
| A61P 3/06 | (2006.01) | |
| A61K 38/10 | (2006.01) | |
| A61K 38/16 | (2006.01) | |
| A61K 38/17 | (2006.01) | |
| C07K 1/04 | (2006.01) | |
| A61K 45/00 | (2006.01) | |
| C07K 14/775 | (2006.01) | |
| A61K 38/18 | (2006.01) | |
| A61K 47/50 | (2017.01) | |

(52) U.S. Cl.
CPC .......... *A61K 38/1709* (2013.01); *A61K 38/17* (2013.01); *A61K 38/18* (2013.01); *A61K 45/00* (2013.01); *A61K 47/50* (2017.08); *C07K 1/04* (2013.01); *C07K 1/042* (2013.01); *C07K 14/775* (2013.01); *Y10T 428/2982* (2015.01)

(58) Field of Classification Search
None
See application file for complete search history.

(56) References Cited

U.S. PATENT DOCUMENTS

| | | |
|---|---|---|
| 5,116,739 A | 5/1992 | Teranishi et al. |
| 5,874,075 A | 2/1999 | Collins et al. |
| 5,876,968 A | 3/1999 | Sirtori et al. |
| 6,090,608 A | 7/2000 | Oppenheim et al. |
| 6,090,921 A | 7/2000 | Winge et al. |
| 6,287,590 B1 | 9/2001 | Dasseux |
| 6,306,433 B1 | 10/2001 | Andersson et al. |
| 6,413,744 B1 | 7/2002 | Morris et al. |
| 6,455,088 B1 | 9/2002 | Dasseux |
| 6,503,498 B1 | 1/2003 | Gerard et al. |
| 6,617,134 B1 | 9/2003 | Sirtori et al. |
| 6,852,510 B2 | 2/2005 | Bremel et al. |
| 6,953,840 B2 | 10/2005 | Zhu et al. |
| 7,157,557 B2 | 1/2007 | Sassenfeld et al. |
| 7,179,484 B2 | 2/2007 | Singh |
| 7,189,411 B2 | 3/2007 | Dasseux |
| 7,223,726 B2 | 5/2007 | Oda et al. |
| 7,332,333 B2 | 2/2008 | Bremel et al. |
| 7,378,273 B2 | 5/2008 | Bleck |
| 7,994,120 B2 | 8/2011 | Dasseux et al. |
| 8,206,750 B2 | 6/2012 | Dasseux |
| 8,617,615 B2 | 12/2013 | Dasseux |
| 9,187,551 B2 * | 11/2015 | Dasseux .............. C07K 14/775 530/412 |
| 2006/0217312 A1 | 9/2006 | Dasseux |
| 2008/0293633 A1 | 11/2008 | Bisgaier et al. |
| 2011/0293557 A1 | 12/2011 | Prieto Valtuena et al. |
| 2012/0323005 A1 | 9/2012 | Satyanarayana Reddy et al. |
| 2014/0206600 A1 * | 7/2014 | Dasseux ................ A61K 9/127 514/1.9 |
| 2014/0213501 A1 | 7/2014 | Dasseux et al. |

FOREIGN PATENT DOCUMENTS

| | | |
|---|---|---|
| WO | WO 1986/04144 A1 | 7/1986 |
| WO | WO 1988/03166 A1 | 5/1988 |
| WO | WO 1990/12879 A2 | 11/1990 |

(Continued)

OTHER PUBLICATIONS

U.S. Appl. No. 14/884,115, filed Oct. 2015, Dasseux; Jean-Louis.*
UniProt Database, Accession No. P02647, 17 pages (1986) (Year: 1986).*
PCT International Search Report and Written Opinion of the International Searching Authority from PCT/US2012/024020 dated May 9, 2012.
"Effect of CER-001 on Atherosclerosis in Acute Coronary Syndrome (ACS) Patients—Efficacy and Safety: The CHI Square Trial," www.clinicaltrials.gov, 2011.

(Continued)

*Primary Examiner* — James H Alstrum-Acevedo
*Assistant Examiner* — Thea D'Ambrosio
(74) *Attorney, Agent, or Firm* — Biospark Intellectual Property Law

(57) ABSTRACT

The present disclosure relates to lipoprotein complexes and lipoprotein populations and their use in the treatment and/or prevention of dyslipidemic diseases, disorders, and/or conditions. The disclosure further relates to recombinant expression of apolipoproteins, purification of apolipoproteins, and production of lipoprotein complexes using thermal cycling-based methods.

25 Claims, 37 Drawing Sheets

Figure 2:
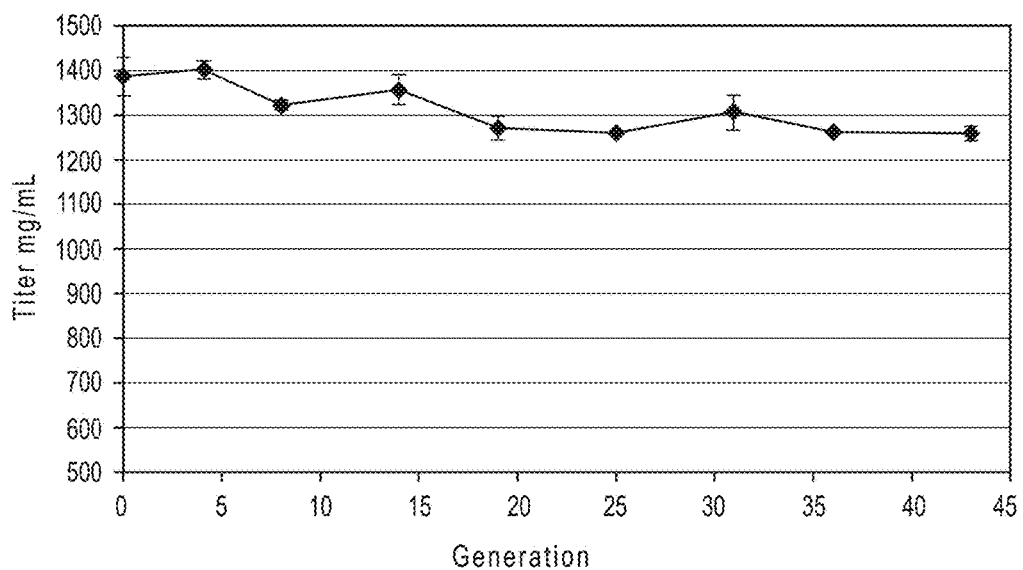

Specification includes a Sequence Listing.

(56) References Cited

FOREIGN PATENT DOCUMENTS

| | | |
|---|---|---|
| WO | WO 1993/00443 A1 | 1/1993 |
| WO | WO 1993/12143 A1 | 6/1993 |
| WO | WO 1994/13819 A1 | 6/1994 |
| WO | WO 1995/25786 A1 | 9/1995 |
| WO | WO 1995/30762 A1 | 11/1995 |
| WO | WO 1996/27608 A1 | 9/1996 |
| WO | WO 2002/02738 A2 | 1/2002 |
| WO | WO 2003/096983 A2 | 11/2003 |
| WO | WO 2005/007803 A2 | 1/2005 |
| WO | WO 2005/072129 A2 | 8/2005 |
| WO | WO 2006/012632 A2 | 2/2006 |
| WO | WO 2006/100567 A1 | 9/2006 |
| WO | WO 2007/023476 A2 | 3/2007 |
| WO | WO 2008/104890 A2 | 9/2008 |
| WO | 2008/141230 A1 | 11/2008 |
| WO | WO 2009/055538 A1 | 4/2009 |
| WO | WO 2010/093918 A1 | 8/2010 |

OTHER PUBLICATIONS

Altamirano C et al., 2006 "Specific nutrient supplementation of defined serum-free medium for the improvement of CHO cells growth and t-PA production." *Electronic Journal of Biotechnology* 9(1).

Asztalos B et al., 1997 "Role of Free Apolipoprotein A-1 in Cholesterol Efflux," *Arterioscier Thromb Basc Biol* 17(9):1630-1637.

Benjwal S et al., 2006 "Monitoring protein aggregation during thermal unfolding in circular dichroism experiments," *Protein Science* 15:635-639.

Bielicki J et al., 1992 "Efflux of lipid from fibroblasts to apolipoproteins: dependence on elevated levels of cellular unesterified cholesterol," *Journal of Lipid Research* 33:1699-1709.

Brewer H et al., 1986 "Isolation and Characterization of Apolipoproteins A-I, A-II, and A-IV," *Methods in Enzymology* 128:223-246.

Brissette L et al., 1991 "Expression of Recombinant Human Apolipoprotein A-I in Chinese Hamster Ovary Cells and *Escherichia coli*," *Protein Expression and Purification* 2:296-303.

Chau P et al., 2006 "Mechanism of Prebeta-HDL Formation and Activation," *Biochemistry* 45:3981-3987.

Chau P et al., 2007 "Bone Morphogenetic Protein-1 (BMP-1) Cleaves Human Proapolipoprotein A1 and Regulates Its Activation for Lipid Binding," *Biochemistry* 46:8445-8450.

Cuellar et al., 2014 "Aoikuoioriteub A-1 configuration and cell cholesterol efflux activity of discoidal lipoproteins depend on the reconstitution process," *Biochimica et Biophysica Acta* 1841:180-189.

DeSilva, et al., 1990. "Purification and characterization of apolipoprotein J." *J. Biol. Chem.* 265(24):14292-14297.

Dixon J et al., 1989 "Expression and secretion of chicken apolipoprotein AI in—transfected COS cells," *Biochemica et Biophysica Acta* 109:.

Dufourcq J et al., 1986 "Morphological changes of phosphatidylcholine bilayers induced by melittin: vesicularization, fusion, discoidal particles," *Biochimica et Biophysica Acta* 859:33-48.

Duong P et al., 2008 "Characterization and properties of preβ-HDL particles formed by ABCA1-mediated cellular lipid efflux to apoA-I," *Journal of Lipid Research* 49(5):1006-1014.

Edelstein C et al., 1980 "Effect of Guanidine Hydrochloride on the Hydrodynamic and Thermodynamic Properties of Human Apolipoprotein A-I in Solution," *Journal of Biological Chemistry* 255(12):5747-5754.

Fennewald S et al., 1988 "Expression of Human PreproapoAI AND Pre(Δpro)apoAI in a Murine Pituitary Cell Line (AtT-20)," *Journal of Biological Chemistry* 263(3):15568-15577.

Feng M et al., 2006 "High yield and secretion of recombinant human apolipoprotein AI in Pichia pastoris," *Protein Expression and Purification* 46:337-342.

Fielding C et al., 1995 "Molecular physiology of reverse cholesterol transport," *Journal of Lipid Research* 36(2):221-228.

Formisano S et al., 1978 "Effect of Pressure and Ionic Strength on the Self-association of Apo-A-I from the Human High Density Lipoprotein Complex." *Journal of Biological Chemistry* 253(2):354-360.

Forte T et al., 1987 "Lipid-poor apolipoprotein A-I in Hep G2 cells: formation of lipid-rich particles by incubation with dimyristoylphosphatitlylcholine,"*Biochimica et Biophysica Acta* 920:185-194.

Forte T et al., 1990 "Physical and chemical characteristics of apolipoprotein A-I-lipid complexes produced by Chinese hamster ovary cells transfected with human apolipoprotein A-I gene," *Biochintica et Biophysica Acta* 1047:11-18.

Forte T et al., 1993 "Apolipoprotein A-I-cell membrane interaction: extracellular assembly of heterogeneous nascent HDL particles," *Journal of Lipid Research* 34(2):317-324.

Forte T et al., 1995 "Recruitment of cell phospholipids and cholesterol by apolipoproteins A-II and A-I: formation of nascent apolipoprotein-specific HDL that differ in size, phospholipid composition, and reactivity with LCAT," *Journal of Lipid Research* 36:148-157.

Forte T et al., 1996 "Structural relationships between nascent apoA-I-containing particles that are extracellularly assembled in cell culture," *Journal of Lipid Research* 37:1076-1085.

Frank P et al., 2000 "Apolipoprotein A-I: structure-function relationships," *Journal of Lipid Research* 41(6):853-872.

Germershausen J et al., 1981 "Preparative High Speed Gel Permeation Chromatography of Proteins on Toyopearl HW55F," *Biochemical and Biophysical Research Communications* 99(3):1020-1027.

Gursky O et al., 1996 "Thermal unfolding of human high-density apolipoprotein A-1: Implications for a lipid-free molten globular state," *Proc. Natl. Acad. Sci. USA* 93(7):2991-2995.

Jayaraman S et al., 2005 "Kinetic Stabilization and Fusion of Apolipoprotein A-2:DMPC Disks: Comparison with apoA-1 and apoC-1," *Biophysical Journal* 88:2907-2918.

Jonas A, 1986 "Reconstitution of High-Density Lipoproteins," *Methods in Enzymology* 128:553-582.

Kim et al., 2013 "Single Step Reconstitution of Multifunctional High-Density Lipoprotein-Derived Nanomaterials Using Microfluidics," *ACS Nano* 7(11):9975-9983.

Kunitake S et al., 1992 "Interconversion between apolipoprotein A-I-containing lipoproteins of pre-beta, and alpha electrophoretic mobilities." *Journal of Lipid Research* 33(12):1807-1816.

Kunitake S et al., 1990, "Pre-Beta High Density Lipoprotein—Unique Disposition of Apolipoprotein A-I Increases Susceptibility to Proteolysis," *Arteriosclerosis* 10:25-30.

Lamon-Fava S et al., 1987 "Secretion of Apolipoprotein A-I in Lipoprotein Particles Following Transfection of the Human Apolipoprotein A-I Gene into 3T3 Cells," *Journal of Biological Chemistry* 262(19):8944-8947.

Law et al., 1984 "Nucleotide sequence and the encoded amino acids of human apolipoprotein A-I mRNA," *Proc. Natl. Acad Sci USA* 81:66-70.

Li et al., 2004 "Double Belt Structure of Discoidal High Density Lipoproteins: Molecular Basis for Size Heterogeneity," *J Mol. Biol.* 343(5):1293-1311.

Lorenzetti R et al., 1986 "Expression of the human apolipoprotein AI gene fused to the *E. coli* gene for β-galactosidase," *Federation of European Biochemical Societies* 194(2):343-350.

Mallory J et al., 1987 "Expression and Characterization of Human Apolipoprotein A-I in Chinese Hamster Ovary Cells," *Journal of Biological Chemistry* 262(9):4241-4247.

Marcel Y et al., 2003 "Structure-function relationships of apolipoprotein A-I: a flexible protein with dynamic lipid associations," *Curr Opin Lipidol* 14(2):151-157.

McGuire K et al., 1996 "High yield overexpression and characterization of human recombinant proapolipoprotein A-I," *Journal of Lipid Research* 37:1519-1528.

Nanjee M et al., "Acute Effects of Intravenous Infusion of ApoA1/Phosphatidylcholine Discs on Plasma Lipoproteins in Humans," *Arterioscler Thromb Basc Biol* 19:979-989.

(56) References Cited

OTHER PUBLICATIONS

Nanjee M et al., 2001 "Intravenous apoA-I/Lecithin discs increase pre-β-HDL concentration in tissue fluid and stimulate reverse cholesterol transport in humans," *Journal of Lipid Research* 42:1586-1593.

Persson J et al., 1999 "Thermo-separating water/polymer system: a novel one-polymer aqueous two-phase system for protein purification,"*Biotechnol Bioeng* 66(4):247-257 (Abstract).

Pyle L et al., 1997 "Production of Mature Human Apolipoprotein A-I in a Baculovirus-Insect Cell System: Propeptide Is Not Essential for Intracellular Processing but May Assist Rapid Secretion," *Analytical Biochemistry* 253:253-258.

Roberts L et al., 1997 "Structural Analysis of Apolipoprotein A-I: Limited Proteolysis of Methionine-Reduced and—Oxidized Lipid-Free and Lipid-Bound Human Apo A-I," *Biochemistry* 36:7615-7624.

Ryan R et al., 2003 "Optimized bacterial expression of human apolipoprotein A-I," *Protein Expression and Purification* 27:98-103.

Sartor M, "Dynamic Light Scattering," *San Diego, University of California* 2002:21.

Schmidt H et al., 1997 "Expression and Purification of Recombinant Human Apolipoprotein A-I in Chinese Hamster Ovary Cells," *Protein Expression and Purification* 10:226-236.

Schmidt H et al., 1997 "In vivo kinetics as sensitive method for testing physiologically intact human recombinant apolipoprotein A-I: comparison of three different expression systems," *Clinica Chimica Acta* 268:41-60.

Scorci-Thomas M et al., 1996 "High level secretion of wild-type and mutant forms of human proapoA-I using baculovirus-mediated Sf-9 cell expression," *Journal of Lipid Research* 37(3):673-683.

Scott R. 2007 "Quantitative Chromatography Analysis," part of the Chrom-Ed Series, available online at http://www.chromatography-online.org/quant/Chromatographic%20Data/Data%20Processing/Peak%20Area%20Measurements.html 2 pages.

Sigalov et al., "Oxidation of methionine residues affects the structure and stability of apolipoprotein A-1 in reconstituted high density lipoprotein particles," Chem. and Phys. Lipids 113:133-146 (2001).

Spieker L et al., 2002 "High-Density Lipoprotein Restores Endothelial Function in Hypercholesterolemic Men," *Circulation* 1399-1402.

Sviridov D et al., 1999 "Effectivity of Expression of Mature Forms of Mutant Human Apolipoprotein A-I," *Protein Expression and Purification* 17:231-238.

Sviridov D et al., 2000 "Deletion of the propeptide of apolipoprotein A-I reduces protein expression but stimulates effective conversion of preβ-high density lipoprotein to α-high density lipoprotein," *Journal of Lipid Research* 41(11):1872-1882.

Swaney, JB., 1983, "Reconstitution of apolipoprotein A-I from human high density lipoprotein with bovine brain sphingomyelin." *J. Biol. Chem.* 258(2): 1254-1259.

Tardif J et al., 2007 "Effects of Reconstituted High-Density Lipoprotein Infusions on Coronary Atherosclerosis—A Randomized Controlled Trial," *JAMA* 297(15)1675-1682.

Thompson et al., "Physical Stability of Liposomes Prepared from Milk Fat Globule Membrane and Soya Phospholipids," J. Agric. Food Chem. 54:6390-6397 (2006).

Vitello L et al., 1976 "Studies on Human Serum High Density Lipoproteins—Self-association of apolipoprotein A-I in aqueous solutions," *Journal of Biological Chemistry* 251(4):1131-1136.

Weiss P et al., 2006 "Flexible Methodology for Developing Mammalian Cell Lines," *BioPharm International*.

Weinberg R et al., 1988 "Analytic and preparative separation of apolipoproteins A-I, A-II and A-IV by reverse phase liquid chromatography," Journal of Lipid Research 29(6):819-824.

Yetukuri 2010 "Compositions and lipid spatial distribution of HDL particles in subjects with low and high HDL-cholesterol," *Journal of Lipid Research* 51:2341-2351.

Zhang X, Chen B. Recombinant high density lipoprotein reconstituted with apolipoprotein A1 cysteine mutants as delivery vehicles for 10-hydroxycamptothecin. *Cancer Letters* 298 (2010) 26-33.

"Definition of Suspension", available online at www.chemicool.com/definition/suspension.html, 1 page (2014).

"Solution", available online at www.thefreedictionary.com/p/Solution%20(chemistry), 5 pages (2014).

Zheng et al., "Chap. 23: Bioseparation Techniques and Their Applications," Handbook of Molecular and Cellular Methods in Biology and Medicine, 2nd Ed., Cseke et al., eds., CRC Press, pp. 329-353 (2004).

Nykiforuk et al., 2011, "Expression and recovery of biologically active recombinant Apolipoprotein $AI_{Milano}$ from transgenic safflower (*Carthamus tinctorius*) seeds," Plant Biotechnology Journal 9:250-263.

Written Opinion dated May 27, 2015 in connection with Singapore application No. 20130605012.

Notice dated Jan. 5, 2016 issued by the Australian Patent Office regarding a Notice of Opposition filed in connection with Australian patent application No. 2012214672.

Notice dated Apr. 5, 2016 issued by the Australian Patent Office regarding a Notice of Opposition withdrawn in connection with Australian patent application No. 2012214672.

"homogenization (chemistry)," 2014, Encyclopedia Britannica Online, http://www.britannica.com/Ebchecked/topic/270516/homogenization.

Horowitz et al., 1993, "Increased Plasma and Renal Clearance of an Exchangeable Pool of Apolipoprotein A-I in Subjects with Low Levels of High Density Lipoprotein Cholesterol," J. Clin. Invest. 91:1743-1752.

Mehnert and Mader, 2001, "Solid lipid nanoparticles production, characterization and applications," Advanced Drug Delivery Reviews 47:165-196.

Ross et al., 2015, "Proinflammatory high-density lipoprotein results from oxidized lipid mediators in the pathogenesis of both idiopathic and associated types of pulmonary arterial hypertension," Pulmonary Circulation 5(4):640-648.

Shao et al., 2008, "Methionine oxidation impairs reverse cholesterol transport by apolipoprotein A-I," PNAS 105(34):12224-12229.

Tardy et al., 2014, "CER-001, a HDL-mimetic, stimulates the reverse lipid transport and atherosclerosis regression in high cholesterol diet-fed LDL-receptor deficient mice," Atherosclerosis 232:110e118.

* cited by examiner

```
          1          2          3          4
 1234567890 1234567890 1234567890 1234567890
 MKAAVLTLAV LFLTGSQARH FWQQDEPPQS PWDRVKDLAT 5          6          7          8
 1234567890 1234567890 1234567890 1234567890
 VYVDVLKDSG RDYVSQFEGS ALGKQLNLKL LDNWDSVTST
                     1          1          1
          9          0          1          2
 1234567890 1234567890 1234567890 1234567890
 FSKLREQLGP VTQEFWDNLE KETEGLRQEM SKDLEEVKAK
          1          1          1          1
          3          4          5          6
 1234567890 1234567890 1234567890 1234567890
 VQPYLDDFQK KWQEEMELYR QKVEPLRAEL QEGARQKLHE 1          1          1          2
          7          8          9          0
 1234567890 1234567890 1234567890 1234567890
 LQEKLSPLGE EMRDRARAHV DALRTHLAPY SDELRQRLAA
          2          2          2          2
          1          2          3          4
 1234567890 1234567890 1234567890 1234567890
 RLEALKENGG ARLAEYHAKA TEHLSTLSEK AKPALEDLRQ
          2          2
          5          6
 1234567890 1234567890 1234567
 GLLPVLESFK VSFLSALEEY TKKLNTQ
```

FIG. 1

30min

60min

10min

20min

20min

40min

60min

120min

LIPOPROTEIN COMPLEXES AND MANUFACTURING AND USES THEREOF

1. CROSS REFERENCE TO RELATED APPLICATIONS

This application claims the benefit under 35 U.S.C. § 119(e) of provisional application No. 61/440,371, filed Feb. 7, 2011, provisional application No. 61/452,630, filed Mar. 14, 2011, and provisional application No. 61/487,263, filed May 17, 2011, the contents of all of which are incorporated herein in their entireties by reference thereto.

2. TECHNICAL FIELD

The present disclosure provides lipoprotein complexes, pharmaceutical compositions comprising the complexes, methods of producing and purifying apolipoproteins for such complexes, methods of making the complexes and methods of using the complexes to treat or prevent cardiovascular diseases, disorders, and/or conditions associated therewith.

3. BACKGROUND

3.1. Overview

Circulating cholesterol is carried by plasma lipoproteins—complex particles of lipid and protein composition that transport lipids in the blood. Four major classes of lipoprotein particles circulate in plasma and are involved in the fat-transport system: chylomicrons, very low density lipoprotein (VLDL), low density lipoprotein (LDL) and high density lipoprotein (HDL). Chylomicrons constitute a short-lived product of intestinal fat absorption. VLDL and, particularly, LDL are responsible for the delivery of cholesterol from the liver (where it is synthesized or obtained from dietary sources) to extrahepatic tissues, including the arterial walls. HDL, by contrast, mediates reverse cholesterol transport (RCT), the removal of cholesterol lipids, in particular from extrahepatic tissues to the liver, where it is stored, catabolized, eliminated or recycled. HDL also plays a beneficial role in inflammation, transporting oxidized lipids and interleukin, which may in turn reduce inflammation in blood vessel walls.

Lipoprotein particles have a hydrophobic core comprised of cholesterol (normally in the form of a cholesteryl ester) and triglycerides. The core is surrounded by a surface coat comprising phospholipids, unesterified cholesterol and apolipoproteins. Apolipoproteins mediate lipid transport, and some may interact with enzymes involved in lipid metabolism. At least ten apolipoproteins have been identified, including: ApoA-I, ApoA-II, ApoA-IV, ApoA-V, ApoB, ApoC-I, ApoC-II, ApoC-III, ApoD, ApoE, ApoJ and ApoH. Other proteins such as LCAT (lecithin:cholesterol acyltransferase), CETP (cholesteryl ester transfer protein), PLTP (phospholipid transfer protein) and PON (paraoxonase) are also found associated with lipoproteins.

Cardiovascular diseases such as coronary heart disease, coronary artery disease and atherosclerosis are linked overwhelmingly to elevated serum cholesterol levels. For example, atherosclerosis is a slowly progressive disease characterized by the accumulation of cholesterol within the arterial wall. Compelling evidence supports the theory that lipids deposited in atherosclerotic lesions are derived primarily from plasma LDLs; thus, LDLs have popularly become known as "bad" cholesterol. In contrast, HDL serum levels correlate inversely with coronary heart disease. Indeed, high serum levels of HDLs are regarded as a negative risk factor. It is hypothesized that high levels of plasma HDLs are not only protective against coronary artery disease, but may actually induce regression of atherosclerotic plaque (see, e.g., Badimon et al., 1992, Circulation 86 (Suppl. III):86-94; Dansky and Fisher, 1999, Circulation 100:1762-63; Tangirala et al., 1999, Circulation 100(17): 1816-22; Fan et al., 1999, Atherosclerosis 147(1):139-45; Deckert et al., 1999, Circulation 100(11):1230-35; Boisvert et al., 1999, Arterioscler. Thromb. Vasc. Biol. 19(3):525-30; Benoit et al., 1999, Circulation 99(1):105-10; Holvoet et al., 1998, J. Clin. Invest. 102(2):379-85; Duverger et al., 1996, Circulation 94(4):713-17; Miyazaki et al., 1995, Arterioscler. Thromb. Vasc. Biol. 15(11):1882-88; Mezdour et al., 1995, Atherosclerosis 113(2):237-46; Liu et al., 1994, J. Lipid Res. 35(12):2263-67; Plump et al., 1994, Proc. Nat. Acad. Sci. USA 91(20):9607-11; Paszty et al., 1994, J. Clin. Invest. 94(2):899-903; She et al, 1992, Chin. Med. J. (Engl). 105(5):369-73; Rubin et al., 1991, Nature 353(6341):265-67; She et al., 1990, Ann. NY Acad. Sci. 598:339-51; Ran, 1989, Chung Hua Ping Li Hsueh Tsa Chih (also translated as: Zhonghua Bing Li Xue Za Zhi) 18(4):257-61; Quezado et al., 1995, J. Pharmacol. Exp. Ther. 272(2).604-11; Duverger et al., 1996, Arterioscler. Thromb. Vasc. Biol. 16(12):1424-29; Kopfler et al., 1994, Circulation; 90(3): 1319-27; Miller et al., 1985, Nature 314(6006):109-11; Ha et al., 1992, Biochim. Biophys. Acta 1125(2):223-29; Beitz et al., 1992, Prostaglandins Leukot. Essent. Fatty Acids 47(2):149-52). As a consequence, HDLs have popularly become known as "good" cholesterol, (see, e.g., Zhang, et al., 2003 Circulation 108:661-663).

The "protective" role of HDL has been confirmed in a number of studies (e.g., Miller et al., 1977, Lancet 1(8019): 965-68; Whayne et al., 1981, Atherosclerosis 39:411-19). In these studies, the elevated levels of LDL appear to be associated with increased cardiovascular risk, whereas high HDL levels seem to confer cardiovascular protection. In vivo studies have further demonstrated the protective role of HDL, showing that HDL infusions into rabbits may hinder the development of cholesterol induced arterial lesions (Badimon et al., 1989, Lab. Invest. 60:455-61) and/or induce their regression (Badimon et al., 1990, J. Clin. Invest. 85:1234-41).

3.2. Reverse Cholesterol Transport, HDL And Apolipoprotein A-I

The reverse cholesterol transport (RCT) pathway functions to eliminate cholesterol from most extrahepatic tissues and is crucial to maintaining the structure and function of most cells in the body. RCT consists mainly of three steps: (a) cholesterol efflux, i.e., the initial removal of cholesterol from various pools of peripheral cells; (b) cholesterol esterification by the action of lecithin:cholesterol acyltransferase (LCAT), preventing a re-entry of effluxed cholesterol into cells; and (c) uptake of HDL-cholesterol and cholesteryl esters to liver cells for hydrolysis, then recycling, storage, excretion in bile or catabolism to bile acids.

LCAT, the key enzyme in RCT, is produced by the liver and circulates in plasma associated with the HDL fraction. LCAT converts cell-derived cholesterol to cholesteryl esters, which are sequestered in HDL destined for removal (see Jonas 2000, Biochim. Biophys. Acta 1529(1-3):245-56). Cholesteryl ester transfer protein CETP) and phospholipid transfer protein (PLTP) contribute to further remodeling of the circulating HDL population. CETP moves cholesteryl esters made by LCAT to other lipoproteins, particularly ApoB-comprising lipoproteins, such as VLDL and LDL. PLTP supplies lecithin to HDL. HDL triglycerides are catabolized by the extracellular hepatic triglyceride lipase, and lipoprotein cholesterol is removed by the liver via several mechanisms.

The functional characteristics of HDL particles are mainly determined by their major apolipoprotein components such as ApoA-I and ApoA-II. Minor amounts of ApoC-I, ApoC-II, ApoC-III, ApoD, ApoA-IV, ApoE, and ApoJ have also been observed associated with HDL. HDL exists in a wide variety of different sizes and different mixtures of the above-mentioned constituents, depending on the status of remodeling during the metabolic RCT cascade or pathway.

Each HDL particle usually comprises at least 1 molecule, and usually two to 4 molecules, of ApoA-I. HDL particles may also comprise only ApoE (gamma-LpE particles), which are known to also be responsible for cholesterol efflux, as described by Prof. Gerd Assmann (see, e.g., von Eckardstein et al., 1994, Curr Opin Lipidol. 5(6):404-16). ApoA-I is synthesized by the liver and small intestine as preproApolipoprotein A-I, which is secreted as proApolipoprotein A-I (proApoA-I) and rapidly cleaved to generate the plasma form of ApoA-I, a single polypeptide chain of 243 amino acids (Brewer et al., 1978, Biochem. Biophys. Res. Commun. 80:623-30). PreproApoA-I that is injected experimentally directly into the bloodstream is also cleaved into the plasma form of ApoA-I (Klon et al., 2000, Biophys. J. 79(3):1679-85; Segrest et al., 2000, Curr. Opin. Lipidol. 11(2):105-15; Segrest et al., 1999, J. Biol. Chem. 274 (45):31755-58).

ApoA-I comprises 6 to 8 different 22-amino acid alpha-helices or functional repeats spaced by a linker moiety that is frequently proline. The repeat units exist in amphipathic helical conformation (Segrest et al., 1974, FEBS Lett. 38: 247-53) and confer the main biological activities of ApoA-I, i.e., lipid binding and lecithin cholesterol acyl transferase (LCAT) activation.

ApoA-I forms three types of stable complexes with lipids: small, lipid-poor complexes referred to as pre-beta-1 HDL; flattened discoidal particles comprising polar lipids (phospholipid and cholesterol) referred to as pre-beta-2 HDL; and spherical particles, comprising both polar and nonpolar lipids, referred to as spherical or mature EIDL ($HDL_3$ and $HDL_2$). Most HDL in the circulating population comprises both ApoA-I and ApoA-II (the "AI/AII-IIDL fraction"). However, the fraction of HDL comprising only ApoA-I (the "AI-HDL fraction") appears to be more effective in RCT. Certain epidemiologic studies support the hypothesis that the ApoA-I-HDL fraction is anti-atherogenic (Parra et al., 1992, Arterioscler. Thromb. 12:701-07; Decossin et al., 1997, Eur. J. Clin. Invest. 27:299-307).

HDL particles are made of several populations of particles that have different sizes, lipid composition and apolipoprotein composition. They can be separated according to their properties, including their hydrated density, apolipoprotein composition and charge characteristics. For example, the pre-beta-HDL fraction is characterized by a lower surface charge than mature alpha-HDL. Because of this charge difference, pre-beta-HDL and mature alpha-HDL have different electrophoretic mobilities in agarose gel (David et al., 1994, J. Biol. Chem. 269(12):8959-8965).

The metabolism of pre-beta-HDL and mature alpha-HDL also differs. Pre-beta-HDL has two metabolic fates: either removal from plasma and catabolism by the kidney or remodeling to medium-sized HDL that are preferentially degraded by the liver (Lee et al., 2004, J. Lipid Res. 45(4):716-728).

Although the mechanism for cholesterol transfer from the cell surface (i.e., cholesterol efflux) is unknown, it is believed that the lipid-poor complex, pre-beta-1 HDL, is the preferred acceptor for cholesterol transferred from peripheral tissue involved in RCT (see Davidson et al., 1994, J. Biol. Chem. 269:22975-82; Bielicki et al., 1992, J. Lipid Res. 33:1699-1709; Rothblat et al., 1992, J. Lipid Res. 33:1091-97; and Kawano et al., 1993, Biochemistry 32:5025-28; Kawano et al., 1997, Biochemistry 36:9816-25). During this process of cholesterol recruitment from the cell surface, pre-beta-1 HDL is rapidly converted to pre-beta-2 HDL. PLTP may increase the rate of pre-beta-2 HDL disc formation, but data indicating a role for PLTP in RCT are lacking. LCAT reacts preferentially with discoidal, small (pre-beta) and spherical (i.e., mature) HDL, transferring the 2-acyl group of lecithin or other phospholipids to the free hydroxyl residue of cholesterol to generate cholesteryl esters (retained in the HDL) and lysolecithin. The LCAT reaction requires ApoA-I as an activator; i.e., ApoA-I is the natural cofactor for LCAT. The conversion of cholesterol sequestered in the HDL to its ester prevents re-entry of cholesterol into the cell, the net result being that cholesterol is removed from the cell.

Cholesteryl esters in the mature HDL particles in the ApoAI-HDL fraction (i.e., comprising ApoA-I and no ApoA-II) are removed by the liver and processed into bile more effectively than those derived from HDL comprising both ApoA-I and ApoA-II (the Al/AII-HDL fraction). This may be owed, in part, to the more effective binding of ApoAI-HDL to the hepatocyte membrane. The existence of an HDL receptor has been hypothesized, and a scavenger receptor, class B, type I (SR-BI) has been identified as an HDL receptor (Acton et al., 1996, Science 271:518-20; Xu et al., 1997, Lipid Res. 38:1289-98). SR-BI is expressed most abundantly in steroidogenic tissues (e.g., the adrenals), and in the liver (Landschulz et al., 1996, J. Clin. Invest. 98:984-95; Rigotti et al., 1996, J. Biol. Chem. 271:33545-49). For a review of HDL receptors, see Broutin et al., 1988, Anal. Biol. Chem. 46:16-23.

Initial lipidation by ATP-binding cassette transporter AI appears to be critical for plasma HDL formation and for the ability of pre-beta-HDL particles to effect cholesterol efflux (Lee and Parks, 2005, Curr. Opin. Lipidol. 16(1):19-25). According to these authors, this initial lipidation enables pre-beta-HDL to function more efficiently as a cholesterol acceptor and prevents ApoA-I from rapidly associating with pre-existing plasma HDL particles, resulting in greater availability of pre-beta-HDL particles for cholesterol efflux.

CETP may also play a role in RCT. Changes in CETP activity or its acceptors, VLDL and LDL, play a role in "remodeling" the HDL population. For example, in the absence of CETP, the HDLs become enlarged particles that are not cleared. (For reviews of RCT and HDLs, see Fielding and Fielding, 1995, J. Lipid Res. 36:211-28; Barrans et al., 1996, Biochem. Biophys. Acta 1300:73-85; Hirano et al., 1997, Arterioscler. Thromb. Vasc. Biol. 17(6):1053-59).

HDL also plays a role in the reverse transport of other lipids and apolar molecules, and in detoxification, i.e., the transport of lipids from cells, organs, and tissues to the liver for catabolism and excretion. Such lipids include sphingomyelin (SM), oxidized lipids, and lysophophatidylcholine. For example, Robins and Fasulo (1997, J. Clin. Invest. 99:380-84) have shown that HDLs stimulate the transport of plant sterol by the liver into bile secretions.

The major component of HDL, ApoA-I, can associate with SM in vitro. When ApoA-I is reconstituted in vitro with bovine brain SM (BBSM), a maximum rate of reconstitution occurs at 28° C., the temperature approximating the phase transition temperature for BBSM (Swaney, 1983, J. Biol. Chem. 258(2), 1254-59). At BBSM:ApoA-I ratios of 7.5:1 or less (wt/wt), a single reconstituted homogeneous HDL particle is formed that comprises three ApoA-I molecules per particle and that has a BBSM:ApoA-I molar ratio of 360:1. It appears in the electron microscope as a discoidal complex similar to that obtained by recombination of ApoA-I with phosphatidylcholine at elevated ratios of phospholipid:protein. At BBSM:ApoA-I ratios of 15:1 (wt/wt), however, larger-diameter discoidal complexes form that have a higher phospholipid:protein molar ratio (535:1). These complexes are significantly larger, more stable, and more resistant to denaturation than ApoA-I complexes formed with phosphatidylcholine.

Sphingomyelin (SM) is elevated in early cholesterol acceptors (pre-beta-HDL and gamma-migrating ApoE-comprising lipoprotein), suggesting that SM might enhance the ability of these particles to promote cholesterol efflux (Dass and Jessup, 2000, J. Pharm. Pharmacol. 52:731-61; Huang et al., 1994, Proc. Natl. Acad. Sci. USA 91:1834-38; Fielding and Fielding 1995, J. Lipid Res. 36:211-28).

3.3. Protective Mechanism of HDL and ApoA-I

Studies of the protective mechanism(s) of HDL have focused on Apolipoprotein A-I (ApoA-I), the major component of HDL. High plasma levels of ApoA-I are associated with absence or reduction of coronary lesions (Maciejko et al., 1983, N. Engl. J. Med. 309:385-89; Sedlis et al., 1986, Circulation 73:978-84).

The infusion of ApoA-I or of HDL in experimental animals exerts significant biochemical changes, as well as reduces the extent and severity of atherosclerotic lesions. After an initial report by Maciejko and Mao (1982, Arteriosclerosis 2:407a), Badimon et al., (1989, Lab. Invest. 60:455-61; 1989, J. Clin. Invest. 85:1234-41) found that they could significantly reduce the extent of atherosclerotic lesions (reduction of 45%) and their cholesterol ester content (reduction of 58.5%) in cholesterol-fed rabbits, by infusing HDL (d=1.063-1.325 g/ml). They also found that the infusions of HDL led to a close to a 50% regression of established lesions. Esper et al. (1987, Arteriosclerosis 7:523a) have shown that infusions of HDL can markedly change the plasma lipoprotein composition of Watanabe rabbits with inherited hypercholesterolemia, which develop early arterial lesions. In these rabbits, HDL infusions can more than double the ratio between the protective HDL and the atherogenic LDL.

The potential of HDL to prevent arterial disease in animal models has been further underscored by the observation that ApoA-I can exert a fibrinolytic activity in vitro (Saku et al., 1985, Thromb. Res. 39:1-8). Ronneberger (1987, Xth Int. Congr. Pharmacol., Sydney, 990) demonstrated that ApoA-I can increase fibrinolysis in beagle dogs and in Cynomologous monkeys. A similar activity can be noted in vitro on human plasma. Ronneberger was able to confirm a reduction of lipid deposition and arterial plaque formation in ApoA-I treated animals.

In vitro studies indicate that complexes of ApoA-I and lecithin can promote the efflux of free cholesterol from cultured arterial smooth muscle cells (Stein et al., 1975, Biochem. Biophys. Acta, 380:106-18). By this mechanism, HDL can also reduce the proliferation of these cells (Yoshida et al., 1984, Exp. Mol Pathol. 41:258-66).

Infusion therapy with HDL comprising ApoA-I or ApoA-I mimetic peptides has also been shown to regulate plasma HDL levels by the ABC1 transporter, leading to efficacy in the treatment of cardiovascular disease (see, e.g., Brewer et al., 2004, Arterioscler. Thromb. Vasc. Biol. 24:1755-1760).

Two naturally occurring human polymorphism of ApoA-I have been isolated in which an arginine residue is substituted with cysteine. In Apolipoprotein A-$I_{Milano}$ (ApoA-$I_M$), this substitution occurs at residue 173, whereas in Apolipoprotein A-$I_{Paris}$ (ApoA-$I_P$), this substitution occurs at residue 151 (Franceschini et al., 1980, J. Clin. Invest. 66:892-900; Weisgraber et al., 1983, J. Biol. Chem. 258:2508-13; Bruckert et al., 1997, Atherosclerosis 128:121-28; Daum et al., 1999, J. Mol. Med. 77:614-22; Klon et al., 2000, Biophys. J. 79(3):1679-85). Yet a further naturally occurring human polymorphism of ApoA-I has been isolated, in which a leucine is substituted with an arginine at position 144. This polymorphism has been termed Apolipoprotein A-I Zaragoza (ApoA-$I_Z$) and is assocated with severe hypoalphalipoproteinemia and an enhanced effect of high density lipoprotein (HDL) reverse cholesterol transport (Recalde et al., 2001, Atherosclerosis 154(3):613-623; Fiddyment et al., 2011, Protein Expr. Purif. 80(1):110-116).

Reconstituted HDL particles comprising disulfide-linked homodimers of either ApoA-$I_M$ or ApoA-$I_P$ are similar to reconstituted HDL particles comprising wild-type ApoA-I in their ability to clear dimyristoylphosphatidylcholine (DMPC) emulsions and their ability to promote cholesterol efflux (Calabresi et al., 1997b, Biochemistry 36:12428-33; Franceschini et al., 1999, Arterioscler. Thromb. Vasc. Biol. 19:1257-62; Daum et al., 1999, J. Mol. Med. 77:614-22). In both mutations, heterozygous individuals have decreased levels of HDL but paradoxically, are at a reduced risk for atherosclerosis (Franceschini et al., 1980, J. Clin. Invest. 66:892-900; Weisgraber et al., 1983, J. Biol. Chem. 258: 2508-13; Bruckert et al., 1997, Atherosclerosis 128:121-28). Reconstituted HDL particles comprising either variant are capable of LCAT activation, although with decreased efficiency when compared with reconstituted HDL particles comprising wild-type ApoA-I (Calabresi et al., 1997, Biochem. Biophys. Res. Commun. 232:345-49; Daum et al., 1999, J. Mol. Med. 77:614-22).

The ApoA-$I_M$ mutation is transmitted as an autosomal dominant trait; eight generations of carriers within a family have been identified (Gualandri et al., 1984, Am. J. Hum. Genet. 37:1083-97). The status of an ApoA-$I_M$ carrier individual is characterized by a remarkable reduction in HDL-cholesterol level. In spite of this, carrier individuals do not apparently show any increased risk of arterial disease. Indeed, by examination of genealogical records, it appears that these subjects may be "protected" from atherosclerosis (Sirtori et al., 2001, Circulation, 103: 1949-1954; Roma et al., 1993, J. Clin. Invest. 91(4):1445-520).

The mechanism of the possible protective effect of ApoA-$I_M$ in carriers of the mutation seems to be linked to a modification in the structure of the mutant ApoA-$I_M$, with loss of one alpha-helix and an increased exposure of hydrophobic residues (Franceschini et al., 1985, J. Biol. Chem. 260:1632-35). The loss of the tight structure of the multiple alpha-helices leads to an increased flexibility of the molecule, which associates more readily with lipids, compared to normal ApoA-I. Moreover, lipoprotein complexes are more susceptible to denaturation, thus suggesting that lipid delivery is also improved in the case of the mutant.

Bielicki, et al. (1997, Arterioscler. Thromb. Vasc. Biol. 17 (9):1637-43) has demonstrated that ApoA-$I_M$ has a limited capacity to recruit membrane cholesterol compared with wild-type ApoA-I. In addition, nascent HDL formed by the association of ApoA-$I_M$ with membrane lipids was predominantly 7.4-nm particles rather than larger 9- and 11-nm complexes formed by wild-type ApoA-I. These observations indicate that the $Arg_{173} \rightarrow Cys_{173}$ substitution in the ApoA-I primary sequence interfered with the normal process of cellular cholesterol recruitment and nascent HDL assembly. The mutation is apparently associated with a decreased efficiency for cholesterol removal from cells. Its antiatherogenic properties may therefore be unrelated to RCT.

The most striking structural change attributed to the $Arg_{173} \rightarrow Cys_{173}$ substitution is the dimerization of ApoA-$I_M$ (Bielicki et al., 1997, Arterioscler. Thromb. Vasc. Biol. 17 (9):1637-43). ApoA-$I_M$ can form homodimers with itself and heterodimers with ApoA-II. Studies of blood fractions comprising a mixture of apolipoproteins indicate that the presence of dimers and complexes in the circulation may be responsible for an increased elimination half-life of apolipoproteins. Such an increased elimination half-life has been observed in clinical studies of carriers of the mutation (Gregg et al., 1988, NATO ARW on Human Apolipoprotein Mutants: From Gene Structure to Phenotypic Expression, Limone S G). Other studies indicate that ApoA-$I_M$ dimers (ApoA-$I_M$/ApoA-$I_M$) act as an inhibiting factor in the interconversion of HDL particles in vitro (Franceschini et al., 1990, J. Biol. Chem. 265:12224-31).

3.4. Current Treatments for Dyslipidemia and Related Disorders

Dyslipidemic disorders are diseases associated with elevated serum cholesterol and triglyceride levels and lowered serum HDL:LDL ratios, and include hyperlipidemia, especially hypercholesterolemia, coronary heart disease, coronary artery disease, vascular and perivascular diseases, and cardiovascular diseases such as atherosclerosis. Syndromes associated with atherosclerosis such as transient ischemic attack or intermittent claudication, caused by arterial insufficiency, are also included. A number of treatments are currently available for lowering the elevated serum cholesterol and triglycerides associated with dyslipidemic disorders. However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), colestipol hydrochloride (Colestid®, The Upjohn Company), and colesevelam hydrochloride (Welchol®, Daiichi-Sankyo Company). When taken orally, these positively-charged resins bind to the negatively charged bile acids in the intestine. Because the resins cannot be absorbed from the intestine, they are excreted carrying the bile acids with them. The use of such resins at best, however, only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

Statins are cholesterol lowering agents that block cholesterol synthesis by inhibiting HMGCoA reductase, the key enzyme involved in the cholesterol biosynthetic pathway. Statins, e.g., lovastatin (Mevacor®), simvastatin (Zocor®), pravastatin (Pravachol®), fluvastatin (Lescol®) and atorvastatin (Lipitor®), are sometimes used in combination with bile-acid-binding resins. Statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (The Physicians Desk Reference, 56$^{th}$ Ed., 2002, Medical Economics).

Niacin (nicotinic acid) is a water soluble vitamin B-complex used as a dietary supplement and antihyperlipidemic agent. Niacin diminishes production of VLDL and is effective at lowering LDL. In some cases, it is used in combination with bile-acid binding resins. Niacin can increase HDL when used at adequate doses, however, its usefulness is limited by serious side effects when used at such high doses. Niaspan® is a form of extended-release niacin that produces fewer side effects than pure niacin. Niacin/Lovastatin (Nicostatin®) is a formulation containing both niacin and lovastatin and combines the benefits of each drug.

Fibrates are a class of lipid-lowering drugs used to treat various forms of hyperlipidemia (i.e., elevated serum triglycerides) that may also be associated with hypercholesterolemia. Fibrates appear to reduce the VLDL fraction and modestly increase HDL, however the effect of these drugs on serum cholesterol is variable. In the United States, fibrates such as clofibrate (Atromid-S®), fenofibrate (Tricor®) and bezafibrate (Bezalip®) have been approved for use as antilipidemic drugs, but have not received approval as hypercholesterolemia agents. For example, clofibrate is an antilipidemic agent that acts (via an unknown mechanism) to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®) is a lipid regulating agent that moderately decreases serum triglycerides and VLDL cholesterol, and moderately increases HDL cholesterol—the $HDL_2$ and $HDL_3$ subfractions as well as both ApoA-I and A-II (i.e., the AI/AMT-HDL fraction). However, the lipid response is heterogeneous, especially among different patient populations. Moreover, while prevention of coronary heart disease was observed in male patients between 40-55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates including toxicity such as malignancy (especially gastrointestinal cancer), gallbladder disease and an increased incidence in non-coronary mortality.

Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

Other agents useful for the treatment of hyperlipidemia include ezetimibe (Zetia®; Merck), which blocks or inhibits cholesterol absorption. However, inhibitors of ezetimibe have been shown to exhibit certain toxicities.

HDL, as well as recombinant forms of ApoA-I complexed with phospholipids can serve as sinks/scavengers for apolar or amphipathic molecules, e.g., cholesterol and derivatives (oxysterols, oxidized sterols, plant sterols, etc.), cholesterol esters, phospholipids and derivatives (oxidized phospholipids), triglycerides, oxidation products, and lipopolysaccharides (LPS) (see, e.g., Casas et al., 1995, J. Surg. Res. November 59(5):544-52). HDL can also serve as also a scavenger for TNF-alpha and other lymphokines. HDL can also serve as a carrier for human serum paraoxonases, e.g., PON-1, -2, -3. Paraoxonase, an esterase associated with HDL, is important for protecting cell components against oxidation. Oxidation of LDL, which occurs during oxidative stress, appears directly linked to development of atherosclerosis (Aviram, 2000, Free Radic. Res. 33 Suppl:S85-97). Paraoxonase appears to play a role in susceptibility to atherosclerosis and cardiovascular disease (Aviram, 1999, Mol. Med. Today 5(9):381-86). Human serum paraoxonase (PON-1) is bound to high-density lipoproteins (HDLs). Its activity is inversely related to atherosclerosis. PON-1 hydrolyzes organophosphates and may protect against atherosclerosis by inhibition of the oxidation of HDL and low-density lipoprotein (LDL) (Aviram, 1999, Mol. Med. Today 5(9): 381-86). Experimental studies suggest that this protection is associated with the ability of PON-1 to hydrolyze specific lipid peroxides in oxidized lipoproteins. Interventions that preserve or enhance PON-1 activity may help to delay the onset of atherosclerosis and coronary heart disease.

HDL further has a role as an antithrombotic agent and fibrinogen reducer, and as an agent in hemorrhagic shock (Cockerill et al., WO 01/13939, published Mar. 1, 2001). HDL, and ApoA-I in particular, has been show to facilitate an exchange of lipopolysaccharide produced by sepsis into lipid particles comprising ApoA-I, resulting in the functional neutralization of the lipopolysaccharide (Wright et al., WO9534289, published Dec. 21, 1995; Wright et al., U.S. Pat. No. 5,928,624 issued Jul. 27, 1999; Wright et al., U.S. Pat. No. 5,932,536, issued Aug. 3, 1999).

There are a variety of methods available for making lipoprotein complexes in vitro. U.S. Pat. Nos. 6,287,590 and 6,455,088 disclose a method entailing co-lyophilization of apolipoprotein and lipid solutions in organic solvent (or solvent mixtures) and formation of charged lipoprotein complexes during hydration of the lyophilized powder. Lipoprotein complexes can also be formed by a detergent dialysis method; e.g., a mixture of a lipid, a lipoprotein and a detergent such as cholate is dialyzed and reconstituted to form a complex (see, e.g., Jonas et al., 1986, Methods Enzymol. 128:553-82). Example 1 of U.S. publication 2004/0067873 discloses a cholate dispersion method, in which a lipid dispersion is combined with cholate under conditions for forming micelles, and these in turn are incubated with an apoliprotein solution to form complexes. Ultimately, the cholate, which is toxic, has to be removed, e.g., by dialysis, ultrafiltration or adsorption absorption onto an affinity bead or resin. U.S. Pat. No. 6,306,433 discloses lipoprotein complex formation by subjecting a fluid mixture of a protein and lipid to high pressure homogenization. However, proteins that are sensitive to high shear forces can lose activity when exposed to high pressure homogenization.

Thus, currently available manufacturing methods result in wastage of starting materials, such as protein degradation, and/or require purification of the resulting product, such as removal of a toxic agent, and thus are inefficient and costly. Additionally, preparations of lipoprotein complexes can be heterogeneous, containing a mixture of complexes varying in size and in composition. See, e.g., U.S. Pat. No. 5,876, 968. Accordingly, there is a need to develop new methods for production of lipoprotein complexes that are efficient and yield more homogeneous complexes, preferably having a high degree of purity. Such processes could allow more economical production on a large scale while generating a more uniform pharmaceutically acceptable product with fewer risks of side effects due to contaminants.

Moreover, the therapeutic use of ApoA-I, ApoA-I$_M$, ApoA-I$_P$ and other variants, as well as reconstituted HDL, is presently limited, however, by the large amount of apolipoprotein required for therapeutic administration and by the cost of protein production, considering the low overall yield of production and the occurrence of protein degradation in cultures of recombinantly expressed proteins. (See, e.g., Mallory et al., 1987, J. Biol. Chem. 262(9):4241-4247; Schmidt et al., 1997, Protein Expression & Purification 10:226-236). It has been suggested by early clinical trials that the dose range is between 1.5-4 g of protein per infusion for treatment of cardiovascular diseases. The number of infusions required for a full treatment is unknown. (See, e.g., Eriksson et al., 1999, Circulation 100(6):594-98; Carlson, 1995, Nutr. Metab. Cardiovasc. Dis. 5:85-91; Nanjee et al., 2000, Arterioscler. Thromb. Vasc. Biol. 20(9):2148-55; Nanjee et al., 1999, Arterioscler. Thromb. Vasc. Biol. 19(4):979-89; Nanjee et al., 1996, Arterioscler. Thromb. Vasc. Biol. 16(9):1203-14).

Recombinant human ApoA-I has been expressed in heterologous hosts, however, the yield of mature protein has been insufficient for large-scale therapeutic applications, especially when coupled to purification methods that further reduce yields and result in impure product.

Weinberg et al., 1988, J. Lipid Research 29:819-824, describes the separation of apolipoproteins A-I, A-II and A-IV and their isoforms purified from human plasma by reverse phase high pressure liquid chromatography.

WO 2009/025754 describes protein separation and purification of alpha-1-antitrypsin and ApoA-I from human plasma.

Hunter et al., 2009, Biotechnol. Prog. 25(2):446-453, describes large-scale purification of the ApoA-I Milano variant that is recombinantly expressed in E. coli.

Caparon et al., 2009, Biotechnol. And Bioeng. 105(2): 239-249 describes the expression and purification of ApoA-I Milano from an E. coli host which was genetically engineered to delete two host cell proteins in order to reduce the levels of these proteins in the purified apolipoprotein product.

U.S. Pat. No. 6,090,921 describes purification of ApoA-I or apolipoprotein E (ApoE) from a fraction of human plasma containing ApoA-I and ApoE using anion-exchange chromatography.

Brewer et al., 1986, Meth. Enzymol. 128:223-246 describes the isolation and characterization of apolipoproteins from human blood using chromatographic techniques.

Weisweiler et al., 1987, Clinica Chimica Acta 169:249-254 describes isolation of ApoA-I and ApoA-II from human HDL using fast-protein liquid chromatography.

deSilva et al., 1990, J. Biol. Chem. 265(24):14292-14297 describes the purification of apolipoprotein J by immunoaffinity chromatography and reverse phase high performance liquid chromatography.

Lipoproteins and lipoprotein complexes are currently being developed for clinical use, with clinical studies using different lipoprotein-based agents establishing the feasibility of lipoprotein therapy (Tardif, 2010, Journal of Clinical Lipidology 4:399-404). One study evaluated autologous delipidated HDL (Waksman et aL, 2010, J Am. Coll. Cardiol. 55:2727-2735). Another study evaluated ETC-216, a complex of recombinant ApoA-$I_M$ and palmitoyl-oleoyl-PC (POPC) (Nissen et al., 2003, JAMA 290:2292-2300). CSL-111 is a reconstituted human ApoA-I purified from plasma complexed with soybean phosphatidylcholine (SBPC) (Tardif et al., 2007, JAMA 297:1675-1682). Current exploratory drugs have shown efficacy in reducing the atherosclerotic plaque but the effect was accompanied by secondary effects such as increase in transaminases or formation of ApoA-I antibodies (Nanjee et al., 1999, Arterioscler. Vasc. Throm. Biol. 19:979-89; Nissen et al., 2003, JAMA 290:2292-2300; Spieker et al., 2002, Circulation 105:1399-1402; Nieuwdorp et al., 2004, Diabetologia 51:1081-4; Drew et al., 2009, Circulation 119, 2103-11; Shaw et al., 2008, Circ. Res. 103:1084-91; Tardiff et al., 2007, JAMA 297:1675-1682; Waksman, 2008, Circulation 118:S 371; Cho, U.S. Pat. No. 7,273,849 B2, issued Sep. 25, 2007). For example, the ERASE clinical trial (Tardiff et al., 2007, JAMA 297:1675-1682) utilized two doses of CSL-111: 40 mg/kg and 80 mg/kg of ApoA-I. The 80 mg/kg dose group had to be stopped due to liver toxicity (as shown by serious transaminase elevation). Even in the 40 mg/kg dose group several patient experience transaminase elevation.

The need therefore exists for safer drugs that are more efficacious in lowering serum cholesterol, increasing HDL serum levels, preventing and/or treating dyslipidemia and/or diseases, conditions and/or disorders associated with dyslipidemia. There is a need in the art for lipoprotein formulations that are not associated with liver toxicity, and preferably induce only minimal (or no) increase in triglycerides, LDL-triglycerides, or VLDL-triglycerides, as well as for robust production methods that can be used to reliably make these lipoprotein formulations on a commercial scale.

4. SUMMARY

The present disclosure provides lipoprotein complexes, comprising a protein fraction (e.g., an apolipoprotein fraction) and a lipid fraction, and populations thereof that are especially suited to treating and/or preventing dyslipidemia and diseases, disorders and/or conditions associated with dyslipidemia. It has been discovered that populations of complexes which have greater purity and/or homogeneity, and/or comprise particular ratios of lipids and proteins, as described herein, have increased ability to mobilize cholesterol combined with reduced risk of side effects.

The lipoprotein complexes comprise a protein fraction (e.g., an apolipoprotein fraction) and a lipid fraction (e.g., a phospholipid fraction). The protein fraction includes one or more lipid-binding proteins, such as apolipoproteins, peptides, or apolipoprotein peptide analogs or mimetics capable of mobilizing cholesterol when present in a lipoprotein complex. Non-limiting examples of such apolipoproteins and apolipoprotein peptides include preproapolipoproteins, preproApoA I, proApoA-I, ApoA-I, preproApoA-II, proApoA-II, ApoA-II, preproApoA-IV, proApoA-IV, ApoA-IV, ApoA-V, preproApoE, proApoE, ApoE, preproApoA-$I_M$, proApoA-$I_M$, ApoA-$I_M$, preproApoA-$I_P$, proApoA-$I_P$, ApoA-$I_P$, preproApoA-$I_Z$, proApoA-$I_Z$, and ApoA-$I_Z$. The apolipoprotein(s) can be in the form of monomers, dimers, or trimers, or mixtures thereof. In a specific embodiment, the apolipoprotein fraction consists essentially of ApoA-I, most preferably of a single isoform. ApoA-I in lipoprotein complexes can have at least 90% or at least 95% sequence identity to a protein corresponding to amino acids 25 to 267 of SEQ ID NO:1. Optionally, ApoA-I further comprises an aspartic acid at the position corresponding to the full length ApoA-I amino acid 25 of SEQ ID NO:1 (and position 1 of the mature protein). Preferably, at least 75%, at least 80%, at least 85%, at least 90% or at least 95% of the ApoA-I is correctly processed, mature protein (i.e., lacking the signal and propeptide sequences) and not oxidized, deamidated and/or truncated.

The present disclosure also provides mammalian host cells engineered to express ApoA-I, cell cultures comprising ApoA-I, and methods of producing mature, biologically active ApoA-I. It has been discovered that it is possible to engineer mammalian host cells to express large quantities of mature ApoA-I, that is substantially free of both immature ApoA-I (proApoA-I) and truncated forms of ApoA-I generated by protease degradation. These results are surprising. First, host cell machinery for protein processing could be expected to be overwhelmed by overexpression of a heterologous protein such as ApoA-I, leading to the production of the unprocessed, immature protein. Second, ApoA-I secreted into the culture medium is subject to degradation by proteases and yet, only low levels of truncated ApoA-I are observed in the culture medium. The mammalian host cells, cell culture and the methods of producing ApoA-I are particularly suited to the production of mature protein, useful in therapeutic applications, in commercially relevant quantities.

As provided herein, a mammalian host cell is engineered to express a protein that preferably comprises (or consists of) an amino acid sequence having at least 95%, at least 96%, at least 97%, at least 98%, at least 99%, or 100% identity to positions 25 to 267 of SEQ ID NO:1. The protein preferably has an aspartic acid residue at the position corresponding to position 25 of SEQ ID NO:1. The mammalian host cell can optionally further secrete such a protein. In some instances, the protein expressed and/or secreted by the mammalian host cell can further comprise an 18-amino acid signal sequence (MKAAVLTLAVLFLTGSQA, SEQ ID NO:2) and/or a 6-amino acid propeptide sequence (RHFWQQ, SEQ ID NO:3). In some instances, the host cell is engineered to express a protein comprising an amino acid sequence having at least 95%, at least 96%, at least 97%, at least 98%, at least 99%, or 100% identity to SEQ ID NO:1.

The host cell can be from any mammalian cell line, including but not limited to Chinese hamster ovary (e.g., CHO-K1 or CHO-S), VERO, BHK, BHK 570, HeLa, COS-1, COS-7, MDCK, 293, 3T3, PC12 and W138, or from an amyeloma cell or cell line (e.g., a murine myeloma cell or cell line).

The mammalian host cell can further contain multiple copies of a nucleic acid encoding an ApoA-I protein, e.g., a protein comprising or consisting of positions 25 to 267 of SEQ ID NO:1. For example, the mammalian host cell can contain at least about 5, 6, 7, 8, or more copies, and up to about 10, 11, 12, 13, or 14 copies of the nucleic acid. The nucleic acid can further be operably linked to a promoter capable of expressing the protein at a high level in the mammalian host cell, such as, for example, a simian cytomegalovirus promoter or more specifically, immediate early simian cytomegalovirus promoter.

The mammalian host cells are preferably capable of producing at least about 0.5, 1, 2, or 3 g/L ApoA-I in culture and/or up to about 20 g/L ApoA-I in culture, e.g., up to 4, 5, 6, 7, 8, 9, 10, 12, or 15 g/L ApoA-I in culture. The culture can be of any scale, ranging from about 150 mL to about 500 L, 1000 L, 2000 L, 5000 L, 10,000 L, 25,000 L, or 50,000 L or more. In varying embodiments, the culture volume can range from 10 L to 50 L, from 50 L to 100 L, from 100 L to 150 L, from 150 L to 200 L, from 200 L to 300 L, from 300 L to 500 L, from 500 L to 1000 L, from 1000 L to 1500 L, from 1500 L to 2000 L, from 2000 L to 3000 L, from 3000 L to 5000 L, from 5000 L to 7500 L, from 7500 L to 10,000 L, from 10,000 L to 20,000 L, from 20,000 L to 40,000 L, from 30,000 L to 50,000 L. In some instances, the culture is a large scale culture, such as 15 L, 20 L, 25 L, 30 L, 50 L, 100 L, 200 L, 300 L, 500 L, 1000 L, 5000 L, 10,000 L, 15,000 L, 20,000 L, 25,000 L, up to 50,000 L or more.

The mammalian host cells of the present disclosure can be grown in culture. Thus, the present disclosure further provides a mammalian cell culture, comprising a plurality of mammalian host cells as described above or in Section 6.1.2 below. The cell culture can include one or more of the following features: (a) the culture (which is optionally a large scale batch culture of at least 10 liters, at least 20 liters, at least 30 liters, at least 50 liters, at least 100 liters, 300 L, 500 L, 1000 L, 5000 L, 10,000 L, 15,000 L, 20,000 L, 25,000 L, up to 50,000 L or a continuous culture of at least 10 liters, at least 20 liters, at least 30 liters, at least 50 liters, at least 100 liters, 300 L, 500 L, 1000 L, 5000 L, or up to 10,000 L) comprises at least about 0.5, 1.0, 1.5, 2.0, 2.5, 3.0, 3.5, 4.0 g/L or more of mature ApoA-I protein comprising or consisting of an amino sequence corresponding to amino acids 25 to 267 of SEQ ID NO:1; (b) at least 75%, at least 80%, at least 85%, at least 90%, at least 95%, at least 98%, or at least 99% of the protein in the culture medium is an ApoA-I protein lacking a signal sequence; (c) at least 75%, at least 80%, at least 85%, at least 90%, at least 95%, at least 98%, or at least 99% of the protein in the culture medium is a mature ApoA-I protein lacking a signal sequence and a propeptide sequence; and (d) at least 75%, at least 80%, at least 85%, at least 90%, at least 95% of the mature ApoA-I is not truncated, oxidized, or deamidated.

The present disclosure also provides methods of producing mature, biologically active ApoA-I. Generally, the methods comprise culturing any of the mammalian host cells described above or in Section 6.1.2 under conditions in which ApoA-I is expressed and secreted. The method can further include a step of recovering from the supernatant of a cultured mammalian host cell, and optionally purifying, the mature, biologically active ApoA-I (such as by the methods disclosed in Sections 6.1.3 and 6.1.4 below).

ApoA-I obtained or obtainable by the methods described above can further be complexed with lipid to form a lipoprotein complex as described herein, and/or incorporated into pharmaceutical compositions in therapeutically effective amounts. The pharmaceutical compositions preferably are phosphate buffered solutions that also contain sucrose and/or mannitol as excipients.

It has further been discovered that, by purifying ApoA-I using a new combination of chromatography and filtration steps, large quantities of pure ApoA-I can be produced that contains levels of host cell proteins, host cell DNA, endotoxins and truncated forms of the protein that are low enough to confer one or more attributes, including reduced risk of side effects and low or no toxicity, rendering the protein particularly suitable for therapeutic uses. Preferably, ApoA-I purified by the methods described herein is produced recombinantly in mammalian cells and is secreted into the growth medium. Accordingly, the present disclosure relates to a method of purifying ApoA-I comprising the steps of: (a) contacting an ApoA-I containing solution with an anion exchange matrix under conditions such that the ApoA-I does not bind to the matrix; (b) filtering the ApoA-I containing solution obtained in step (a) through a membrane having a pore size sufficient to remove viruses or viral particles; (c) passing the filtrate obtained in step (b) through a first reverse phase chromatography column under conditions such that the ApoA-I binds to the matrix; (d) eluting from the first reverse phase chromatography matrix a first ApoA-I containing reverse phase eluate using a gradient of increasing concentrations of an organic solvent; (e) passing the first ApoA-I reverse phase eluate from step (d) through a second reverse phase chromatography column under conditions such that the ApoA-I binds to the matrix; and (f) eluting from the second reverse phase chromatography matrix a second ApoA-I containing reverse phase eluate using a gradient of increasing concentrations of an organic solvent. The order in which the steps are performed is not critical, for example, in an exemplary embodiment the step of filtering through a membrane to remove viruses or viral particles is performed after step (f) above, rather than after step (a).

Also provided herein is a substantially pure ApoA-I product obtained or obtainable by the purification methods described herein in which the concentration of ApoA-I is at least 10 g/L. The substantially pure ApoA-I product produced by the purification methods described herein preferably comprises less than about 10 pg of host cell DNA per mg of ApoA-I, less than about 100 ng of host cell proteins per mg of ApoA-I, and/or less than 0.1 EU of endotoxin per mg of ApoA-I. The ApoA-I product can be at least 95% pure, at least 96% pure, at least 97% pure, at least 98% pure or at least 99% pure.

Furthermore, the substantially pure ApoA-I product can be incorporated into any of the pharmaceutical compositions and/or lipoprotein complexes described herein that comprise ApoA-I.

The lipid fraction typically includes one or more phospholipids which can be neutral, negatively charged, positively charged, or a combination thereof. The fatty acid chains on phospholipids are preferably from 12 to 26 or 16 to 26 carbons in length and can vary in degree of saturation from saturated to mono-unsaturated. Exemplary phospholipids include small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, egg sphingomyelin, milk sphingomyelin, palmitoyl sphingomyelin, phytosphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. Phospholipid fractions including SM and palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives.

Most preferably the lipid fraction contains at least one neutral phospholipid and, optionally, one or more negatively charged phospholipids. In lipoprotein complexes that include both neutral and negatively charged phospholipids, the neutral and negatively charged phospholipids can have fatty acid chains with the same or different number of carbons and the same or different degree of saturation. In some instances, the neutral and negatively charged phospholipids will have the same acyl tail, for example a C16:0, or palmitoyl, acyl chain.

When the lipid component of the complex comprises or consists of neutral and negatively charged phospholipids, the weight-to-weight (wt:wt) ratio of neutral to negatively charged phospholipid(s) is preferably in a wt:wt ratio ranging from about 99:1 to about 90:10, more preferably from about 99:1 to about 95:5, and most preferably from about 98:2 to about 96:4. In one embodiment, the neutral phospholipid(s) and the negatively charged phospholipid(s) are present in a weight-to-weight (wt:wt) ratio of neutral phospholipid(s) to negatively charged phospholipid(s) of about 97:3.

The neutral phospholipid can be natural or synthetic. Preferably, the phospholipid is a sphingomyelin ("SM"), such as palmitoyl sphingomyelin, a phytosphingomyelin, a diphytosphingomyelin, a phosphosphingolipid, or a glycosphingolipid, optionally with saturated or mono-unsaturated fatty acids with chain lengths from 16 to 26 carbon atoms. SM can be from any source. For example, the SM can be obtained from milk, egg, brain, or made synthetically. In a specific embodiment, the SM is obtained from chicken egg ("egg SM"). In another specific embodiment, the SM is palmitoylsphingomyelin.

Any phospholipid that bears at least a partial negative charge at physiological pH can be used as the negatively charged phospholipid. Non-limiting examples include negatively charged forms, e.g., salts, of phosphatidylinositol, a phosphatidylserine, a phosphatidylglycerol and a phosphatidic acid. In a specific embodiment, the negatively charged phospholipid is 1,2-dipalmitoyl-sn-glycero-3-[phospho-rac-(1-glycerol)], or DPPG, a phosphatidylglycerol. Preferred salts include potassium and sodium salts.

The phospholipids used to manufacture the complexes of the disclosure are preferably at least 95% pure and are more preferably at least 99% pure, and/or have levels of oxidation levels under 4 meq O/kg, more preferably under 3 meq O/kg (e.g., under 2 meq O/kg). The major initial reaction product of oxygen and fatty acids is hydroperoxide. Using an iodometric method, it is possible to measure oxidation levels by assaying the presence of peroxide in a sample.

The lipoprotein complexes of the present disclosure preferably have ratios of apolipoprotein to lipid that result in more complete and homogeneous complex formation, as shown in the examples below. The lipoprotein complexes are characterized by an apolipoprotein fraction:lipid fraction molar ratio ranging from 1:80 to 1:120, from 1:100 to 1:115, or from 1:105 to 1:110, where the apolipoprotein is expressed in ApoA-I equivalents. In specific embodiments, the molar ratio of the apolipoprotein fraction:lipid fraction is 1:80 to 1:90 (e.g., 1:82, 1:85 or 1:87), from 1:90 to 1:100 (e.g., 1:95 or 1:98), from 1:100 to 1:110 (e.g., 1:105 or 1:108).

In specific embodiments, particularly those in which egg SM is used as the neutral lipid, the weight ratio of the apolipoprotein fraction:lipid fraction ranges from about 1:2.7 to about 1:3 (e.g., 1:2.7).

The lipoprotein complexes of the present disclosure can also be used as carriers to deliver hydrophobic, lipophilic or apolar active agents. For such applications, the lipid fraction can further include, or the lipoprotein complex can be loaded with, one or more hydrophobic, lipophilic or apolar active agents, including but not limited to fatty acids, drugs, nucleic acids, vitamins, and/or nutrients. Specific examples of active agents are described in Section 6.2.

The present disclosure also provides populations of the lipoprotein complexes. Typically:
- the populations contain a plurality of lipoprotein complexes, each comprising a protein fraction and a lipid fraction;
- the protein fractions contain a lipoprotein or lipoprotein analog as described above, and in Section 6.1 or in Section 6.5.3; most preferably a protein fraction comprises or consists essentially of lipoprotein (e.g., ApoA-I protein) that is obtained or obtainable by the methods described in Section 6.1.2 and/or purified by the methods described in Section 6.1.4;
- the lipid fractions contain a lipid as described above, and in Section 6.2 or in Section 6.5.2;
- the lipoprotein complexes are preferably produced by the thermal cycling methods described in Section 6.5.4.

Applicants have discovered several features that are thought to contribute individually or in combination to the potency and the safety profile of lipoprotein complex populations. These features include:
- the homogeneity in the size of the complexes in a population, mostly ranging between 4 nm and 15 nm (e.g., between 5 nm and 12 nm, between 6 nm and 15 nm, or between 8 nm and 10 nm);
- the purity of the apolipoprotein used to make the complex (e.g., lack of oxidized, deamidated, truncated, and/or immature forms of apolipoprotein and/or lack of endotoxin, and/or lack of proteins other than apolipoprotein(s) (such as host cell proteins), and/or host cell DNA that are often present in recombinant production);
- the purity of the complexes themselves in the population (characterized by the lack of contaminants, such as solvents or detergents use to prepare the complexes; the lack of oxidized lipids; the lack of deamidated, oxidized or truncated proteins; and/or reduced amounts or lack of uncomplexed apolipoprotein and/or lipids).

Of these features, the homogeneity of the complexes and the prevalence of mature, unmodified apolipoprotein in complexes, is thought to increase potency. Purity of apolipoproteins, lipids, and the complexes reduces the risk of side effects such as liver damage reflected by increases in liver enzymes (e.g., transaminases). Additionally, the inventors have made it feasible to make populations of lipoprotein complexes by methods that result in the incorporation of most of the apolipoprotein into complexes, and the reduction in the amount of uncomplexed apolipoprotein is also beneficial in that it reduces the risk of an immunogenic response in a subject that could be caused by the administration of a heterologous protein.

Accordingly, the present disclosure provides populations of lipoprotein complexes that are characterized by one or more, or even all, of the following features:
(a) at least 75%, at least 80%, at least 85%, at least 90%, or at least 95% by weight of the lipoprotein, typically ApoA-I, in said population is in mature form;
(b) no more than 25%, no more than 20%, no more than 15%, no more than 10% or no more than 5% by weight of the lipoprotein, typically ApoA-I, in said population is in immature form;
(c) the population contains no more than 100 picograms, no more than 50 picograms, no more than 25 picograms, no more than 10 picograms or no more than 5 picograms host cell DNA per milligram of the lipoprotein, typically ApoA-I;
(d) the population contains no more than 500 nanograms, no more than 200 nanograms, no more than 100 nanograms, no more than 50 nanograms, or no more than 20 nanograms host cell protein per milligram of the lipoprotein, typically ApoA-I;
(e) no more than 25%, no more than 20%, no more than 15%, no more than 10% or no more than 5% by weight of the lipoprotein, typically ApoA-I, in the population is in truncated form;
(f) the lipoprotein component comprises or consists of mature ApoA-I, and no more than 20%, no more than 15%, no more than 10%, no more than 5%, no more than 3%, no more than 2% or no more than 1% of each of methionine 112 and methionine 148 in said ApoA-I in said population is oxidized;
(g) at least 80%, at least 85%, at least 90% or at least 95% of the lipoprotein complexes are in the form of particles of 4 nm to 15 nm in size, e.g., 6 nm to 15 nm in size, or 8 to 12 nm in size, yet more preferably 5 nm to 12 nm in size, as measured by gel permeation chromatography ("GPC") or dynamic light scattering ("DLS");
(i) the population contains no more than 1 EU, no more than 0.5 EU, no more than 0.3 EU or no more than 0.1 EU of endotoxin per milligram of the lipoprotein, typically ApoA-I;
(j) no more than 15%, no more than 10%, no more than 5%, no more than 4%, no more than 3%, no more than 2% or no more than 1% of the amino acids in the lipoprotein, typically ApoA-I, in said population is deamidated;
(k) no more than 15%, no more than 10%, no more than 5%, no more than 2% or 0% by weight of the lipid in the lipid fraction in said complexes is cholesterol;
(l) the population contains no more than 200 ppm, 100 ppm, 50 ppm of a non-aqueous solvent;
(m) the population does not contain any detergent (e.g., cholate);
(n) the population can be at least 80%, at least 85%, at least 90%, at least 95%, at least 97%, at least 98%, or at least 99% homogeneous, as measured by percent of the population in a single peak in gel permeation chromatography;
(o) the population is in a composition in which at least 80%, at least 85%, at least 90%, at least 95% or at least 97% of the protein is in complexed form;
(p) no more than 5%, no more than 4%, no more than 3%, no more than 2% or no more than 1% of the lipid in said population is oxidized; and
(q) no more than 15%, no more than 10%, no more than 5%, no more than 4%, no more than 3%, no more than 2% or no more than 1% of methionine and/or tryptophan residues in said population are oxidized.

In specific embodiments, the population has features selected from the following groups:
Group I: features (a), (b) and (e) above;
Group II: features (c), (d) and (i) above;
Group III: features (f), (j), (e), (p) and (q) above;
Group IV: features (g), (n) and (o) above;
Group V: features (l) and (m) above; and
Group VI: feature (k) above.

In certain aspects, the population is characterized by one or two features independently selected from each of Group I and Group IV; optionally, the population is characterized by three features independently selected from each of Group I and Group IV. The population can additionally be characterized by one, two or three features independently selected from each of Group II and/or Group III. The population can yet be further characterized one or two features independently selected from Group V and/or one feature independently selected from Group VI.

Certain lipid and protein components can form a plurality of different but homogeneous lipoprotein complexes. Accordingly, the present disclosure also provides compositions comprising two, three, or four populations of lipoprotein complexes comprising different amounts of apolipoprotein molecules (e.g., two, three or four ApoA-I molecules or ApoA-I equivalents). In an exemplary embodiment, a composition comprises two lipoprotein complex populations, a first population comprising lipoprotein complexes having 2 ApoA-I molecules or ApoA-I equivalents per lipoprotein complex, a second population comprising lipoprotein complexes having 3 or 4 ApoA-I molecules or ApoA-I equivalents per lipoprotein complex and optionally a third population comprising lipoprotein complexes having 4 or 3 ApoA-I molecules or ApoA-I equivalents per lipoproprotein complex, respectively.

The compositions comprising two or more populations of lipoprotein complexes preferably have low levels of uncomplexed lipoprotein and/or lipid. Accordingly, preferably no more than 15%, no more than 12%, than 10%, no more than 9%, no more than 8%, no more than 7%, no more than 6%, no more than 5%, no more than 4%, no more than 3%, no more than 2%, or no more than 1% of the lipid in the composition is in uncomplexed form and/or no more than 15%, no more than 12%, no more than 10%, no more than 9%, no more than 8%, no more than 7%, no more than 6%, no more than 5%, no more than 4%, no more than 3%, no more than 2%, or no more than 1% of the lipoprotein in the composition is in uncomplexed form.

The disclosure provides methods for making lipoprotein complexes. The methods are based, inter alia, on the discovery that subjecting a suspension containing uncomplexed lipids and lipid-binding proteins or peptides to thermal cycling conditions results in the formation of lipoprotein complexes with advantageous results relative to other methods, such those in which lipoprotein complexes are produced by incubating the components at a fixed temperature.

The present disclosure provides thermal-cycling methods for preparing lipoprotein complexes, such as those described in Sections 6.5.1 to 6.5.4. The methods typically comprise subjecting a suspension comprising lipid particles (a "lipid component") and lipid-binding proteins or peptides (a "protein component") to a plurality of thermal cycles until most of the protein component is incorporated into lipoprotein complexes. The methods generally entail cycling the suspension between a temperature in a first, higher, temperature range and a temperature in a second, lower, temperature range until lipoprotein complexes are formed. The high and low temperature ranges of the thermocycling process are based on the phase transition temperatures of the lipid and protein components of the lipoprotein complexes. Alternatively, where the lipid component does not exhibit a defined or discrete phase transition, as could occur when using phospholipids having unsaturated fatty acid chains or a mixture of phospholipids, the high and low temperature ranges of the thermocycling differ by at least about 20° C., up to about 40° C. or even more. For example, in some embodiments, the low and high temperature ranges differ by 20° C.-30° C., 20° C.-40° C., 20° C.-50° C., 30° C.-40° C., 30° C.-50° C., 25° C.-45° C., 35° C.-55° C.

For a lipid, the phase transition involves a change from a closely packed, ordered structure, known as the gel state, to a loosely packed, less-ordered structure, known as the fluid state. Lipoprotein complexes are typically formed in the art by incubating lipid particles and apolipoproteins at temperatures near the transition temperature of the particular lipid or mixture of lipids used. The phase transition temperature of the lipid component (which can be determined by calorimetry) +/−12° C., more preferably +/−10° C., represents the "low" temperature range in the methods of the disclosure. In certain embodiments, the low temperature range is +/−3° C., +/−5° C., or +/−8° C. of the phase transition temperature of the lipid component. In one specific embodiment, the low temperature range is from no less than 5° C. or no less than 10° C. below to 5° C. above the phase transition temperature of the lipid component.

For a protein, the phase transition temperature involves a change from the tertiary structure into the secondary structure. The phase transition temperature of the protein component +/−12° C., more preferably +/−10° C., represents the "high" temperature range in the methods of the disclosure. In specific embodiments, the high temperature range is +/−3° C., +/−5° C., or +/−8° C. of the phase transition temperature of the protein component. In one specific embodiment, the low temperature range is from 10° C. below to no more than 5° C., no more than 10° C., or no more than 15° C. above the phase transition temperature of the protein component.

The lipid component of the starting suspension, i.e., a suspension that has not yet been subjected to thermal cycling, preferably comprises particles of lipids, e.g., is predominantly composed of lipids that are not complexed to lipid-binding proteins. The make-up of the lipid component is generally as described in Section 6.5.2 below.

The protein component of the starting suspension preferably contains lipid-binding peptides and/or proteins that are uncomplexed to lipids, or are combined with lipids in protein/peptide to lipid ratio that is at least 5-fold greater (e.g., at least 5-fold, at least 10-fold or at least 20-fold greater) than the protein/peptide to lipid ratio in the desired complex. The make-up of the protein component is generally as described in Section 6.1 and in Section 6.5.3 below. The protein component is preferably made according to the methods described in Section 6.1.2 and/or purified according to the methods described in Section 6.1.3 or 6.1.4.

In the methods of the disclosure, a suspension containing the protein component and lipid component is typically thermally cycled between the high temperature range and the low temperature range, preferably starting at a temperature in the high temperature range, until lipoprotein complexes are formed. Using suitable quantities of lipid and protein components (e.g., as described in U.S. Patent Publication No. 2006-0217312 A1, the contents of which are incorporated herein by reference in their entireties), substantially complete complexation of the lipid and protein components can be reached after several cycles. Further details of the protein and lipid stoichiometry suitable for thermal cycling methods are described in Section 6.5.4.

The complexes produced by the methods are typically supramolecular assemblies shaped as micelles, vesicles, spherical or discoidal particles in which the protein component is physically bound to the lipid component at a specific stoichiometric range and with a homogenous size distribution. The present methods advantageously result in substantially complete complexation of the lipids and/or proteins in the starting suspension, resulting in a composition that is substantially without free lipids and/or free protein, as observed by separation methods such as chromatography. Thus, the methods of the disclosure can be performed in the absence of a purification step.

The lipid component in the starting suspension is typically in particle form. It is preferred that the particles are predominantly at least 45 nm, at least 50 nm, at least 55 nm or at least 60 nm in size ranging up to 65 nm, up to 70 nm, up to 75 nm, up to 80 nm in size, up to 100 nm, up to 120 nm, up to 150 nm, up to 200 nm, up to 250 nm, up to 300 nm, up to 500 nm, for example, in the 45 nm to 100 nm or 45 to 250 nm size range, more preferably in the 50 nm to 90 nm size range, and most preferably in the 55 nm to 75 nm size range. In a preferred embodiment, the lipid particles are predominantly composed of egg-sphingomyelin and are 55 to 75 nm in size. In another preferred embodiment, the lipid particles are predominantly composed of one or more synthetic sphingomyelin (e.g., palmitoylsphingomyelin or phytosphingomyelin) and are 175 nm to 250 nm in size. In yet another preferred embodiment, the lipid particles are predominantly composed of one or more synthetic lipids (e.g., palmitoyl sphingomyelin or phytosphingomyelin) and are 250 nm to 1000 nm in size. In yet another preferred embodiment, the lipid particles are predominantly composed of one or more synthetic lipids (e.g., palmitoyl sphingomyelin or phytosphingomyelin) and are 1000 nm to 4000 nm in size. The sizes referred to herein are zeta (Z) average sizes as determined by dynamic light scattering. High pressure homogenization, for example microfluidization, advantageously produces lipid particles of suitable sizes. Other methods for forming particles are disclosed in Section 6.5.2 below, and can be used as an alternative to homogenization. If such methods produce particles outside the preferred size ranges, the particles can be subject to size filtration to obtain particles of a suitable size.

The methods of preparing lipoprotein complexes described herein advantageously produce complexes that are homogeneous in their size distribution, circumventing the need for size fractionation. Moreover, the methods of the disclosure result in substantially complete incorporation (e.g., at least 95%, at least 96%, at least 97%, at least 98% or at least 99%) of the starting protein into lipoprotein particles. Accordingly, the disclosure provides a composition comprising lipoprotein complexes and in which at least 95%, at least 96%, at least 97%, at least 98% or at least 99% of the lipid-binding protein in the composition is complexed to lipid, for example as determined using gel permeation chromatography. In specific embodiments, the disclosure provides a composition comprising lipoprotein complexes which have 4 nm to 20 nm zeta average size, e.g., a 4 nm to 20 nm zeta average size, a 4 nm to 15 nm zeta average size, a 4 nm to 12 nm zeta average size, a 5 nm to 15 nm zeta average size, a 5 nm to 12 nm zeta average size, a 5 nm to 10 nm zeta average size, a 5 nm to 20 nm zeta average size, a 6 nm to 15 nm zeta average size, or an 8 nm to 12 nm zeta average size, and in which at least 95%, at least 96%, at least 97%, at least 98% or at least 99% of the lipid-binding protein in the composition is complexed to lipid, for example as determined using gel permeation chromatography. Subjecting lipid particles to thermal cycling with a lipoprotein according to the methods described herein typically results in a population of lipoprotein particles of 4 nm to 15 nm in size, for example a population of lipoprotein particles of 6 nm to 15 nm in size, 5 nm to 12 nm in size, or 8 nm to 12 nm in size. The size of the lipid particles subjected to thermal cycling can range from 50 nm to 250 nm. In a preferred embodiment, the lipid particles are predominantly composed of egg-sphingomyelin and are 55 to 75 nm in size. In another preferred embodiment, the lipid particles are predominantly composed of one or more synthetic sphingomyelin (e.g., phytosphingomyelin) and are 175 nm to 250 nm in size.

One or more steps in the methods of preparing lipoprotein complexes can be carried out under an inert gas. Doing so can reduce or prevent oxidation of apolipoproteins and/or lipids, thereby reducing risk of side effects, such as liver damage. Suitable inert gases include nitrogen, helium, and argon.

The lipoprotein complexes obtained or obtainable by the methods described above are particularly suited to therapeutic uses because no further purification step is needed after the complexes are formed.

The present disclosure also provides populations of lipoprotein complexes, and pharmaceutical compositions comprising lipoprotein complexes or populations thereof, as described herein, and may optionally include one or more pharmaceutically acceptable carriers, excipients and/or diluents. In some embodiments, the pharmaceutical compositions are packaged in unit dosage amounts suitable for administration. For example, in some embodiments, the compositions comprise unit dosage amounts of dried (for example lyophilized) lipoprotein complexes packaged in sealed vials. Such compositions are suitable for reconstitution with water, physiological solution (such as saline) or buffer, and administration via injection. Such compositions may optionally include one or more anti-caking and/or anti-agglomerating agents to facilitate reconstitution of the charged complexes, or one or more buffering agents, isotonicity agents (e.g., sucrose and/or mannitol), sugars or salts (e.g., sodium chloride) designed to adjust the pH, osmolality and/or salinity of the reconstituted suspension. The populations of lipoprotein complexes and/or pharmaceutical compositions described above can be manufactured under conditions that minimize oxidation, thereby reducing the risk of side effects, such as liver damage, caused by oxidized products. For example, pharmaceutical compositions can be manufactured under an inert gas, such as nitrogen, helium, or argon.

For commercial applications, it is useful to make large-scale preparations of the lipoprotein complexes and pharmaceutical compositions. Accordingly, the present disclosure also provides a preparation of at least 1 L, 2 L, 5 L or 10 L and up to 15 L, 20 L, 30 L, 50 L, or more (e.g., a preparation of 5 L to 30 L, 10 L to 15 L, or 30 L to 50 L) comprising lipoprotein complexes in an amount sufficient to achieve a concentration of lipid-binding protein of at least about 3 mg/mL, at least about 4 mg/mL, or at least about 5 mg/mL, and up to about 10 mg/mL, about 15 mg/mL, or about 20 mg/mL, preferably ranging from about 8 mg/mL to about 12 mg/mL, most preferably about 8 mg/mL. In a specific embodiment, the preparation has a volume of 15 L to 25 L and contains about 100 g to about 250 g of ApoA-I. In another specific embodiment, the preparation has a volume of 30 L to 50 L and contains about 240 g to about 780 g of ApoA-I.

The lipoprotein complexes described herein are useful to treat dyslipidemic disorders in animals, most preferably in humans. Such conditions include, but are not limited to hyperlipidemia, and especially hypercholesterolemia (including heterozygous and homozygous familial hypercholesterolemia), and cardiovascular disease such as atherosclerosis (including treatment and prevention of atherosclerosis) and the myriad clinical manifestations of atherosclerosis, such as, for example, stroke, ischemic stroke, transient ischemic attack, myocardial infarction, acute coronary syndrome, angina pectoris, intermittent claudication, critical limb ischemia, valve stenosis, and atrial valve sclerosis; restenosis (e.g., preventing or treating atherosclerotic plaques which develop as a consequence of medical procedures such as balloon angioplasty); and other disorders, such as endotoxemia, which often results in septic shock.

Lipoprotein complexes and compositions as described herein have been found to effect and/or facilitate cholesterol efflux when administered at doses lower than those used for other lipoprotein complexes in studies to date. See, e.g., Spieker et al., 2002, Circulation 105:1399-1402 (using a dose of 80 mg/kg); Nissen et al., 2003, JAMA 290:2292-2300 (using doses of 15 mg/kg or 40 mg/kg); Tardif et al., 2007 JAMA 297:1675-1682 (using doses of 40 mg/kg to 80 mg/kg), using doses that range from 15 mg/kg to 80 mg/kg. Additionally, the lipoprotein complexes as described herein have been found to have reduced side effects. As shown in the examples below, it has been discovered that lipoprotein complexes of the disclosure effectively mobilize cholesterol at doses as low as 2 mg/kg, and, in contrast lipoprotein complexes previously administered to human patients, do not significantly raise the levels of triglycerides, VLDL, and liver enzymes such as transaminases Nanjee et al., 1999, Arterioscler. Vasc. Throm. Biol. 19:979-89). Moreover, the reduced side effects are observed even as doses are increased up to about 15 mg/kg (lack of triglyceride elevation) or even as high as 45 mg/kg (lack of transaminase increase) in normal subjects with normal liver and/or kidney function. Thus, the ability of the complexes of the present disclosure to be administered without side effects is preferably assessed in an individual with normal liver function, normal kidney function, or both.

Without being bound by theory, the inventors attribute the benefits of the lipoprotein complexes of the disclosure to a more homogeneous size distribution of complexes and reduced amounts of damaged protein and/or lipid (e.g., oxidized protein, deamidated protein, and oxidized lipid) as compared to prior treatments. It is further believed that the negatively charged phospholipids comprising the lipid fraction will impart the complexes and compositions described herein with improved therapeutic properties over conventional lipoprotein complexes. One of the key differences between small discoidal pre-beta HDL particles, which are degraded in the kidney, and large discoidal and/or spherical HDL, which are recognized by the liver where their cholesterol is either stored, recycled, metabolized (as bile acids) or eliminated (in the bile), is the charge of the particles. The small, discoidal pre-beta HDL particles have a lower negative surface charge than large, discoidal and/or spherical HDL particles that are negatively charged. It is believed that the higher negative charge is one of the factors that trigger the recognition of the particles by the liver, and that therefore avoids catabolism of the particles by the kidney. Furthermore, it has been shown that the kidney does not absorb readily absorb charged particles (see Hacker et al., 2009, *Pharmacology: Principles and Practice*, 183). Thus, owing in part to the presence of the charged phospholipids(s), it is believed that negatively charged lipoprotein complexes and compositions described herein will stay in the circulation longer than conventional lipoprotein complexes, or that the charge will affect the half-life of the lipoprotein in a charge-dependent manner. It is expected that their longer circulation (residence) time, combined with a reduction in the rate and/or extent to which the complexes aggregate and fuse with existing HDL as a result of the negative charge, will facilitate cholesterol mobilization (by giving the complexes more time to accumulate cholesterol) and esterification (by providing more time for the LCAT to catalyze the esterification reaction). The charge may also increase the rate of cholesterol capture and/or removal, thereby facilitating removal of cholesterol in larger quantities. As a consequence, it is expected that the negatively charged lipoprotein complexes and compositions described herein will provide therapeutic benefit over conventional lipoprotein therapies, as less complex and/or composition will need to be administered, and less often, with reduced side effects.

Accordingly, the methods provided herein generally involve administering to a subject a therapeutically effective amount of a lipoprotein complex, a population of lipoprotein complexes, or pharmaceutical composition described herein to treat or prevent a dyslipidemic disorder. The lipoprotein complex can be administered at a dose ranging from about 0.25 mg/kg ApoA-I equivalents to about 45 mg/kg, e.g., a dose of about 0.5 mg/kg to about 30 mg/kg or about 1 mg/kg ApoA-I equivalents up to about 15 mg/kg ApoA-I equivalents per injection. The dose can further be tailored to the individual being treated by selecting a dose that minimizes the increase in the level of triglycerides, VLDL-cholesterol and/or VLDL-triglyceride. In specific embodiments, the dose is about 3 mg/kg, about 6 mg/kg, or about 12 mg/kg.

The methods further comprise administering the lipoprotein complex at an interval ranging from 5 to 14 days, or from 6 to 12 days, such as an interval of one or two weeks. The methods can further comprise administering the lipoprotein complex 4, 5, 6, 7, 8, 9, 10, 11, 12, or up to 52 times at any of the intervals described above, and preferably at an interval of one week. For example, in one embodiment, the lipoprotein complex is administered six times, with an interval of 1 week between each administration. For chronic conditions, more than 52 administrations can be carried out. Optionally, the methods can be preceeded by an initial induction phase where the lipoprotein complex is administered more frequently.

Complexes and/or pharmaceutical compositions thereof, can be administered parenterally, e.g., intravenously. Intravenous administration can be done as an infusion over a period of time ranging from about 1 to about 24 hours, or about 1 to 4 hours, about 0.5 to 2 hours, or about 1 hour.

The examples below show small increases in triglyceride levels following administration of doses 30 mg/kg and 45 mg/kg, which is explained by the increase in VLDL and LDL resulting from the high degree of cholesterol mobilization. Those parameters can be controlled during the treatment, as they are routinely measured in hospital laboratories with standard lipid panels. Based on examples below, the dose selection can be achieved to minimize the increase in the level of triglycerides and VLDL-cholesterol and VLDL-triglyceride dependent on the patient reaction to the medicine, which allows a personalized-type medicine.

The complexes and/or compositions can be administered alone (as monotherapy) or, alternatively, they can be adjunc-tively administered with other therapeutic agents useful for treating and/or preventing dyslipidemia and/or its associated conditions, diseases and/or disorders. Non-limiting examples of therapeutic agents with which the negatively charged lipoprotein complexes and compositions described herein can be adjunctively administered include bile acid-binding resins, HMG CoA-reductase inhibitors (statins), niacin, resins, inhibitors of cholesterol absorption, platelet aggregation inhibitors, fibrates, anticoagulants, CETP inhibitors (e.g., anacetrapib and dalcetrapib), and/or PCSKG antibodies or ligands.

5. BRIEF DESCRIPTION OF THE FIGURES

FIG. 1: the amino acid sequence of human prepro-Apo-lipoprotein A-I (SEQ ID NO: 1; GenBank Accession no. AAB59514.1). Amino acids 1-18, in bold font, correspond to the signal sequence of ApoA-I, and amino acids 19-24 correspond to the propeptide sequence, underlined. Both the signal sequence and the propeptide are cleaved in cells to produce the full-length mature human ApoA-I (amino acids 25-267).

FIG. 2: ApoA-I titers in 12-day fed batch cultures of recombinant S-CHO cells expressing ApoA-I. Cells were continuously cultured by serial passage from generation 0 to generation 43. The ApoA-I production was monitored in generations 4, 8, 14, 19, 25, 21, 36 and 43 by reverse phase HPLC. The amount of ApoA-I in the culture medium varied from 1259 mg/L to 1400 mg/L.

Figure 3A:
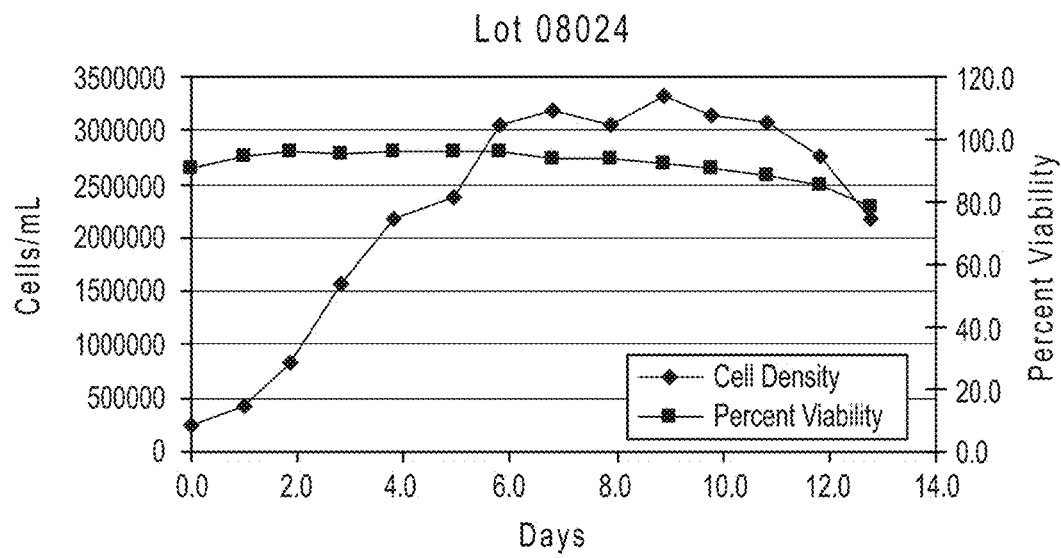
Figure 3B:
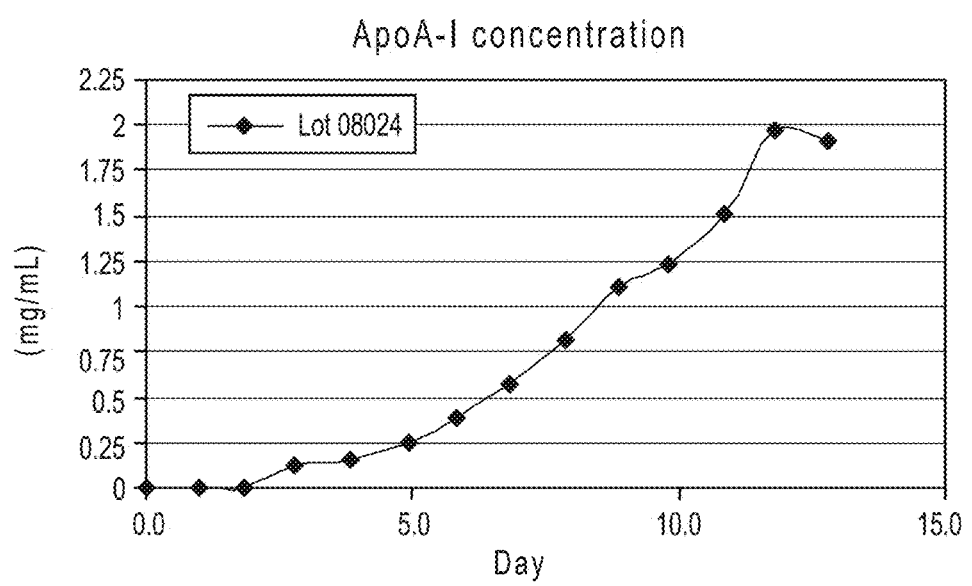

FIGS. 3A-3B: FIG. 3A shows the viable cell density in a 200 L 13-day culture of recombinant S-CHO cells expressing ApoA-I. Viable cell density peaked on day 9 at 33.20× 105 cells/mL with a viability of 92.5%. FIG. 3B shows the concentration of ApoA-I in the culture medium of the 13-day culture. The concentration of ApoA-I in the culture medium peaked on day 12 at around 2 mg/mL.

Figure 4:
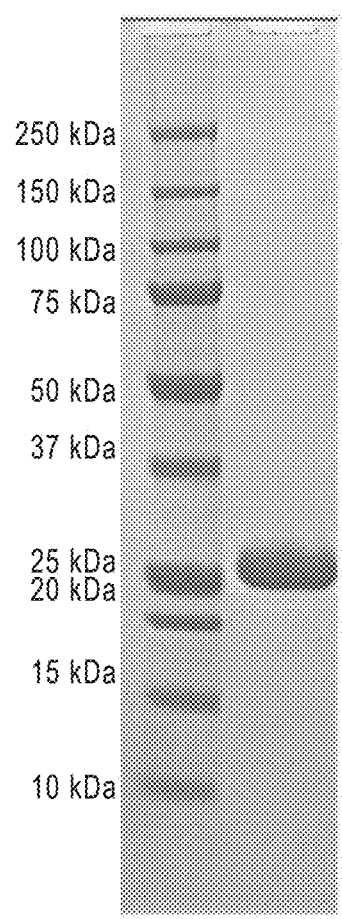

FIG. 4: SDS polyacrylamide gel of ApoA-I purified by the methods described herein. The left-hand lane shows molecular weight markers. The right-hand lane shows purified ApoA-I having a molecular weight of approximately 28 kD.

Figure 5A:
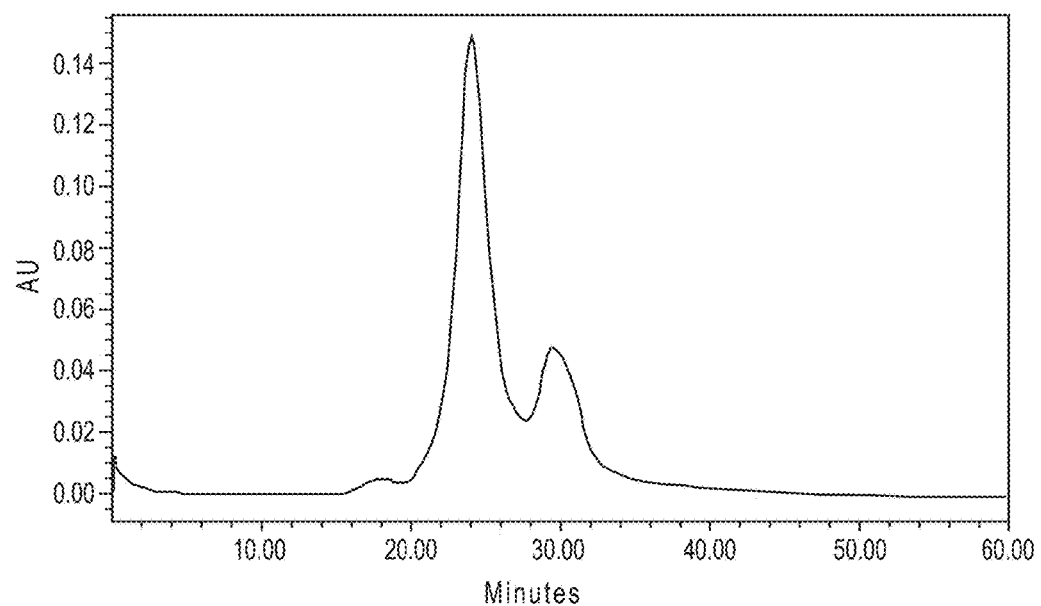
Figure 5B:
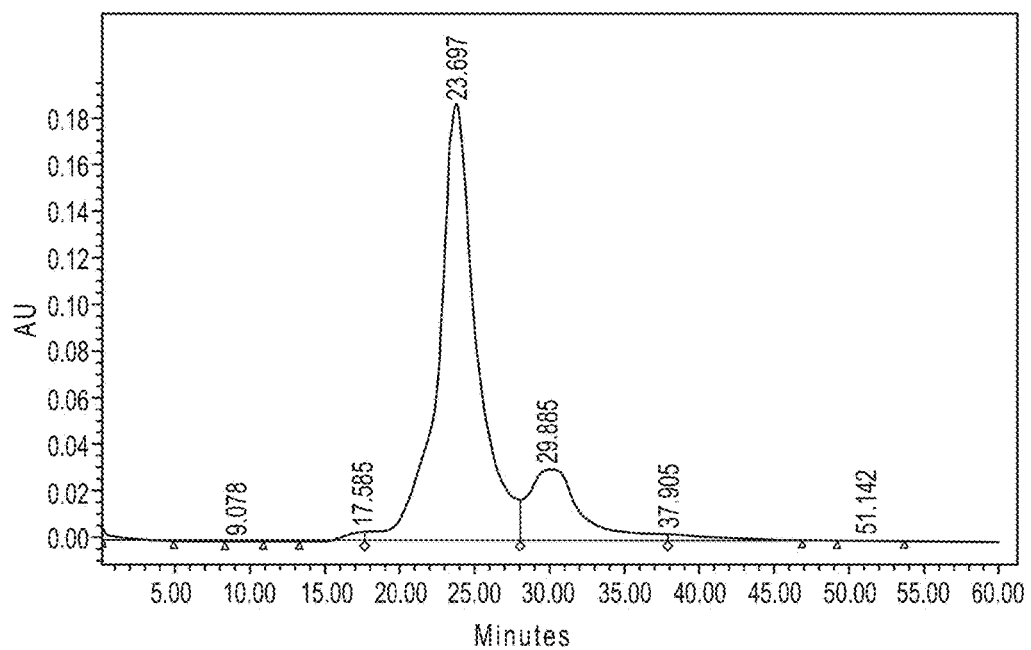
Figure 5C:
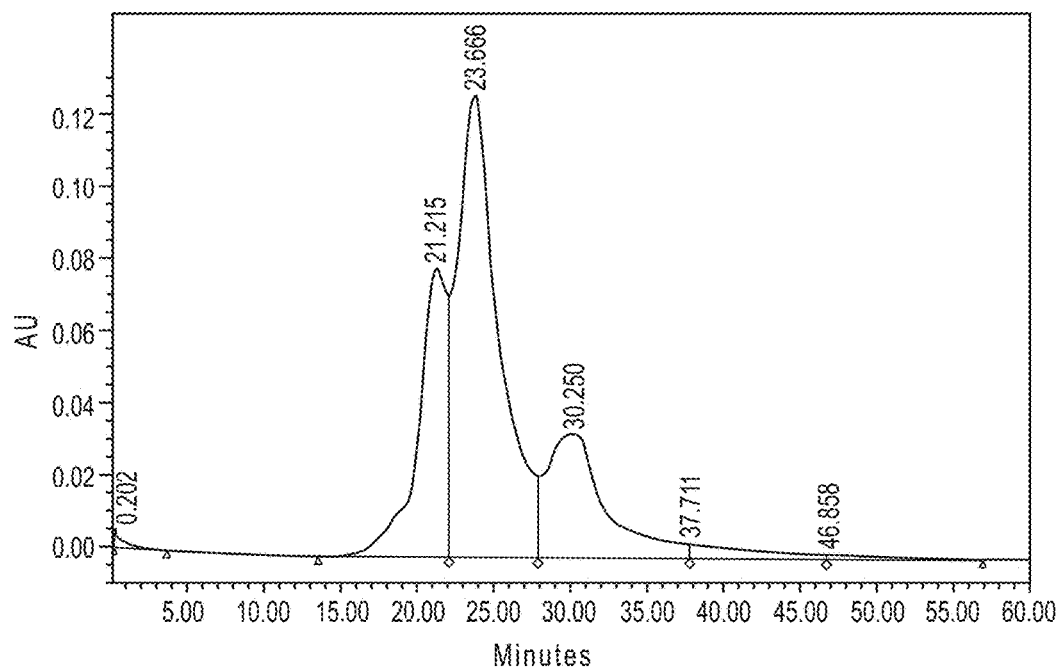
Figure 5D:
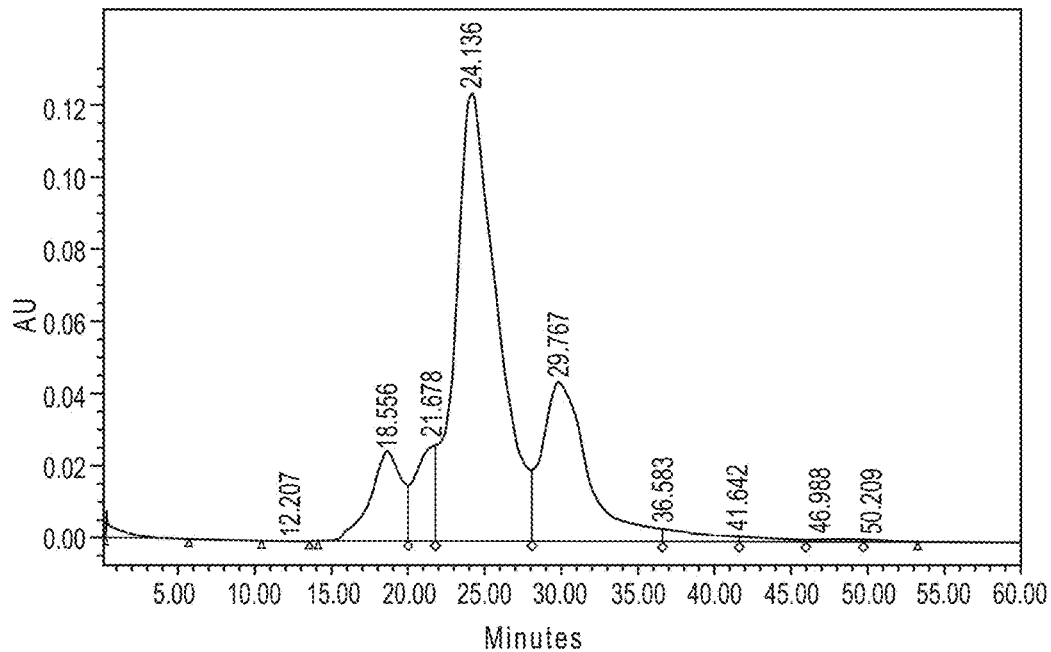
Figure 6A:
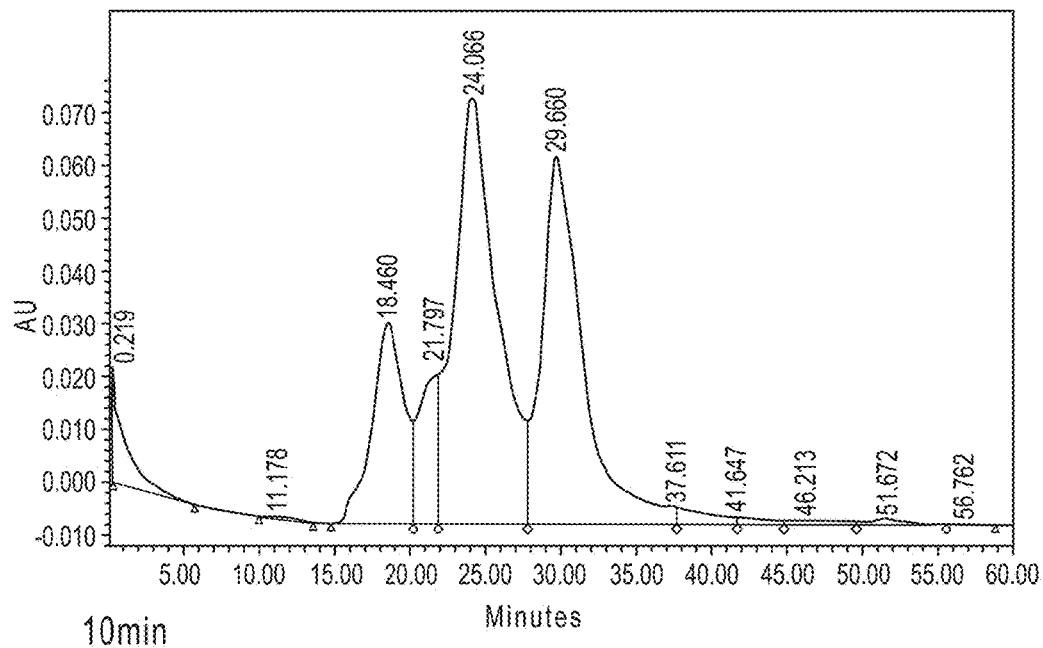
Figure 6B:
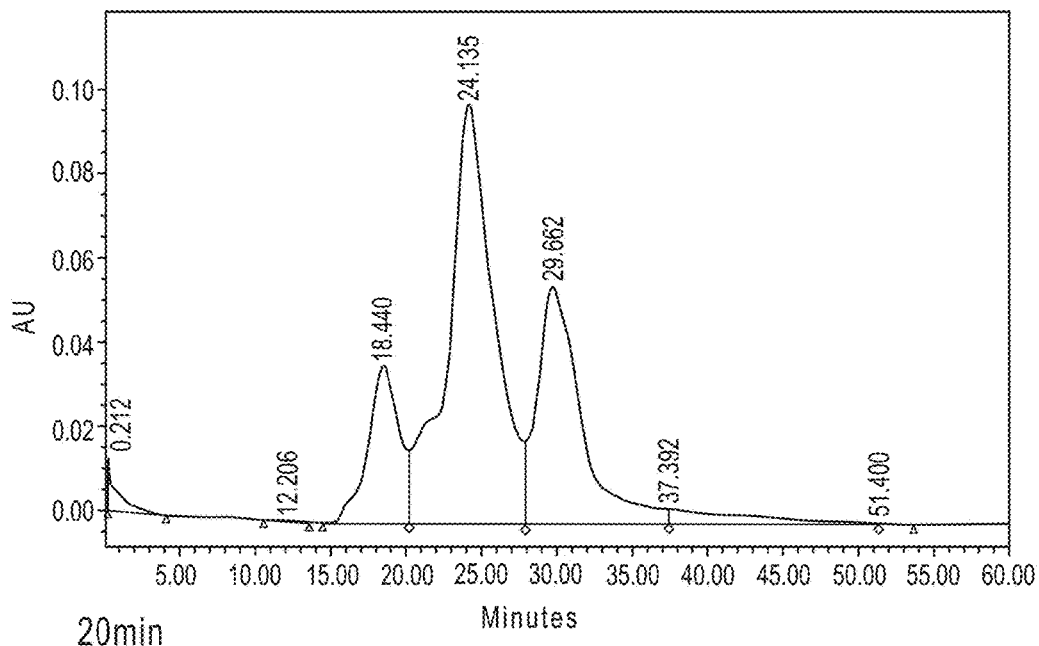
Figure 6C:
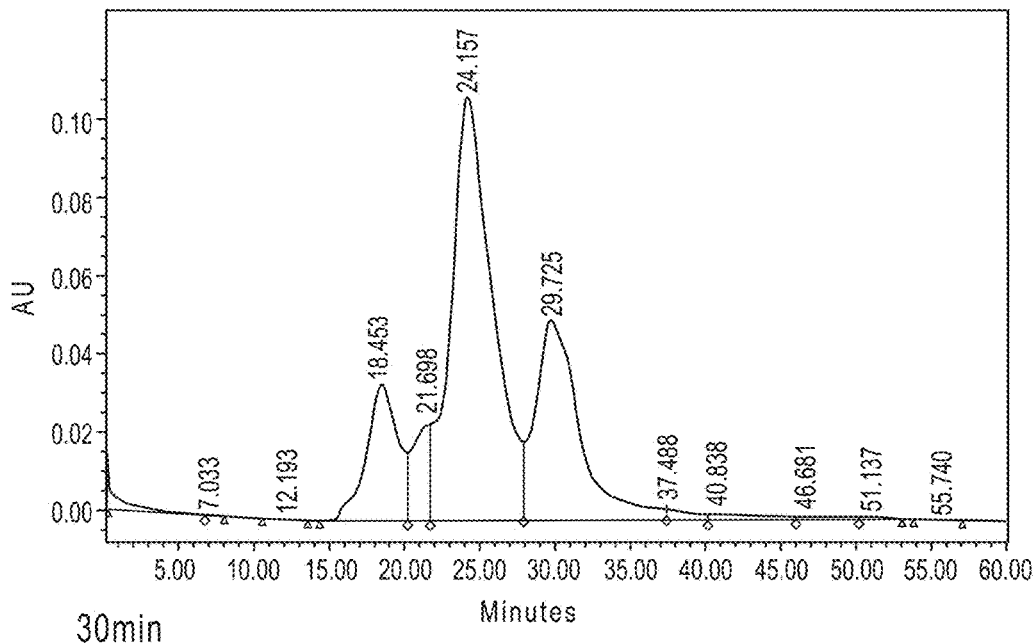
Figure 6D:
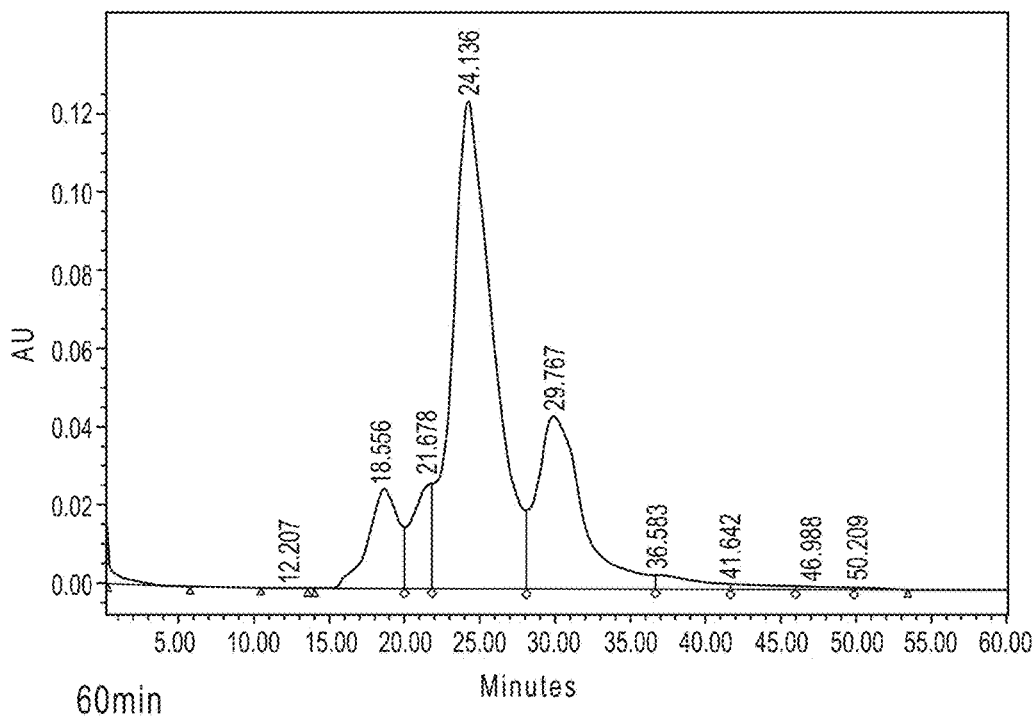
Figure 7A:
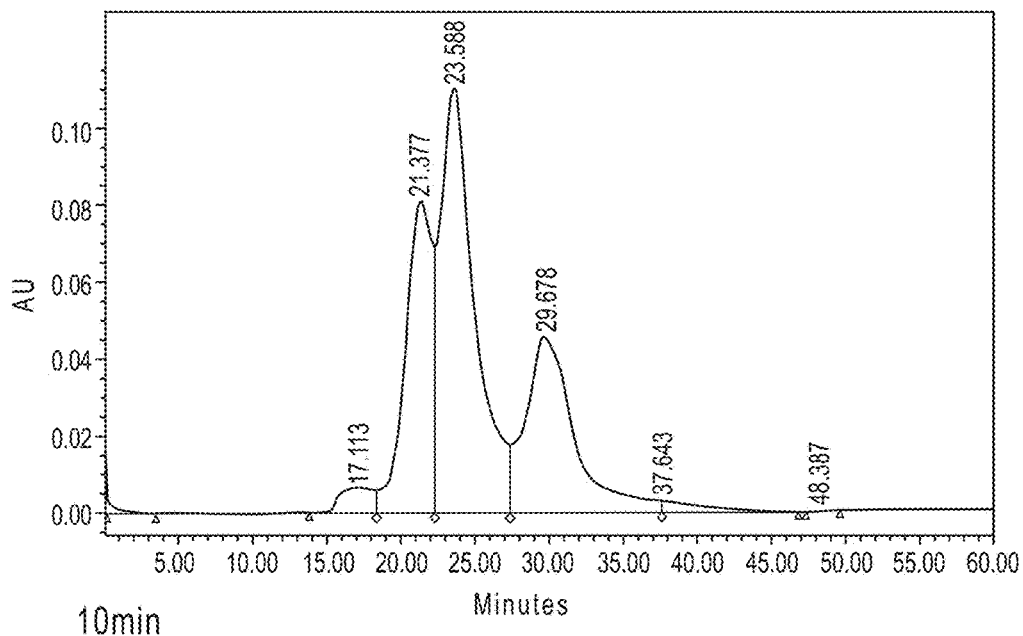
Figure 7B:
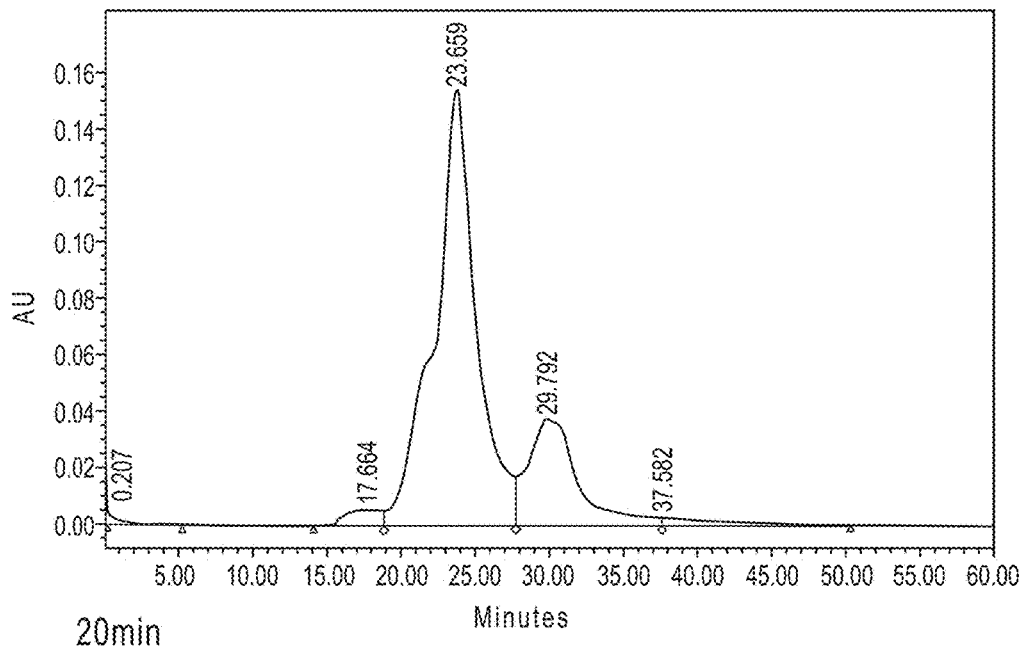
Figure 7C:
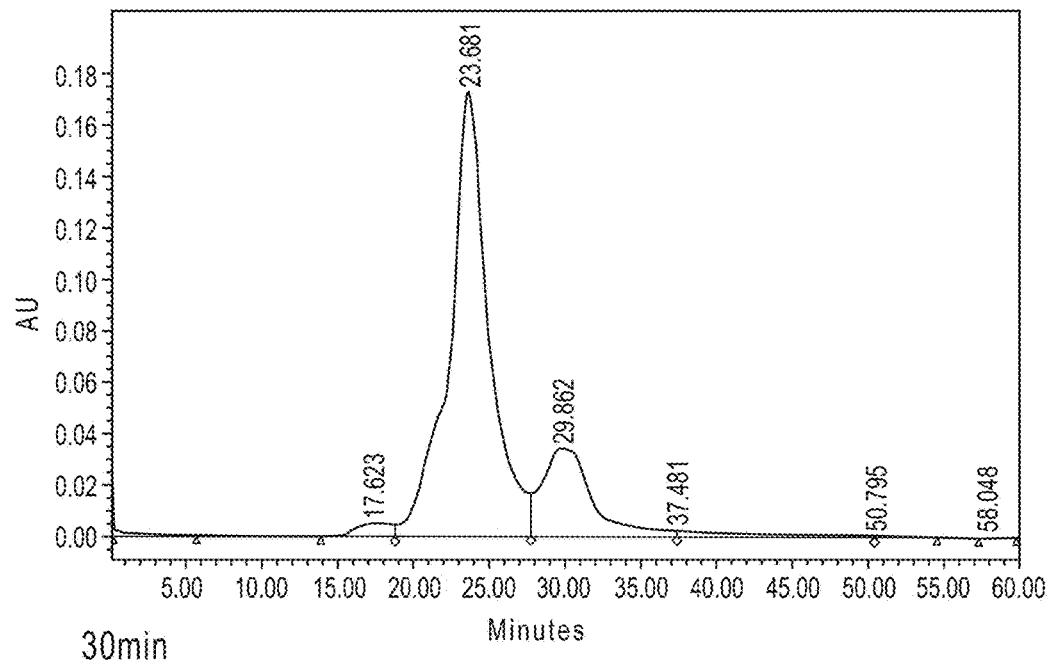
Figure 7D:
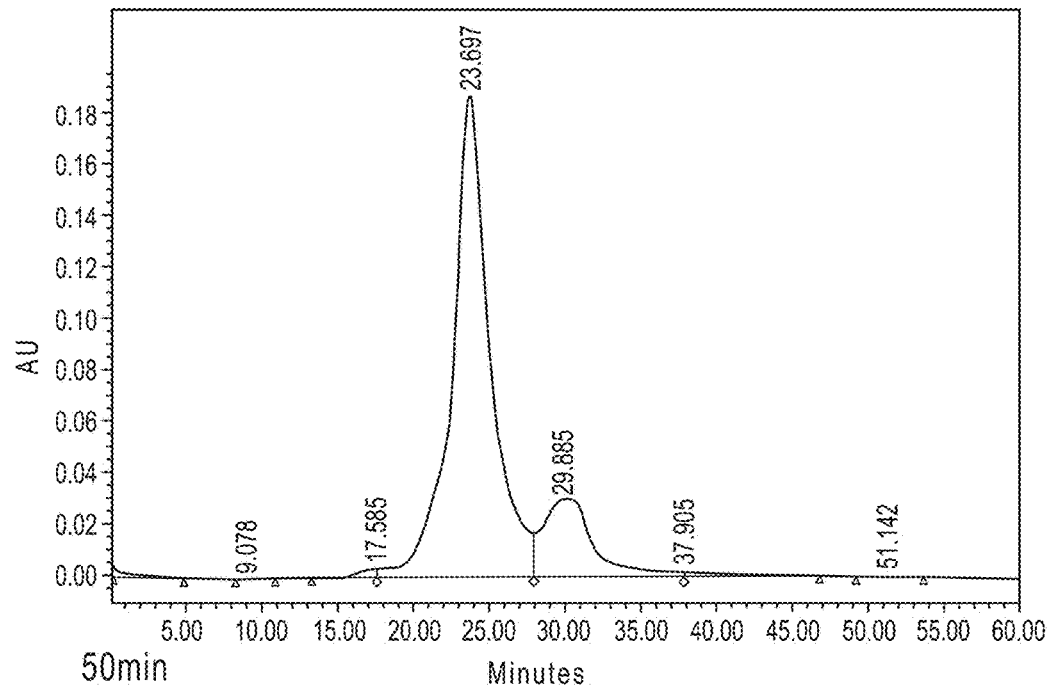
Figure 8A:
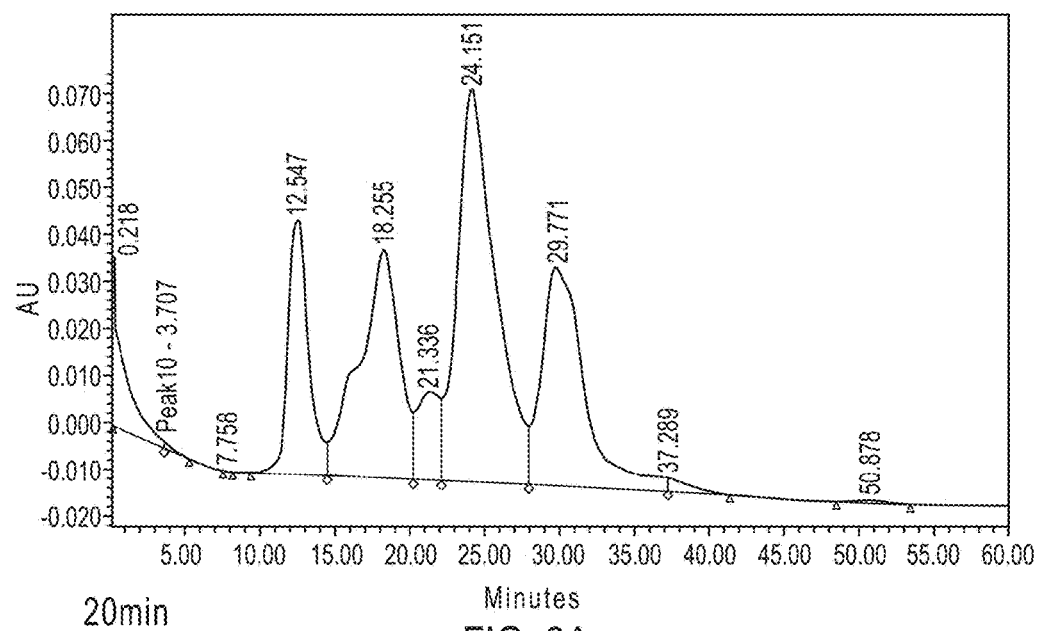
Figure 8B:
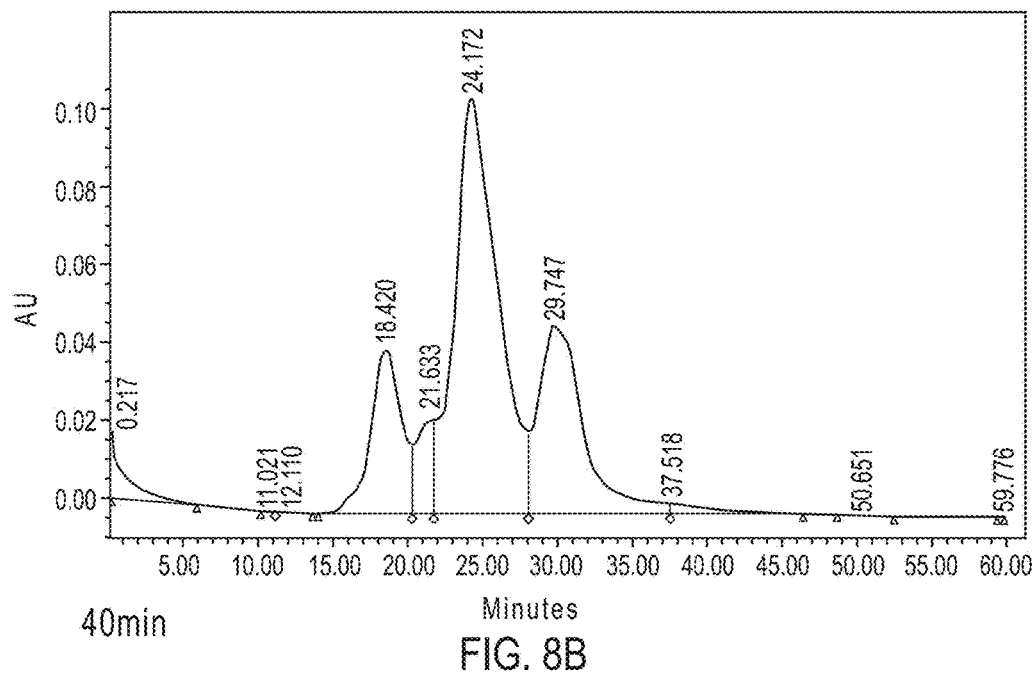
Figure 8C:
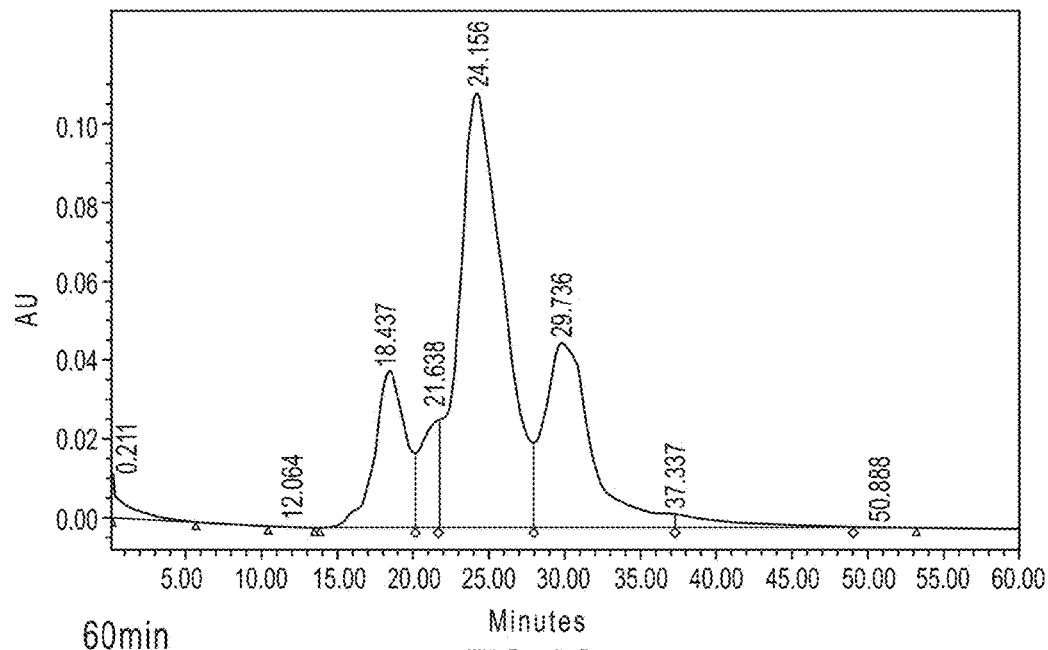
Figure 8D:
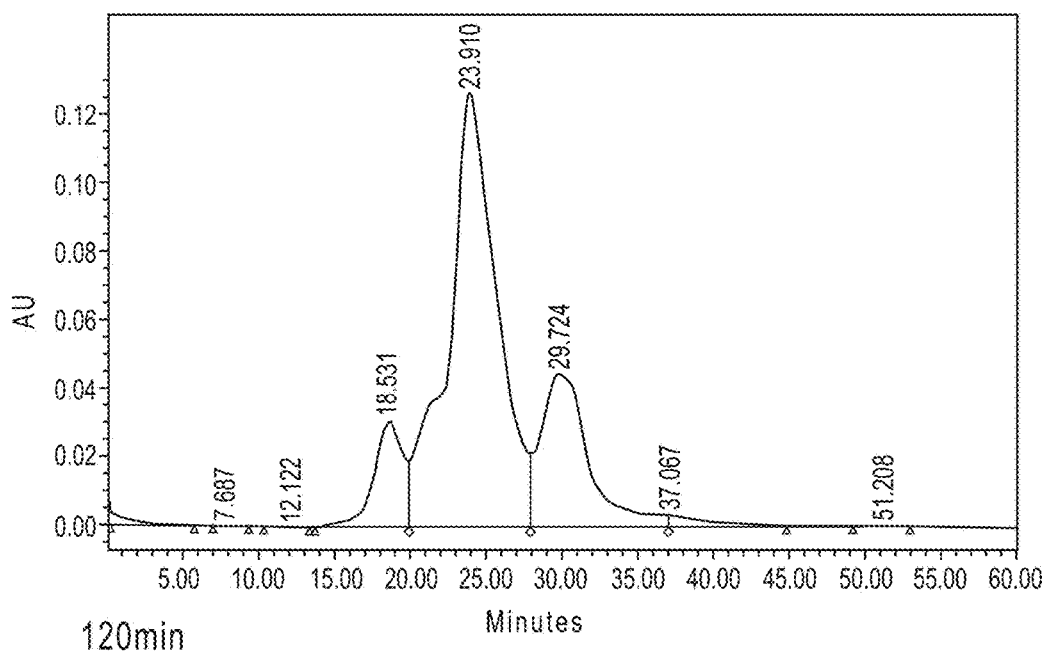

FIGS. 5A-5D: HPLC chromatograms of proApoA-I/SM complexes at protein:lipid weight ratios of 1:2.5 (Formula A; FIG. 5A), 1:2.7 (Formula B; FIG. 5B), 1:3.1 (Formula C; FIG. 5C), and proApoA-I/SM/DPPC complexes at a protein: lipid weight ratio of 1:2.7 (Formula D; FIG. 5D).

FIGS. 6A-6D: HPLC chromatograms of lipoprotein complexes of Formula D at 10, 20, 30, and 60 minutes, respectively.

FIGS. 7A-7D: HPLC chromatograms of lipoprotein complexes of Formula B at 10, 20, 30, and 50 minutes, respectively.

FIGS. 8A-8D: HPLC chromatograms of lipoprotein complexes of Formula F at 20, 40, 60, and 120 minutes, respectively.

Figure 9:
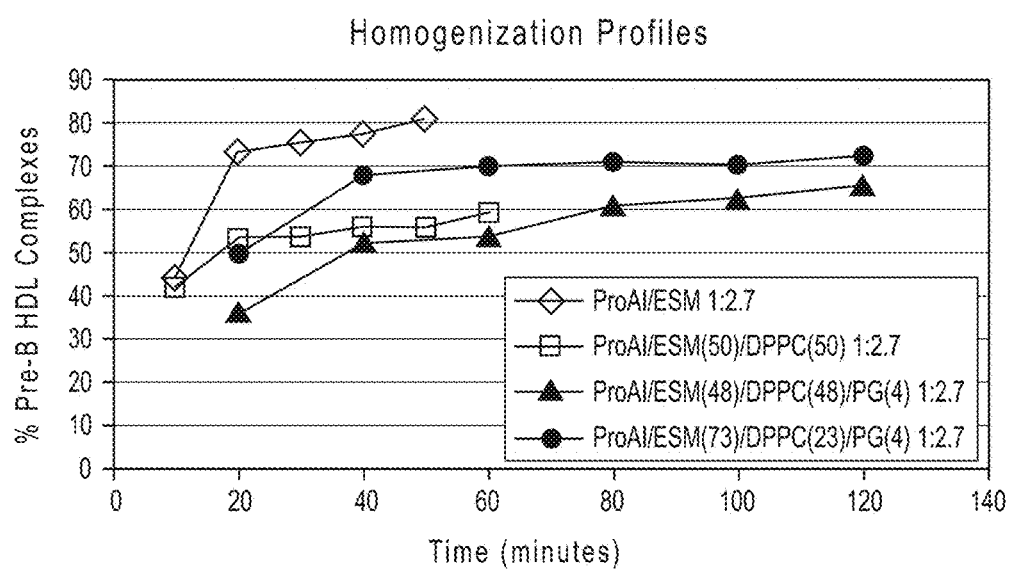
Figure 10A:
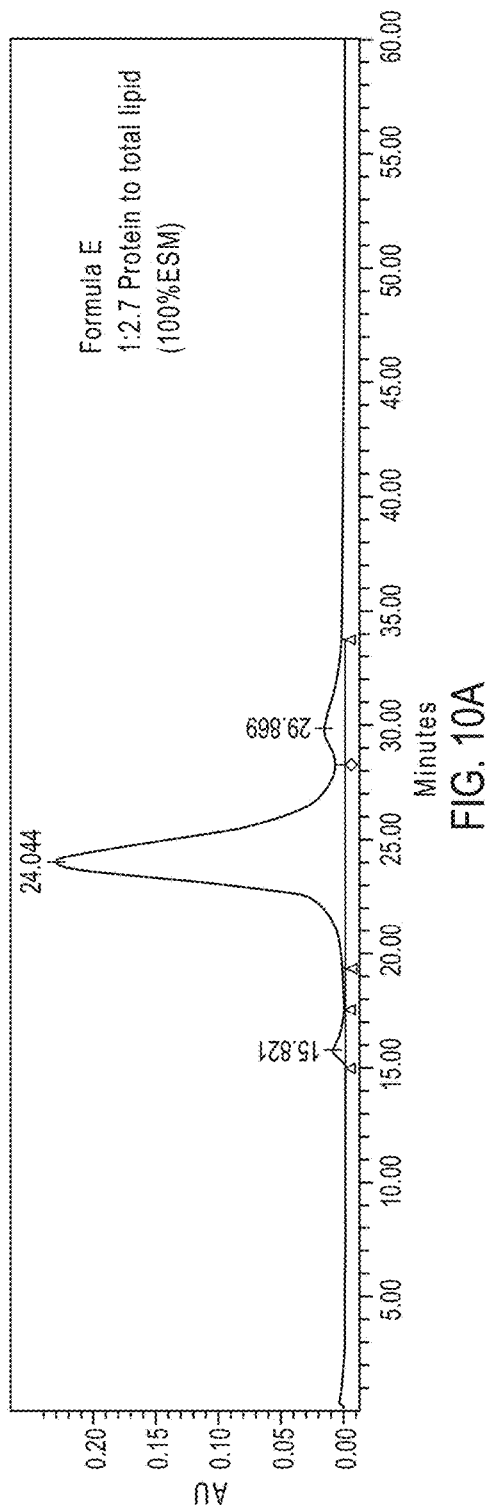
Figure 10B:
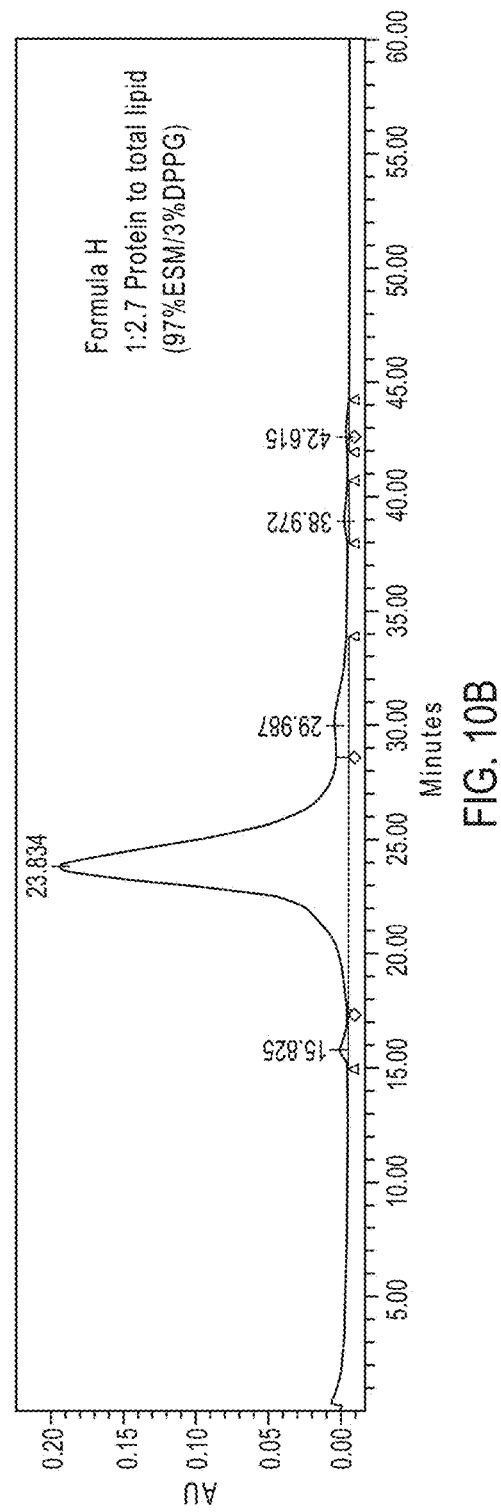
Figure 10C:
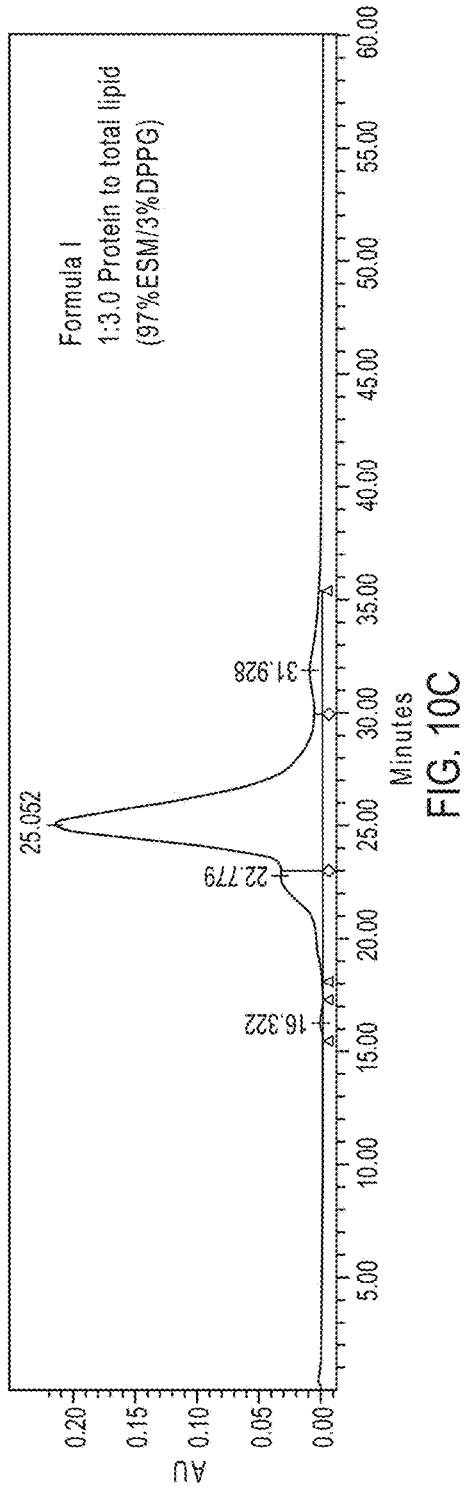
Figure 10D:
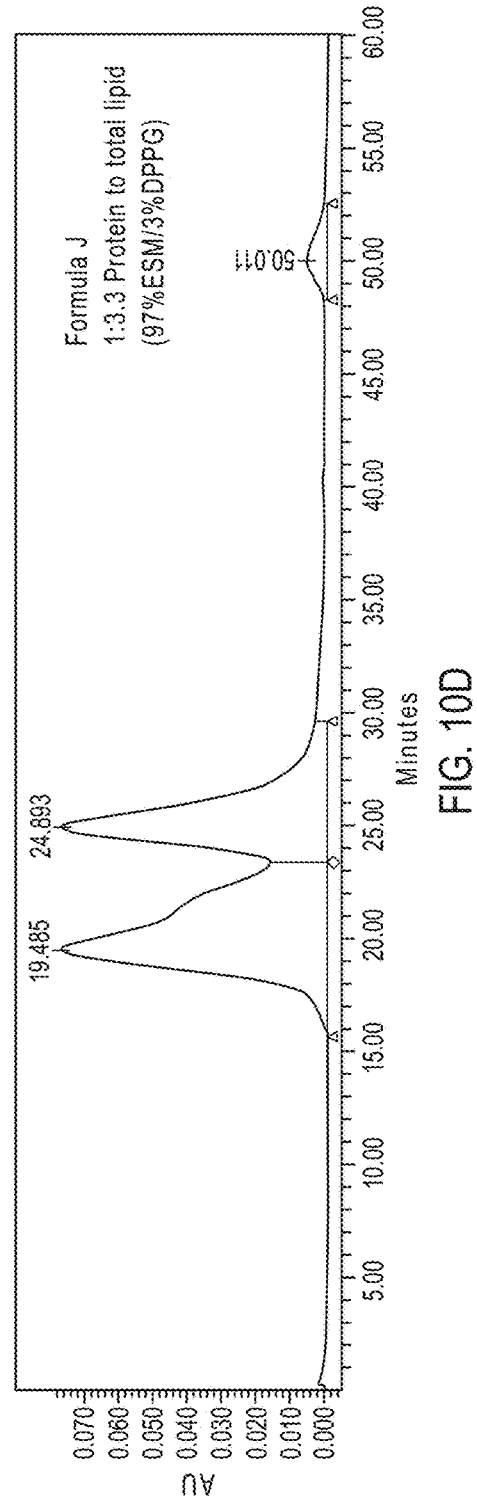

FIG. 9: Chart of pre-beta HDL complex formation over time illustrating formation of lipoprotein complexes with a 1:2.7 lipoprotein:total phospholipid wt:wt ratio comprising proApoA-I and SM (Formula B), proApoA-I, SM, DPPC and DPPG with a SM:DPPC:DPPG wt:wt ratio of 48:48:4 (Formula F), and proApoA-I, SM, DPPC and DPPG with a SM:DPPC:DPPG wt:wt ratio of 73:23:4 (Formula G).

FIG. 10A-10D: HPLC chromatograms for Formulae E, H, I, and J, respectively.

Figure 11:
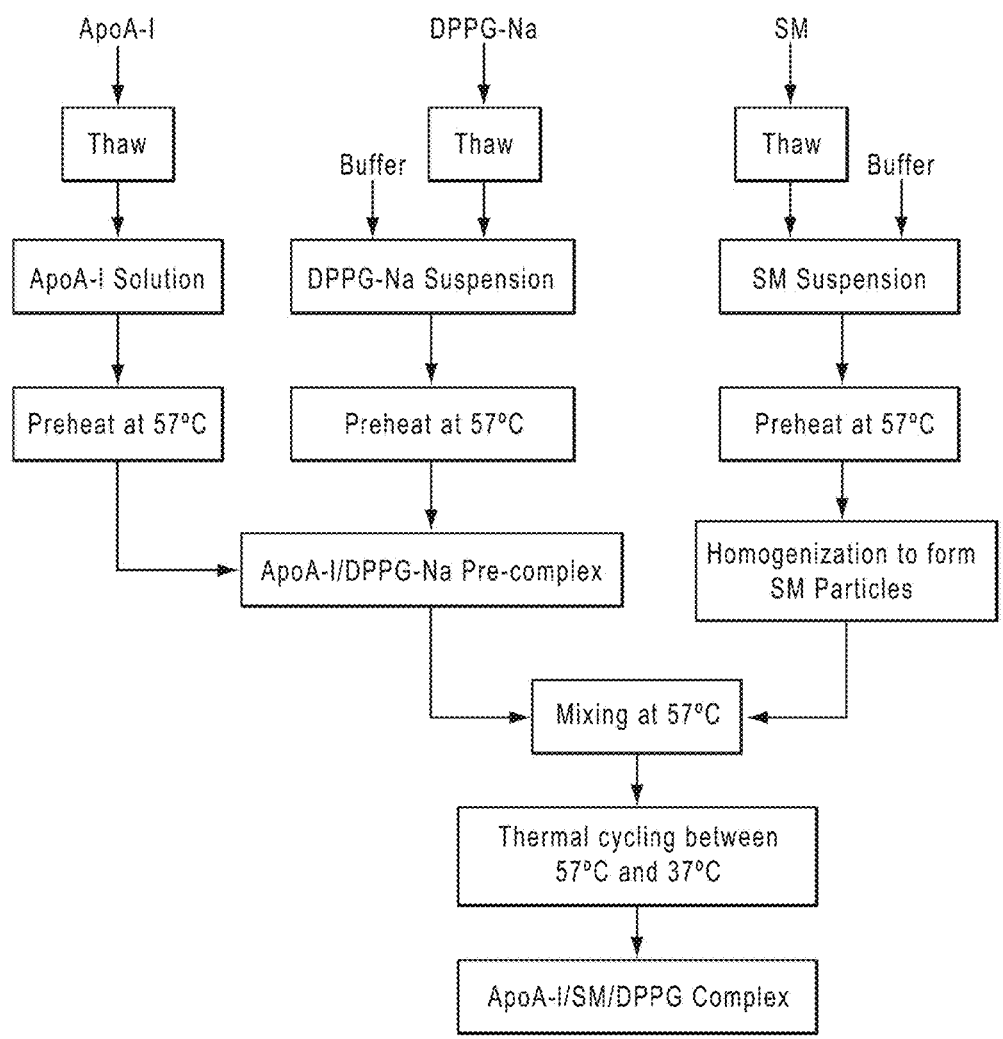

FIG. 11: Schematic diagram of exemplary process for making lipoprotein complexes.

Figure 12:
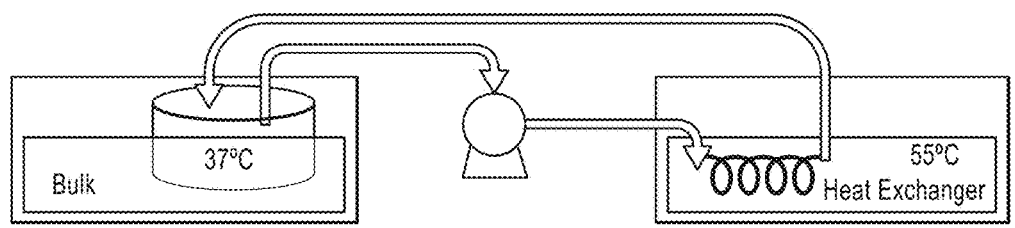

FIG. 12: Exemplary thermal cycling apparatus used for non-commercial scale thermal cycling runs.

Figure 13A:
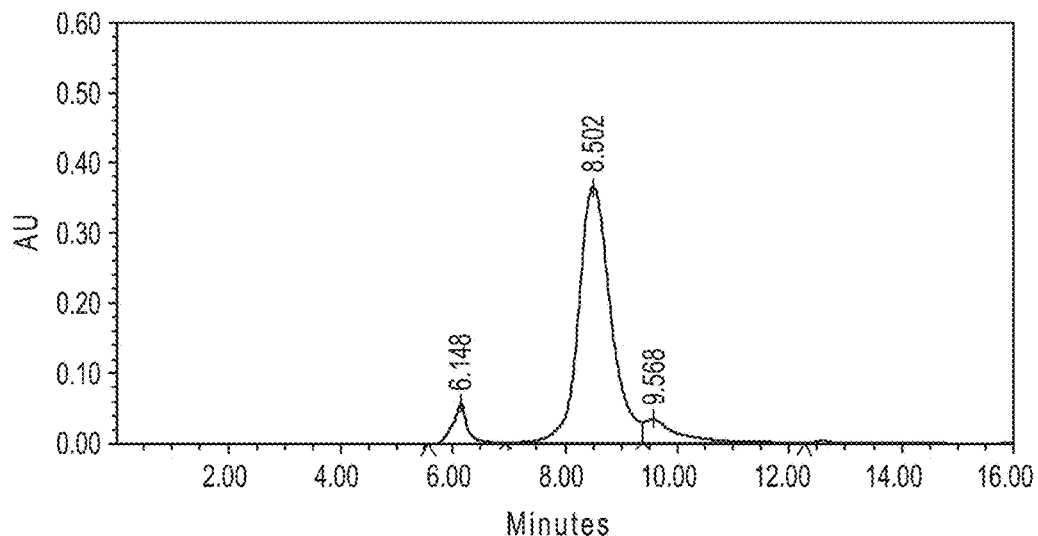
Figure 13B:
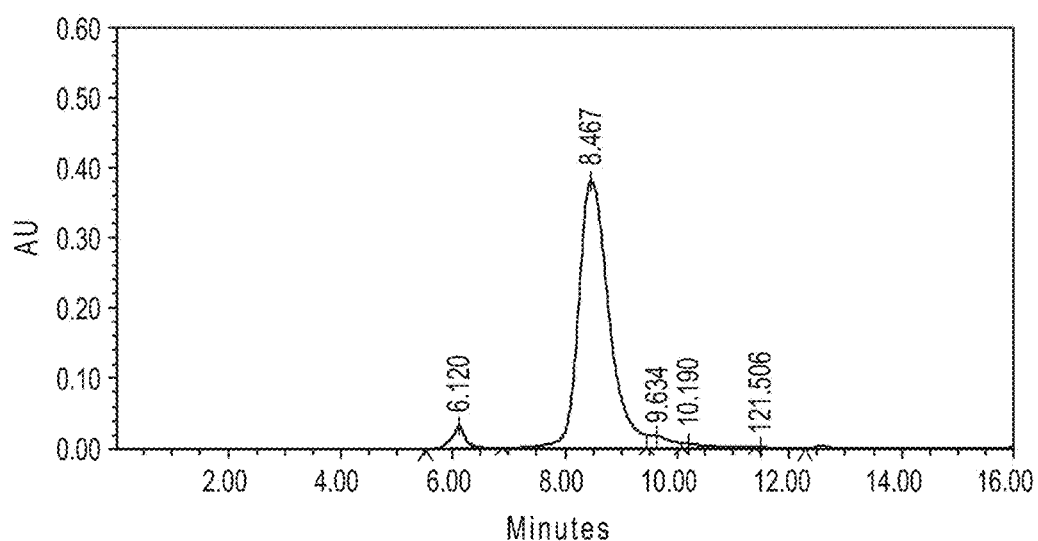
Figure 13C:
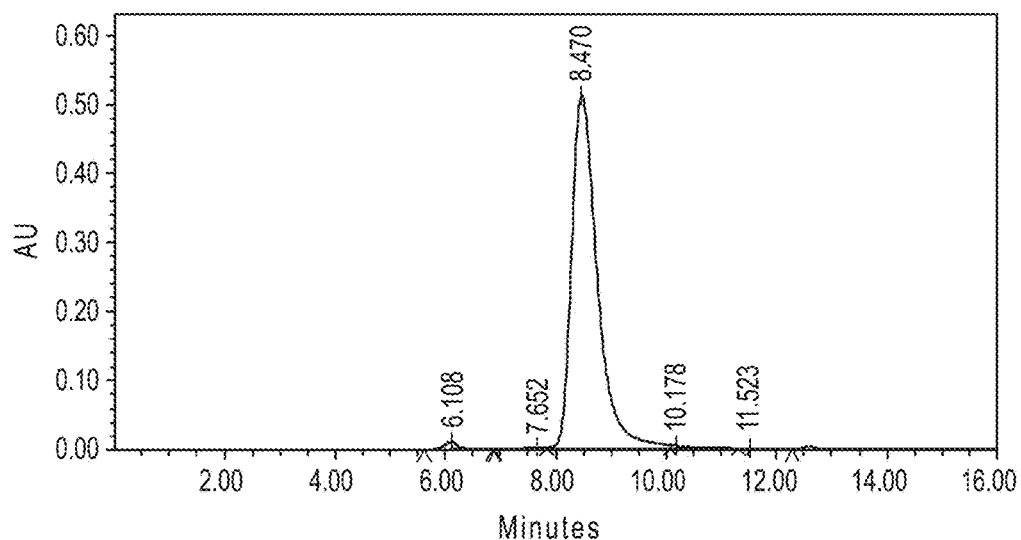
Figure 13D:
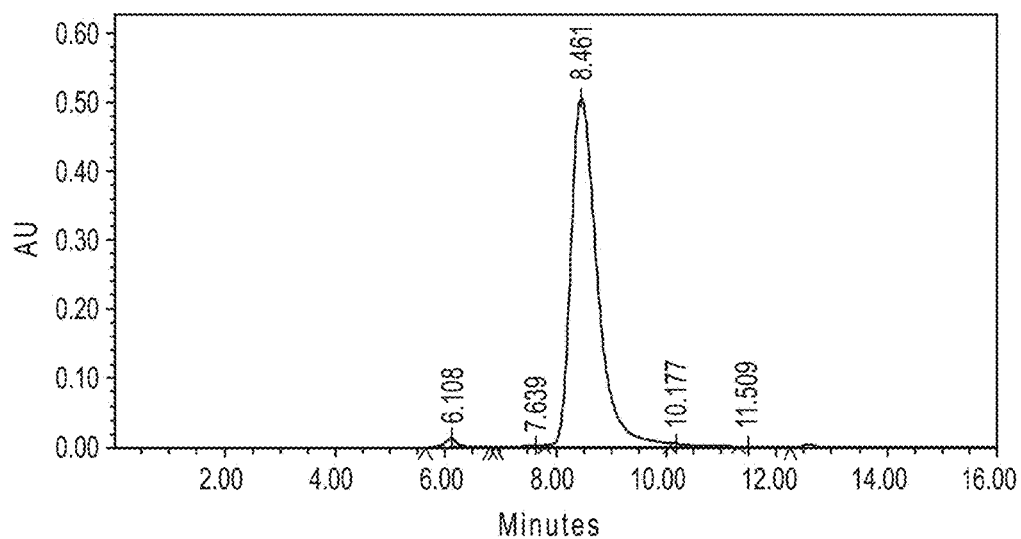
Figure 13E:
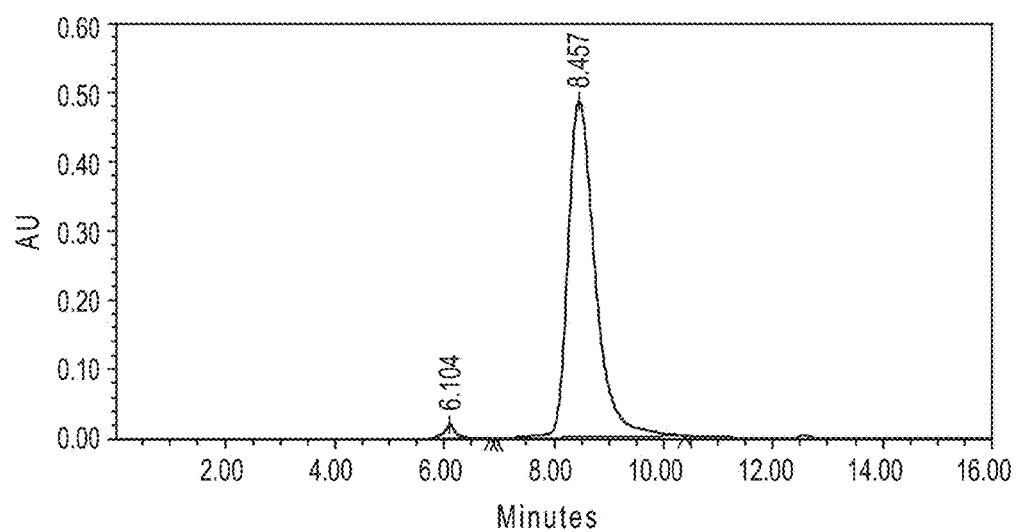

FIGS. 13A-13E: Gel permeation chromatogram of SM/DPPG/ApoA-I protein complexes with increasing number of thermal cycles. The components were subject to thermal cycling between 57° C. and 37° C. for 5 minutes at each temperature, for a total of 30 minutes (FIG. 13A), 60 minutes (FIG. 13B), 120 minutes (FIG. 13C), 180 minutes (FIG. 13D) or 210 minutes (FIG. 13E).

Figure 14:
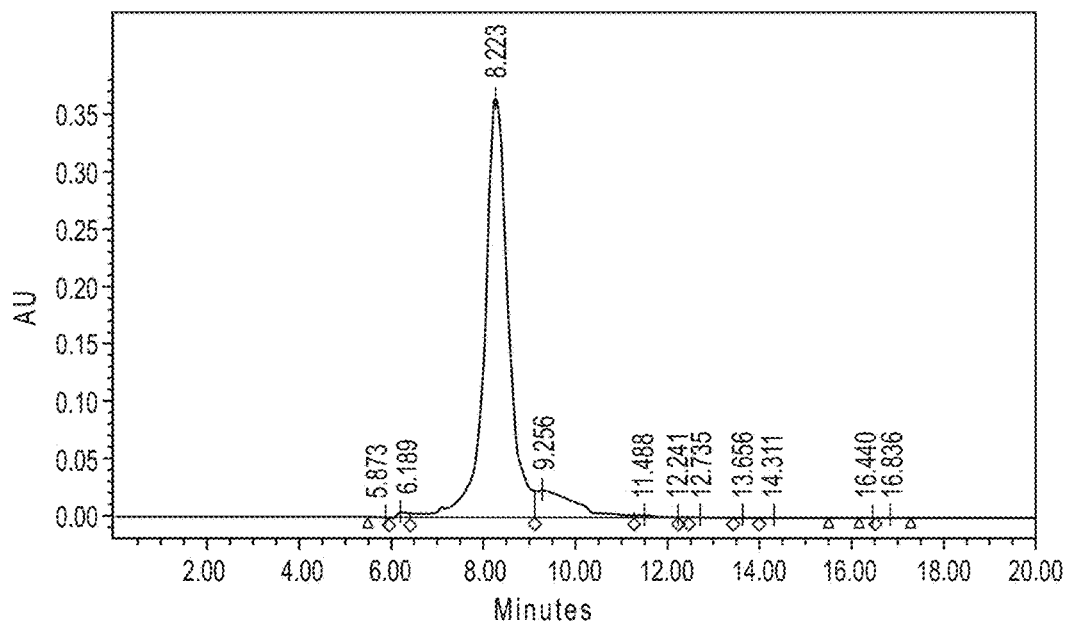

FIG. 14: Gel permeation chromatogram of SM/ApoA-I complexes.

Figure 15:
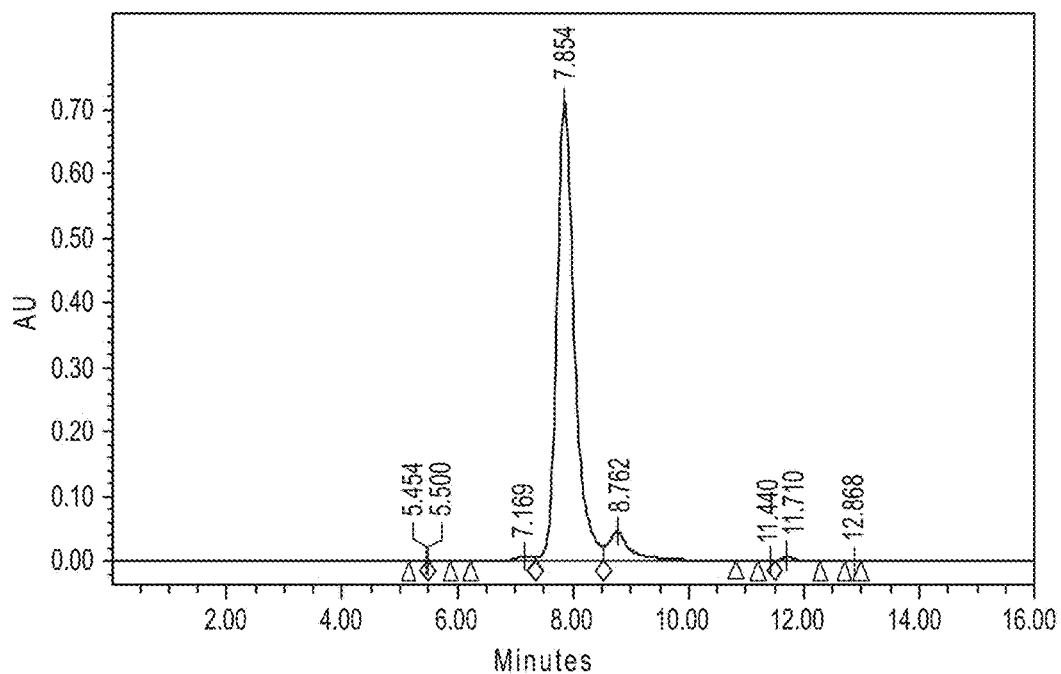

FIG. 15: Gel permeation chromatogram of N-palmitoyl-4-hydroxysphinganine-1-phosphocholine (a form of plant SM or phytosphingomyelin)/DPPG/ApoA-I complexes.

Figure 16:
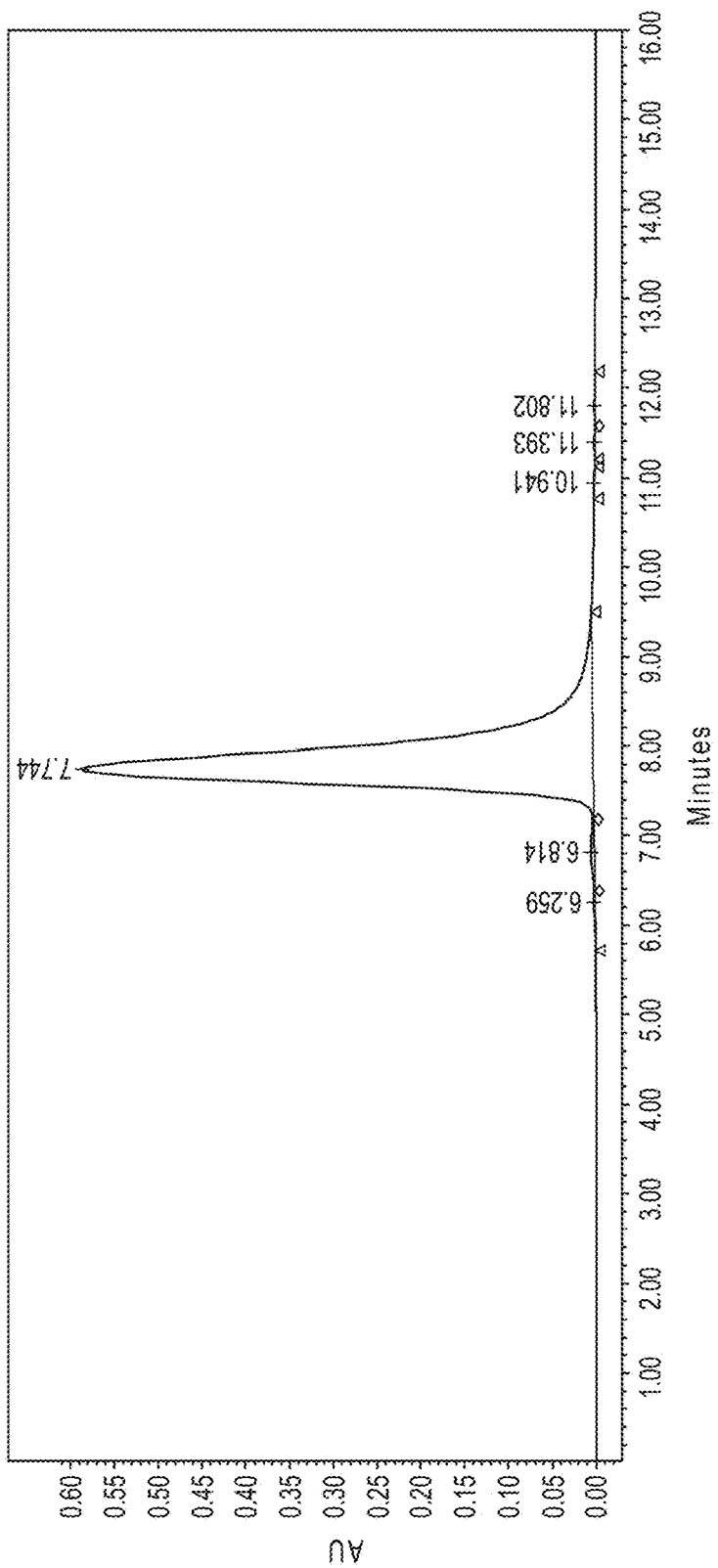

FIG. 16: Gel permeation chromatogram of synthetic palmitoyl SM/DPPG/ApoA-I complexes.

Figure 17:
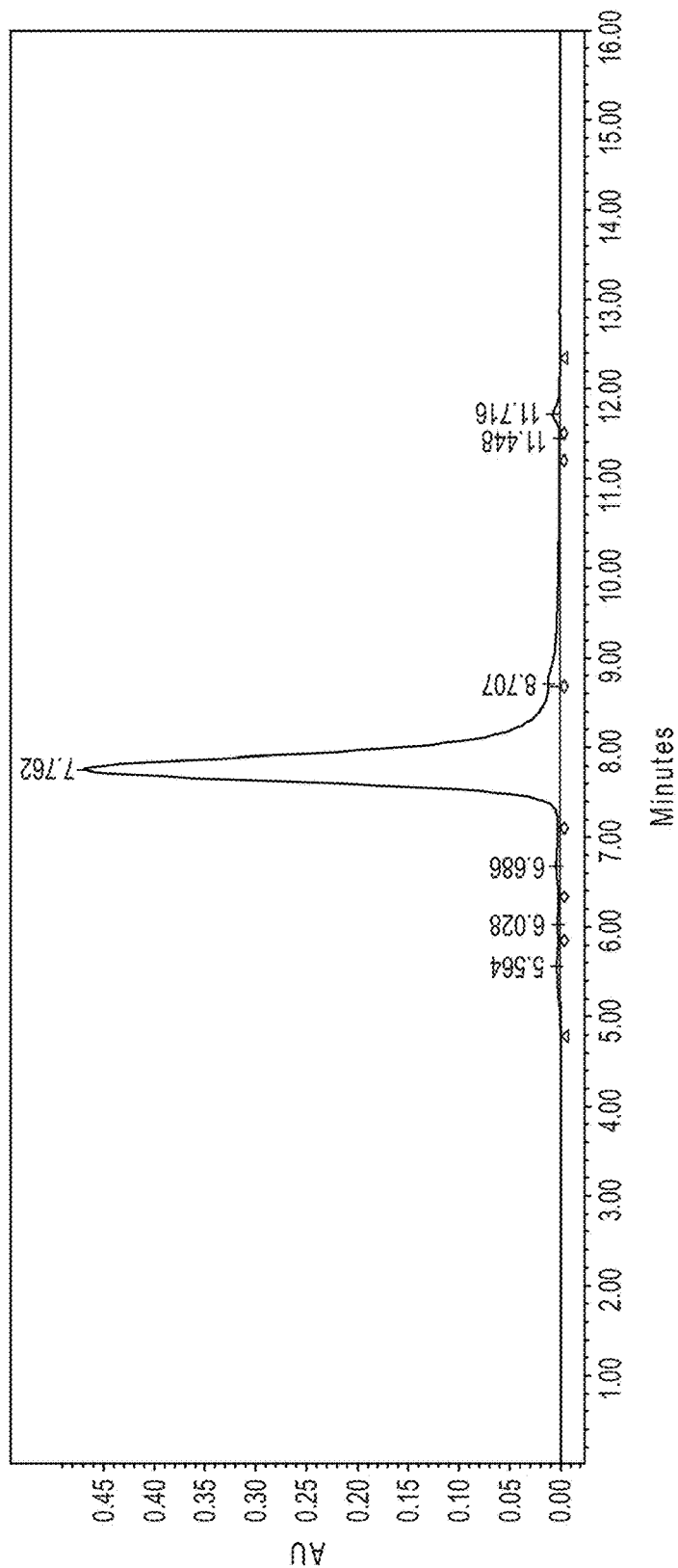

FIG. 17: Gel permeation chromatogram of phytosphingomyelin/DPPG/ApoA-I complexes.

Figure 18:
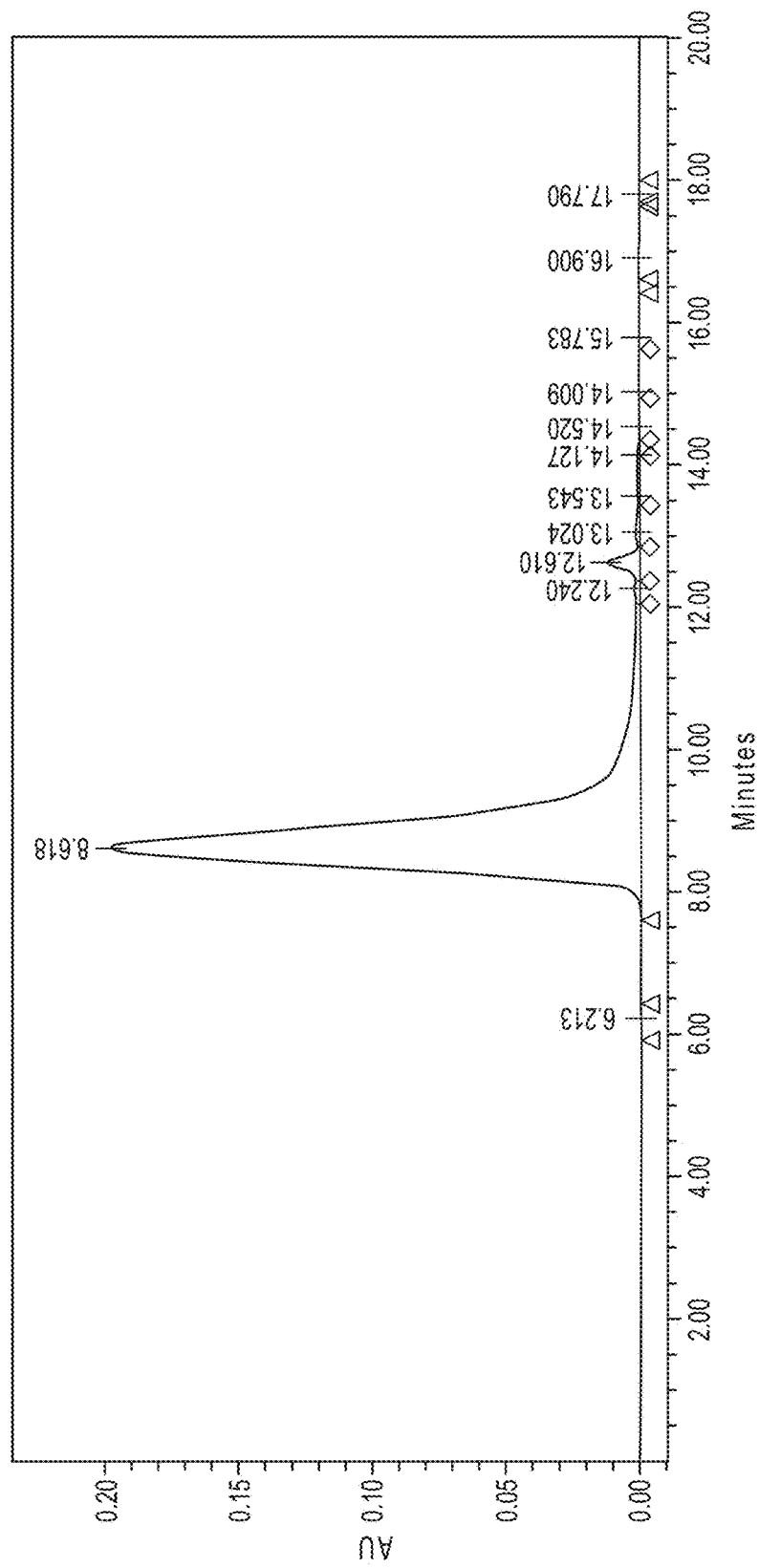

FIG. 18: Gel permeation chromatogram of SM/DPPC/DPPG/ApoA-I peptide complexes.

Figure 19A:
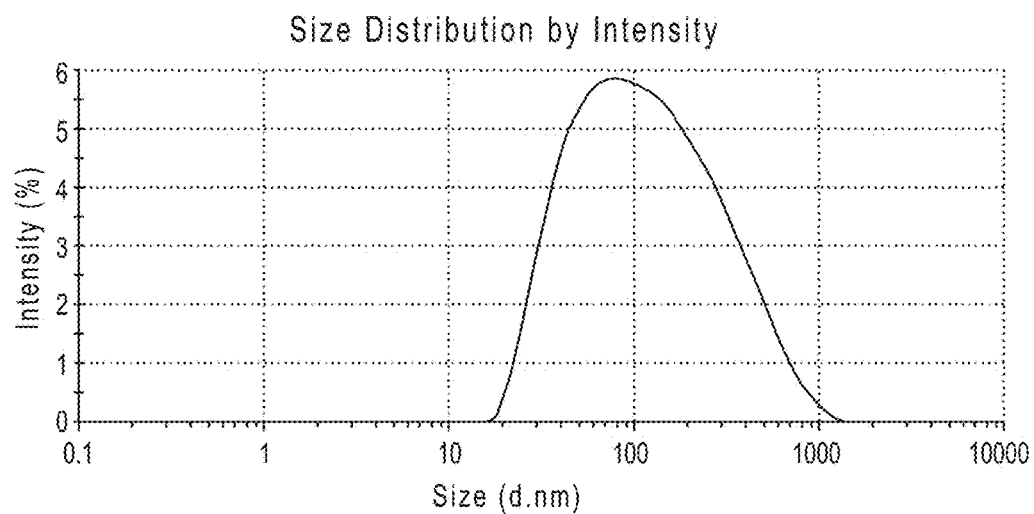
Figure 19B:
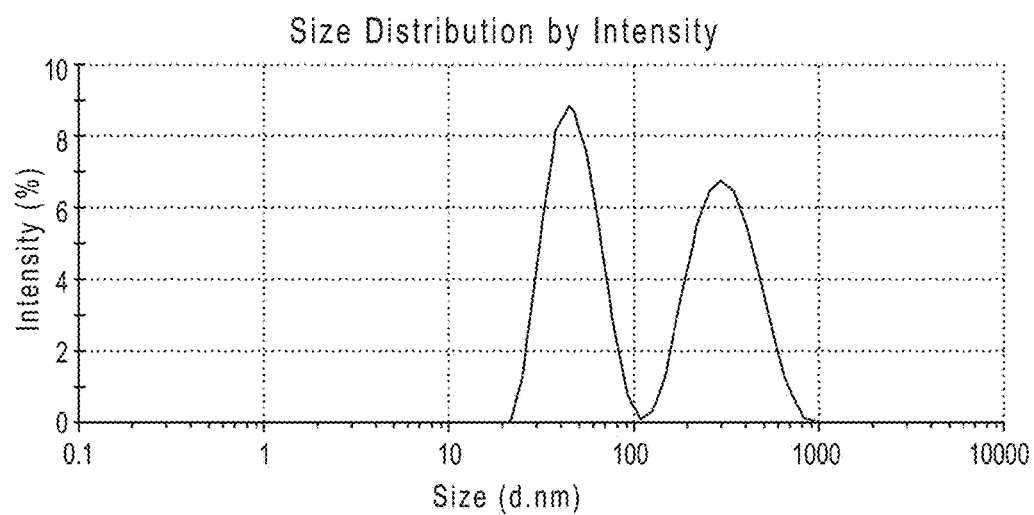
Figure 19C:
Figure 19D:
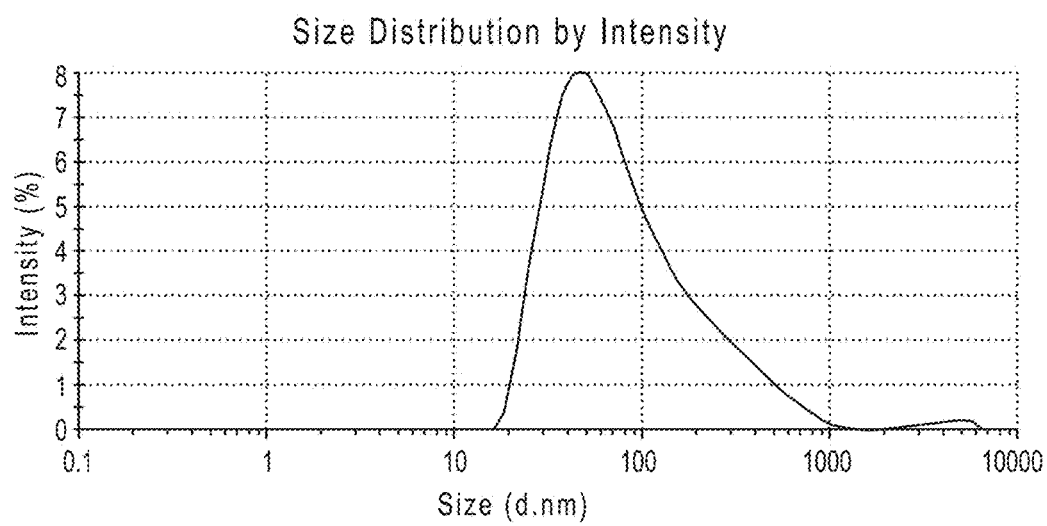
Figure 20A:
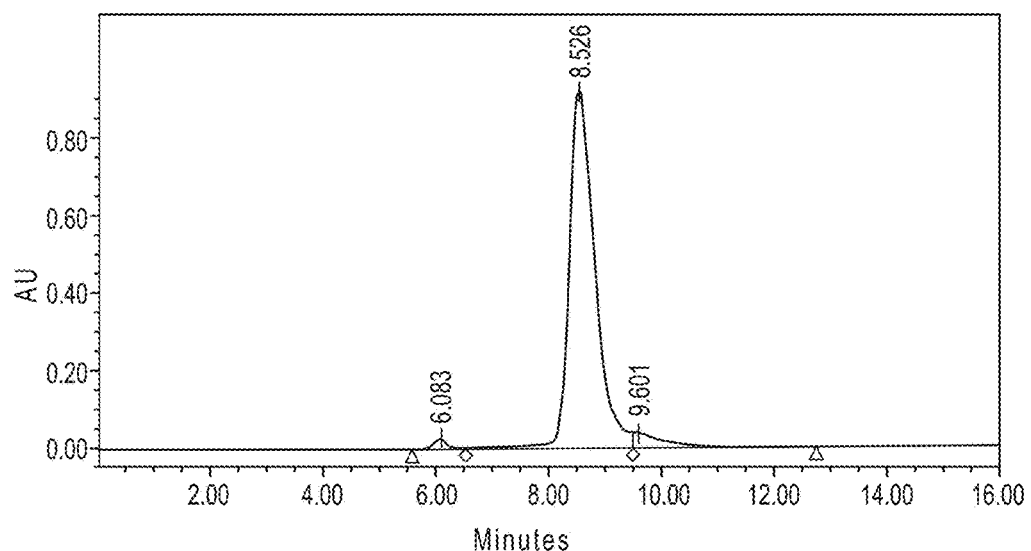
Figure 20B:
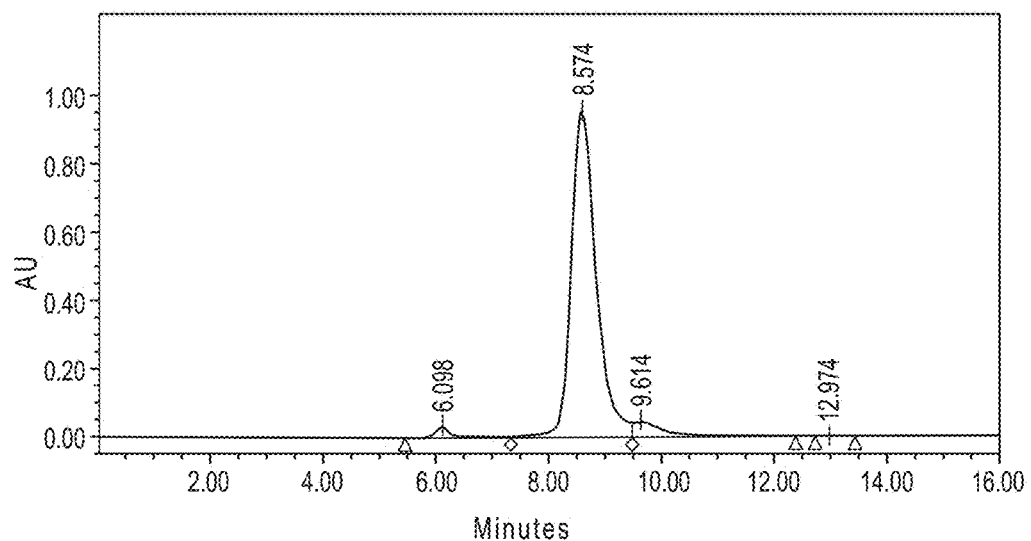
Figure 20C:
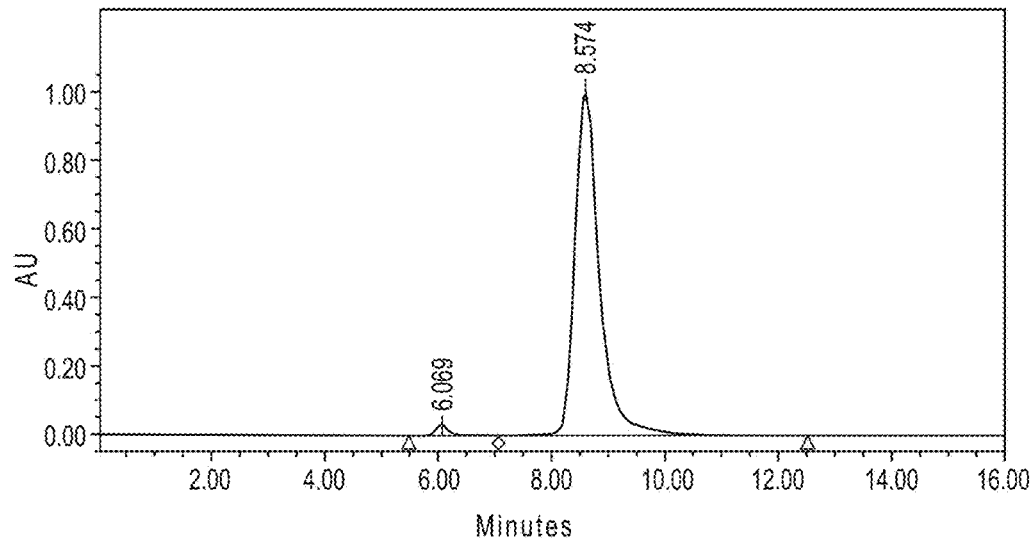
Figure 20D:
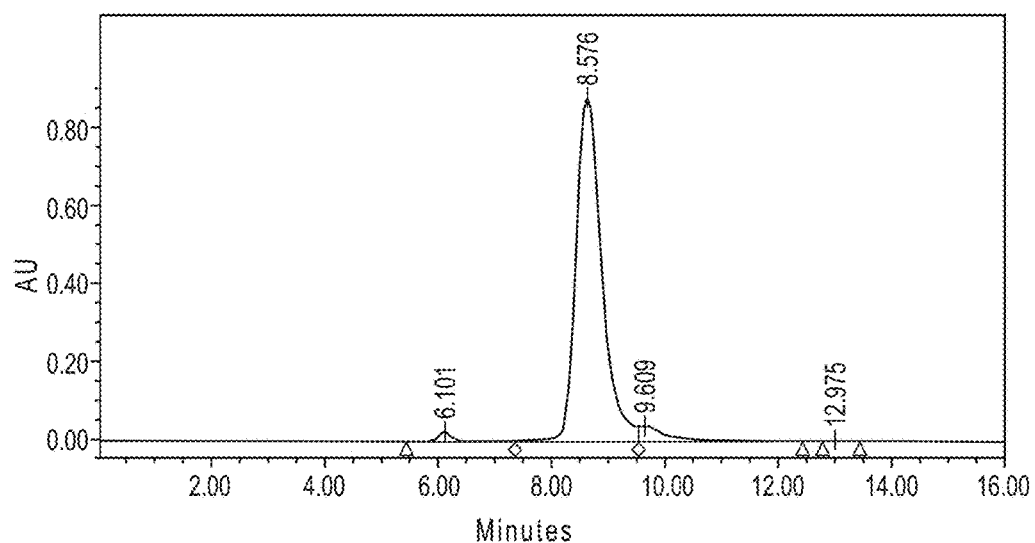

FIGS. 19A-19D: Characterization of lipid particles by a Dynamic Light Scattering system using a Malvern Instruments Zetasizer (Malvern Instruments Inc.). In FIG. 19A, the Z average is 84.49 nm (the "84 nm particles"); in FIG. 19B, the Z average is 76.76 nm (the "77 nm particles"); in FIG. 19C, the Z average is 66.21 nm (the "66 nm particles"); and in FIG. 19D, the Z average is 59.50 nm (the "60 nm particles").

FIGS. 20A-20D: Gel permeation chromatograms of complexes after five thermal cycles with 84 nm (FIG. 20A), 77 nm (FIG. 20B), 66 nm (FIG. 20C) and 60 nm (FIG. 20D) lipid particles.

Figure 21A:
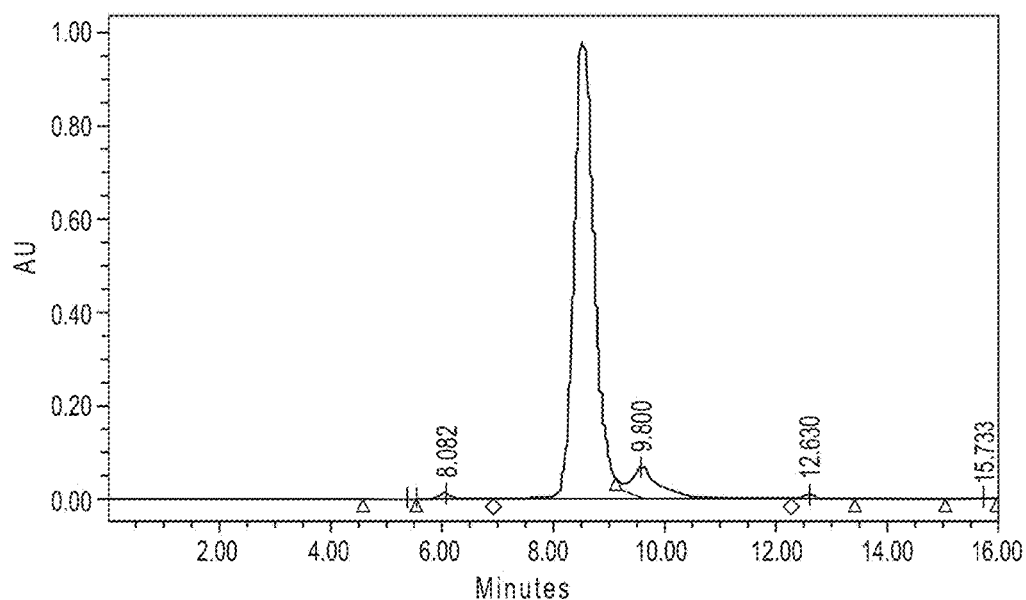
Figure 21B:
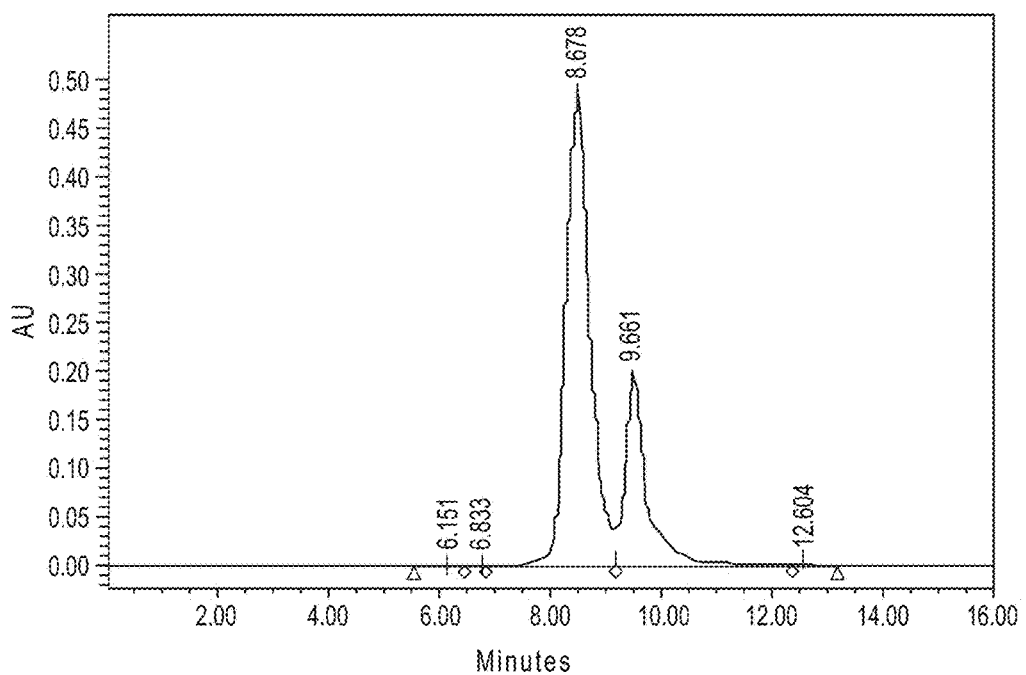

FIGS. 21A-21B: Gel permeation chromatograms of complexes after six thermal cycles starting with 450 nm (FIG. 21A) and 40 nm (FIG. 21B) lipid particles.

Figure 22:
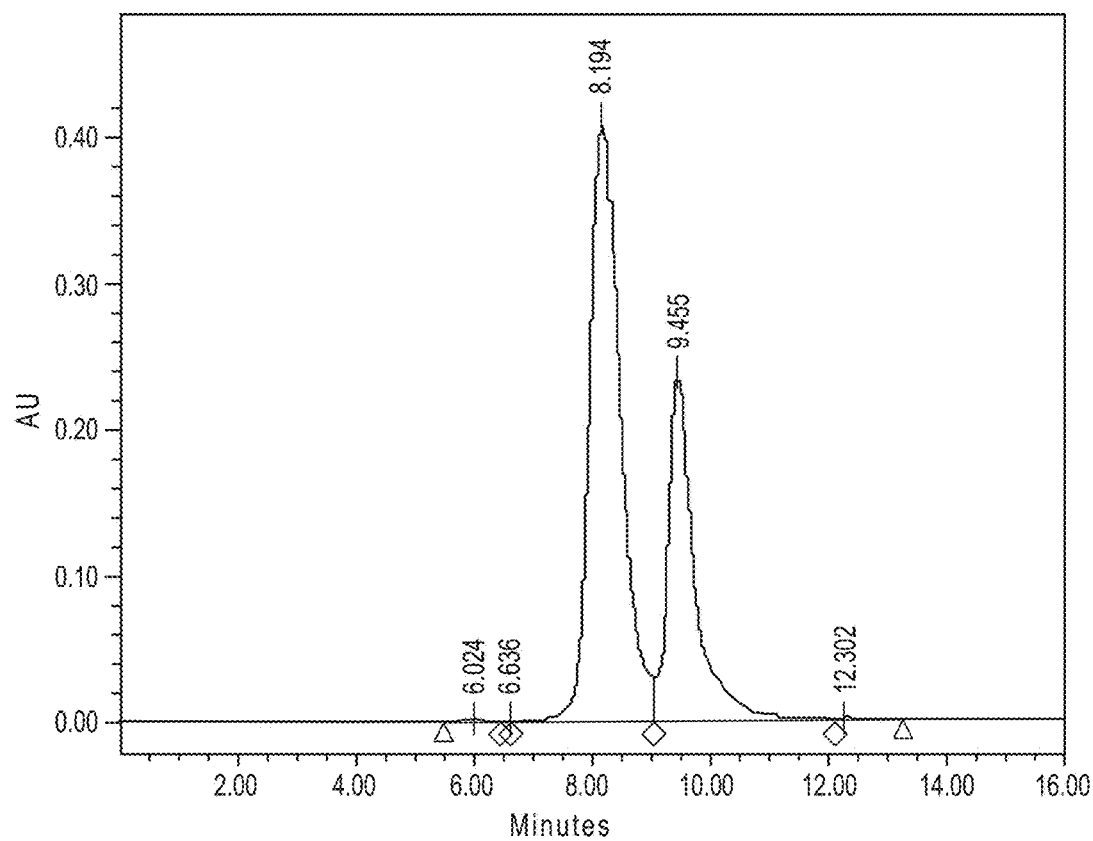

FIG. 22: Gel permeation chromatogram of complexes after six thermal cycles starting with 65 nm lipid particles, with the first cycle initiated at the "low temperature" of 37° C.

Figure 23:
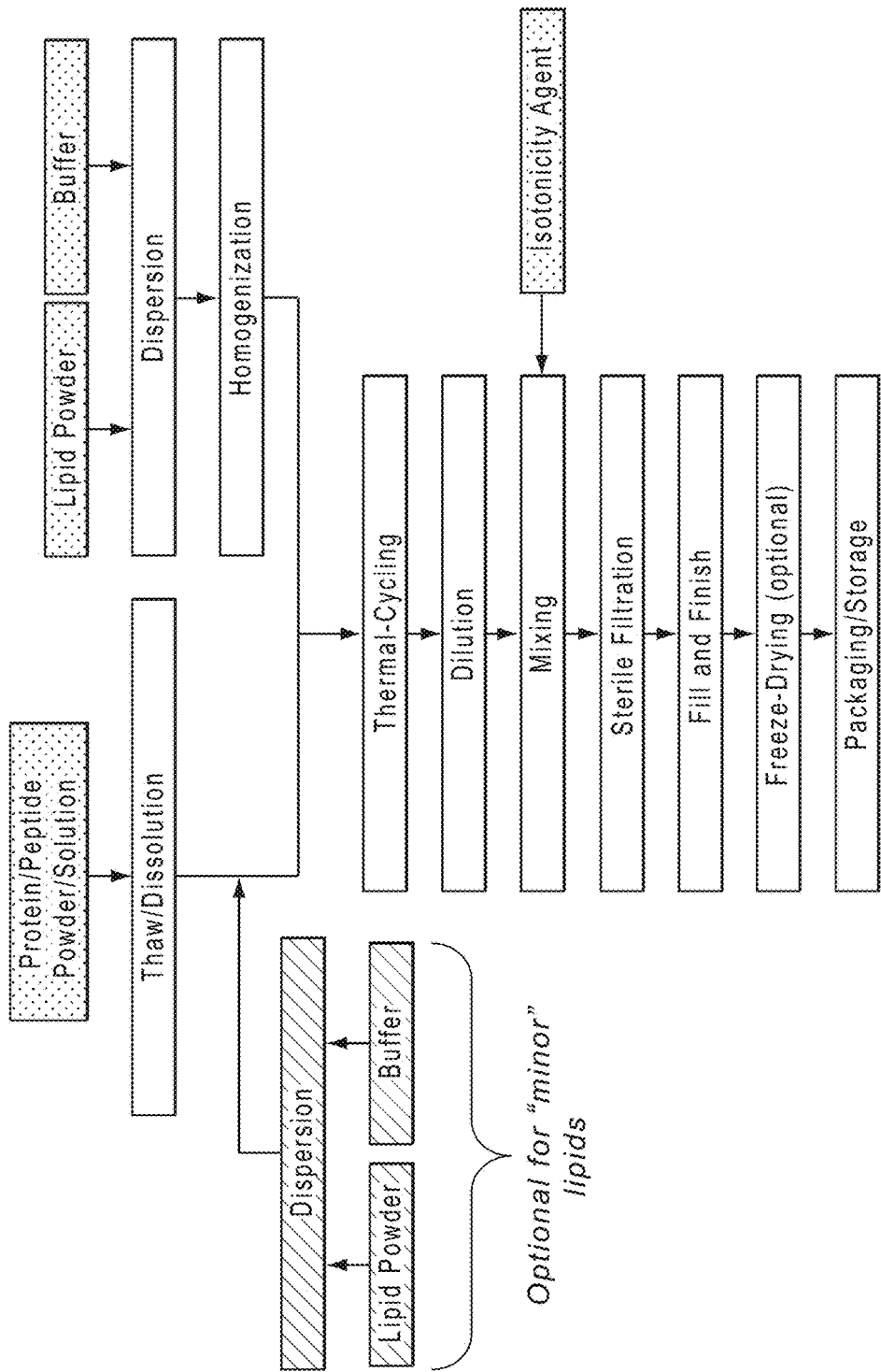

FIG. 23: Schematic diagram of exemplary embodiment for making pharmaceutical compositions comprising lipoprotein complexes, which includes formulating the lipoprotein complexes produced by the methods of the disclosure into commercially useful pharmaceutical compositions.

Figure 24:
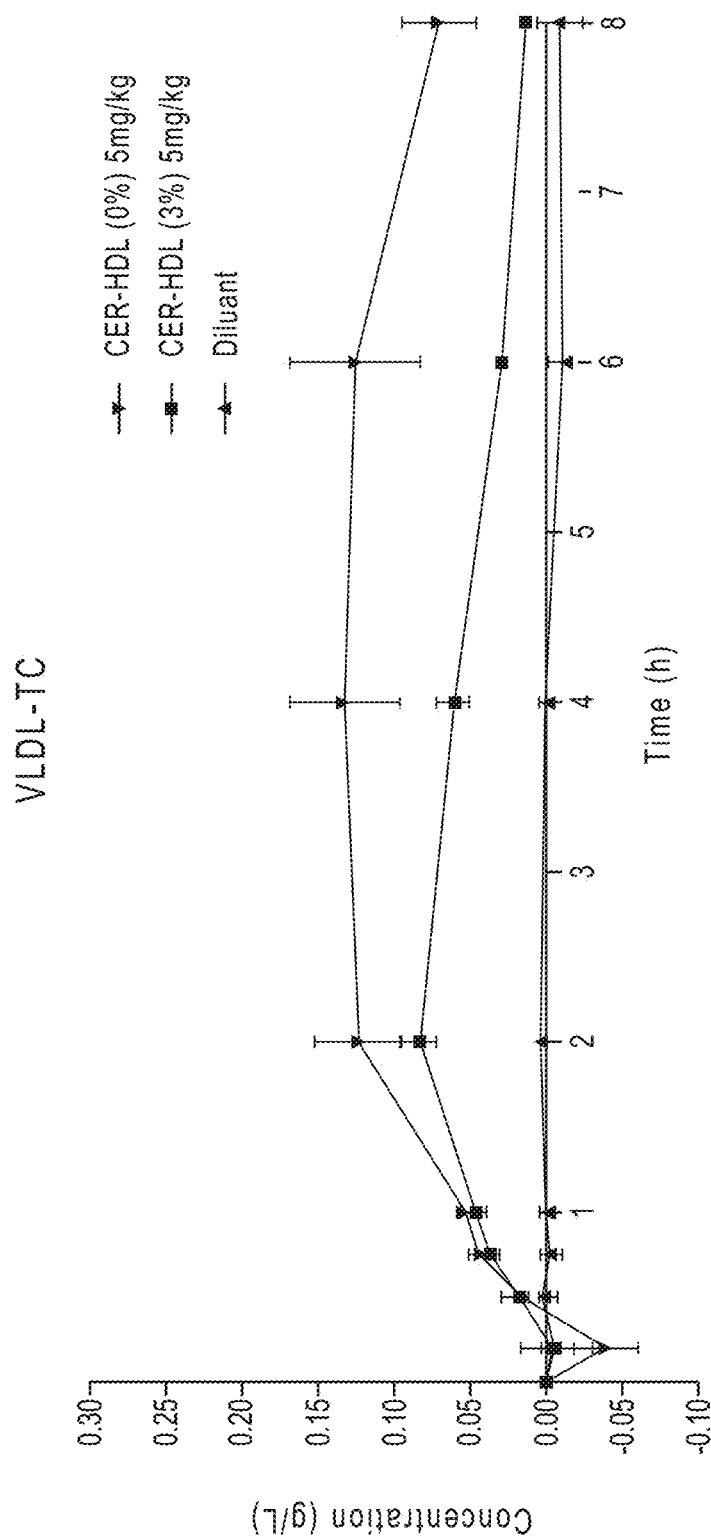

FIG. 24: Increase in plasma VLDL-total cholesterol levels following infusion of a lipoprotein complex according to Formula B and Formula H. Lipoprotein complexes according to Formula H (■) and Formula B (▼) were infused into fasted rabbits at doses of 5 mg/kg. Baseline values, ranging from 0.03 to 0.3 g/L for the three groups, were subtracted to determine the increase in plasma VLDL-total cholesterol levels.

Figure 25:
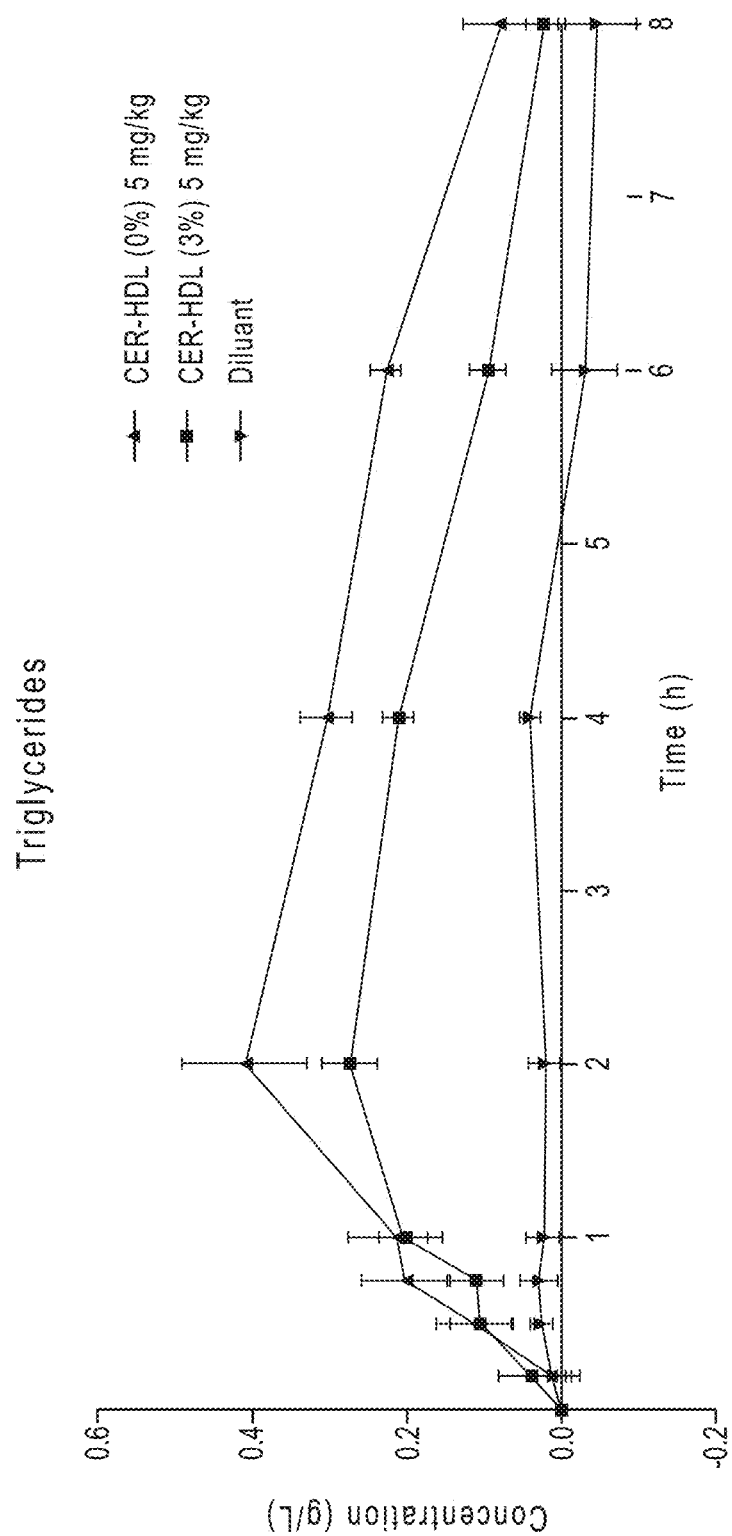
Figure 26A:
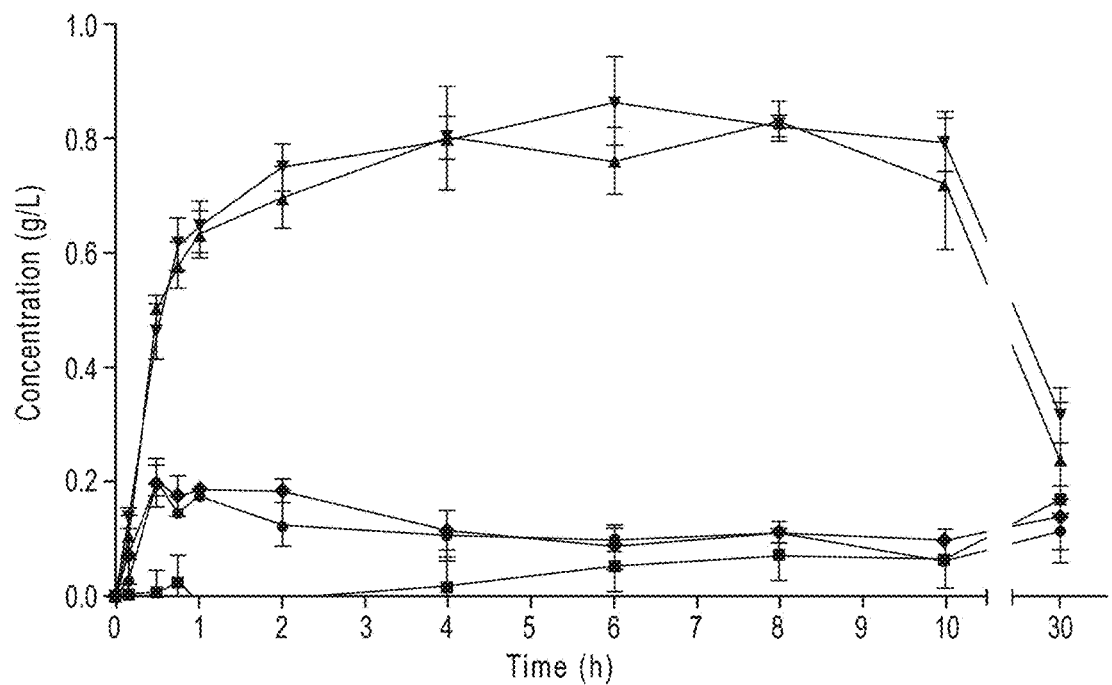
Figure 26B:
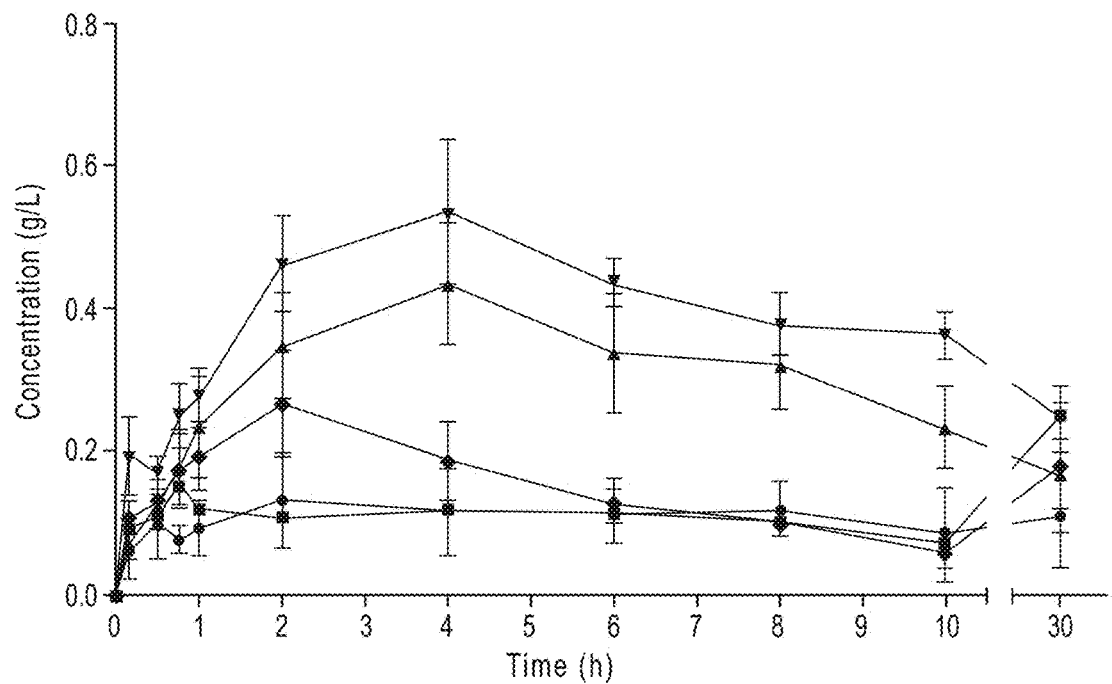
Figure 26C:
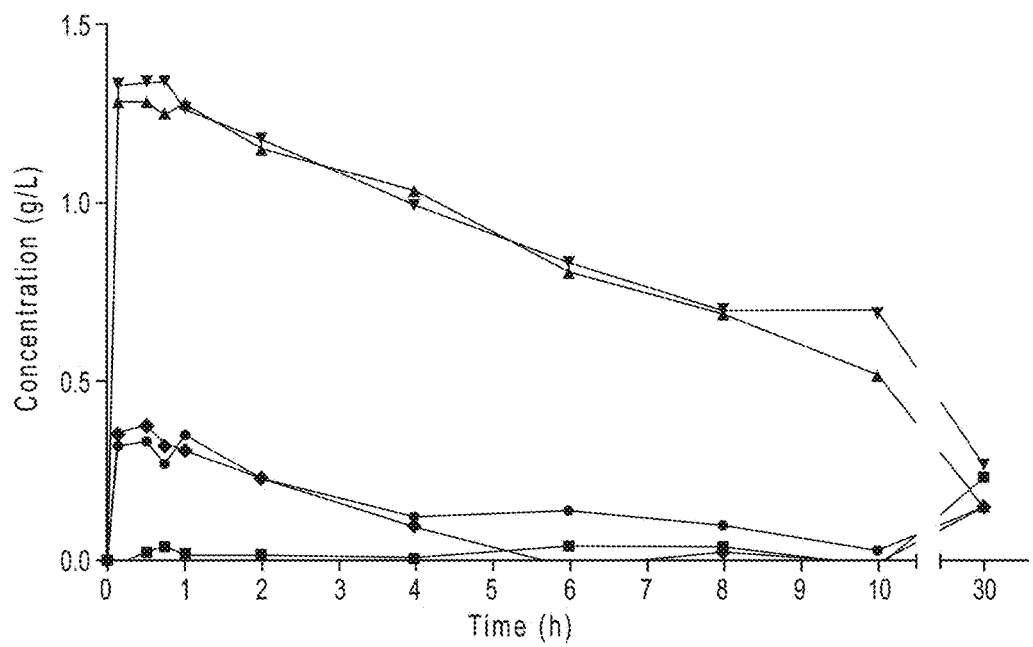
Figure 26D:
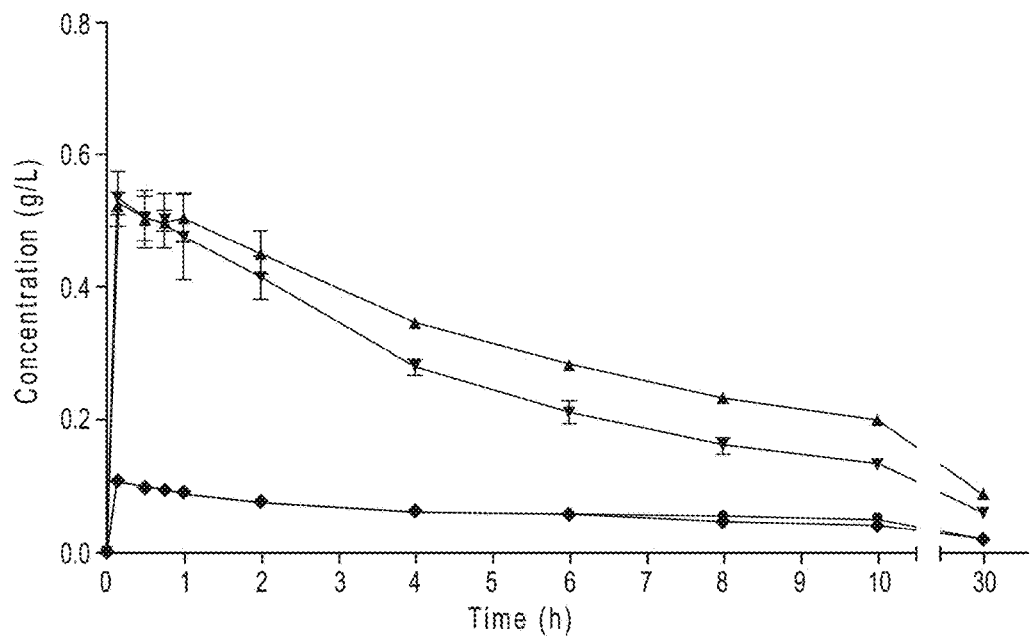

FIG. 25: Increase in plasma triglyceride levels following infusion of a lipoprotein complex according to Formula B and Formula H. Lipoprotein complexes according to Formula H (■) and Formula B (▲) were infused into fasted rabbits at doses of 5 mg/kg. Baseline values, ranging from 0.31 to 0.71 g/L for the three groups, were subtracted to determine the increase in plasma triglyceride levels.

FIG. 26A-26D: Increase in plasma total cholesterol (FIG. 26A), triglycerides (FIG. 26B), phospholipids (FIG. 26C), and ApoA-I (FIG. 26D) following infusion of 5 mg/kg or 20 mg/kg of and 20 mg/kg in rabbits of ApoA-I/eggSM complexes (●, ▲) or ApoA-I/synthetic SM complexes (♦, ▼), as compared to diluent (■). Baseline values ranged as follows for the different plasma lipids measured: from 0.28 to 0.4 g/L for plasma cholesterol, from 0.23 to 0.29 g/L for plasma triglycerides, and from 0.45 to 0.61 g/L for plasma phospholipids.

Figure 27A:
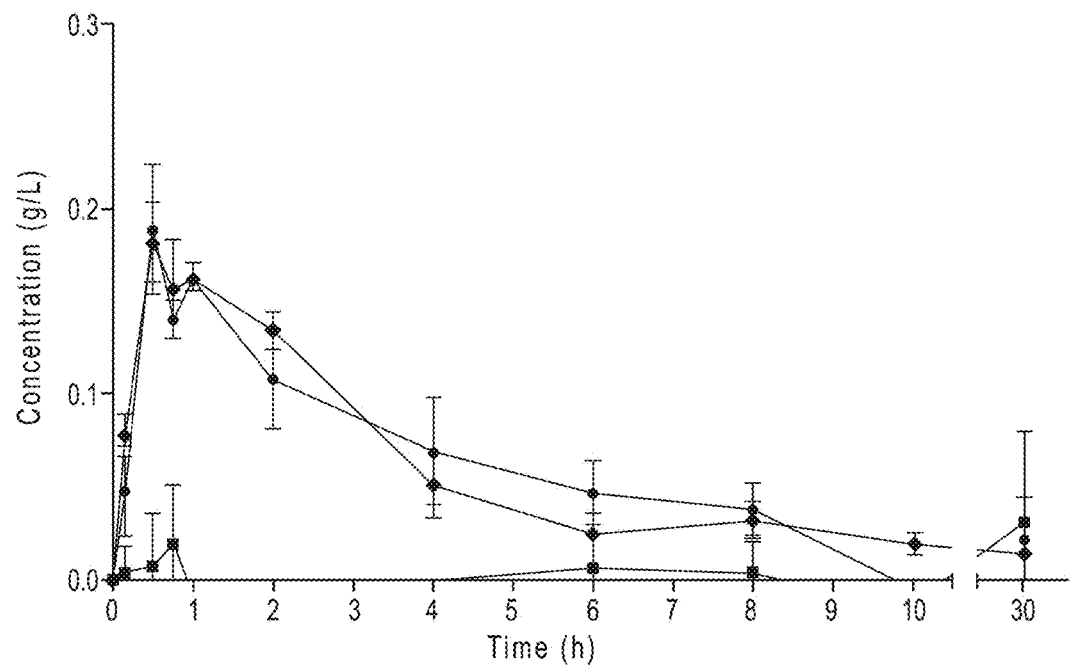
Figure 27B:
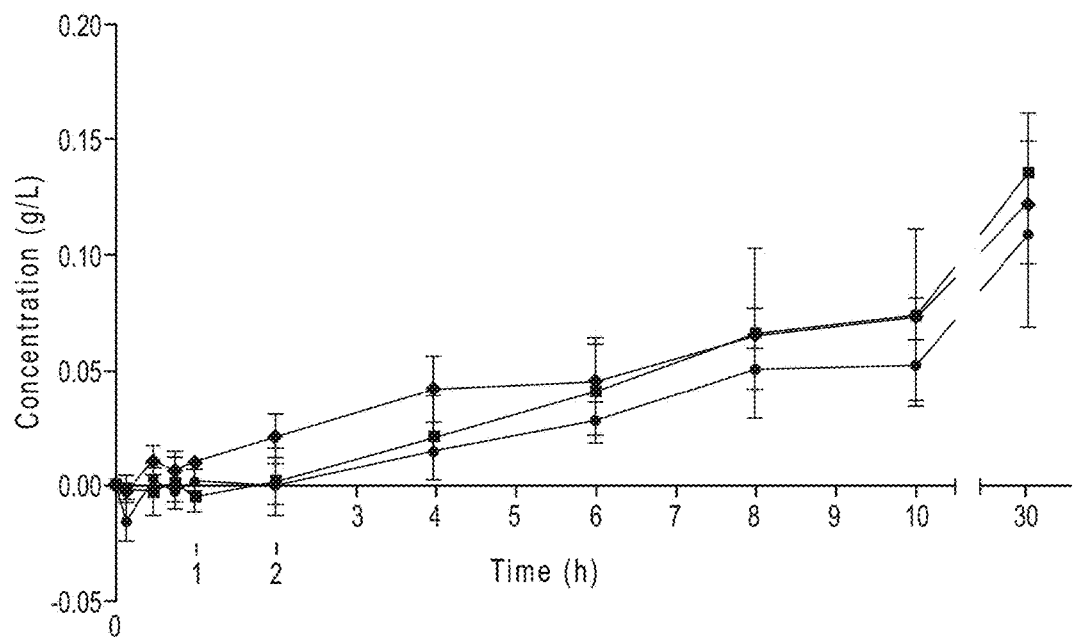
Figure 27C:
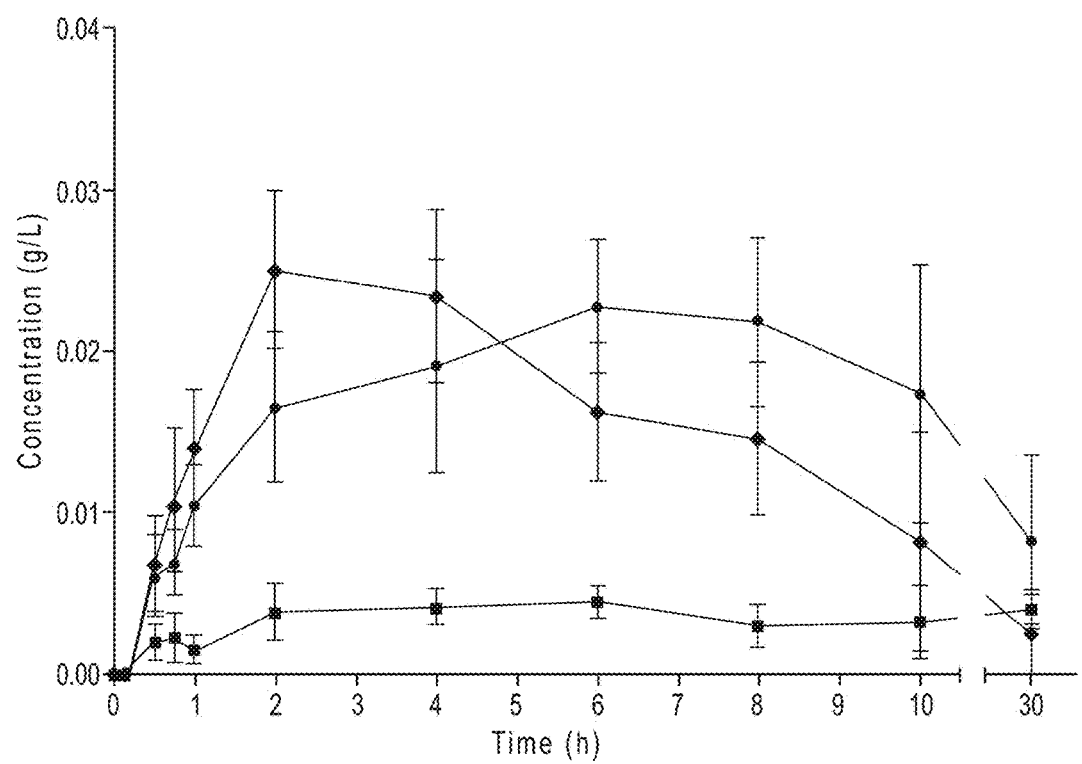

FIG. 27A-27C: Increase in plasma HDL-total cholesterol (FIG. 27A), LDL-total cholesterol (FIG. 27B), and VLDL-total cholesterol (FIG. 27C) following infusion in rabbits of 5 mg/kg ApoA-I/eggSM complexes (●) and ApoA-I/synthetic SM complexes (♦) as compared to diluent (■). Baseline values ranged as follows: between 0.20 to 0.31 g/L for plasma HDL-total cholesterol, between 0.06 to 0.09 g/L for plasma LDL-total cholesterol, and between 0.007 to 0.011 g/L for plasma VLDL-total cholesterol.

6. DETAILED DESCRIPTION

The present disclosure provides lipoprotein complexes, populations thereof, along with methods of making the lipoprotein complexes. The complexes, and populations and compositions (e.g., pharmaceutical compositions) thereof, are useful for, among other things, the treatment and/or prophylaxis of dyslipidemia and/or diseases, disorders and/or conditions associated with dyslipidemia. As discussed in the Summary section, the lipoprotein complexes comprise two major fractions, an apolipoprotein fraction and a phospholipid fraction, preferably in defined weight or molar ratios, and preferably including a specified amount of a neutral phospholipid and, optionally, one or more negatively charged phospholipids.

6.1. The Protein Fraction

The present disclosure provides lipoprotein complexes which comprise a protein fraction. The present disclosure further provides methods of making lipoprotein complexes. The protein component of the lipoprotein complexes is not critical for success in the present methods. Virtually any lipid-binding protein, such as an apolipoprotein and/or derivative or analog thereof that provides therapeutic and/or prophylactic benefit can be included in the complexes. Moreover, any alpha-helical peptide or peptide analog, or any other type of molecule that "mimics" the activity of an apolipoprotein (such as, for example ApoA-I) in that it can activate LCAT or form discoidal particles when associated with lipids, can be included in the lipoprotein complexes, and is encompassed by the term "lipid-binding protein."

6.1.1. Lipid Binding Proteins

The present disclosure further provides methods of purifying recombinantly produced protein, e.g., for use in making lipoprotein complexes. The recombinantly produced protein is most suitably an apolipoprotein. Suitable proteins include apolipoproteins ApoA-I, ApoA-II, ApoA-IV, ApoA-V and ApoE; preferably in mature form. Lipid-binding proteins also active polymorphic forms, isoforms, variants and mutants as well as truncated forms of the foregoing apolipoproteins, the most common of which are Apolipoprotein A-I$_{Milano}$ (ApoA-I$_M$), Apolipoprotein A-I$_{Paris}$ (ApoA-I$_P$), and Apolipoprotein A-I$_{Zaragoza}$ (ApoA-I$_Z$). Apolipoproteins mutants containing cysteine residues are also known, and can also be used (see, e.g., U.S. Publication No. 2003/0181372). The apolipoproteins may be in the form of monomers or dimers, which may be homodimers or heterodimers. For example, homo- and heterodimers (where feasible) of ApoA-I (Duverger et al., 1996, Arterioscler. Thromb. Vasc. Biol. 16(12):1424-29), ApoA-I$_M$ (Franceschini et al., 1985, J. Biol. Chem. 260:1632-35), ApoA-I$_P$ (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-

35), ApoA-IV (Duverger et al., 1991, Euro. J. Biochem. 201(2):373-83), ApoE (McLean et al., 1983, J. Biol. Chem. 258(14):8993-9000), ApoJ and ApoH may be used. The apolipoproteins may include residues corresponding to elements that facilitate their isolation, such as His tags, or other elements designed for other purposes, so long as the apolipoprotein retains some biological activity when included in a complex.

Such apolipoproteins can be purified from animal sources (and in particular from human sources) or produced recombinantly as is well-known in the art, see, e.g., Chung et al., 1980, J. Lipid Res. 21(3):284-91; Cheung et al., 1987, J. Lipid Res. 28(8):913-29. See also U.S. Pat. Nos. 5,059,528, 5,128,318, 6,617,134; U.S. Publication Nos. 20002/0156007, 2004/0067873, 2004/0077541, and 2004/0266660; and PCT Publications Nos. WO/2008/104890 and WO/2007/023476. Other methods of purification are also possible, for example as described in Sections 6.1.3 and 6.1.4 below.

Non-limiting examples of peptides and peptide analogs that correspond to apolipoproteins, as well as agonists that mimic the activity of ApoA-I, ApoA-I$_M$, ApoA-II, ApoA-IV, and ApoE, that are suitable for use as apolipoproteins in the complexes and compositions described herein are disclosed in U.S. Pat. Nos. 6,004,925, 6,037,323 and 6,046,166 (issued to Dasseux et al.), U.S. Pat. No. 5,840,688 (issued to Tso), U.S. Publication Nos. 2004/0266671, 2004/0254120, 2003/0171277 and 2003/0045460 (to Fogelman), U.S. Publication No. 2003/0087819 (to Bielicki) and PCT Publication No. WO/2010/093918 (to Dasseux et al.), the disclosures of which are incorporated herein by reference in their entireties. These peptides and peptide analogues can be composed of L-amino acid or D-amino acids or mixture of L- and D-amino acids. They may also include one or more non-peptide or amide linkages, such as one or more well-known peptide/amide isosteres. Such "peptide and/or peptide mimetic" apolipoproteins can be synthesized or manufactured using any technique for peptide synthesis known in the art, including, e.g., the techniques described in U.S. Pat. Nos. 6,004,925, 6,037,323 and 6,046,166.

The complexes can include a single type of lipid-binding protein, or mixtures of two or more different lipid-binding proteins, which may be derived from the same or different species. Although not required, the lipoprotein complexes will preferably comprise lipid-binding proteins that are derived from, or correspond in amino acid sequence to, the animal species being treated, in order to avoid inducing an immune response to the therapy. Thus, for treatment of human patients, lipid-binding proteins of human origin are preferably used in the complexes of the disclosure. The use of peptide mimetic apolipoproteins may also reduce or avoid an immune response.

In certain preferred embodiments, the lipid-binding protein is a protein having an amino acid sequence with at least 95% sequence identity to a mature human ApoA-I protein, e.g., a protein having an amino acid sequence corresponding to positions 25 to 267 of SEQ ID NO:1. In certain embodiments, the mature human ApoA-I protein has an amino acid sequence with at least 96%, at least 97%, at least 98%, or at least 99% sequence identity to positions 25 to 267 of SEQ ID NO:1. In some embodiments, the mature human ApoA-I protein has an amino acid sequence having an aspartic acid at position 1 (i.e. the position corresponding to position 25 of SEQ ID NO:1). In a specific embodiment, the mature human ApoA-I protein has an amino acid sequence corresponding to positions 25 to 267 of SEQ ID NO:1. In a preferred embodiment, the ApoA-I protein is recombinantly produced in mammalian host cells, most preferably Chinese Hamster Ovary ("CHO") cells, as described in the following subsection.

6.1.2. Recombinant Expression of Apolipoproteins

The present disclosure provides recombinant expression methods for producing lipid binding proteins such as ApoA-I, and related nucleic acids, mammalian host cells, cell cultures. The resulting recombinant lipid binding protein can be purified and/or incorporated into lipoprotein complexes as described herein.

Generally, for recombinant production, a polynucleotide sequence encoding a lipid-binding protein or peptide is inserted into an appropriate expression vehicle, i.e., a vector that contains the necessary elements for the transcription and translation of the inserted coding sequence, or in the case of an RNA viral vector, the necessary elements for replication and translation. The expression vector can be derived from viruses such as adenovirus, adeno-associated virus, herpesvirus, retrovirus or lentivirus. The expression vehicle is then transfected into a suitable target cell which will express the protein or peptide. Suitable host cells include, but are not limited to, bacterial species, mammalian or insect host cell systems including baculovirus systems (see, e.g., Luckow et al., Bio/Technology, 6, 47 (1988)), and established cell lines such 293, COS-7, C127, 3T3, CHO, HeLa, BHK, etc. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

Where ApoA-I is the lipid binding protein, ApoA-I protein is expressed from a recombinant nucleotide sequence encoding ApoA-I. In some embodiments, the nucleotide sequence encoding ApoA-I is human. Non-limiting examples of human ApoA-I nucleotide sequences are disclosed in U.S. Pat. Nos. 5,876,968; 5,643,757; and 5,990,081, and WO 96/37608; the disclosures of which are incorporated herein by reference in their entireties. In certain embodiments, the nucleotide sequence encodes the amino acid sequence of a mature ApoA-I protein, preferably operably linked to a signal sequence (e.g., amino acids 1-18 of SEQ ID NO:1) for secretion of the ApoA-I from the host cell and/or a proprotein sequence (e.g., amino acids 19-25 of SEQ ID NO:1). Other signal sequences suitable for directed secretion of ApoA-I can be either heterologous to ApoA-I, e.g., a human albumin signal peptide or a human IL-2 signal peptide, or homologous to ApoA-I.

Preferably, the nucleotide sequence encodes a mature human ApoA-I polypeptide, for example a polypeptide having an amino acid sequence that is at least 95%, at least 96%, at least 97%, at least 98% or at least 99% identical to the amino acid sequence corresponding to positions 25 to 267 of SEQ ID NO:1, optionally wherein the amino acid sequence comprises an aspartic acid at position 25. In a preferred embodiment, the nucleotide sequence encodes a polypeptide having an amino acid sequence of SEQ ID NO:1. The nucleotide sequence can also encode a polypeptide having an amino acid sequence that is at least 95%, at least 96%, at least 97%, at least 98% or at least 99% identical to the amino acid sequence of human ApoA-I protein set forth in one of GenBank Accession Nos. NP 000030, AAB59514, P02647, CAA30377, AAA51746 or AAH05380.1, optionally comprising an aspartic acid at the position corresponding to the first amino acid of the mature human ApoA-I protein.

The ApoA-I encoding polynucleotides can be codon optimized for expression in recombinant host cells. Preferred host cells are mammalian host cells, including, but not limited, Chinese hamster ovary cells (e.g. CHO-K1; ATCC No. CCL 61; CHO-S (GIBCO Life Technologies Inc., Rockville, Md., Catalog #11619012)), VERO cells, BHK (ATCC No. CRL 1632), BHK 570 (ATCC No. CRL 10314), HeLa cells, COS-1 (ATCC No. CRL 1650), COS-7 (ATCC No. CRL 1651), MDCK cells, 293 cells (ATCC No. CRL 1573; Graham et al., J. Gen. Virol. 36:59-72, 1977), 3T3 cells, myeloma cells (especially murine), PC12 cells and W138 cells. In certain embodiments, the mammalian cells, such as CHO-S cells (Invitrogen™, Carlsbad Calif.), are adapted for growth in serum-free medium. Additional suitable cell lines are known in the art and available from public depositories such as the American Type Culture Collection, Manassas, Va.

For recombinant expression of ApoA-I, the polynucleotides encoding ApoA-I are operably linked to one or more control sequences, e.g., a promoter or terminator, that regulate the expression of ApoA-I in the host cell of interest. The control sequence(s) can be native or foreign to the ApoA-I-encoding sequence, and also native or foreign to the host cell in which the ApoA-I is expressed. Control sequences include, but are not limited to, promoters, ribosome binding sites, leaders, polyadenylation sequences, propeptide sequences, signal peptide sequences, and transcription terminators. In some embodiments, the control sequences include a promoter, ribosome binding site, and transcriptional and translational stop signals. The control sequences can also include one or more linkers for the purpose of introducing specific restriction sites facilitating ligation of the control sequences with the coding region of the nucleotide sequence encoding ApoA-I.

The promoters driving the recombinant expression of ApoA-I can be constitutive promoters, regulated promoters, or inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See e.g., Nevoigt et al. (2006) Appl. Environ. Microbiol. 72:5266-5273, the disclosure of which is herein incorporated by reference in its entirety.

One or more of the control sequences can be derived from viral sources. For example, in certain aspects, promoters are derived from polyoma or adenovirus major late promoter. In other aspects, the promoter is derived from Simian Virus 40 (SV40), which can be obtained as a fragment that also contains the SV40 viral origin of replication (Fiers et al., 1978, Nature, 273:113-120), or from cytomegalovirus, e.g., simian cytomegalovirus immediate early promoter. (See U.S. Pat. No. 4,956,288). Other suitable promoters include those from metallothionein genes (See U.S. Pat. Nos. 4,579, 821 and 4,601,978).

Also provided herein are recombinant ApoA-I expression vectors. A recombinant expression vector can be any vector, e.g., a plasmid or a virus, that can be manipulated by recombinant DNA techniques to facilitate expression of a heterologous ApoA-I in a recombinant host cell. The expression vector can be integrated into the chromosome of the recombinant host cell and comprises one or more heterologous genes operably linked to one or more control sequences useful for production of ApoA-I. In other embodiments, the expression vector is an extrachromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent). In various embodiments, the expression vector includes a selectable marker, such as a gene that confers antibiotic resistance (e.g., ampicillin, kanamycin, chloramphenicol or tetracycline resistance) to the recombinant host organism that comprises the vector. In particular aspects, the DNA constructs, vectors and polynucleotides are suitable for expression of ApoA-I in mammalian cells. Vectors for expression of ApoA-I in mammalian cells can include an origin of replication, a promoter and any necessary ribosome binding sites, RNA splice sites, polyadenylation site, and transcriptional terminator sequences that are compatible with the host cell systems. In some aspects, an origin of replication is heterologous to the host cell, e.g., is of viral origin (e.g., SV40, Polyoma, Adeno, VSV, BPV). In other aspects, an origin of replication is provided by the host cell chromosomal replication mechanism.

Methods, reagents and tools for introducing foreign DNA into mammalian host cells are known in the art and include, but are not limited to, calcium phosphate-mediated transfection (Wigler et al., 1978, Cell 14:725; Corsaro et al., 1981, Somatic Cell Genetics 7:603; Graham et al., 1973, Virology 52:456), electroporation (Neumann et al., 1982, EMBO J. 1:841-5), DEAE-dextran mediated transfection (Ausubel et al. (eds.), Short Protocols in Molecular Biology, 3rd Edition (John Wiley & Sons 1995)), and liposome-mediated transfection (Hawley-Nelson et al., 1993, Focus 15:73; Ciccarone et al., 1993, Focus 15:80).

For high-yield production, stable expression of ApoA-I is preferred. For example, following the introduction of foreign DNA into the host cells, the host cells may be allowed to grow for 1-2 days in an enriched media, and then are switched to a selective media. Rather than using expression vectors that contain viral origins of replication, host cells can be transformed with vector comprising a nucleotide sequence comprising the ApoA-I-coding sequence controlled by appropriate expression control elements and a selectable marker. The selectable marker in the vector confers resistance to the selection and allows cells to stably integrate the vector into their chromosomes and grow to form foci which in turn can be cloned and expanded into cell lines. A number of selection systems may be used, including but not limited to the herpes simplex virus thymidine kinase (Wigler et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy et al., 1980, Cell 22: 817) genes can be employed in tk⁻, hgprt⁻ or aprt⁻ cells, respectively. Also, antimetabolite resistance can be used as the basis of selection by using, for example, dhfr, which confers resistance to methotrexate (Wigler et al., 1980, Natl. Acad. Sci. USA 77: 3567; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072; neo, which confers resistance to the aminoglycoside G-418 (Colberre-Garapin et al., 1981, J. Mol. Biol. 150: 1); and/or hyg, which confers resistance to hygromycin (Santerre et al., 1984, Gene 30: 147).

Stable, high yield expression can also be achieved using retroviral vectors that integrate into the host cell genome (see, e.g., U.S. Patent Publications No. 2008/0286779 and 2004/0235173). Alternatively, stable, high yield expression of ApoA-I can be achieved by gene activation methods, which entail activating expression of and amplifying an endogenous ApoA-I gene in genomic DNA of a mammalian cell of choice, for example as described in WO 1994/012650. Increasing the copy number of an ApoA-I gene (containing an ApoA-I coding sequence and one or more control elements) can facilitate the high yield expression of ApoA-I. Preferably, the mammalian host cell in which ApoA-I is expressed has an ApoA-I gene copy index of at least 2, at least 3, at least 4, or at least 5. In specific embodiments, the mammalian host cell in which ApoA-I is expressed has an ApoA-I gene copy index of at least 6, at least 7, at least 8, at least 9, or at least 10.

In certain embodiments, the mammalian cells are adapted to produce ApoA-I in quantities of at least 0.5 g/L, at least 1 g/L, at least 1.5 g/L, at least 2 g/L, at least 2.5 g/L, at least 3 g/L, at least 3.5 g/L, and optionally up to 4 g/L, up to 4.5 g/L, up to 5 g/L, up to 5.5 g/L, or up to 6 g/L. The mammalian host cells are preferably capable of producing at least about 0.5, 1, 2, or 3 g/L ApoA-I in culture and/or up to about 20 g/L ApoA-I in culture, e.g., up to 4, 5, 6, 7, 8, 9, 10, 12, or 15 g/L ApoA-I in culture.

In certain embodiments, the mammalian cells are adapted for growth in serum-free medium. In these embodiments, the ApoA-I is secreted from the cells. In other embodiments, the ApoA-I is not secreted from the cells.

The mammalian host cells provided herein can be used to produce ApoA-I. Generally, the methods comprise culturing a mammalian host cell as described herein under conditions in which ApoA-I is expressed. Furthermore, the methods can comprise recovering and, optionally, purifying mature ApoA-I from the supernatant of the mammalian cell culture.

The culture conditions, including the culture medium, temperature, pH, can be suited to the mammalian host cell being cultured and the mode of culture chosen (shake flask, bioreactor, roller bottle, etc. . . . ). Mammalian cells can be grown in large scale batch culture, in continuous or semi-continuous culture.

Also provided herein is a mammalian cell culture comprising a plurality of a ApoA-I-producing mammalian host cells described herein. In some embodiments, the mammalian cell culture comprises at least 0.5 g/L, at least 1 g/L, at least 1.5 g/L, at least 2 g/L, at least 2.5 g/L, at least 3 g/L, at least 3.5 g/L, and optionally up to 4 g/L, up to 4.5 g/L, up to 5 g/L, up to 5.5 g/L, or up to 6 g/L of ApoA-I. The culture can be of any scale, ranging from about 150 mL to about 500 mL, 1 L, 10 L, 15 L, 50 L, 100 L, 200 L, 250 L, 300 L, 350 L, 400 L, 500 L, 750 L, 1000 L, 1500 L, 2000 L, 2500 L, 3000 L, 5000 L, 7500 L, 10000 L, 15000 L, 20000 L, 25000 L, 50000 L or more. In some instances, the culture is a large scale culture, such as 15 L, 20 L, 25 L, 30 L, 50 L, 100 L, 200 L, 300 L, 500 L, 1000 L, 5000 L, 10000 L, 15000 L, 20000 L, 25000 L, up to 50000 L or more.

6.1.3. Purification of Apolipoproteins

The present disclosure relates to methods of obtaining highly purified apolipoprotein, that is useful in making lipoprotein complexes and compositions thereof as described herein. The methods can be applied to any apolipoprotein, including but not limited to, ApoA-I, -II, -III or -IV; ApoB48 and ApoB100; ApoC-I, -II, -III or -IV; ApoD; ApoE, ApoH; ApoJ. More specifically, the present disclosure relates to methods of obtaining highly purified ApoA-I. In some embodiments, the ApoA-I is a human protein having a sequence selected from, but not limited to, the sequences set forth in Genbank Accession Nos. NP 000030, AAB59514, P02647, CAA30377, AAA51746 and AAH05380.1. In certain embodiments, the ApoA-I is a human protein as described above in Section 6.1.2. In other embodiments, the methods of the present disclosure can be used to purify ApoA-I obtained from non-human animals (see, e.g., U.S. Publication No. 2004/0077541), for example, cows, horses, sheep, monkeys, baboons, goats, rabbits, dogs, hedgehogs, badgers, mice, rats, cats, guinea pigs, hamsters, duck, chicken, salmon and eel (Brouillette et al., 2001, Biochim. Biophys. Acta. 1531:4-46; Yu et al., 1991, Cell Struct. Funct. 16(4):347-55; Chen and Albers, 1983, Biochim Biophys Acta. 753(1):40-6; Luo et al., 1989, J Lipid Res. 30(11):1735-46; Blaton et al., 1977, Biochemistry 16:2157-63; Sparrow et al., 1995, J Lipid Res. 36(3):485-95; Beaubatie et al., 1986, J. Lipid Res. 27:140-49; Januzzi et al., 1992, Genomics 14(4):1081-8; Goulinet and Chapman, 1993, J. Lipid Res. 34(6):943-59; Collet et al., 1997, J Lipid Res. 38(4):634-44; and Frank and Marcel, 2000, J. Lipid Res. 41(6):853-72).

Examples of ApoA-I proteins that can be purified by the methods disclosed herein include, but are not limited to, the preproapolipoprotein form of ApoA-I, pro- and mature forms of ApoA-I, and active polymorphic forms, isoforms, variants and mutants as well as truncated forms, e.g., ApoA-$I_M$, ApoA-$I_Z$, and ApoA-$I_P$. ApoA-$I_M$ is the R173C molecular variant of ApoA-I (see, e.g., Parolini et al., 2003, J Biol Chem. 278(7):4740-6; Calabresi et al., 1999, Biochemistry 38:16307-14; and Calabresi et al., 1997, Biochemistry 36:12428-33). ApoA-$I_P$ is the R151C molecular variant of ApoA-I (see, e.g., Daum et al., 1999, J Mol Med. 77(8):614-22). ApoA-$I_L$ is an L144R molecular variant of ApoA-I (see Recalde et al., 2001, Atherosclerosis 154(3):613-623; Fiddyment et al., 2011, Protein Expr. Purif. 80(1):110-116). Apolipoprotein A-I mutants containing cysteine residues are also known, and can also be purified by the methods described herein (see, e.g., U.S. Publication No. 2003/0181372). ApoA-I for use in the methods described herein can be in the form of monomers, homodimers, or heterodimers. For example, homo- and heterodimers of pro- and mature ApoA-I that can be prepared include, among others, ApoA-I (Duverger et al., 1996, Arterioscler Thromb Vasc Biol. 16(12):1424-29), ApoA-$I_M$ (Franceschini et al., 1985, J Biol Chem. 260:1632-35), and ApoA-$I_P$ (Daum et al., 1999, J Mol Med. 77:614-22).

The purification methods described herein can be performed on any scale convenient for the skilled practitioner.

In some aspects, ApoA-I protein that can be purified by the methods described herein has an amino acid sequence that is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical or at least 100% identical to amino acids 25-267 of SEQ ID NO: 1.

Apolipoprotein can be from any source, including from blood plasma or from recombinant expression in prokaryotic or eukaryotic cells. In particular embodiments, the apolipoprotein is ApoA-I, e.g., human ApoA-I. In some aspects, the ApoA-I is expressed in the cytoplasm or periplasm of prokaryotic or eukaryotic host cells. In these embodiments, the cells are disrupted to release ApoA-I into the supernatant prior to purifying the ApoA-I. Cell disruption methods are well-known in the art. Exemplary methods of disrupting cells include, but are not limited to, enzymatic methods, sonication, detergent methods, and mechanical methods. In certain preferred aspects, ApoA-I is expressed in mammalian cells, preferably CHO cells, and is secreted into the growth medium. In these embodiments, ApoA-I is purified from the clarified cell-free medium. It will be understood that, although the purification methods are described in detail herein in connection with human ApoA-I, it is within the skill in the art to adapt the purification conditions to other apolipoproteins, as well as to non-human ApoA-I, polymorphic forms, isoforms, variants, mutants and truncated forms of ApoA-I or other apolipoproteins, depending on specific protein characteristics that are readily ascertainable by the skilled artisan (e.g., molecular weight, isoelectric point, Stokes radius, hydrophobicity, multimeric state, etc.).

Where ApoA-I, is prepared from blood plasma, it can be separated from blood plasma by any known method, including but not limited to, cold fractionation processes such as those described by Cohn et al., 1946, J. Am. Chem. Soc. 68:459-475 ("Cohn process") or by Oncley et al., 1949, J. Am. Chem. Soc. 71:541-550 ("Cohn-Oncley process"). Other methods for isolating apolipoprotein from blood plasma include variations of the Cohn and Cohn-Oncley processes, such as the Kistler-Nitschmann process. (See Nitschmann et al., 1954, Helv. Chim. Acta 37:866-873; Kistler et al., 1962, Vox Sang. 7:414-424).

In these embodiments, apolipoprotein is obtained by precipitation from plasma with cold alcohol, e.g., ethanol. Other alcohols for use in cold fractionation of plasma include C1-C6 straight or branched chain alcohols, such as methanol, n-propanol, isopropanol, n-butanol, sec-butanol, isobutanol and tert-butanol. In various embodiments, agents other than alcohols that reduce protein solubility can be used to precipitate apolipoprotein from plasma. Such agents include, but are not limited to, ethers, ammonium sulfate, 7-ethoxyacridine-3,9-diamine (rivanol) and polyethylene glycols. Precipitated proteins can be separated from the supernatant by any method known in the art, including, but not limited to, sedimentation, centrifugation and filtration.

ApoA-I can be recovered from any fraction of blood plasma that contains the protein. In some embodiments, ApoA-I is recovered from a serum fraction of human plasma from which the amount of fibrinogen has been reduced by precipitation with about 8% (w/w) ethanol. In other embodiments, apolipoprotein is recovered from a serum fraction of human plasma from which the concentrations of other serum proteins (e.g., β-globulins and γ-gamma globulins) have been reduced by precipitation with about 25% (w/w) ethanol. In still other embodiments, apolipoprotein is recovered as a precipitate from human serum obtained by increasing the ethanol concentration to about 38% to about 42% (w/w). In a particular embodiment, apolipoprotein is recovered as a precipitate from human serum obtained by increasing the ethanol concentration to about 40% (w/w) (Cohn's fraction IV). Precipitated ApoA-I can be recovered from serum fractions by any method known in the art, including but not limited to centrifugation and filtration.

In some embodiments, the temperature of plasma fractions from which apolipoprotein is recovered is sufficiently low to prevent denaturation of the protein. In these embodiments, the temperature of the ApoA-I fractions ranges from about −10° C. to about 0° C., such as from about −8° C. to about −2° C. In various embodiments, the pH of plasma fractions from which ApoA-I is recovered is in a range that prevents denaturation of the protein. In these embodiments, the pH of fractions that contain ApoA-I ranges from about 5 to about 7, such as from about 5.5 to about 6.5.

6.1.4. Improved Lipoprotein Purification Processes

Applicants have further discovered an improved process of purification, described below and illustrated in the Examples, that produces lipoproteins that are mature, intact, and substantially free of contaminants. The purification methods described herein can be performed on any scale convenient for the skilled practitioner.

The methods can be applied to any apolipoprotein, including but not limited to, ApoA-I, -II, -III or -IV; ApoB48 and ApoB100; ApoC-I, -II, -III or -IV; ApoD; ApoE, ApoH; ApoJ. More specifically, the present disclosure relates to methods of obtaining highly purified ApoA-I. In some embodiments, the ApoA-I is a human protein having a sequence selected from, but not limited to, the sequences set forth in Genbank Accession Nos. NP 000030, AAB59514, P02647, CAA30377, AAA51746 and AAH05380.1. In certain embodiments, the ApoA-I is a human protein as described above in Section 6.1.2. In other embodiments, the methods of the present disclosure can be used to purify ApoA-I obtained from non-human animals (see, e.g., U.S. Publication 2004/0077541), for example, cows, horses, sheep, monkeys, baboons, goats, rabbits, dogs, hedgehogs, badgers, mice, rats, cats, guinea pigs, hamsters, duck, chicken, salmon and eel (Brouillette et al., 2001, Biochim Biophys Acta. 1531:4-46; Yu et al., 1991, Cell Struct Funct. 16(4):347-55; Chen and Albers, 1983, Biochim Biophys Acta. 753(1):40-6; Luo et al., 1989, J Lipid Res. 30(11): 1735-46; Blaton et al., 1977, Biochemistry 16:2157-63; Sparrow et al., 1995, J Lipid Res. 36(3):485-95; Beaubatie et al., 1986, J Lipid Res. 27:140-49; Januzzi et al., 1992, Genomics 14(4):1081-8; Goulinet and Chapman, 1993, J Lipid Res. 34(6):943-59; Collet et al., 1997, J Lipid Res. 38(4):634-44; and Frank and Marcel, 2000, J Lipid Res. 41(6):853-72).

Examples of ApoA-I proteins that can be purified by the methods disclosed herein include, but are not limited to, the preproapolipoprotein form of ApoA-I, pro- and mature forms of ApoA-I, and active polymorphic forms, isoforms, variants and mutants as well as truncated forms, e.g., ApoA-$I_M$, ApoA-$I_Z$, and ApoA-$I_P$. Apolipoprotein A-I mutants containing cysteine residues are also known, and can also be purified by the methods described herein (see, e.g., U.S. Publication 2003/0181372). ApoA-I for use in the methods described herein can be in the form of monomers, homodimers, or heterodimers. For example, homo- and heterodimers of pro- and mature ApoA-I that can be prepared include, among others, ApoA-I (Duverger et al., 1996, Arterioscler Thromb Vasc Biol. 16(12):1424-29), ApoA-$I_M$ (Franceschini et al., 1985, J Biol Chem. 260:1632-35), and ApoA-$I_P$ (Daum et al., 1999, J Mol Med. 77:614-22).

In some aspects, ApoA-I protein that can be purified by the methods described herein has an amino acid sequence that is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical or at least 100% identical to amino acids 25-267 of SEQ ID NO: 1.

Apolipoprotein can be from any source, including from blood plasma or from recombinant expression in prokaryotic or eukaryotic cells. In particular embodiments, the apolipoprotein is ApoA-I, e.g., human ApoA-I. In some aspects, the ApoA-I is expressed in the cytoplasm or periplasm of prokaryotic or eukaryotic host cells. In these embodiments, the cells are disrupted to release ApoA-I into the supernatant prior to purifying the ApoA-I. Cell disruption methods are well-known in the art. Exemplary methods of disrupting cells include, but are not limited to, enzymatic methods, sonication, detergent methods, and mechanical methods. In certain preferred aspects, ApoA-I is expressed in mammalian cells, preferably CHO cells, and is secreted into the growth medium. In these embodiments, ApoA-I is purified from the clarified cell-free medium. It will be understood that, although the purification methods are described in detail herein in connection with human ApoA-I, it is within the skill in the art to adapt the purification conditions to other apolipoproteins, as well as to non-human ApoA-I, polymorphic forms, isoforms, variants, mutants and truncated forms of ApoA-I or other apolipoproteins, depending on specific protein characteristics that are readily ascertainable by the skilled artisan (e.g., molecular weight, isoelectric point, Stokes radius, hydrophobicity, multimeric state, etc.).

Generally, the purification methods comprise the steps of: (a) contacting an ApoA-I containing solution with an anion exchange matrix under conditions such that the ApoA-I does not bind to the matrix; (b) filtering the ApoA-I containing solution obtained in step (a) through a membrane having a pore size sufficient to remove viruses or viral particles; (c) passing the filtrate obtained in step (b) through a first reverse phase chromatography column under conditions such that the ApoA-I binds to the matrix; (d) eluting from the first reverse phase chromatography matrix a first ApoA-I containing reverse phase eluate using a gradient of increasing concentrations of an organic solvent; (e) passing the first ApoA-I reverse phase eluate from step (d) through a second reverse phase chromatography column under conditions such that the ApoA-I binds to the matrix; and (f) eluting from the second reverse phase chromatography matrix a second ApoA-I containing reverse phase eluate using a gradient of increasing concentrations of an organic solvent. The order in which the steps are performed is not critical. As will be apparent to the person of skill in the art, a variety of permutations in the order of the steps are possible, some of which are described below.

In certain aspects, the ApoA-I containing solution is conditioned before contacting it with an anion exchange matrix in step (a). Conditioning is performed to adjust the pH of the protein solution so that it is in a range where ApoA-I does not bind to the anion exchange matrix in step (a) (i.e, the protein does not have a net negative charge and step (a) is run in negative mode). In these aspects, the pH of the ApoA-I containing solution is from about 5 to about 7, preferably from about 5.0 to about 5.6. In particular aspects, the pH is from about 5.1 to about 5.5. In still other aspects, the pH is about 5.3. Adjustments in pH can be performed by adding an appropriate acid (e.g., hydrochloric acid) or base (e.g., sodium hydroxide) until a pH within the desired range is obtained. In some embodiments, the ApoA-I containing solution is filtered before the conditioning step to remove cells and cell debris. In other embodiments, when a conditioning step is absent, the ApoA-I containing solution is optionally filtered before step (a) to remove cells and cell debris.

In some embodiments, step (a) of contacting an ApoA-I containing solution with an anion exchange matrix is performed by passing the protein solution through a chromatography column. In these embodiments, the column is packed at a bed height of from about 10 cm to about 50 cm, preferably from about 10 cm to about 30 cm, and more preferably at a bed height of about 20 cm. In certain aspects, the column is loaded with a protein solution comprising from about 10 g to about 50 g, such as from about 10 g to about 30 g, such as from about 25 g to about 35 g of ApoA-I per liter. In particular embodiments, the column is loaded with a protein solution comprising up to about 32 g of ApoA-I per liter. In other embodiments, step (a) is performed in batch mode, i.e., by adding an anion exchange matrix to a protein solution in a flask, mixing for a period of time sufficient for binding contaminants to the matrix, and then separating the matrix material from the protein solution, e.g., by filtration or centrifugation. In certain embodiments, the protein solution is filtered to remove particulates in the solution prior to contacting it with the anion exchange matrix.

Anion exchange matrices for use in step (a) of the methods described herein can be any anion exchange matrix known in the art. Suitable anion exchange matrices include, but are not limited to, Q-Sepharose FF, Q-Spherosil, DEAE-Sepharose FF, Q-Cellulose, DEAE-Cellulose and Q-Spherodex. In a particular embodiment, the anion exchange matrix is Q-Sepharose FF (GE Healthcare). In certain aspects, before contacting the protein solution in step (a) with an anion exchange matrix, the matrix is equilibrated in a buffer having a pH within the preferred ranges discussed above such that the ApoA-I does not bind to the matrix. Buffers useful for equilibrating anion exchange matrices prior to step (a) and for performing step (a) are known to the skilled artisan. In particular embodiments, the buffer is TAMPA (20 mM sodium phosphate, pH 5.3).

In various embodiments, step (a) is used to purify ApoA-I with respect to proteins other than ApoA-I (e.g., host cell proteins), host cell DNA and endotoxin, which bind to the anion exchange matrix and are thereby separated from ApoA-I, which does not bind to matrix under the pH and salt conditions described above. In some aspects, at least 75%, at least 80%, at least 85%, or at least 90% or more of the amount of ApoA-I in the starting solution is recovered from the anion exchange step.

In various embodiments, the purification methods comprise a step (b) in which the ApoA-I solution from step (a) is filtered using a filter with a pore size that is sufficient to trap viruses and viral particles. Optionally, the step (b) of filtering through a membrane to remove viruses or viral particles is performed after step (f) above, rather than after step (a). In certain aspects, the pH of the eluate from the anion exchange matrix is adjusted before viral filtration step (b) by the addition of sodium hydroxide or other suitable base. The ApoA-I containing solution from step (a) is adjusted to a pH of from about 7.8 to about 8.2. In a particular aspect, the ApoA-I containing solution is adjusted to a pH of about 8.0. The filter used in step (b) can be any filter with an appropriate pore size for trapping viruses, e.g., with a pore size of from about 15 nm to about 75 nm. In particular embodiments, the pore size of the filter is about 20 nm (e.g., Planova 20N, Asahi Kasei Medical). The skilled artisan will appreciate that the flow rate of the protein solution through the viral filter is determined by the properties of the solution (e.g., its viscosity, the concentration of particulates, etc.). A typical flow rate for viral filtration is about 12.5 L/h/m2, however, the flow rate can be adjusted higher or lower to maintain a filter pressure of 1 bar or less. The filtrate from step (b) contains ApoA-I. In certain aspects, recovery of ApoA-I from the viral filtration step is at least 80%, at least 85%, at least 90%, at least 95% or at least 98% or more of the amount of the ApoA-I in the anion exchange eluate from step (a).

In particular embodiments, the purification methods described herein comprise a step (c) after step (b) in which the filtrate from step (b) is passed through a first reverse phase chromatography column under buffer and salt conditions that allow the Apolipoprotein A-I to bind to the matrix. In these embodiments, the ApoA-I is purified with respect to host cell DNA, host cell proteins, endotoxin and truncated forms using a gradient of increasing concentrations of organic solvent. Reverse phase chromatography can be performed using a wide variant of matrices known in the art, including but not limited to silica, polystyrene, or cross-linked agarose based media onto which C4 to C18 hydrophobic ligands are grafted. Commercially available hydrophobic matrices useful in the methods described herein include, but are not limited to Butyl Sepharose-FF, Octyl Sepharose-FF, Dianon HP20ss, C18 Hypersil and Source 30 RPC. In particular embodiments, the matrix used in step (c) is Source 30 RPC (GE Healthcare). In certain aspects, the reverse phase chromatography column has a bed height of from about 10 cm to about 50 cm, such as from about 10 cm to about 30 cm. In a particular aspect, the reverse phase chromatography column has a bed height of about 25 cm.

In some embodiments, the ApoA-I filtrate from the viral filtration step (b) is loaded onto the reverse phase column at a concentration of about 1 to about 20 g ApoA-I, such as at a concentration of about 1.5 g to about 5 g of ApoA-I, and more preferably at a concentration of about 2.5 g to about 3.5 g ApoA-I per liter. In a particular aspect, the ApoA-I filtrate from step (b) is loaded onto the reverse phase column at a concentration of about 3.4 g of ApoA-I per liter. Buffer conditions that can be used to equilibrate the reverse phase column before loading ApoA-I and to insure that the protein will bind to the column upon loading will be readily ascertainable to those of skill in the art. Preferably, the column equilibration buffer is a strong buffer that can reduce the column pH to about 9.5. In certain embodiments, the equilibration buffer is TAMP D (20 mM ammonium carbonate). Preferably, after equilibration, ApoA-I containing filtrate from step (b) (at a pH of about 8.0) is loaded onto the column at a flow rate of about 0.5 cm to about 5.0 cm per minute, such as from about 2.0 cm to about 4.0 cm per minute. In a particular embodiment, the ApoA-I containing filtrate is loaded onto the column at a flow rate of about 2.8 cm per minute.

After ApoA-I is bound to the reverse phase matrix in step (c), the protein is eluted in step (d) by exposure to a gradient of increasing concentrations of organic solvent in buffer, such as from about 35% to about 50% acetonitrile in TAMP D buffer. In some aspects, a linear gradient of from about 35% to about 50% acetonitrile over a period of about 60 to about 90 minutes, such as about 70 minutes or more preferably about 80 minutes can be used to elute the ApoA-I from the column. In certain aspects, the linear gradient is followed by about 10 minutes of isocratic elution with 50% acetonitrile. The exact conditions for eluting ApoA-I from the reverse phase column will be readily ascertainable to the skilled artisan. In various embodiments, about 60%, such as about 65%, about 70%, about 75% or about 80% or more of ApoA-I in the column load is present in the column eluate in step (d).

In certain aspects, the purification methods described herein further comprise after step (d) a step (e) of passing the Apolipoprotein A-I reverse phase eluate from step (d) through a second reverse phase chromatography column in order to further remove DNA, host cell proteins and truncated forms of ApoA-I from the full-length protein. Preferably, the reverse phase eluate from step (d) is loaded on the second reverse phase column under conditions that allow the Apolipoprotein A-I to bind to the matrix. The reverse phase matrix for use in step (e) can be the same type of matrix or a different type of matrix as used in step (d). In particular embodiments, the reverse phase matrix used in step (e) is a C18 silica matrix, such as a Daisogel SP-300-BIO C18 matrix (300 Å, 10 µM; Daiso Co., Ltd.). Buffer conditions that can be used to equilibrate the C18 column before loading ApoA-I and to insure that the protein will bind to the column upon loading will be readily ascertainable to those of skill in the art. Preferably, the column equilibration buffer is a strong buffer that can reduce the column pH to about 9.5. In certain embodiments, the equilibration buffer is TAMP E (100 mM ammonium carbonate). In various embodiments, the reverse phase column used in step (e) of the purification methods described herein has a bed height of from about 10 cm to about 50 cm, such as from about 10 cm to about 30 cm. In particular embodiments, the reverse phase column used in step (e) has a bed height of about 25 cm.

In various embodiments, the ApoA-I eluate from step (d) is loaded onto the C18 reverse phase column at a concentration of about 0.5 g to about 30 g ApoA-I, such as at a concentration of about 1 g to about 10 g of ApoA-I, and more preferably at a concentration of about 4 g to about 5 g of ApoA-I per liter. In particular embodiments, the ApoA-I eluate from step (d) is loaded onto the C18 column at a concentration of about 4.7 g of ApoA-I per liter. Preferably, after equilibration, ApoA-I containing eluate from step (d) is loaded onto the column at a flow rate of from about 0.5 cm to about 5.0 cm per minute, such as from about 1.0 cm to about 3.0 cm per minute. In a particular embodiment, the ApoA-I containing filtrate is loaded onto the column at a flow rate of about 2.1 cm per minute.

After ApoA-I is bound to the reverse phase matrix in step (e), the protein is eluted in step (f) using a gradient of increasing concentrations of organic solvent in buffer, such as from about 40% to about 50% acetonitrile in TAMP E buffer. In some aspects, a linear gradient of from about 40% to about 50% acetonitrile is used to elute the ApoA-I from the column over a period of about 40 to about 80 minutes, such as about 50 minutes, about 60 minutes or about 70 minutes. In particular embodiments, a linear gradient of from about 40% to about 50% acetonitrile in TAMP E buffer over a period of about 60 minutes is used to elute the ApoA-I from the reverse phase matrix. In certain aspects, the linear gradient is followed by about 15 minutes of isocratic elution with 50% acetonitrile. The exact conditions for eluting ApoA-I from the reverse phase column will be readily ascertainable to the skilled artisan. In various embodiments, about 60%, such as about 65%, about 70%, about 75% or about 80% or more of ApoA-I in the column load is recovered in the column eluate in step (f).

In certain embodiments, the organic solvent is removed from the ApoA-I containing eluate obtained in step (f) of the methods described herein. Solvent removal can be accomplished by any method known in the art, including, but not limited to, concentrating the ApoA-I containing eluate obtained in step (f) and diafiltering the concentrate into an aqueous buffer. In certain embodiments, the eluate from step (f) is concentrated by about 2-fold, by about 2.5-fold, by about 3-fold, by about 3.5-fold, by about 4-fold, by about 4.5-fold or by about 5-fold as compared to the volume of eluate from the reverse phase column in step (f). In a particular embodiment, the eluate is concentrated by about 2.5-fold and is then diafiltered against approximately 10, 15, or 20, preferably 15 volumes of a suitable aqueous buffer. Suitable aqueous buffers are known in the art. A particularly preferred buffer is TAMP C (3 mM sodium phosphate, pH 8.0).

In some embodiments the order of chromatography columns is reversed.

Optionally, after concentration and buffer exchange, the aqueous ApoA-I solution is further purified by anion exchange chromatography in negative mode (i.e., under conditions where the ApoA-I does not bind to the anion exchange matrix) to remove residual DNA and other negatively charged contaminants such as host cell proteins. (Step (g)). In some embodiments, the anion exchange step is performed in batch mode. In other embodiments, the anion exchange step is performed by column chromatography. Suitable anion exchange matrices for use in batch mode or in column chromatography include, but are not limited to, Q Sepharose-FF or any of the anion exchange matrices discussed above for use in step (a). In particular aspects, the anion exchange step is performed by passing the ApoA-I solution through an anion exchange membrane, such as a membrane having a large surface-area and a strong cationic charge, e.g., Sartobind Q or Mustang Q. Preferably, the anion exchange step is performed using a Mustang Q anion exchange membrane (Pall Life Sciences). In certain aspects, the pH of the aqueous ApoA-I solution is reduced to about 5.5, to about 6.0 or to about 6.5 before this anion exchange step using any suitable acid. In particular aspects, the pH of the aqueous ApoA-I solution is reduced to about 6.0 using dilute phosphoric acid. In preferred embodiments, the ApoA-I solution is passed through a Mustang Q cartridge at approximately 12.5 L/m2/h.

In some embodiments, the anion exchange membrane filtrate is concentrated and optionally dialfiltered to exchange the solvent to one that is suitable for storage or for further processing of the ApoA-I, such as complexing with lipids as described below in Section 6.5.1 and/or formulation in pharmaceutical compositions as described below in Section 6.6. Suitable buffers for storage or further processing of ApoA-I are readily ascertainable to the skilled artisan. In particular embodiments, the purified ApoA-I is exchanged into TAMP C buffer. Any ultrafiltration membrane can be used in this step, provided that the membrane has a molecular weight cutoff that is below the molecular weight of full-length mature ApoA-I such that it allows the passage of buffer but not protein. In particular embodiments, a polyethersulphone membrane (e.g., Filtron Omega series) of 10,000 nominal molecular weight cut-off is used. Preferably, the ApoA-I concentration in the solution after ultrafiltration is at least 10 g/L, at least 12 g/L, at least 15 g/L, at least 20 g/L, at least 25 g/L, at least 30 g/L, at least 35 g/L, at least 40 g/L, at least 45 g/L or at least 50 g/L.

6.1.5. Apolipoprotein Products

The present disclosure also provides substantially pure mature full-length apolipoproteins. As used herein, the term "substantially pure" refers to a protein that is at least 95% pure. In certain embodiments, the substantially pure protein is at least 96%, at least 97%, at least 98%, at least 99%, at least 99.5%, at least 99.9% or 100% pure. In certain aspects, the substantially pure apolipoprotein product produced by the purification methods described herein is a clear to slightly opalescent colorless solution free of visible particles when visually inspected using a light source against a white background. In various embodiments, substantially pure apolipoprotein obtained or obtainable by the methods described in Section 6.1.4 above, comprises low or undetectable amounts of one or more of host cell DNA, proteins other than the apolipoprotein (e.g., host cell proteins), endotoxin, residual solvent, as well as low bioburden (i.e., low number of microbes on or in the sample), as described in further detail below. The purity of the apolipoprotein product can be determined by any method known in the art, including, but not limited to, N-terminal Edman sequencing, MALDI-MS, gel electrophoresis, HPLC, and/or immunoassay.

In various embodiments, the substantially pure apolipoprotein product obtained by the methods described herein is full-length mature human ApoA-I having a mass that is about 28.1 kilodaltons. The mass of ApoA-I in the product can be determined by any method known in the art, including, but not limited to, MALDI-MS. In various embodiments, at least 75%, at least 80%, at least 85%, at least 90%, at least 91%, at least 92%, at least 93%, at least 94%, at least 95%, at least 96%, at least 97%, at least 98%, or at least 99% of the ApoA-I protein in the product is mature full-length ApoA-I (e.g., ApoA-I comprising amino acids 25 to 267 of SEQ ID NO: 1). In certain aspects, the substantially pure ApoA-I product comprises about 15% or less, about 10% or less, about 5% or less, about 4% or less, about 3% or less, about 2% or less or about 1% or less by weight of N-terminally extended ApoA-I isoforms (e.g., proApoA-I). As will be appreciated by the skilled artisan, any N-terminally extended ApoA-I in the product will be rapidly converted to mature ApoA-I in the blood upon administration. In various embodiments, the ApoA-I product comprises about 25% or less, about 20% or less, about 15% or less, about 10% or less, about 5% or less, about 4% or less, about 3% or less, about 2% or less, about 1% or less, about 0.75% or less, about 0.5% or less, about 0.25% or less, or about 0.1% or less by weight of truncated forms of ApoA-I. The amount of truncated or extended ApoA-I can be determined, for example, by N-terminal Edman sequencing and/or MALDI-MS and/or by running and scanning an SDS-PAGE gel to determine the ratio of the intensity of the purified ApoA-I band area to the total intensity of all bands, if present. In various embodiments, the ApoA-I product comprises about 20% or less, about 10% or less, about 5% or less, about 4% or less, about 3% or less, about 2% or less, about 1% or less, about 0.75% or less, about 0.5% or less, about 0.25% or less, or about 0.1% or less by weight of oxidized forms of ApoA-I, in particular ApoA-I oxidized at position $Met_{112}$ and/or $Met_{148}$.

In certain embodiments, the substantially pure apolipoprotein produced by the methods described herein comprises host cell proteins in an amount that is less than about 100 ppm (e.g., ng/mg), such as less than about 75 ppm, less than about 50 ppm, less than about 40 ppm, less than about 30 ppm, less than about 20 ppm, or less than about 10 ppm. In particular embodiments, the substantially pure apolipoprotein product comprises less than about 20 ppm of host cell proteins. More preferably, the apolipoprotein product comprises less than about 10 ppm of host cell proteins. The presence and amount of host cell proteins in an apolipoprotein sample can be determined by any method known in the art. When apolipoprotein is produced recombinantly in, e.g., mammalian cells, commercially available ELISA kits (e.g., Kit F015 from Cygnus Technologies) can be used to detect and quantitate levels of host cell proteins.

In some aspects, the substantially pure apolipoprotein product purified as described herein comprises host cell DNA in an amount that is less than about 50 pg/mg of apolipoprotein, such as less than about 40 pg/mg, less than about 30 pg/mg, less than about 20 pg/mg, less than about 10 pg/mg, or less than about 5 pg/mg of apolipoprotein. In preferred embodiments, the substantially pure apolipoprotein product comprises less than about 10 pg of host cell proteins per mg of apolipoprotein. The presence and amount of host cell DNA in an apolipoprotein sample can be determined by any method known in the art, including real time-PCR or detection of complexes with single stranded binding protein using an anti-SSB antibody (Glycotype Biotechnology), preferably by quantitative PCR.

In certain embodiments, the substantially pure apolipoprotein product produced by the methods described herein comprises endotoxin in an amount that is less than about 0.5 EU per mg of apolipoprotein, such as less than about 0.4 EU per mg, less than about 0.3 EU per mg, less than about 0.2 EU per mg or less than about 0.1 EU per mg of apolipoprotein. Preferably, the substantially pure apolipoprotein product described herein comprises less than about 0.1 EU of endotoxin per mg of apolipoprotein. Detection and quantitation of endotoxin can be achieved by any method known in the art, for example using the Limulus Amebocyte Lysate (LAL) qualitative test for gram-negative bacterial endotoxins. (Cambrex; sensitivity 0.125 EU/mL).

The substantially pure apolipoprotein product described herein has a low bioburden. The term "bioburden" refers to the level of aerobic bacteria, anaerobic bacteria, yeast and molds in the product. In various embodiments, the bioburden of the substantially pure apolipoprotein product purified as described herein is less than about 1 CFU per mL. Bioburden testing can be performed according to any known method, for example according to the European Pharmacopoeia Chapter 2.6.12.B, 2.6.1 and USB Chapter 61 harmonized method.

The substantially pure apolipoprotein product described herein comprises low amounts of residual solvents. In particular embodiments, residual solvent is present in an amount that is less than about 50 ppm, less than about 45 ppm, less than about 40 ppm, less than about 35 ppm, less than about 30 ppm, less than about 25 ppm, less than about 20 ppm, less than about 15 ppm or less than about 10 ppm for 10 mg/L of apolipoprotein. Preferably, residual solvent is present at an amount that is less than about 41 ppm for 10 mg/L of apolipoprotein. The amount of residual solvent can be assayed by any method known in the art, including, but not limited to, GC-MS and HPLC.

Preferably, the apolipoprotein is ApoA-I (e.g., ApoA-I comprising amino acids 25-267 of SEQ ID NO: 1). In some embodiments, the mature human ApoA-I protein has an amino acid sequence having an aspartic acid at position 1 (i.e., the position corresponding to position 25 of SEQ ID NO:1).

6.2. The Lipid Fraction

The lipoprotein complexes and compositions of the present disclosure comprise a lipid fraction. The lipid fraction includes one or more lipids. In various embodiments, one or more lipids can be saturated and/or unsaturated, and natural or synthetic lipids. The lipid fraction preferably includes at least one phospholipid.

Suitable lipids that can be present in the lipid fraction include, but are not limited to, small alkyl chain phospholipids, egg phosphatidylcholine, soybean phosphatidylcholine, dipalmitoylphosphatidylcholine, dimyristoylphosphatidylcholinc, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, palmitoylsphingomyelin, dipalmitoylsphingomyelin, egg sphingomyelin, milk sphingomyelin, phytosphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. Synthetic lipids, such as synthetic palmitoylsphingomyelin or N-palmitoyl-4-hydroxysphinganine-1-phosphocholine (a form of phytosphingomyelin) can be used to minimize lipid oxidation. Phospholipid fractions including palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives.

In preferred embodiments, the lipid fraction includes two types of phospholipids: a sphingomyelin (SM) and a negatively charged phospholipid. SM is a "neutral" phospholipid in that it has a net charge of about zero at physiological pH. The identity of the SM used is not critical for success. Thus, as used herein, the expression "SM" includes sphingomyelins derived or obtained from natural sources, as well as analogs and derivatives of naturally occurring SMs that are impervious to hydrolysis by LCAT, as is naturally occurring SM. SM is a phospholipid very similar in structure to lecithin, but, unlike lecithin, it does not have a glycerol backbone, and hence does not have ester linkages attaching the acyl chains. Rather, SM has a ceramide backbone, with amide linkages connecting the acyl chains. SM is not a substrate for LCAT, and generally cannot be hydrolyzed by it. It can act, however, as an inhibitor of LCAT or can decrease LCAT activity by diluting the concentration of the substrate phospholipid. Because SM is not hydrolyzed, it remains in the circulation longer. It is expected that this feature will permit the negatively charged lipoprotein complexes described herein to have a longer duration of pharmacological effect (mobilization of cholesterol) and to pick up more lipids, in particular cholesterol, than apolipoprotein complexes that do not include SM. This effect may result in less frequent or smaller doses being necessary for treatment than are required for lipoprotein complexes that do not include SM.

The SM may be obtained from virtually any source. For example, the SM may be obtained from milk, egg or brain. SM analogues or derivatives may also be used. Non-limiting examples of useful SM analogues and derivatives include, but are not limited to, palmitoylsphingomyelin, N-palmitoyl-4-hydroxysphinganine-1-phosphocholine (a form of phytosphingomyelin), palmitoylsphingomyelin, stearoylsphingomyelin, D-erythro-N-16:0-sphingomyelin and its dihydro isomer, D-erythro-N-16:0-dihydro-sphingomyelin. Synthetic SM such as synthetic palmitoylsphingomyelin or N-palmitoyl-4-hydroxysphinganine-1-phosphocholine (phytosphingomyelin) can be used in order to produce more homogeneous complexes and with fewer contaminants and/or oxidation products than sphingolipids of animal origin.

Exemplary sphingomyelins palmitoylsphingomyelin and phytosphingomyelin are shown below.

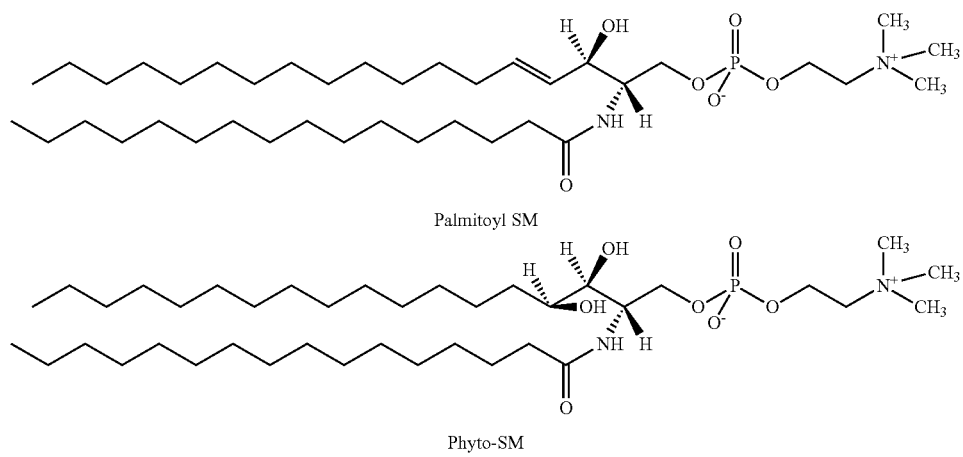

Palmitoyl SM

Phyto-SM

Sphingomyelins isolated from natural sources may be artificially enriched in one particular saturated or unsaturated acyl chain. For example, milk sphingomyelin (Avanti Phospholipid, Alabaster, Ala.) is characterized by long saturated acyl chains (i.e., acyl chains having 20 or more carbon atoms). In contrast, egg sphingomyelin is characterized by short saturated acyl chains (i.e., acyl chains having fewer than 20 carbon atoms). For example, whereas only about 20% of milk sphingomyelin comprises C16:0 (16 carbon, saturated) acyl chains, about 80% of egg sphingomyelin comprises C16:0 acyl chains. Using solvent extraction, the composition of milk sphingomyelin can be enriched to have an acyl chain composition comparable to that of egg sphingomyelin, or vice versa.

The SM may be semi-synthetic such that it has particular acyl chains. For example, milk sphingomyelin can be first purified from milk, then one particular acyl chain, e.g., the C16:0 acyl chain, can be cleaved and replaced by another acyl chain. The SM can also be entirely synthesized, by e.g., large-scale synthesis. See, e.g., Dong et al., U.S. Pat. No. 5,220,043, entitled Synthesis of D-erythro-sphingomyelins, issued Jun. 15, 1993; Weis, 1999, Chem. Phys. Lipids 102 (1-2):3-12.

The lengths and saturation levels of the acyl chains comprising a semi-synthetic or a synthetic SM can be selectively varied. The acyl chains can be saturated or unsaturated, and can contain from about 6 to about 24 carbon atoms. Each chain may contain the same number of carbon atoms or, alternatively each chain may contain different numbers of carbon atoms. In some embodiments, the semi-synthetic or synthetic SM comprises mixed acyl chains such that one chain is saturated and one chain is unsaturated. In such mixed acyl chain SMs, the chain lengths can be the same or different. In other embodiments, the acyl chains of the semi-synthetic or synthetic SM are either both saturated or both unsaturated. Again, the chains may contain the same or different numbers of carbon atoms. In some embodiments, both acyl chains comprising the semi-synthetic or synthetic SM are identical. In a specific embodiment, the chains correspond to the acyl chains of a naturally-occurring fatty acid, such as for example oleic, palmitic or stearic acid. In another embodiment, SM with saturated or unsaturated functionalized chains is used. In another specific embodiment, both acyl chains are saturated and contain from 6 to 24 carbon atoms. Non-limiting examples of acyl chains present in commonly occurring fatty acids that can be included in semi-synthetic and synthetic SMs are provided in Table 1, below:

TABLE 1

| Length:Number of Unsaturations | Common Name |
|---|---|
| 14:0 | myristic acid |
| 16:0 | palmitic acid |
| 18:0 | stearic acid |
| 18:1 cis$\Delta^9$ | oleic acid |
| 18:2 cis$\Delta^{9, 12}$ | linoleic acid |
| 18:3 cis$\Delta^{9, 12, 15}$ | linonenic acid |
| 20:4 cis$\Delta^{5, 8, 11, 14}$ | arachidonic acid |
| 20:5 cis$\Delta^{5, 8, 11, 14, 17}$ | eicosapentaenoic acid (an omega-3 fatty acid) |

In preferred embodiments, the SM is palmitoyl SM, such as synthetic palmitoyl SM, which has C16:0 acyl chains, or is egg SM, which includes as a principal component palmitoyl SM.

In a specific embodiment, functionalized SM, such as a phytosphingomyelin, is used.

The lipid fraction preferably includes a negatively charged phospholipid. As used herein, "negatively charged phospholipids" are phospholipids that have a net negative charge at physiological pH. The negatively charged phospholipid may comprise a single type of negatively charged phospholipid, or a mixture of two or more different, negatively charged, phospholipids. In some embodiments, the charged phospholipids are negatively charged glycerophospholipids. The identity(ies) of the charged phospholipids(s) are not critical for success. Specific examples of suitable negatively charged phospholipids include, but are not limited to, a 1,2-dipalmitoyl-sn-glycero-3-[phospho-rac-(1-glycerol)], a phosphatidylglycerol, a phospatidylinositol, a phosphatidylserine, and a phosphatidic acid. In some embodiments, the negatively charged phospholipid comprises one or more of phosphatidylinositol, phosphatidylserine, phosphatidylglycerol and/or phosphatidic acid. In a specific embodiment, the negatively charged phospholipid consists of 1,2-dipalmitoyl-sn-glycero-3-[phospho-rac-(1-glycerol)], or DPPG.

Like the SM, the negatively charged phospholipids can be obtained from natural sources or prepared by chemical synthesis. In embodiments employing synthetic negatively charged phospholipids, the identities of the acyl chains can be selectively varied, as discussed above in connection with SM. In some embodiments of the negatively charged lipoprotein complexes described herein, both acyl chains on the negatively charged phospholipids are identical. In some embodiments, the acyl chains on the SM and the negatively charged phospholipids are all identical. In a specific embodiment, the negatively charged phospholipid(s), and/or SM all have C16:0 or C16:1 acyl chains. In a specific embodiment the fatty acid moiety of the SM is predominantly C16:1 palmitoyl. In one specific embodiment, the acyl chains of the charged phospholipid(s) and/or SM correspond to the acyl chain of palmitic acid.

The phospholipids used are preferably at least 95% pure, and/or have reduced levels of oxidative agents. Lipids obtained from natural sources preferably have fewer polyunsaturated fatty acid moieties and/or fatty acid moieties that are not susceptible to oxidation. The level of oxidation in a sample can be determined using an iodometric method, which provides a peroxide value, expressed in milli-equivalent number of isolated iodines per kg of sample, abbreviated meq O/kg. See, e.g., Gray, J. I., Measurement of Lipid Oxidation: A Review, Journal of the American Oil Chemists Society, Vol. 55, p. 539-545 (1978); Heaton, F. W. and Uri N., Improved Iodometric Methods for the Determination of Lipid Peroxides, Journal of the Science of food and Agriculture, vol 9. P, 781-786 (1958). Preferably, the level of oxidation, or peroxide level, is low, e.g., less than 5 meq O/kg, less than 4 meq O/kg, less than 3 meq O/kg, or less than 2 meq O/kg.

Lipid fractions including SM and palmitoylsphingomyelin can optionally include small quantities of additional lipids. Virtually any type of lipids may be used, including, but not limited to, lysophospholipids, galactocerebroside, gangliosides, cerebrosides, glycerides, triglycerides, and cholesterol and its derivatives.

When included, such optional lipids will typically comprise less than about 15 wt % of the lipid fraction, although in some instances more optional lipids could be included. In some embodiments, the optional lipids comprise less than about 10 wt %, less than about 5 wt %, or less than about 2 wt %. In some embodiments, the lipid fraction does not include optional lipids.

In a specific embodiment, the phospholipid fraction contains egg SM or palmitoyl SM or phytosphingomyelin and DPPG in a weight ratio (SM:negatively charged phospholipid) ranging from 90:10 to 99:1, more preferably ranging from 95:5 to 98:2. In one embodiment, the weight ratio is 97:3.

The lipoprotein complexes of the present disclosure can also be used as carriers to deliver hydrophobic, lipophilic or apolar active agents for a variety of therapeutic or diagnostic applications. For such applications, the lipid fraction can further include one or more hydrophobic, lipophilic or apolar active agents, including but not limited to fatty acids, drugs, nucleic acids, vitamins, and/or nutrients. Suitable hydrophobic, lipophilic or apolar active agents are not limited by therapeutic category, and can be, for example, analgesics, anti-inflammatory agents, antihelmimthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarial, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, nucleic acids (e.g., small interfering RNAs), opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable hydrophobic, lipophilic, or apolar active agents are: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritonavir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Salts, isomers and derivatives of the above-listed agents may also be used, as well as mixtures.

6.3. Lipoprotein Complexes

The present disclosure provides lipoprotein complexes comprising a protein fraction and a lipid fraction, the composition of each of which has been described above in Sections 6.1 and 6.2, respectively.

Generally, the protein fraction includes one or more lipid-binding protein, such as an apolipoprotein and/or derivative or analog thereof that provides therapeutic and/or prophylactic benefit. The complexes can include a single type of lipid-binding protein, or mixtures of two or more different lipid-binding proteins, which can be derived from the same or different species. Suitable lipid-binding proteins are described above in Section 6.1. Although not required, the lipoprotein complexes will preferably comprise lipid-binding proteins that are derived from, or correspond in amino acid sequence to, the animal species being treated, in order to avoid inducing an immune response to the therapy. Thus, for treatment of human patients, lipid-binding proteins of human origin are preferably used in the complexes of the disclosure. The use of peptide mimetic apolipoproteins can also reduce or avoid an immune response.

The use of apolipoprotein that has a high degree of purity (e.g., mature and not truncated, oxidized, deamidated, contaminated with endotoxin and/or contaminated with other proteins or with nucleic acids) is thought to enhance the therapeutic potency and/or enhance safety of lipoprotein complex. Accordingly, the protein fraction can comprise at least 75%, at least 80%, at least 85%, at least 90%, at least 95%, at least 96%, at least 97%, at least 98%, at least 99% mature, full-length ApoA-I, optionally, having no more than 25%, no more than 20%, no more than 15%, no more than 10%, no more than 5%, or about 0% oxidized methionine-112 or methionine-148, and/or no more than 15%, no more than 10%, no more than 5%, or about 0% deaminated amino acids. The apolipoprotein can be purified according to any of the methods described herein. Preferably, the apolipoprotein can be made as described in Section 6.1.4.

In a specific embodiment, the protein fraction comprises or consists essentially of ApoA-I, for example, substantially pure mature, full-length ApoA-I, as described above in Section 6.1.5.

The lipid fraction includes one or more lipids, which can be saturated, unsaturated, natural and synthetic lipids and/or phospholipids. Suitable lipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, egg sphingomyelin, milk sphingomyelin, phytosphingomyelin, palmitoylsphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. Phospholipid fractions including SM and palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives. Synthetic lipids are preferred, such as synthetic palmitoyl sphingomyelin or N-palmitoyl-4-hydroxysphinganine-1-phosphocholine (phytosphingomyelin). Further lipids are described above in Section 6.2. Preferably, lipoprotein complexes comprise sphingomyelin.

Optionally, the lipoprotein complexes of the present disclosure can be loaded with hydrophobic, lipophilic or apolar active agents, including but not limited to fatty acids, drugs, nucleic acids, vitamins, and/or nutrients, for a variety of therapeutic or diagnostic applications. Suitable agents are described above in Section 6.2.

The lipoprotein complexes can be made using any of the methods described herein. Preferably, the complexes are made as described in Sections 6.5.1 to 6.5.4.

The molar ratio of the lipid fraction to the protein fraction of the negatively charged lipoprotein complexes described herein can vary, and will depend upon, among other factors, the identity(ies) of the apolipoprotein comprising the protein fraction, the identities and quantities of the charged phospholipids comprising the lipid fraction, and the desired size of the charged lipoprotein complex. Because the biological activity of apolipoproteins such as ApoA-I are thought to be mediated by the amphipathic helices comprising the apolipoprotein, it is convenient to express the apolipoprotein fraction of the lipid:apolipoprotein molar ratio using ApoA-I protein equivalents. It is generally accepted that ApoA-I contains 6-10 amphipathic helices, depending upon the method used to calculate the helices. Other apolipoproteins can be expressed in terms of ApoA-I equivalents based upon the number of amphipathic helices they contain. For example, ApoA-$I_M$, which typically exists as a disulfide-bridged dimer, can be expressed as 2 ApoA-I equivalents, because each molecule of ApoA-$I_M$ contains twice as many amphipathic helices as a molecule of ApoA-I. Conversely, a peptide apolipoprotein that contains a single amphipathic helix can be expressed as a 1/10-1/6 ApoA-I equivalent, because each molecule contains 1/10-1/6 as many amphipathic helices as a molecule of ApoA-I. In general, the lipid:ApoA-I equivalent molar ratio of the lipoprotein complexes (defined herein as "Ri") will range from about 105:1 to 110:1. In some embodiments, the Ri is about 108:1. Ratios in weight can be obtained using a MW of approximately 650-800 for phospholipids.

In some embodiments, the molar ratio of lipid:ApoA-I equivalents ("RSM") ranges from about 80:1 to about 110:1, e.g., about 80:1 to about 100:1. In a specific example, the RSM for lipoprotein complexes can be about 82:1.

The various apolipoprotein and/or phospholipids molecules comprising the negatively charged lipoprotein complexes may be labeled with any art-known detectable marker, including stable isotopes (e.g., $^{13}C$, $^{15}N$, $^{2}H$, etc.); radioactive isotopes (e.g., $^{14}C$, $^{3}H$, $^{125}I$, etc.); fluorophores; chemiluminescers; or enzymatic markers.

In preferred embodiments, the lipoprotein complexes are negatively charged lipoprotein complexes which comprise a protein fraction which is preferably mature, full-length ApoA-I, and a lipid fraction comprising a neutral phospholipid, sphingomyelin (SM), and negatively charged phospholipid.

It has been discovered that composition and relative quantities of SM and negatively charged phospholipid comprising the lipid fraction of lipoprotein complexes affect the homogeneity and stability of compositions comprising the complexes. As illustrated in the Examples section, compositions comprising complexes in which the lipid fraction is composed of SM and negatively charged phospholipid are more homogeneous, and more stable than similar compositions in which the lipid fraction includes DPPC in addition to SM.

Thus, complexes of the present disclosure that contain SM and negatively charged lipid are preferably formed in the absence of a lecithin in order to improve their homogeneity and stability. Once homogeneous complexes containing SM and negatively charged lipids are formed, additional lipids such as lecithin can be incorporated.

When included, optional lipids will typically comprise less than about 15% of the lipid fraction, although in some instances more optional lipids could be included. In some embodiments, the optional lipids comprise than about 10%, less than about 5%, or less than about 2% wt %. In some embodiments, the lipid fraction of the negatively charged lipoprotein complexes does not include optional lipids.

In a specific embodiment, the phospholipid fraction contains eggSM or palmitoyl SM or phytoSM and DPPG in a weight ratio (SM:negatively charged phospholipid) ranging from 90:10 to 99:1, more preferably ranging from 95:5 to 98:2, e.g., 97:3.

Some apolipoproteins exchange in vivo from one lipoprotein complex to another (this is true for apolipoprotein ApoA-I). During the course of such exchange, the apolipoprotein typically carries with it one or more phospholipid molecules. Owing to this property, it is expected that the negatively charged lipoprotein complexes described herein will "seed" negatively charged phospholipids to endogenous HDL, thereby transforming them into alpha particles that are more resistant to elimination by the kidneys. Thus, it is expected that administration of the negatively charged lipoprotein complexes and compositions described herein will increase serum levels of HDL, and/or alter endogenous HDL half-life as well as endogenous HDL metabolism. It is expected that this will result in alteration of cholesterol metabolism and reverse lipid transport.

As illustrated in the Examples section, compositions comprising complexes in which the weight ratio of ApoA-I:SM and DPPG phospholipid is about 1:2.7 were more homogeneous and more stable than similar compositions with other weight:weight ratios. Accordingly, the present disclosure provides lipoprotein compositions in which the protein:lipid weight ratio is optimized for formation of a homogeneous population of complexes. This weight:weight ratio ranges from 1:2.6 to 1:3, and is optimally 1:2.7, for complexes of ApoA-I, SM, and DPPG, and for complexes of components of similar molecular mass. In specific embodiments, the ratio of ApoA-I protein fraction to lipid fraction typically ranges from about 1:2.7 to about 1:3, with 1:2.7 being preferred. This corresponds to molar ratios of ApoA-I protein to phospholipid ranging from approximately 1:90 to 1:140. Accordingly, the present disclosure provides complexes in which the molar ratio protein to lipid is about 1:90 to about 1:120, about 1:100 to about 1:140, or about 1:95 to about 1:125. Specifically at this optimized ratio, the ApoA-I protein fraction and the SM and DPPG lipid fraction form substantially homogeneous complexes with the same size and charge characteristics, as assayed by column chromatography and gel electrophoresis, respectively, as natural HDL.

The size of the negatively charged lipoprotein complex can be controlled by varying the Ri. That is, the smaller the Ri, the smaller the disk. For example, large discoidal disks will typically have an Ri in the range of about 200:1 to 100:1, whereas small discoidal disks will typically have an Ri in the range of about 100:1 to 30:1.

In some specific embodiments, the negatively charged lipoprotein complexes are large discoidal disks that contain 2-4 ApoA-I equivalents (e.g., 2-4 molecules of ApoA-I, 1-2 molecules of ApoA-I$_M$ dimer or 12-40 single helix peptide molecules), 1 molecule of negatively charged phospholipid and 400 molecules of SM. In other specific embodiments, the negatively charged lipoprotein complexes are small discoidal disks that contain 2-4 ApoA-I equivalents; 1-10, more preferably 3-6, molecule of negatively charged phospholipid; and 90-225 molecules, more preferably 100-210 molecules, of SM.

6.3.1. Measurement of Complexes and Particle Size

The composition of lipoprotein complexes, as well as their size and that of lipid particles used in the preparation of the lipoprotein complexes, can be determined using a variety of techniques known in the art.

Protein and lipid concentration of lipoprotein complexes in solution can be measured by any method known in the art, including, but not limited to, protein and phospholipid assays, chromatographic methods such as HPLC, gel filtration, GC coupled with various detectors including mass spectrometry, UV or diode-array, fluorescent, elastic light scattering and others. The integrity of lipid and proteins can be also determined by the same chromatographic techniques as well as by peptide mapping, SDS-page gel electrophoresis, N- and C-terminal sequencing of ApoA-I, and standard assays for determining lipid oxidation.

The lipoprotein complex as well as lipid particles used in the preparation of the lipoprotein complexes, can range in size as described herein. Lipid particle size and/or lipid and protein complex size can be determined using methods known in the art. Exemplary methods include dynamic light scattering and gel permeation chromatography.

Dynamic light scattering (DLS), also known as photon correlation spectroscopy, measures and the shift in wavelength of a light beam hitting a particle moving in solution by Brownian motion. Specifically, the moving particles scatter light when illuminated by a laser and the resulting intensity fluctuations in the scattered light can be used to calculate the sphere size distribution in the solution. See, Zetasizer Nano Series User Manual, MAN0317 Issue 2.1 (July 2004). DLS determines the intensity distribution and average of the particles in solution, based on which particle volume and number distribution and average can be calculated. The DLS technique can be used to determine the size of lipid particles used to make lipoprotein complexes, as well as the size of the lipoprotein complexes themselves. A suitable DLS instrument is the Zetasizer Nano by Malvern Instruments.

Gel permeation chromatography (GPC) can also be used to determine the size of protein-containing complexes. Gel permeation chromatography separates components in a mixture based on molecular size. The size of a lipid-protein complex can be determined by comparing the elution profile of the complex to that of known standards or reference samples, typically by comparison to a calibration curve. Reference samples are available commercially and can include both protein and non-protein standards, such as albumin, ferritin, and vitamin $B_{12}$. Current Protocols in Molecular Biology (1998), Section IV, 10.9.1-10.9.2.

Lipid particles useful in the preparation of the lipoprotein complexes of the disclosure can be at least 45 nm, at least 50 nm, at least 55 nm, at least 60 nm in size, as measured by DLS (e.g., using intensity based measured). Furthermore, lipid particle can be up to 65 nm, up to 70 nm, up to 80 nm, up to 90 nm, up to 100 nm, up to 120 nm, up to 150 nm, up to 200 nm, up to 250 nm, up to 300 nm, or up to 500 nm in size, as measured by DLS.

The lipoprotein complexes of the disclosure can range in size from 4 nm to 15 nm, 6 nm to 15 nm, 4 nm to 12 nm, 5 to 12 nm, 6 nm to 12 nm, 8 nm to 12 nm, or 8 nm to 10 nm as measured by the techniques described herein.

6.4. Populations of Lipoprotein Complexes

The present disclosure further provides populations of the lipoprotein complexes described herein. The populations comprise a plurality of lipoprotein complexes as described herein, each comprising a protein fraction and a lipid fraction, e.g. as described above in Section 6.3. Applicants have discovered several features that are thought to contribute individually or in combination to the potency and the safety profile of populations of lipoprotein complexes. Populations of lipoprotein complexes can incorporate any number of the features, described herein alone or in combination.

First, the homogeneity of the lipoprotein complexes in a population, i.e., the prevalence of one or more discrete lipoprotein complex(es) in the population, as indicated by the one or more discrete peaks of lipoprotein complexes in a population, and the prevalence in lipoprotein complexes of mature, unmodified apolipoprotein, are thought to increase potency. Accordingly, the population of lipoprotein complexes can comprise a protein fraction comprising or consisting essentially of an apolipoprotein, e.g., ApoA-I, and a lipid fraction, where the population is at least 80%, at least 85%, at least 90%, at least 95%, at least 96%, at least 97%, at least 98%, or at least 99% homogeneous as measured by the percent of the population in a single peak in gel permeation chromatography.

In some embodiments, lipoprotein complex size in a population can range between 4 nm and 15 nm, e.g., between 5 nm and 12 nm, between 6 nm and 15 nm, or between 8 nm and 10 nm.

The apolipoprotein, e.g., ApoA-I, in the population can be mature, preferably full length (untruncated) ApoA-I, and the population can contain at least 75%, at least 80%, at least 85%, at least 90%, at least 95%, at least 96%, at least 97%, at least 98%, at least 99% by weight mature, preferably full length (untruncated) ApoA-I. In some embodiments, the population includes no more than 25%, no more than 20%, no more than 15%, no more than 10%, or no more than 5% by weight of immature or incompletely processed ApoA-I and/or no more than 20%, no more than 15%, no more than 10%, or no more than 5% by weight of truncated ApoA-I.

Second, the purity of apolipoprotein and lipids in the complexes and the relative absence of contaminants in the lipoprotein complexes, also referred to as the purity of the lipoprotein complexes, is thought to reduce the risk of side effects such as liver damage, reflected by increases in liver enzymes (e.g., transaminase). The purity of apolipoprotein can be measured by the relative lack of oxidation and/or deamidation. Accordingly, in certain embodiments, populations of lipoprotein complexes can have reduced amounts of oxidized apolipoprotein, such as no more than 20%, no more than 15%, no more than 10%, no more than 5%, no more than 4%, no more than 3%, no more than 2%, no more than 1% oxidized methionine, especially methionine-112 or methionine-148, or no more than 15%, no more than 10%, no more than 5%, no more than 4%, no more than 3%, no more than 2%, or no more than 1% oxidized tryptophan. Populations of lipoprotein complexes can also have a reduced percentage of deamidated amino acids, for example no more than 15%, no more than 10%, no more than 5%, no more than 4%, no more than 3%, no more than 2%, or no more than 1% deamidated amino acids.

It is also desirable to control the purity of the lipids in the lipoprotein complex. Accordingly, in some embodiments, no more than 5%, no more than 4%, no more than 3%, no more than 2% or no more than 1% of the lipid in said population is oxidized.

Another measure of the purity of the complexes and populations thereof is a reduction in, or absence of, contaminants that result from the methods of producing or purifying the apolipoprotein or the methods of making the lipoprotein complexes themselves. Accordingly, where the apolipoprotein is purified from host cells, for example mammalian host cells, the populations of lipoprotein complexes are preferably free of host cell DNA or proteins. In specific embodiments, the population contains no more than 500 nanograms, no more than 200 nanograms, no more than 100 nanograms, no more than 50 nanograms, or no more than 20 nanograms host cell protein per milligram of the lipoprotein, and/or no more than 100 picograms, no more than 50 picograms, no more than 25 picograms, no more than 10 picograms or no more than 5 picograms host cell DNA per milligram of the lipoprotein, typically ApoA-I.

Other contaminants that can occur and are to be avoided are endotoxin, which can be present, inter alia, in cell cultures and in plasma samples, and solvents and detergents, which can be present depending on the process used to make and/or purify the lipoprotein complex. Populations of lipoprotein complexes can contain at most about 1 EU, about 0.5 EU, about 0.3 EU, or about 0.1 EU of endotoxin per milligram lipoprotein, e.g. ApoA-I. Populations of lipoprotein complexes can also be limited to containing no more than 200 ppm, 250 ppm, 100 ppm or a non-aqueous solvent. In a specific embodiment, the population does not contain any detergent, e.g., cholate.

Additionally, using the methods disclosed herein, it is possible to incorporate most of the apolipoprotein starting material into complexes, limiting the amount of uncomplexed apolipoprotein present in a population. The reduction in the amount of uncomplexes apolipoprotein is beneficial in that it reduces the risk of an immunogenic response due to exposure to a heterologous protein. The population of lipoprotein complexes can be in a composition in which at least 80%, at least 85%, at least 90%, at least 95%, at least 97%, at least 98%, at least 99% or 100% of the protein is in the lipoprotein complex, i.e., the complexed form. Optionally, the population of lipoprotein complexes can be in a composition in which at least 80%, at least 85%, at least 90%, at least 95%, at least 97%, at least 98%, at least 99% or 100% of the lipid is in the lipoprotein complex.

Optionally, the population can comprise complexes in which the lipid fraction comprises no more than 15%, no more than 10%, no more than 5%, no more than 4%, no more than 3%, no more than 2%, no more than 1%, or 0% cholesterol by weight of lipid.

Certain lipid and protein components can form a plurality of different but homogeneous lipoprotein complexes. Accordingly, the present disclosure also provides compositions comprising two, three, or four populations of lipoprotein complexes comprising different amounts of apolipoprotein molecules (e.g., two, three or four ApoA-I molecules or ApoA-I equivalents). In an exemplary embodiment, a composition comprises two lipoprotein complex populations, a first population comprising lipoprotein complexes having 2 ApoA-I molecules or ApoA-I equivalents per lipoprotein complex, a second population comprising lipoprotein complexes having 3 or 4 ApoA-I molecules or ApoA-I equivalents per lipoprotein complex and optionally a third population comprising lipoprotein complexes having 4 or 3 ApoA-I molecules or ApoA-I equivalents per lipoproprotein complex, respectively.

The compositions comprising two or more populations of lipoprotein complexes preferably have low levels of uncomplexed lipoprotein and/or lipid. Accordingly, preferably no more than 15%, no more than 12%, than 10%, no more than 9%, no more than 8%, no more than 7%, no more than 6%, no more than 5%, no more than 4%, no more than 3%, no more than 2%, or no more than 1% of the lipid in the composition is in uncomplexed form and/or no more than 15%, no more than 12%, no more than 10%, no more than 9%, no more than 8%, no more than 7%, no more than 6%, no more than 5%, no more than 4%, no more than 3%, no more than 2%, or no more than 1% of the lipoprotein in the composition is in uncomplexed form.

Also provided herein are large-scale preparations of lipoprotein complexes, or populations thereof, that are particularly useful for commercial applications, such as large scale manufacturing of lipoprotein complexes for therapeutic purposes. The preparations contemplated herein comprise a population of lipoprotein complexes, e.g., negatively charged lipoprotein complexes, as described herein.

The preparations are provided in volumes, amounts and resulting concentration of lipoprotein complexes suitable for the manufacturing of compositions, e.g., pharmaceutical compositions and dosage forms, on a commercial scale. Typical preparation volumes range from about 5 L to about 50 L, or more, for example, about 10 L to about 40 L, about 15 L to about 35 L, about 15 L to about 30 L, about 20 L to about 40 L, about 20 L to about 30 L, about 25 L to about 45 L, about 25 L to about 35 L. Preparations can have a volumne of about 5 L, about 6 L, about 7 L, about 8 L, about 9 L, about 10 L, about 11 L, about 12 L, about 13 L, about 14 L, about 15 L, about 16 L, about 17 L, about 18 L, about 19 L, about 20 L, about 25 L, about 30 L, about 35 L, about 40 L, about 45 L, or about 50 L. In a preferred embodiment, the preparation has a volume of about 20 L.

Preparations further contain lipoprotein complexes, or a population thereof, in amounts sufficient to achieve a concentration of apolipoprotein ranging from about 5 mg/mL up to about 15 mg/mL, from 5 mg/mL to about 10 mg/mL, from about 10 mg/mL to about 15 mg/mL, or about 8 mg/mL to about 12 mg/mL of apolipoprotein. Depending on the volume of the preparation, amounts can range from about 25 g up to about 350 g, expressed as the amount of apolipoprotein, e.g., ApoA-I, in the preparation. In a specific embodiment, the preparation contains about 8 mg/mL of ApoA-I.

In a specific embodiment, the preparation has a volume of 15 L to 25 L and contains about 100 g to about 250 g of ApoA-I. In another specific embodiment, the preparation has a volume of 30 L to 50 L and contains about 240 g to about 780 g of ApoA-I.

6.5. Methods of Making Lipoprotein Complexes

6.5.1. Thermal Cycling Based Methods of Making Lipoprotein Complexes

It has been discovered that methods using thermal cycling of protein and lipid components as described herein can be used to generate lipoprotein complexes with advantages over other methodologies. In the thermal cycling methods provided herein, a protein component and a lipid component, that are subjected to thermal cycling until the majority of the protein component (e.g., at least 60%, at least 70%, at least 80%, or at least 90%) is complexed with the lipid component, forming a lipoprotein complex. As will be appreciated by skilled artisans, the advantages of the present methods over other methods for production of lipoprotein complexes include a high complexing efficiency resulting in a substantially homogeneous and pure end product, without few to no byproducts (e.g., uncomplexed protein) or manufacturing impurities (e.g., detergents or surfactants, degraded proteins, oxidized components) present in the resulting product, circumventing the need for costly and wasteful purification steps. Thus, the methods are efficient and result in little-to-no wastage of starting materials. Furthermore, the processes are easy to scale up and have a low equipment cost. The ability to conduct these processes without industrial solvents makes them environmentally friendly also.

Preferably, to minimize oxidation of the protein and lipid components, one, more than one or all steps of complex formation (including homogenization of the lipid component) are carried out under an inert gas (e.g., nitrogen, argon or helium) blanket.

6.5.2. The Lipid Component

The thermal cycling methods of the disclosure can utilize a variety of lipids, alone or in combination, including saturated, unsaturated, natural and synthetic lipids and/or phospholipids, as described above in Section 6.2.

The lipids can be prepared for thermal cycling with the protein component using any method that generates lipid particles, such as multilamellar vesicles ("MLVs"), small unilamellar vesicles ("SUVs"), large unilamellar vesicles ("LUVs"), micelles, dispersions and the like.

A range of technologies is known for producing lipid particles. Lipid particles have been produced using a variety of protocols, forming different types of vesicles. It is preferred that the particles used in the thermal cycling methods of the disclosure are predominantly in the 45-80 nm size range, most preferably in the 55 nm to 75 nm size range.

High pressure homogenization, for example microfluidization, advantageously produces particles of suitable sizes. The homogenization pressure is preferably at least 1,000 bars, at least 1,200 bars, at least 1,400 bars, at least 1,600 bars, at least 1,800 bars, and is most preferably at least 2,000 bars, for example at least 2,200 bars, at least 2,400 bars, at least 2,600 bars, at least 2,800 bars, at least 3,000 bars, at least 3,200 bars, at least 3,400 bars, at least 3,600 bars, at least 3,800 bars, or at least 4,000 bars. In specific embodiments, the homogenization pressure is in a range between any pair of the foregoing values, e.g., 1,600 to 3,200 bars; 1,800 to 2,800 bars; 1,900 to 2,500 bars; 2,000 to 2,500 bars; 2,000 to 3,000 bars; 2,400 to 3,800 bars; 2,800 to 3,400 bars; and so on and so forth. One bar equals 100 kPa, 1,000,000 dynes per square centimeter (baryes), 0.987 atm (atmospheres), 14.5038 psi, 29.53 inHg and 750.06 torr.

In one suitable homogenization method, an emulsion of the lipids is transferred into the feed vessel of a Microfluidizer Model 110Y (Microfluidics Inc, Newton, Mass.). The unit is immersed in a bath to maintain the process temperature (e.g., 55° C., 58° C., 62° C., etc.) during homogenization, and is flushed with an inert gas such as argon before use. After priming, the emulsion is passed through the homogenizer in continuous re-cycle for 5-20 minutes at a pressure gradient across the interaction head. Homogenization of the lipid component in the absence of the protein component avoids the destruction of the protein component by high shear used in homogenization techniques.

Other methods can suitably be used, provided that particles of a suitable size can be obtained. For example, hydration of lipids by aqueous solution can result in the dispersion of lipids and spontaneous formation of multimellar vesicles ("MLVs"). An MLV is a particle with multiple lipid bilayers surrounding the central aqueous core. These types of particles are larger than small unilamellar vesicles (SUVS) and may be 350-400 nm in diameter. MLVs can be prepared by solubilizing lipids in chloroform in a round-bottom flask and evaporating the chloroform until the lipid formed a thin layer on the wall of the flask. The aqueous solution is added and the lipid layer is allowed to rehydrate. Vesicles formed as the flask is swirled or vortexed. Deamer et al., 1983, in Liposomes (Ostro, Ed.), Marcel Dekker, Inc. New York (citing Bangham et al., 1965, J. Mol. Biol. 13:238). This method can also be used to generate single lamellar vesicles. Johnson et al., 1971, Biochim. Biophys. Acta 233:820.

A small unilamellar vesicle (SUV) is a particle with a single lipid bilayer enclosing an aqueous core. Depending on the method employed to generate the SUVS, they can range in size from 25-110 nm in diameter. The first SUVs were prepared by drying a phospholipid preparation in chloroform under nitrogen, adding the aqueous layer to produce a lipid concentration in the millimolar range, and sonicating the solution at 45° C. to clarity. Deamer et al., 1983, in Liposomes (Ostro, Ed.), Marcel Dekker, Inc. New York. SUVs prepared in this fashion yield particles in the range of 25-50 nm in diameter.

Another method of making SUVs is rapidly injecting an ethanol/lipid solution into the aqueous solution to be encapsulated. Deamer et al., 1983, in Liposomes (Ostro, Ed.), Marcel Dekker, Inc. New York (citing Batzri et al., 1973, Biochim. Biophys. Acta 298:1015). SUVs produced by this method range in size from 30-110 nm in diameter.

SUVs can also be produced by passing multilamellar vesicles through a French Press four times at 20,000 psi. The SUVs produced will range in size from 30-50 nm in diameter. Deamer et al., 1983, in Liposomes (Ostro, Ed.), Marcel Dekker, Inc. New York (citing Barenholz et al., 1979, FEBS Letters 99:210).

Multilamellar and unilamellar phospholipid vesicles can also be formed by extrusion of aqueous preparations of phospholipids at high pressure through small-pore membranes (Hope et al., 1996, Chemistry and Physics of Lipids, 40:89-107)

Large unilamellar vesicles are similar to SUVs in that they are single lipid bilayers surrounding the central aqueous core, but LUVs are much larger that SUVs. Depending on their constituent parts and the method used to prepare them, LUVs can range in size from 50-1000 nm in diameter. Deamer et al., 1983, in Liposomes (Ostro, Ed.), Marcel Dekker, Inc. New York. LUVs are usually prepared using one of three methods: detergent dilution, reverse-phase evaporation, and infusion.

In the detergent dilution technique, detergent solutions such as cholate, deoxycholate, octyl glucoside, heptyl glucoside and Triton X-100 are used to form micelles from the lipid preparation. The solution is then dialyzed to remove the detergent. Deamer et al., 1983, in Liposomes (Ostro, Ed.), Marcel Dekker, Inc. New York.

The reverse-phase evaporation technique solubilizes lipid in aqueous-nonpolar solutions, forming inverted micelles. The nonpolar solvent is evaporated and the micelles aggregate to form LUVs. This method generally requires a great deal of lipid.

The infusion method injects a lipid solubilized in a non-polar solution into the aqueous solution to be encapsulated. As the nonpolar solution evaporates, lipids collect on the gas/aqueous interface. The lipid sheets form LUVs and oligolamellar particles as the gas bubbles through the aqueous solution. Particles are sized by filtration. Deamer et al., 1983, in Liposomes (Ostro, Ed.), Marcel Dekker, Inc. New York (citing Deamer et al., 1976, Biochim. Biophys. Acta 443:629 and Schieren et al., 1978, Biochim. Biophys. Acta 542:137).

An aliquot of the resulting lipid preparation can be characterized to confirm that the lipid particles are suitable for use as the lipid component in the thermocyling methods disclosed herein. Characterization of the lipid preparation can be performed using any method known in the art, including, but not limited to, size exclusion filtration, gel filtration, column filtration, gel permeation chromatography, and non-denaturating gel electrophoresis.

6.5.3. The Protein Component

The protein component of the lipoprotein complexes is not critical for success in the present thermal cycling methods. Virtually any lipid-binding protein, such as an apolipoprotein and/or derivative or analog thereof that provides therapeutic and/or prophylactic benefit can be included in the complexes. Moreover, any alpha-helical peptide or peptide analog, or any other type of molecule that "mimics" the activity of an apolipoprotein (such as, for example ApoA-I) in that it can activate LCAT or form discoidal particles when associated with lipids, can be included in the lipoprotein complexes, and is therefore included within the definition of "lipid-binding protein." The lipid-binding proteins that can be used in the thermal cycling methods include those in described in Section 6.1 above. The lipid-binding proteins can be recombinantly produced as described in Section 6.1.2 above. The lipid-binding proteins can be purified by any of the methods described herein, including as described in Section 6.1.3 or Section 6.1.4 above.

The protein component can be purified from animal sources (and in particular from human sources), chemically synthesized or produced recombinantly as is well-known in the art, see, e.g., Chung et al., 1980, J. Lipid Res. 21(3): 284-91; Cheung et al., 1987, J. Lipid Res. 28(8):913-29. See also U.S. Pat. Nos. 5,059,528, 5,128,318, 6,617,134; U.S. Publication Nos. 20002/0156007, 2004/0067873, 2004/0077541, and 2004/0266660; and PCT Publications Nos. WO/2008/104890 and WO/2007/023476.

The protein component can include lipids in protein/peptide to lipid ratio that is at least 5-fold greater (e.g., at least 5-fold, at least 10-fold or at least 20-fold greater) than the protein/peptide to lipid ratio in the desired complex. For example, to produce a lipoprotein complex in which the desired protein to lipid ratio is 1:200 on a molar basis, the protein in the protein component can be combined with a lipid, typically one that will represent only a small fraction of the lipid in the final complex, e.g., in a ratio of 1:10 to 1:20. Without implying any mechanism, this "pre-" complexing of the protein to a small amount of lipid is useful when the desired complex has more than one type of lipid, allowing more homogeneous distribution of a lipid that is present in small quantities in the lipoprotein complex produced by thermal cycling (e.g., 10% or less by weight of total lipid, 5% or less by weight of total lipid, 3% or less by weight of total lipid, 2% or less by weight of total lipid, or 1% or less by weight of total lipid in the desired lipoprotein complex).

6.5.4. Generating Lipoprotein Complexes by Thermal Cycling

The methods generally entail thermally cycling a suspension comprising lipid particles and lipid binding proteins between a "high" temperature range and a "low" temperature range until lipoprotein complexes are formed.

The suspension that is thermally cycled is contains a lipid component and a protein component that are brought together, preferably at a temperature in the high temperature range, to form a "starting" suspension that is then subject to thermal cycling.

The optimum ratio of lipids and proteins in the starting suspension is determined by the desired stoichiometry of the components in the ultimate lipoprotein complexes to be produced. As will be recognized by skilled artisans, the molar ratio of the lipid fraction to the protein fraction will depend upon, among other factors, the identity(ies) of the proteins and/or peptides in the protein component, the identities and quantities of the lipids in the lipid fraction, and the desired size of the lipoprotein complex. Suitable lipid to protein ratios in the lipoprotein complexes can be determined using any number of functional assays known in the art, including, but not limited to, gel electrophoresis mobility assay, size exclusion chromatography, interaction with HDL receptors, recognition by ATP-binding cassette transporter (ABCA1), uptake by the liver, and pharmacokinetics/pharmacodynamics. For example, gel electrophoresis mobility assays can be used to determine the optimum ratio of lipid component to protein component in the complexes. Where the complexes produced by the methods of the disclosure are charged, as a result of inclusion of phospholipids in the lipid component, the complexes can be designed to exhibit an electrophoretic mobility that is similar to natural pre-beta-HDL or alpha-HDL particles. Thus, in some embodiments, natural pre-beta-HDL or alpha-HDL particles can be used as standard for determining the mobility of the complexes.

In a preferred embodiment, the ultimate complex has at least one apolipoprotein or apoliprotein mimic (most preferably mature human ApoA-I or ApoA-I peptide, respectively), at least one neutral lipid, and at least one negatively charged lipid, such as those described in PCT WO2006/100567, the contents of which are incorporated by reference herein.

Because the biological activity of apolipoproteins such as ApoA-I are thought to be mediated by the amphipathic helices comprising the apolipoprotein, it is convenient to express the apolipoprotein fraction of the lipid:apolipoprotein molar ratio using ApoA-I protein equivalents. It is generally accepted that ApoA-I contains 6-10 amphipathic helices, depending upon the method used to calculate the helices. Other apolipoproteins can be expressed in terms of ApoA-I equivalents based upon the number of amphipathic helices they contain. For example, ApoA-$I_M$, which typically exists as a disulfide bridged dimer, can be expressed as 2 ApoA-I equivalents, because each molecule of ApoA-$I_M$ contains twice as many amphipathic helices as a molecule of ApoA-I. Conversely, a peptide apolipoprotein that contains a single amphipathic helix can be expressed as a 1/10 to 1/6 ApoA-I equivalent, because each molecule contains 1/10 to 1/6 as many amphipathic helices as a molecule of ApoA-I.

In general, the lipid:ApoA-I equivalent molar ratio of the lipoprotein complexes (defined herein as "Ri") will range from about 2:1 to 200:1. In some embodiments, the Ri is about from 50:1 to 150:1, or from 75:1 to 125:1, from 10:1 to 175:1. Ratios in weight can be obtained using a MW of approximately 650-800 for phospholipids.

In certain embodiments, the molar ratio of the components is 2-6 (negatively charged lipid, e.g., DPPG): 90-120 (neutral lipid, e.g., SM): 1 (ApoA-I equivalents). In a specific embodiment, described in Example 1, the complex comprises DPPG, SM and ApoA-I in a lipid to protein molar ratio of approximately 108:1, with DPPG representing 3% (+/−1%) of the total lipid by weight and SM representing 97% (+/−5%) of the lipid by weight.

The concentration of the lipid and protein components in the starting suspension prior to the initiation of thermocycling can range from 1 to 30 mg/ml concentration of ApoA-I equivalents and from 1 to 100 mg/ml concentrations of lipid. In specific embodiments, the concentration of the protein component is selected from 1 to 30 mg/ml, 2 to 20 mg/ml, from 5 to 20 mg/ml, from 2 to 10 mg/ml, from 5 to 15 mg/ml, from 5 to 20 mg/ml, and from 10 to 20 mg/ml, and the concentration of the lipid component is independently selected from 10 to 100 mg/ml, from 10 to 75 mg/ml, from 25 to 50 mg/ml, from 10 to 75 mg/ml, from 25 to 100 mg/ml, from 25 to 75 mg/ml, and from 1 to 75 mg/ml.

The high and low temperature ranges of the thermocycling process are based on the phase transition temperatures of the lipid and protein components of the lipoprotein complexes. Alternatively, where the lipid component does not exhibit a defined or discrete phase transition, as could occur when using phospholipids having unsaturated fatty acid chains or a mixture of phospholipids, the high and low temperature ranges of the thermocycling differ by at least about 20° C., up to about 40° C. or even more. For example, in some embodiments, the low and high temperature ranges differ by 20° C.-30° C., 20° C.-40° C., 20° C.-50° C., 30° C.-40° C., 30° C.-50° C., 25° C.-45° C., 35° C.-55° C.

For a lipid, the phase transition involves a change from a closely packed, ordered structure, known as the gel state, to a loosely packed, less-ordered structure, known as the fluid state. Lipoprotein complexes are typically formed in the art by incubating lipid particles and apolipoproteins at temperatures near the transition temperature of the particular lipid or mixture of lipids used. The phase transition temperature of the lipid component (which can be determined by calorimetry) +/−5° C.-10° C. represents the "low" temperature range in the methods of the disclosure.

For a protein, the phase transition temperature involves a change from the folded three dimensional structure into a two-dimensional structure. For a lipid, the phase transition involves a change from a closely packed, ordered structure, known as the gel state, to a loosely packed, less-ordered structure, known as the fluid state. Lipoprotein complexes are typically formed in the art by incubating lipid particles and apolipoproteins at temperatures near the transition temperature of the particular lipid or mixture of lipids used.

The phase transition temperature of the lipid component (which can be determined by calorimetry) +/−12° C., more preferably +/−10° C., represents the "low" temperature range in the methods of the disclosure. In certain embodiments, the low temperature range is +/−3° C., +/−5° C., or +/−8° C. of the phase transition temperature of the lipid component. In one specific embodiment, the low temperature range is from no less than 5° C. or no less than 10° C. below to 5° C. above the phase transition temperature of the lipid component.

For a protein, the phase transition temperature involves a change from the tertiary structure into the secondary structure. The phase transition temperature of the protein component +/−12° C., more preferably +/−10° C., represents the "high" temperature range in the methods of the disclosure. In specific embodiments, the high temperature range is +/−3° C., +/−5° C., or +/−8° C. of the phase transition temperature of the protein component. In one specific embodiment, the low temperature range is from 10° C. below to no more than 5° C., no more than 10° C., or no more than 15° C. above the phase transition temperature of the protein component.

The starting suspension is subjected to thermal cycling between the high temperature and the low temperature, preferably starting at the high temperature, until at least 70%, at least 80%, at least 90%, at least 95%, at least 96%, at least 97%, at least 98% or at least 99% of the protein in the starting suspension is incorporated into lipoprotein complexes. Using suitable stoichiometric quantities of lipid and protein components, substantially complete complexation of the lipid and protein components can be reached after several cycles. The number of cycles will depend on the protein and lipid components, the duration of the cycles, but typically 5 or more cycles, 10 or more cycles, or 15 or more cycles (at both the high and low temperatures) will be required for substantially complete complexation. The cycles typically range from 2 minutes to 60 minutes. In specific embodiments, the cycles range from 5 to 30 minutes, from 10 to 20 minutes, from 5 to 20 minutes, from 2 to 45 minutes, or from 5 to 45 minutes at each temperature.

The complexes produced by the methods are typically supramolecular assemblies shaped as micelles, vesicles, spherical or discoidal particles in which the protein component is physically bound to phospholipids at a specific stoichiometric range between the phospholipid and protein and with a homogeneous size distribution. The present methods advantageously result in substantially complete complexation of the lipids and/or proteins in the starting suspension, resulting in a composition that is substantially free lipids and/or free protein, as observed by separation methods such as chromatography. Thus, the methods of the disclosure can be performed in the absence of a purification step.

The methods of the disclosure advantageously produce complexes that are homogenous in their size distribution, circumventing the need for size fractionation.

In some embodiments of the disclosure, the lipoprotein complexes will contain more than one type of lipid, including one or more lipids in relatively small quantities (e.g., less than 10%, less than 5%, less than 3% or less than 1% of the lipid component). To optimize dispersion, lipids used in small quantities can be pre-blended with the protein component rather than incorporated into the lipid particles in the lipid component.

An aliquot of the resulting lipoprotein complexes can be characterized to confirm that the complexes possess the desired characteristics, e.g., substantially complete (e.g., >90%, >95%, >97% or >98%) incorporation of the protein component into the lipid component. Characterization of the complexes can be performed using any method known in the art, including, but not limited to, size exclusion filtration, gel filtration, column filtration, gel permeation chromatography, and non-denaturing gel electrophoresis.

The homogeneity and/or stability of the lipoprotein complexes or composition described herein can be measured by any method known in the art, including, but not limited to, chromatographic methods such as gel filtration chromatography. For example, in some embodiments a single peak or a limited number of peaks can be associated with a stable complex. The stability of the complexes can be determined by monitoring the appearance of new of peaks over time. The appearance of new peaks is a sign of reorganization among the complexes due to the instability of the particles.

Preferably, to minimize oxidation of the protein and lipid components, the thermocycling is carried out under an inert gas (e.g., nitrogen, argon or helium) blanket.

6.5.5. Other Methods of Making Lipoprotein Complexes

The lipoprotein complexes described herein, including negatively charged lipoprotein complexes, can be prepared in a variety of forms, including, but not limited to vesicles, liposomes, proteoliposomes, micelles, and discoidal particles. In addition to the thermal cycling methods described above, a variety of methods known to those skilled in the art can be used to prepare the lipoprotein complexes. Various techniques for preparing liposomes or proteoliposomes may be used. For example, apolipoprotein can be co-sonicated (using an ultrasonic bath or ultrasonic probe) with the appropriate phospholipids to form complexes. Alternatively, apolipoprotein, e.g., ApoA-I, can be combined with pre-formed lipid vesicles resulting in the spontaneous formation of lipoprotein complexes. The lipoprotein complexes can also be formed by a detergent dialysis method; e.g., a mixture of apolipoprotein, charged phospholipid(s), and SM and a detergent such as cholate is dialyzed to remove the detergent and reconstituted to form negatively charged lipoprotein complexes (see, e.g., Jonas et al., 1986, Methods in Enzymol. 128:553-82), or by using an extruder device or by homogenization.

In some embodiments, complexes are prepared by homogenization using high pressure (e.g., about 32000 p.s.i.) for about 40, about 50, or about 60 minutes. In a specific embodiment, a complex comprising ApoA-I, SN, and DPPG is prepared as follows. ApoA-I is dissolved in phosphate buffer and incubated at 50° C. with a dispersion of DPPG in phosphate buffer made using a high shear mixer. The ApoA-I/DPPG mixture is then combined with a dispersion of SM, and homogenized at pressures over 30,000 p.s.i. at 30-50° C. until complex formation is substantially complete, as monitored by dynamic light scattering or gel permeation chromatography.

In some embodiments, lipoprotein complexes can be prepared by the cholate dispersion method described in Example 1 of U.S. publication 2004/0067873, the disclosure of which is incorporated herein by reference. Briefly, dry lipid is hydrated in $NaHCO_3$ buffer, then vortexed and sonicated until all lipid is dispersed. Cholate solution is added, the mixture is incubated for 30 minutes, with periodic vortexing and sonicating, until it turns clear, indicating that the lipid cholate micelles are formed. ProApoA-I in $NaHCO_3$ buffer is added, and the solution incubated for 1 hour at approximately 37° C.-50° C.

Cholate can be removed by methods well known in the art. For example cholate can be removed by dialysis, ultrafiltration or by removal of cholate molecules by adsorption absorption onto an affinity bead or resin. In one embodiment, the affinity beads, e.g., BIO-BEADS® (Bio-Rad Laboratories) are added to the preparation of negatively charged lipoprotein complexes and cholate to adsorb the cholate. In another embodiment, the preparation, e.g., a micellar preparation of the lipoprotein complexes and cholate, is passed over a column packed with affinity beads.

In a specific embodiment, cholate is removed from a preparation of lipoprotein complexes by loading the preparation onto BIO-BEADS® within a syringe. The syringe is then sealed with barrier film and incubated with rocking at 4° C. overnight. Before use, the cholate is removed by injecting the solution through BIO-BEADS®, where it is adsorbed by the beads.

The lipoprotein complexes, such as negatively charged lipoprotein complexes described herein, are expected to have an increased half-life in the circulation when the complexes have a similar size and density to HDL, especially to the HDLs in the pre-beta-1 or pre-beta-2 HDL populations. Stable preparations having a long shelf life may be made by lyophilization. In some embodiments, co-lyophilization methods commonly known in the art are used to prepare ApoA-I-lipid complexes. Briefly, the co-lyophilization steps include either solubilizing a mixture of ApoA-I and lipid in organic solvent or solvent mixture, or solubilizing ApoA-I and lipid separately and mixing them together. Desirable characteristics of solvents or solvent mixtures for co-lyophilization include: (i) a medium relative polarity to be able to dissolve hydrophobic lipids and amphipathic protein, (ii) class 2 or class 3 solvents according to FDA solvent guidelines (Federal Register, volume 62, No. 247) to avoid potential toxicity associated with residual organic solvent, (iii) low boiling point to assure ease of solvent removal during lyophilization, (iv) high melting point to provide for faster freezing, higher temperatures of condensation and less wear and tear on the freeze-dryer. In some embodiments, glacial acetic acid is used. Combinations of methanol, glacial acetic acid, xylene, or cyclohexane can also be used.

The ApoA-I-lipid solution is then lyophilized to obtain a homogeneous powder. The lyophilization conditions can be optimized to obtain fast evaporation of solvent with minimal amount of residual solvent in the lyophilized apolipoprotein-lipid powder. The selection of freeze-drying conditions can be determined by the skilled artisan, depending on the nature of solvent, type and dimensions of the receptacle, holding solution, fill volume, and characteristics of the freeze-dryer used.

The lyophilized lipoprotein complexes can be used to prepare bulk supplies for pharmaceutical reformulation, or to prepare individual aliquots or dosage units that can be reconstituted to obtain a solution or suspension of lipoprotein complexes. For reconstitution, the lyophilized powder is rehydrated with an aqueous solution to a suitable volume (e.g., 5 mg polypeptide/ml, which is convenient for intravenous injection). In some embodiments, the lyophilized powder is rehydrated with phosphate buffered saline or a physiological saline solution. The mixture can be agitated or vortexed to facilitate rehydration. The reconstitution step can be performed at a temperature equal to or greater than the phase transition temperature of the lipid component of the complexes.

The ApoA-I-lipid complexes can form spontaneously after hydration of lyophilized apolipoprotein-lipid powder with an aqueous medium of appropriate pH and osmolality. In some embodiments, the hydration medium contains stabilizers selected from, but not limited to, sucrose, trehalose and glycerin. In some embodiments, the solution is heated several times above the transition temperature of the lipids in order for complexes to form. The ratio of lipid to protein can be from 1:1 to 200:1 (mole/mole), and is preferably 3:1 to 2:1 lipid:protein (w/w), more preferably 2.7:1 to 2.1:1 lipid:protein (w/w), e.g., 2.7:1 lipid:protein (w/w). The powder is hydrated to obtain a final complex concentration of 5-30 mg/ml expressed in protein equivalents.

In various embodiments, ApoA-I powder can be obtained by freeze-drying the polypeptide solution in $NH_4HCO_3$ aqueous solution. A homogeneous solution of ApoA-I and lipid (e.g., sphingomyelin) is then formed by dissolving the lipid powder and the ApoA-I powder in glacial acetic acid. The solution is then lyophilized, and HDL-like apolipoprotein-lipid complexes are formed by hydration of the resulting powder in an aqueous medium.

In some embodiments, ApoA-I-lipid complexes are formed by co-lyophilization of phospholipid and protein solutions or suspensions. A homogeneous solution of ApoA-I and lipid (e.g., phospholipids) in an organic solvent or organic solvent mixture is lyophilized, and ApoA-I-lipid complexes are subsequently formed spontaneously by hydration of the lyophilized powder in an aqueous buffer. Examples of organic solvents and solvent mixtures for use in this method include, but are not limited to, acetic acid, an acetic acid/xylene mixture, an acetic acid/cyclohexane mixture, and a methanol/xylene mixture.

An aliquot of the resulting reconstituted preparations can be characterized to confirm that the complexes have the desired size distribution; e.g., the size distribution of HDL. An exemplary method for characterizing the size is gel filtration chromatography. A series of proteins of known molecular weight and Stokes' diameter, as well as human HDL, can be used as standards to calibrate the column.

In other embodiments, recombinant ApoA-I-lipid complexes are made by complexing ApoA-I with the lipids disclosed in U.S. patent publication no. 2006/0217312 and international publication no. WO 2006/100567 (PCT/IB2006/000635), the disclosures of which are incorporated herein by reference.

U.S. Pat. Nos. 6,004,925, 6,037,323, 6,046,166 and 6,287,590 (incorporated herein by reference in their entireties) disclose a simple method for preparing negatively charged lipoprotein complexes that have characteristics similar to HDL. This method, which involves co-lyophilization of apolipoprotein and lipid solutions in organic solvent (or solvent mixtures) and formation of negatively charged lipoprotein complexes during hydration of the lyophilized powder, has the following advantages: (1) the method requires very few steps; (2) the method uses inexpensive solvent(s); (3) most or all of the included ingredients are used to form the designed complexes, thus avoiding waste of starting material that is common to the other methods; (4) lyophilized complexes are formed that are very stable during storage such that the resulting complexes may be reconstituted immediately before use; (5) the resulting complexes usually need not be further purified after formation and before use; (6) toxic compounds, including detergents such as cholate, are avoided; and (7) the production method can be easily scaled up and is suitable for GMP manufacture (i.e., in an endotoxin-free environment).

Other suitable methods are described in US published application no. 2006/0217312 and international publication WO 2006/100567 (PCT/IB 2006/000635), the disclosure of each of which is incorporated herein by reference.

Preferably, to minimize oxidation of the protein and lipid components, one, more than one or all steps of complex formation are carried out under an inert gas (e.g., nitrogen, argon or helium) blanket.

Protein and lipid concentration of apolipoprotein-lipid particles in solution can be measured by any method known in the art, including, but not limited to, protein and phospholipid assays, chromatographic methods such as HPLC, gel filtration, GC coupled with various detectors including mass spectrometry, UV or diode-array, fluorescent, elastic light scattering and others. The integrity of lipid and proteins can be also determined by the same chromatographic techniques as well as by peptide mapping, SDS-page gel electrophoresis, N- and C-terminal sequencing of ApoA-I, and standard assays for determining lipid oxidation.

6.6. Pharmaceutical Compositions

The pharmaceutical compositions contemplated by the disclosure comprise negatively charged lipoprotein complexes as the active ingredient in a pharmaceutically acceptable carrier suitable for administration and delivery in vivo. Since peptides may comprise acidic and/or basic termini and/or side chains, peptide mimetic apolipoproteins can be included in the compositions in either the form of free acids or bases, or in the form of pharmaceutically acceptable salts. Modified proteins such as amidated, acylated, acetylated or pegylated proteins, may also be used. Optionally, the pharmaceutical compositions can comprise lipoprotein complexes loaded with one or more hydrophobic, lipophilic, or apolar active agents, as described above in Sections 6.2 and 6.3.

Injectable compositions include sterile suspensions, solutions or emulsions of the active ingredient in aqueous or oily vehicles. The compositions can also comprise formulating agents, such as suspending, stabilizing and/or dispersing agent. In some embodiments, the injectable composition comprises negatively charged lipoprotein complexes in phosphate buffered saline (10 mM sodium phosphate, 80 mg/mL sucrose, pH 8.2). The compositions for injection can be presented in unit dosage form, e.g., in ampules or in multidose containers, and can comprise added preservatives. For infusion, a composition can be supplied in an infusion bag made of material compatible with negatively charged lipoprotein complexes, such as ethylene vinyl acetate or any other compatible material known in the art.

Suitable dosage forms comprise negatively charged lipoprotein complexes at a final concentration of about 5 mg/mL to about 15 mg/mL of lipoprotein. In a specific embodiment, the dosage form comprises negatively charged lipoprotein complexes at a final concentration of about 8 mg/mL to about 10 mg/mL Apolipoprotein A-I, preferably about 8 mg/mL.

Preferably, to minimize oxidation of the protein and lipid components, the pharmaceutical compositions are formulated and/or filled under an inert gas (e.g., nitrogen, argon or helium) blanket.

6.7. Methods of Treatment

The lipoprotein complexes, e.g., negatively charged lipoprotein complexes, and compositions described herein can be used for virtually every purpose lipoprotein complexes have been shown to be useful. Lipoprotein complexes, such as negatively charged lipoprotein complexes, are effective at mobilizing cholesterol, even when administered at doses significantly lower than the amounts of apolipoprotein (20 mg/kg to 100 mg/kg per administration every 2 to 5 days, 1.4 g to 8 g per average sized human) required by currently available treatment regimens.

Consequently, the complexes and compositions of the present disclosure are particularly useful to treat or prevent cardiovascular diseases, disorders, and/or associated conditions. Methods of treating or preventing a cardiovascular disease, disorder, and/or associated condition in a subject generally comprise administering to the subject a low (<15 mg/kg) dose or amount of a lipoprotein complex or pharmaceutical composition described herein according to a regimen effective to treat or prevent the particular indication.

Lipoprotein complexes are administered in an amount sufficient or effective to provide a therapeutic benefit. In the context of treating a cardiovascular disease, disorder, and/or associated condition, a therapeutic benefit can be inferred if one or more of the following occurs: an increase in cholesterol mobilization as compared to a baseline, a reduction in atherosclerotic plaque volume, an increase in high density lipoprotein (HDL) fraction of free cholesterol as compared to a baseline level, without an increase in mean plasma triglyceride concentration or an increase above normal range of liver transaminase (or alanine aminotransferase) levels. A complete cure, while desirable, is not required for therapeutic benefit to exist.

In some embodiments, the lipoprotein complex is administered at a dose of about 2 mg/kg ApoA-I equivalents to about 12 mg/kg ApoA-I equivalents per injection. In some embodiments, the lipoprotein complex is administered at a dose of about 3 mg/kg ApoA-I equivalents. In some embodiments, the lipoprotein complex is administered at a dose of about 6 mg/kg ApoA-I equivalents. In some embodiments, the lipoprotein complex is administered at a dose of about 12 mg/kg ApoA-I equivalents.

Subjects to be treated are individuals suffering from a preventing a cardiovascular disease, disorder, and/or associated condition. Non-limiting examples of such cardiovascular diseases, disorders and/or associated conditions that can be treated or prevented with the lipoprotein complexes and compositions described herein include, peripheral vascular disease, restenosis, atherosclerosis, and the myriad clinical manifestations of atherosclerosis, such as, for example, stroke, ischemic stroke, transient ischemic attack, myocardial infarction, acute coronary syndrome, angina pectoris, intermittent claudication, critical limb ischemia, valve stenosis, and atrial valve sclerosis. Subjects can be individuals with a prior incidence of acute coronary syndrome, such as a myocardial infarction (either with or without ST elevation) or unstable angina. The subject treated may be any animal, for example, a mammal, particularly a human.

In one embodiment, the methods encompass a method of treating or preventing a cardiovascular disease, comprising administering to a subject a charged lipoprotein complex or composition described herein in an amount that does not alter a patient's baseline ApoA-I following administration.

In other embodiments, the methods encompass a method of treating or preventing a cardiovascular disease, comprising administering to a subject a lipoprotein complex (e.g., a charged complex) or composition described herein in an amount that is effective to achieve a serum level of free or complexed apolipoprotein higher than a baseline (initial) level prior to administration by about 5 mg/dL to 100 mg/dL approximately to two hours after administration and/or by about 5 mg/dL to 20 mg/dL approximately 24 hours after administration.

In another embodiment, the methods encompass a method of treating or preventing a cardiovascular disease, comprising administering to a subject a lipoprotein complex (e.g., a charged complex) or composition described herein in an amount effective to achieve a circulating plasma concentrations of a HDL-cholesterol fraction for at least one day following administration that is at least about 10% higher than an initial HDL-cholesterol fraction prior to administration.

In another embodiment, the methods encompass a method of treating or preventing a cardiovascular disease, comprising administering to a subject a lipoprotein complex (e.g., a charged complex) or composition described herein in an amount effective to achieve a circulating plasma concentration of a HDL-cholesterol fraction that is between 30 and 300 mg/dL between 5 minutes and 1 day after administration.

In another embodiment, the methods encompass a method of treating or preventing a cardiovascular disease, comprising administering to a subject a lipoprotein complex (e.g., a charged complex) or composition described herein in an amount effective to achieve a circulating plasma concentration of cholesteryl esters that is between 30 and 300 mg/dL between 5 minutes and 1 day after administration.

In still another embodiment, the methods encompasses a method at treating or protecting a cardiovascular disease, comprising administering to a subject a lipoprotein complex (e.g., a charged complex) or composition described herein in an amount effective to achieve an increase in fecal cholesterol excretion for at least one day following administration that is at least about 10% above a baseline (initial) level prior to administration.

The lipoprotein complexes, including negatively charged lipoprotein complexes, or compositions described herein can be used alone or in combination therapy with other drugs used to treat or prevent the foregoing conditions. Such therapies include, but are not limited to simultaneous or sequential administration of the drugs involved. For example, in the treatment of hypercholesterolemia, such as familial hypercholesterolemia (homozygous or heterozygous) or atherosclerosis, charged lipoprotein formulations can be administered with any one or more of the cholesterol lowering therapies currently in use; e.g., bile-acid resins, niacin, statins, inhibitors of cholesterol absorption and/or fibrates. Such a combined regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the lipoprotein complexes, including negatively charged lipoprotein complexes, described herein affect RCT, increase HDL, and promote cholesterol efflux.

In another embodiment, the lipoprotein complexes, including negatively charged lipoprotein complexes, or compositions described herein may be used in conjunction with fibrates to treat or prevent coronary heart disease; coronary artery disease; cardiovascular disease, restenosis, vascular or perivascular diseases; atherosclerosis (including treatment and prevention of atherosclerosis); Exemplary formulations and treatment regimens are described below.

The lipoprotein complexes, including negatively charged lipoprotein complexes, or compositions described herein can be administered in dosages that increase the small HDL fraction, for example, the pre-beta, pre-gamma and pre-beta-like HDL fraction, the alpha HDL fraction, the HDL3 and/or the HDL2 fraction. In some embodiments, the dosages are effective to achieve atherosclerotic plaque reduction as measured by, for example, imaging techniques such as magnetic resonance imaging (MRI) or intravascular ultrasound (IVUS). Parameters to follow by IVUS include, but are not limited to, change in percent atheroma volume from baseline and change in total atheroma volume. Parameters to follow by MRI include, but are not limited to, those for IVUS and lipid composition and calcification of the plaque.

The plaque regression could be measured using the patient as its own control (time zero versus time t at the end of the last infusion, or within weeks after the last infusion, or within 3 months, 6 months, or 1 year after the start of therapy.

Administration can best be achieved by parenteral routes of administration, including intravenous (IV), intramuscular (IM), intradermal, subcutaneous (SC), and intraperitoneal (IP) injections. In certain embodiments, administration is by a perfusor, an infiltrator or a catheter. In some embodiments, the lipoprotein complexes, e.g., negatively charged lipoprotein complexes, are administered by injection, by a subcutaneously implantable pump or by a depot preparation, in amounts that achieve a circulating serum concentration equal to that obtained through parenteral administration. The complexes could also be absorbed in, for example, a stent or other device.

Administration can be achieved through a variety of different treatment regimens. For example, several intravenous injections can be administered periodically during a single day, with the cumulative total volume of the injections not reaching the daily toxic dose. The methods comprise administering the lipoprotein complex at an interval of 6, 7, 8, 9, 10, 11, or 12 days. In some embodiments, the lipoprotein complex is administered at an interval of a week.

The methods can further comprise administering the lipoprotein complex 4, 5, 6, 7, 8, 9, 10, 11, or 12 times at any of the intervals described above. For example, in one embodiment, the lipoprotein complex is administered six times, with an interval of 1 week between each administration. In some embodiments, administration could be done as a series of injections and then stopped for 6 months to 1 year, and then another series started. Maintenance series of injections could then be administered every year or every 3 to 5 years. The series of injections could be done over a day (perfusion to maintain a specified plasma level of complexes), several days (e.g., four injections over a period of eight days) or several weeks (e.g., four injections over a period of four weeks), and then restarted after six months to a year. For chronic conditions, administration could be carried out on an ongoing basis. Optionally, the methods can be preceded by an induction phase, when the lipoprotein complexes are administered more frequently.

In yet another alternative, an escalating dose can be administered, starting with about 1 to 5 doses at a dose between (50-200 mg) per administration, then followed by repeated doses of between 200 mg and 1 g per administration. Depending on the needs of the patient, administration can be by slow infusion with a duration of more than one hour, by rapid infusion of one hour or less, or by a single bolus injection.

Toxicity and therapeutic efficacy of the various lipoprotein complexes can be determined using standard pharmaceutical procedures in cell culture or experimental animals for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Lipoprotein complexes, such as negatively charged lipoprotein complexes, that exhibit large therapeutic indices are preferred. Non-limiting examples of parameters that can be followed include liver function transaminases (no more than 2× normal baseline levels). This is an indication that too much cholesterol is brought to the liver and cannot assimilate such an amount.

The effect on red blood cells could also be monitored, as mobilization of cholesterol from red blood cells causes them to become fragile, or affect their shape.

Patients can be treated from a few days to several weeks before a medical act (e.g., preventive treatment), or during or after a medical act. Administration can be concomitant to or contemporaneous with another invasive therapy, such as, angioplasty, carotid ablation, rotoblader or organ transplant (e.g., heart, kidney, liver, etc.).

In certain embodiments, negatively charged lipoprotein complexes are administered to a patient whose cholesterol synthesis is controlled by a statin or a cholesterol synthesis inhibitor. In other embodiments, negatively charged lipoprotein complexes are administered to a patient undergoing treatment with a binding resin, e.g., a semi-synthetic resin such as cholestyramine, or with a fiber, e.g., plant fiber, to trap bile salts and cholesterol, to increase bile acid excretion and lower blood cholesterol concentrations.

6.8. Other Uses

The lipoprotein complexes, e.g., negatively charged lipoprotein complexes, and compositions described herein can be used in assays in vitro to measure serum HDL, e.g., for diagnostic purposes. Because ApoA-I, ApoA-II and Apo peptides associate with the HDL component of serum, negatively charged lipoprotein complexes can be used as "markers" for the HDL population, and the pre-beta1 and pre-beta2 HDL populations. Moreover, the negatively charged lipoprotein complexes can be used as markers for the subpopulation of HDL that are effective in RCT. To this end, negatively charged lipoprotein complexes can be added to or mixed with a patient serum sample; after an appropriate incubation time, the HDL component can be assayed by detecting the incorporated negatively charged lipoprotein complexes. This can be accomplished using labeled negatively charged lipoprotein complexes (e.g., radiolabels, fluorescent labels, enzyme labels, dyes, etc.), or by immunoassays using antibodies (or antibody fragments) specific for negatively charged lipoprotein complexes.

Alternatively, labeled negatively charged lipoprotein complexes can be used in imaging procedures (e.g., CAT scans, MRI scans) to visualize the circulatory system, or to monitor RCT, or to visualize accumulation of HDL at fatty streaks, atherosclerotic lesions, and the like, where the HDL should be active in cholesterol efflux.

Examples and data associated with the preparation and characterization of certain proApoA-I-lipid complexes are described in U.S. Patent Publication No. 2004/0067873, the disclosure of which is incorporated herein by reference in its entirety.

Data obtained in an animal model system using certain proApoA-I-lipid complexes are described in U.S. Patent Publication No. 2004/0067873, the disclosure of which is incorporated herein by reference in its entirety.

7. EXAMPLE 1: DEVELOPMENT OF AN APOA-I EXPRESSION SYSTEM

7.1. Cloning and Expression of Human ApoA-I in Chinese Hamster Ovary (CHO) Cells

7.1.1. Preparation of the ApoA-I Expression Vector

The preproApoA-I gene sequence was obtained from NCBI (P02647) and flanking sequences were added for easy cloning and improved expression. The preproApoA-I encoding DNA with the flanking sequences was synthesized and cloned into Bluescript KS+ vector. The 5' flanking sequence contained an optimized Kozak translation sequence. The preproApoA-I insert was excised from the Bluescript KS+ vector with Hind III and Bgl II restriction enzymes. This fragment was gel-purified and ligated into a retroviral expression vector bearing the following genetic elements: human cytomegalovirus promoter fused to a Moloney Murine Sarcoma virus 5' LTR, a MoMuLV/SV packaging region, the immediate-early simian cytomegalovirus promoter, a multicloning site, the 3' LTR from MoMuLV, and a bacterial origin of replication and beta-lactamase gene. Clones of the resulting construct were sequenced through the gene and flanking regions. A final clone (clone #17) was selected based on congruity to the predicted DNA sequence. Retrovector was then prepared for transduction using 293GP cells co-transfected with an expression plasmid for Vesicular Stomatitis Virus envelope glycoprotein. Supernatant recovered from the co-transfected cells and concentrated was used for the CHO-S transduction step described below in Section 7.1.2.

7.1.2. Production of a Mammalian Cell Line for Expression of ApoA-I

Chinese hamster ovary cells adapted for growth in serum-free medium (CHO-S) were subjected to three rounds of transduction (1×, 2×, and 3×) using the retroviral vector described above in Section 7.1.1. The pooled population was expanded for cryopreservation after each transduction and a sample of cells was submitted for gene copy analysis. Gene copy index is shown below in Table 2. The 3× transduced cell line was analyzed for productivity in a 16-day fed batch test in duplication 125 mL flasks. The results are shown in Table 3.

TABLE 2

Gene Copy Index Results of ApoA-I Expression Cell Lines

| Transduction Round | Cell Line Name After Transduction | Gene Copy Index |
|---|---|---|
| 1 | * CHO-S-ApoA-I-R (1X) | 2.53 |
| 1 | * CHO-S-ApoA-I-R (1X) | |
| 2 | ** CHO-S-ApoA-I-R (2X) | 5.50 |
| 2 | ** CHO-S-ApoA-I-R (2X) | |
| 3 | * CHO-S-ApoA-I-R (3X) | 7.23 |

* The 1X cell lines were combined before proceeding to create the 2X cell lines
** The 2X cell lines were combined before proceeding to create the 3X cell lines

TABLE 3

Fed Batch Productivity Data for CHO-S-ApoA-I-R (3X)

| 3X Pooled Population | Day | | | | | |
|---|---|---|---|---|---|---|
| | 2 | 4 | 6 | 8 | 10 | 12 |
| VCD* (×105 cells/mL) | 10.49 | ** | 66.33 | 69.10 | 74.73 | 51.74 |
| µg/mL (by ELISA) | 89 | 459 | 1339 | 2755 | 2775 | 2658 |

*Viable cell density
**d4 cell counts not performed due to collection error

7.1.3. Stability of Cell Line Expressing ApoA-I

A non-GMP characterization study was conducted on CHO-S-ApoA-I-R (3×) clone, 17, the master cell bank producing ApoA-I, in order to assess its stability in viability, growth rate, conservation of the gene inserts, and consistent product secretion during long-term culture.

The cell line was thawed from the master cell bank and cultured in 125 mL shake flasks using PF CHO LS medium (HyClone, Logan Utah). The cells were continuously cultured by serial passage from generation 0 to generation 43. At generations 4, 8, 14, 19, 25, 31, 36 and 43 samples of cells were frozen. At the end of the culturing, samples of cells from all generations were thawed and used to conduct terminal culture runs to compare ApoA-I protein production of the cell line at different generations in the same experiment. The supernatant from each of the samples were tested at day 12 using reverse phase HPLC analysis to determine the level of ApoA-I production. ApoA-I concentration was found to vary from 1259 mg/L to 1400 mg/L for the various samples (FIG. 2).

To compare the stability of gene inserts, samples of the CHO cells at generations 0, 4, 14, 25, 36 and 43 were used for DNA isolation. The number of genetic inserts for each sample was determined using real-time PCR on genomic DNA. As shown in Table 3, the PCR-based indexes of copy number were not significantly different based on overlapping standard deviations between generation 0 and generation 43. The production of ApoA-I and the gene copy index values from the master cell bank cell line were found to be stable over the 43 generations tested.

TABLE 4

Stability of Gene Copy Index

| Generation | Gene Copy Index | Standard Deviation |
|---|---|---|
| 0 | 7.87 | 0.25 |
| 4 | 7.80 | 0.27 |
| 14 | 7.80 | 0.27 |
| 25 | 7.97 | 0.25 |
| 36 | 7.90 | 0.17 |
| 43 | 8.20 | 0.27 |

7.2. Cell Growth and Harvest of ApoA-I 7.2.1. Scale Up to Innoculum and 200 L Bioreactor Production A vial of CHO-S cells stably transfected with the human ApoA-I gene from the master cell bank were thawed in a 37° C. water bath and were added to a single shake flask (250 mL) (Thermo Fisher Scientific) containing 35 mL of HyQ PF-CHO LS cell culture medium. The initial cell count, determined using a hemacytometer, was $2.48 \times 10^5$ cells/mL and 93.8% viability. The culture was then placed on an Orbit shaker (90 rpm) within an incubator maintained at 37° C. in a humidified, 5% $CO_2$ environment. Subculture steps targeted inoculation densities of approximately $1.6 \times 10^5$ cells/mL. The day 4 cell count and percent viability in the flask was $15.01 \times 10^5$ cells/mL with 93.9% viability. The 250 mL flask was subcultured to 1 L flask. The day 3 average viable cell count from the 1 L flask was $13.56 \times 10^5$ cells/mL with 95.3% viability. The 1 L flask was subcultured to a Wave Bioreactor System 20EH with a 10 L disposable Wave Bag (GE Healthcare Bioscience Bioprocess Corp, Somerset, N.J.) at an initial culture volume and an initial target cell density of 1000 mL and $1.75 \times 10^5$ cells/mL, respectively. The Wave Bioreactor operating settings were 37° C. incubation temperature, 15.0 cpm rocker speed, 10.9° rocking angle, and 5.0% $CO_2$ concentration in the aeration gas with a gas flow rate of 0.25 L/minute. After 3 days of culture, the viable cell density in the Wave Bag was $10.73 \times 10^5$ cells/mL, and fresh HyQ PF-CHO LS was added bringing the culture volume to 5000 mL. After an additional three days, the viable cell density was $13.25 \times 10^5$ cells/mL and the volume in the Wave Bag was transferred to the 30 L bioreactor. The operating set-points in the 30 L bioreactor for temperature, pH, dissolved oxygen, pressure, and agitation rate were 37° C., pH 7.0, 40% air saturation, 1 psig pressure, and 50 rpm agitation rate, respectively.

The viable cell density in the 30 L bioreactor was $10.80 \times 10^5$ cells/mL on day three of culture, which was sufficient to inoculate the 200 L bioreactor at an initial target density of $2.40 \times 10^5$ cells/mL. The entire contents of the 30 L were transferred and the post inoculum weight, cell density and viability were respectively 134.5 Kg, $2.37 \times 10^5$ cells/mL and 90.9%. The operating set-points in the 200 L bioreactor for temperature, pH, dissolved oxygen, pressure, and agitation rate were 37° C., pH 7.0, 40% air saturation, 1 psig pressure, and 35 rpm agitation rate, respectively. On day 3, the cell density was $15.71 \times 10^5$ cells/mL, which was sufficient to add 60 L (v/v) of Complete Medium (AGT CD CHO 5×, Invitrogen) and 200 mM L-glutamine (final concentration 10 mM) solution to the bioreactor. On days 8 and 12, the glucose level fell below 5 g/L which triggered an addition of 3 g/L of glucose (20%) solution. The viable cell density peaked on day 9 at $33.20 \times 10^5$ cells/mL with a viability of 92.5%. The bioreactor was harvested on day 13 at a cell viability of 78.5%. The cell counts and viability of the culture throughout the culture period are shown in FIG. 3A and the ApoA-I concentration in the culture medium throughout the culture period are shown in FIG. 3B.

7.2.2. Harvesting, Cell Separation and Storage of Cells

Media from the bioreactor was harvested by passing the bioreactor contents through double Cuno (Rutherford, N.J., USA) 60MO2 Maximizer filters followed by a Millipore 0.22 μm Opticap (Billercia, Mass., USA) into a 200 L bag. The clarified media was then stored at 2-8° C. until the dispensing operation. The clarified media was filtered through a Millipore 0.22 μm filter (Billerica, Mass., USA) and dispensed into 2 L sterile PETG bottles (ThermoFisher, Marietta, Ohio, USA) and then frozen at −20° C. until released for shipment.

8. EXAMPLE 2: DEVELOPMENT OF AN APOA-I PURIFICATION SYSTEM 8.1. Materials and Methods Expression, Primary Separation and Conditioning.

ApoA-I clarified cell growth medium obtained as described in Example 1 (approximately 1.8 L) was thawed by storage at ambient temperature. The thawed medium was conditioned for anion exchange chromatography by reducing the pH 5.3±0.2 with 1M HCl.

Purification of Apo A-I.

A Q-Sepharose FF (GE Healthcare) anion exchange column packed at a bed height of 20 cm was equilibrated with TAMP A buffer (20 mM sodium phosphate, pH 5.3). Equilibration was judged to be complete when the of the column effluent was approximately 5.5. The conditioned filtrate was loaded onto the column at 25-35 g ApoA-I/L of anion exchange resin at a flow rate of 3.7 cm/min. ApoA-I was washed through the column in the TAMP A flow-through, which was collected.

The ApoA-I containing flow-through from the anion-exchange column was pH adjusted to 8.0±0.2 with 1M NaOH. The solution was then filtered through a 0.2 μm Planova 20N filter (Asahi Kasei Medical) at a flow rate of about 12.5 L/h/m² to remove viruses and viral particles.

A Source 30 reverse phase chromatograpy column with a bed height of 25 cm was washed with TAMP D buffer (20 mM ammonium carbonate, pH 9.5) until equilibrated, when the column effluent reached pH 9.5. The ApoA-I containing filtrate from the virus filtration step was loaded onto the column at a flow rate of 2.8 cm/min. ApoA-I in the sample was adsorbed to the matrix and eluted with a gradient of 35-50% acetonitrile in TAMP D buffer.

A reverse phase silica C18 column (300 Å 10 μm) packed at a bed height of 25 cm was washed in TAMP E buffer (100 mM ammonium carbonate, pH 9.5) until equilibrated, when the column effluent reached pH 9.5. The C18 column was then loaded at 4.7 g ApoA-I/L of matrix. The ApoA-I adsorbed to the column matrix was eluted in a 40-50% acetonitrile gradient in TAMP E buffer.

Acetonitrile was removed from the ApoA-I containing fractions eluted from the C18 column by pooling and concentrating the fractions approximately 2.5-fold and then diafiltering the concentration against 15 volumes of TAMP C buffer (3 mM sodium phosphate, pH 8). The pH of the diafiltered ApoA-I solution was decreased to about 6.0 using dilute phosphoric acid and then passed through a Mustang Q anion exchange membrane (Pall Life Sciences) to remove DNA and host cell proteins. The Mustang Q filtrate was diafiltered against 5 volumes of TAMP C buffer.

The diafiltered filtrate was then subjected to a final ultrafiltration using a polyethersulphone membrane (Filtron Omega series) with a 10,000 dalton molecular weight cutoff so that the membrane retains the 28,000 dalton ApoA-I. The protein solution contained The protein solution contained 7.8-17 g/L pure ApoA-I as determined by scanning an SDS-PAGE gel and measuring the ratio of the intensity of the purified ApoA-I band area and the total intensity of all bands.

8.2. Results

Characterization of ApoA-I.

The purity of the ApoA-I product was assayed by SDS-PAGE to be greater than 99% pure, with low levels of DNA and host cell proteins, and no detectable amount of truncated ApoA-I. See FIG. 4.

9. EXAMPLE 3: OPTIMIZATION OF LIPOPROTEIN COMPLEX COMPONENTS

9.1. Preparation of Apolipoprotein and Phospholipid Components proApoA-I:

The protein proApoA-I was supplied by Unité de Biotechnologie, Institut Meurice, Hte Ecole Lucia De Brouckère, 1 Avenue Emile Gryzon, B-1070 Anderlecht, Belgium in lyophilized individual 100 mL flasks containing approximately 90 mg of protein. The batch number was 20060202. The protein was kept at approximately 4° C. until use. Before lyophilization, the content of proApoA-I was 3.225 mg/mL with an urea content about 0.011 mg/mL. A solution of proApoA-I was made by dissolving approximately 630 mg of proApoA-I in 25.6 mL of acetic acid/water 5%. The final concentration of the solution was 25 mg/mL.

ApoA-I:

ApoA-I was prepared as described in Example 1 above.

Sphingomyelin:

Sphingomyelin from egg (Coatsome® NM-10) was supplied by NOF Corporation, 1-56, Oohama-Cho, Amagasaki-Shi, 660-0095, Japan. The batch number was 0502ES1. Sphingomyelin was kept at approximately −20° C. until use. The purity of sphingomyelin was 99.1%. A solution of sphingomyelin was made by dissolving 799.4 mg of purified sphingomyelin in 16 mL of acetic acid/water 5% to yield a final concentration of 50 mg/mL.

Phosphatidylglycerol:

1,2-dipalmitoyl-SN-glycero-3-phosphatidyl glycerol as sodium salt (DPPG-Na, Coatsome® MG-6060 LS) was supplied by NOF Corporation, 1-56, Oohama-Cho, Amagasaki-Shi, 660-0095, Japan. The batch number was 0309651L. DPPG-Na was kept at approximately −20° C. until use. The purity of DPPG-Na was 99.2%. A solution of DPPG-Na was made by dissolving 49.1 mg of DPPG-Na in 1 mL acetic acid/water 5% to yield a final concentration of 50 mg/mL.

Phosphatidylcholine:

di-palmitoyl phosphatidylcholine (DPPC) was obtained from a commercial source.

9.2. Preparation of Lipoprotein Complexes

The following lipoprotein complexes were prepared:
(a) Neutral Lipoprotein Complexes:
  a. Formula A: proApoA-I and SM in a protein:phospholipid weight ratio of 1:2.5;
  b. Formula B: proApoA-I and SM in a protein:phospholipid weight ratio of 1:2.7;
  c. Formula C: proApoA-I and SM in a protein:phospholipid weight ratio of 1:3.1;
  d. Formula D: proApoA-I, SM, and DPPC in a 1:2.7 lipoprotein wt: total phospholipid wt ratio with a SM:DPPC wt ratio of 50:50;
  e. Formula E: ApoA-I and SM in a protein:phospholipid weight ratio of 1:2.7.
(b) Negatively Charged Lipoprotein Complexes:
  a. Formula F: proApoA-I, SM, DPPC and DPPG in a 1:2.7 lipoprotein wt: total phospholipid wt ratio with a SM:DPPC:DPPG wt:wt ratio of 48:48:4;
  b. Formula G: proApoA-I, SM, DPPC and DPPG in a 1:2.7 lipoprotein wt: total phospholipid wt ratio with a SM:DPPC: DPPG wt:wt ratio of 73:23:4;
  c. Formula H: ApoAI, SM, and DPPG in a 1:2.7 lipoprotein wt: total phospholipid wt ratio with a SM:DPPG wt:wt ratio of 97:3;
  d. Formula I: ApoAI, SM, and DPPG in a 1:3.0 lipoprotein wt: total phospholipid wt ratio with a SM:DPPG wt:wt ratio of 97:3;
  e. Formula J: ApoAI, SM, and DPPG in a 1:3.3 lipoprotein wt: total phospholipid wt ratio with a SM:DPPG wt:wt ratio of 97:3;

9.3. Rate of Formation and Homogeneity of Lipoprotein Complexes

Formation of lipoprotein complexes of Formulas A through J was tested by injecting a sample into a HPLC system to check for the size and distribution of lipoprotein complexes. Complexes were produced by co-homogenization and sampled at the indicated times.

FIG. 5 shows exemplary HPLC chromatograms for neutral lipoprotein complexes according to Formulas A through C comprising different lipoprotein:SM wt:wt ratios, and Formula D comprising lipoprotein and neutral phospholipids in a 1:2.7 ratio, where the neutral phospholipid is 50:50 SM:DPPC. The lipoprotein:SM wt:wt ratio of 1:2.7 was optimal. Formula D, which contained a mix of SM and DPPC, showed poor complex formation.

Addition of phosphatidyl choline as a second neutral phospholipid resulted in slow and incomplete complex formation. FIG. 6 shows HPLC chromatograms of lipoprotein complexes of Formula D at 10, 20, 30, and 60 minutes. In contrast, as shown in FIG. 7, Formula B rapidly formed complexes.

Addition of a negatively charged phospholipid, DPPG, to SM and DPPC led to even less complex formation, as shown in the FIG. 8 HPLC chromatograms of lipoprotein complexes of Formula F at 20, 40, 60, and 120 minutes.

As shown in FIG. 9, lipoprotein complexes which contain only SM as a phospholipid, in a protein to lipid weight ratio of 1:2.7 form more pre-B HDL complexes and do so faster than lipoprotein complexes with the same protein to lipid weight ratio but that contain DPPC and/or DPPG. Therefore, lipoprotein complexes comprising only SM as a neutral lipid form more homogeneous lipoprotein complexes at a faster rate than complexes comprising DPPC in addition to SM, with or without addition of DPPG.

Finally, negatively charged lipoprotein complexes comprising an apolipoprotein: phospholipid weight ratio of between 1:2.7 and 1:3, in which the phospholipid fraction contains SM and DPPG in a 97 to 3 weight ratio showed optimal homogeneity and no free lipid peak, as compared to complexes comprising an apolipoprotein: phospholipid weight ratio of 1:3.3 and uncharged lipoprotein complexes. See FIG. 10, showing HPLC chromatograms for Formulae E, H, I, and J. Lipoprotein complexes according to Formulae B and H were chosen for further study in animals (Example 6) and, based on the results of the animal studies, lipoprotein complexes of Formula H were chosen for clinical assessment in human patients (Examples 6 and 8).

10. EXAMPLE 4: FORMATION OF LIPOPROTEIN COMPLEXES USING THERMAL CYCLING-BASED METHODS

10.1. Overview of Procedure for Making ApoA-I/DPPG/Sphingomyelin Complexes

Frozen ApoA-I solution in phosphate buffer (pH 7-9) at a protein concentration of 1 to 30 mg/ml, typically 5 to 20 mg/ml, is prepared by thawing for approximately 24-96 hrs at 2-8° C. and weighed. Sodium monobasic phosphate and sodium dibasic phosphate are added to the ApoA-I solution to obtain a final peptide concentration of 10 mM in pH 7.4 buffer.

DPPG solution is prepared by warming phosphate buffer (10 mM sodium phosphate, pH 8.0) to a target of 50° C. DPPG powder (NOF Corporation) is thawed at ambient temperature for at least 1.5 hrs and then weighed and added to the buffer container. The DPPG is then dispersed at temperature of 50° C. using an ULTRA-TURRAX® high-performance disperser (IKA® Works, Inc.). After dispersion, the DPPG suspension and ApoA-I solution are heated to 57° C. They are combined and heated at 57° C. for 30 minutes under nitrogen. This pre-complex solution is cooled to room temperature.

Sphingomyelin (SM) powder (NOF Corporation) is thawed at ambient temperature then weighed into a glass tank. The phosphate phosphate buffer (10 mM sodium phosphate, pH 8.0) is heated to 50° C. combined with the SM powder for a SM concentration of 220 mg/ml. The SM powder is dispersed in suspension using an ULTRA-TURRAX® and the dispersion is cooled to 4° C. and then passed through the homogenizer. The SM particles are monitored by dynamic light scattering (DLS) to 55 to 70 nm zeta (Z) average size (using an intensity measurement). This can be achieved, e.g., using a Nano DeBee homogenizer at 32000+/−3000 bars, with the temperature at the inlet at 10-18° C. and temperature at the outlet preferably at 30-40° C. (and not exceeding 59° C.), resulting in a particle with Z-average size of 58 nm.

For complexation, the ApoA-I/DPPG mixture and the SM dispersion are warmed separately to 57° C. The warmed SM dispersion is added to the ApoA-I/DPPG mixture with an initial temperature set point of 57° C. After stirring to combine, the solution is cooled to 37° C. and then carried through a series of thermal cycles (57° C. to 37° C.) in order to form ApoA-I/DPPG/SM complexes. This heat-cool process is continued with a contact time between temperatures is from 5 minutes and 30 minutes. The heat-cool cycles are repeated until the majority of the protein component is incorporated into lipoprotein complexes. The size and distribution of complexes during thermocycling is monitored by gel permeation chromatography (GPC).

ApoA-I/DPPG/SM complexes were made according to the procedure described above (and illustrated in FIG. 11). The ApoA-I protein had an amino acid sequence corresponding to positions 25 to 267 of the sequence depicted in FIG. 1. The complexes contain sphingomyelin (SM), and 1,2-dihexadecanoyl-sn-glycero-3-phospho-(1'-rac-glycerol) (Dipalmitoylphosphatidylglycerol or DPPG) in a 97:3 weight ratio. The ratio of ApoA-I protein-to-total lipids is 1:2.7 weight/weight (w/w) which is equivalent to a molar ratio of 1:108. The combined lipid and protein components were cycled between 57° C. and 37° C. for 5 minutes at each temperature using a heat exchanger arranged as depicted in FIG. 5, which includes on the left a Lauda Ecoline Star edition Type 26LE water bath (in which the sample is thermally cycled) and on the right a shell & tube heat exchanger (model EF-050-HE), which has an 18-ml hold volume, connected by a peristaltic pump.

180 mg of DPPG was added to 2.82 grams of 10 mM phosphate buffer pH 8.0. The suspension was dispersed with an ULTRA-TURRAX® disperser for 10 minutes at 50° C. 22 grams of SM powder were combined with 78 grams of 10 mM phosphate buffer pH 8.0. The suspension was dispersed with an ULTRA-TURRAX® disperser for 20 to 40 minutes at 50° C. The SM was homogenized using a NanoBEE set to an average particle size of 60 nm. The DPPG, SM and protein were brought to 57° C. 18 mgs (0.3 ml) of DPPG were added to 214 mg of ApoA-I protein in 10 mM phosphate buffer pH 7.4 at 57° C. After 30 minutes at 57° C., 559 mg of SM particles (2.54 ml) were added. This solution was then subjected to thermal cyling to form a complex.

Gel permeation chromatography showing ApoA-I/DPPG/SM complex formation after thermocycling for 30 minutes, 60 minutes, 120 minutes, 180 minutes and 210 minutes is shown in FIGS. 13A-13E, respectively. A more compact complex is produced with increasing cycle time, as shown by the increasing sharpness of the major GPC peak. The peak corresponding to uncomplexed protein also disappears over time.

10.2. Formation of ApoA-I/Sphingomyelin Complexes

ApoA-I/SM complexes were made according to the procedure described above, but without pre-complexing ApoA-I with DPPG. The protein component was 5 ml of ApoA-I at a concentration of 8.9 mg/ml and the lipid component was 0.5 ml egg sphingomyelin (220 mg/ml) which had been suspended in 10 mM phosphate buffer pH 8.0 and homogenized to form lipid particles of 60 nm. The protein and lipid components were mixed at 50° C. at a ratio of 1:2.5, wt:wt. The resulting suspension was subject to thermal cycling for 18 hours (108 cycles and cycling time of 10 minutes) using a thermal cycling apparatus as depicted in FIG. 5. Gel permeation chromatography shows that the protein/lipid complex formed is essentially homogeneous (see GPC chromatogram of FIG. 14).

10.3. Formation of ApoA-I/DPPG/N-palmitoyl-4-hydroxysphinganine-1-phosphocholine (phytosphingomyelin) Complexes ApoA-I/DPPG/phytosphingomyelin complexes were made according to the procedure described above. The phytosphingomyelin particles were homogenized to a size of about 183 nm (measured by DLS) and added to the 7.8 g/L protein:DPPG mixture to achieve a final protein to lipid (SM and DPPG) ratio of 1:2.7. The suspension containing N-palmitoyl-4-hydroxysphinganine-1-phosphocholine (phyto-sphingomyelin) and a protein:DPPG component was thermally cycled for six cycles of 10 minutes at 37° C. and 10 minutes at 57° C., over a total of two hours. Gel permeation chromatography shows that the protein/lipid complex formed is essentially homogeneous (see GPC chromatogram of FIG. 15).

10.4. Formation of ApoA-I/DPPG/Synthetic Palmitoyl Sphingomyelin

ApoA-I/DPPG/synthetic palmitoyl sphingomyelin complexes were made as follows. An 8.8 mL solution of synthetic palmitoyl sphingomyelin (220 mg/ml) in 10 mM phosphate buffer pH 7.4 was mixed until a particle size of 3300 nm was reached. ApoA-I (945 mg at 14 mg/ml) was combined with 0.03% DPPG (60 mg/ml) by weight and heated at 50° C. for 30 minutes. The synthetic palmitoyl sphingomyelin micelles were combined with the protein/DPPG complex at an apolipoprotein:phospholipid weight ratio of 1:2.7. The suspension of protein and lipid was thermally cycled with heat-cool cycles at 37° C. and 57° C. alternatively every ten minutes for a total of 240 minutes or until the appropriate distribution of the particle size is attained. The size and distribution of complexes during thermocycling was monitored by GPC. After complexation the concentration was brought to 8.0 mg ApoA-I/ml, then sucrose (40 mg/ml) and mannitol (20 mg/ml) were added to the complex for isotonicity. The lipoprotein complexes were assayed by GPC and found to be essentially homogenous (see GPC chromatogram of FIG. 16).

10.5. Formation of ApoA-I/DPPG/Phytosphingomyelin

ApoA-I/DPPG/phytosphingomyelin complexes were made as follows. A 2.0 mL solution of phytosphingomyelin (220 mg/ml) in 10 mM phosphate buffer pH 7.4 was dispersed in an ULTRA-TURRAX® for 40 minutes at 50° C. until a particle size of 990 nm was reached. ApoA-I (15.6 mg at a concentration of 7.8 mg/ml) was combined with 0.03% DPPG (60 mg/ml) by weight and heated at 57° C. for 30 minutes. The phytosphingomyelin solution was combined with the protein/DPPG mixture at an apolipoprotein:phospholipid weight ratio of 1:2.7. The suspension of protein and lipid was then thermally cycled with heat-cool cycles at 37° C. and 57° C. alternatively every ten minutes for a total of 240 minutes or until the appropriate distribution of the particle size was attained. The population of lipoprotein complexes was measured by GPC and found to be about 92.6% homogeneous (see GPC chromatogram in FIG. 17).

10.6. Complex Formation with an ApoA-I Peptide

Complexes of ApoA-I peptide, DPPG and sphingomyelin were generated as described above (see Section 10.1), using an ApoA-I peptide (H-Lys-Leu-Lys-Gln-Lys$^5$-Leu-Ala-Glu-Leu-Leu$^{10}$-Glu-Asn-Leu-Leu-Glu$^{15}$-Arg-Phe-Leu-Asp-Leu$^{20}$-Val-Inp$^{22}$-OH; SEQ ID NO:4) solution. The phospholipid component consists of egg sphingomyelin (SM), 1,2-dipalmitoyl-sn-glycero-3-phosphocholine (Dipalmitoylphosphatidylcholine, DPPC) and 1,2-dipalmitoyl-sn-glycero-3-[phospho-rac-(1-glycerol)] (Dipalmitoylphosphatidyl-glycerol, DPPG) in a 48.5:48.5:3 weight ratio. The ratio of peptide to total phospholipids complex is 1:2.5 (w/w). The drug complex is a solution of the CER-522 complex in phosphate buffered saline (12 mM sodium phosphate, 130 mM sodium chloride, pH 8.2). The complex was formed by subjecting the starting solution to thermal cycling between 50° C. and 37° C. for two hours, flow rate of 1 ml/min.

Gel permeation chromatography shows that the protein/lipid complex formed is essentially homogeneous, with a vast majority of the protein having been incorporated into lipoprotein complexes (see GPC chromatogram of FIG. 18).

10.7. Effect of Lipid Particle Size and Number of Thermal Cycles on Complex Formation The effect of lipid particle size and the number of thermal cycles on particle size was studies. Preparations of four different starting lipid particle sizes (with zeta averages of 85 nm, 77 nm, 66 nm, and 60 nm) (FIGS. 19A through 19D, respectively) were generated by passing SM solutions through the NanoBEE in single passes. Each pass was analyzed for its zeta average. The lipid particle size decreased with each pass and the lipid particles were collected when the desired size was achieved. The four different lipid particle sizes were tested in the complex formation method of Section 10.1, for five or seven cycles of 3 minutes at 37° C. and 10 minutes at 57° C.

When the lipid component is mixed with the protein component, the resulting suspension is cloudy. The cloudiness is reduced, and the solution becomes more transparent, as complexes are formed.

After five cycles, the suspension of complexes produced from 60 nm lipid particles was the most transparent. GPC chromatograms (FIGS. 20A through 20D) show complete or almost complete complexation in all samples, as evidenced by the homogeneity of major peak. When starting with 66 nm lipid particles, there was no uncomplexed protein detectable by GPC in the resulting suspension of lipoprotein complexes, indicating that all the protein was complexed with lipid after five cycles, and the resulting complexes were 98% pure. After seven cycles, all four suspensions became more transparent, showing an even greater extent of complexation. The suspension made using 60 nm lipid particles appeared the clearest.

In a separate study, SM particles of 450 nm and 40 nm were complexed with ApoA-I and DPPG using the method described in Section 10.1. Most, but not all, ApoA-I was incorporated into lipoprotein complexes using 450 nm SM particles as the lipid component, as shown in the GPC chromatogram of FIG. 21A (the 9.8 minute peak). A much smaller fraction of ApoA-I was incorporated into lipoprotein complexes using 40 nm SM particles as the lipid component, as shown in the GPC chromatogram of FIG. 21B (the 9.551 minute peak).

10.8. Effect of Starting Temperature on Complex Formation

The effect of the initial thermal cycling temperature on complex formation was studied. ApoA-I/DPPG/SM complexes were generated described in Section 10.1, except that the lipid component and the protein component were warmed to, and combined at, 37° C. instead of 57° C. A GPC chromatogram of the resulting complex is shown in FIG. 22. Substantially less of the protein component was incorporated into lipoprotein complexes than when thermal cycling was initiated at 57° C., as evidenced by the relatively large protein peak (eluting 9.455 minutes in FIG. 22).

10.9. Commercial Production of Lipoprotein Complexes Using Thermal Cycling Methods For large scale commercial manufacturing, the methods of the disclosure can be scaled up and optionally combined with a formulation step. A commercial embodiment is depicted in FIG. 23. In this embodiment, following the thermocycling steps, the lipoprotein complex is diluted, mixed with one or more isotonicity agents (e.g., sucrose and/or mannitol), filtered, and aliquoted into vials. The contents of the vials can be freeze-dried to prolong shelf-life of the resulting formulation.

ApoA-I/DPPG/SM complexes described in Section 10.1 were produced on a 20-liter scale using DaBEE2000. This complexes were diluted with phosphate buffer (pH 7-8) and mixed with sucrose and mannitol to a final formulation containing phosphate buffer 10 mM pH 7.4, 8 mg/ml ApoA-I, 4% (w/w) sucrose and 2% (w/w) mannitol.

10.10. Comparison of Lipoprotein Complexes Made by Thermal Cycling Vs. Co-Homogenization ApoA-I/DPPG/SM complexes made by the thermal cycling methods disclosed herein were compared to complexes made by co-homogenization of the lipid and protein components. The purity of the complexes made by thermal cycling was improved to 97% compared to the co-homogenization as measured by gel permeation chromatography. Using SDS-PAGE, the complex made by thermal cycling has an increased main band purity of 98% with less truncated protein bands present as compared to co-homogenized complexes.

Oxidation of the ApoA-I is also reduced by the thermal cycling process as compared to co-homogenization. RP-HPLC (C18) shows two oxidation peaks at RT 0.93 and 0.99 in the co-homogenized complexes that are not present in the thermal cycling process. The peptide map also shows a reduction in the oxidation of methionine of ApoA-I at Met 112 and Met 148 in the complexes produced by thermal cycling as compared to the complexes produced by co-homogenization.

A summary of the data is presented in Table 5 below.

TABLE 5

Results of ApoA-I/DPPG/SM Complexes Manufactured using Co-Homogenization and Thermal Cycling

| Test | Co-homogenization Batch A | | Co-homogenization Batch B | | Thermal Cycling Batch A | | Thermal Cycling Batch B | |
|---|---|---|---|---|---|---|---|---|
| Purity of Complexes by GPC | 86% | | 93% | | 96.9% | | 97.5% | |
| Purity of ApoA-I by SDS-PAGE | Band # | % | Band # | % | Band # | % | Band # | % |
| | 1 | 0.3 | 1 | 1.4 | | | | |
| | 2 | 5.4 | 2 | 1.7 | | | 2 | 1.2 |
| | 3 | 3.4 | main | 95.7 | main | 98.1 | main | 98.1 |
| | main | 89.5 | 4 | 1.3 | | | | |
| | 4 | 1.3 | | | | | | |
| Purity of ApoA-I by HP-SEC | RRT | % | RRT | % | RRT | % | RRT | % |
| | 0.97 | 4.9 | 0.97 | 1.5 | 0.97 | 1.2 | 0.96 | 0.7 |
| | 1.00 | 98.2 | 1.00 | 84.9 | 1.00 | 98.2 | 1.00 | 98.7 |
| | 1.10 | 12.8 | 1.10 | 13.6 | 1.10 | 0.6 | 1.11 | 0.6 |
| Heterogeneity ApoA-I by RP-HPLC (C18) | RRT | % | RRT | % | RRT | % | RRT | % |
| | 0.93 | 6.7 | 0.93 | 0.9 | 0.93 | N/A | 0.93 | N/A |
| | 0.94 | N/A | 0.94 | 0.5 | 0.94 | 1.3 | 0.94 | 1.1 |
| | 0.96 | 1.4 | 0.96 | 1.0 | 0.96 | 1.4 | 0.96 | 1.1 |
| | 0.97 | 0.7 | 0.97 | 2.6 | 0.97 | 3.5 | 0.97 | 3.2 |
| | 0.99 | 53.1 | 0.99 | N/A | 0.99 | N/A | 0.99 | N/A |
| | 1.00 | 38.1 | 1.00 | 94.7 | 1.00 | 93.5 | 1.00 | 94.4 |

TABLE 5-continued

Results of ApoA-I/DPPG/SM Complexes Manufactured using
Co-Homogenization and Thermal Cycling

| Test | Batch Results | | | |
|---|---|---|---|---|
| | Co-homogenization Batch A | Co-homogenization Batch B | Thermal Cycling Batch A | Thermal Cycling Batch B |
| Heterogeneity of ApoA-I by Peptide Map/Trypsin, RP-UPLC with UV Fingerprint | $M_{112}$ ox = 73.1%[a] $M_{148}$ ox = 4.4% | $M_{112}$ ox = 5.5%[a] $M_{148}$ ox = 1.0% | $M_{112}$ ox = 4.9%[a] $M_{148}$ ox = 1.5% | $M_{112}$ ox = 3.6%[a] $M_{148}$ ox = 0.9% |

Table 5 Abbreviations:
GPC = Gel Permeation Chromatography
Rt = Retention time;
NMT = Not More Than;
SDS-PAGE = Sodium Dodecyl Sulfate Polyacrylamide Gel Electrophoresis;
HP-SEC = High Performance-Size Exclusion Chromatography;
RP-HPLC = Reverse Phase-High Performance Liquid Chromatography;
RRT = Relative Retention Time;
RP-UPLC = Reverse Phase-Ultra Performance Liquid Chromatography;
$M_{112}$ ox = ApoA-I Residue 112 Methionine Oxidation;
$M_{148}$ ox = ApoA-I Residue 148 Methionine Oxidation.

10.11. Use of Inert Gas in Manufacturing Methods

ApoA-I is a delicate protein that is susceptible to chemical instability (e.g., oxidation). To enhance the stability of ApoA-I in ApoA-I/SM/DPPC-containing pharmaceutical compositions, the pharmaceutical compositions were prepared (including the thermal cycling, filling and finishing steps) under an atmosphere of nitrogen, an inert gas. Below are the results of studies comparing ApoA-I/SM/DPPC complexes made by co-homogenization and ApoA-I/SM/DPPC complexes made by thermal cycling under nitrogen.

TABLE 6

Comparative Analysis of Oxidation Levels of $Met_{112}$ and $Met_{148}$ in ApoA-I/SM/DPPC Complexes Made by Two Different Methods

| Batch No. | Batch Size | Manufacturing Method | Atmosphere | Oxidation Levels |
|---|---|---|---|---|
| 1 | 10 L | Co-homogenization | Air | $M_{112}$ ox = 14.8% $M_{148}$ ox = 0.8% |
| 2 | 9.6 L | Co-homogenization | Air | $M_{112}$ ox = 64.3% $M_{148}$ ox = 2.5% |
| 3 | 9.0 L | Co-homogenization | Air | $M_{112}$ ox = 71.3% $M_{148}$ ox = 2.5% |
| 4 | 19.9 L | Co-homogenization | Air | $M_{112}$ ox = 38.0% $M_{148}$ ox = 0.9% |
| 5 | 18.0 L | Co-homogenization | Air | $M_{112}$ ox = 5.9% $M_{148}$ ox = 0.8% |
| 6 | 17.4 L | Co-homogenization | Air | $M_{112}$ ox = 73.1% $M_{148}$ ox = 4.4% |
| 7 | 12.0 L[2] | Co-homogenization | Air | $M_{112}$ ox = 5.5% $M_{148}$ ox = 1.0% |
| 8 | 21.6 L | Thermal Cycling | Nitrogen | $M_{112}$ ox = 4.9% $M_{148}$ ox = 1.5% |
| 9 | 16.7 L | Thermal Cycling | Nitrogen | $M_{112}$ ox = 3.6% $M_{148}$ ox = 0.9% |

11. EXAMPLE 5: IN VITRO CHOLESTEROL EFFLUX STUDIES

The biological activity of ApoA-I-lipid complexes was studied in Fu5AH rat hepatoma cells, measuring ABCA1-mediated cholesterol efflux.

The Fu5AH rat hepatoma cells have high expression of the scavenger receptor class B type I (SRB1), which facilitate the bidirectional flux of cholesterol between the cells and mature HDL. This model provides a specific assay for IIDL-mediated cholesterol efflux activity. The assay was performed using a method described by Mweva et al., 2006, "Comparison of different cellular models measuring in vitro the whole human serum cholesterol efflux capacity," Eur. J. Clin. Invest. 36, 552-559. Fu5AH cells were labeled with $^3$H-cholesterol for 24 hours. Acceptor media for efflux were prepared for each test sample (ApoA-I/DPPG/palmitoyl SM, ApoA-I/DPPG/egg SM, or ApoA-I/DPPG/phytoSM at 30, 20 and 10 µg/ml, diluted with MEM buffered with 25 mM HEPES) and for the control samples (ApoA-I purified from human plasma (20 µg/mL), $HDL_3$, 2% human serum, medium alone). Acceptor medium containing test or control samples was added to the cells for 4 hours and cholesterol was measured in efflux media and cell monolayers to determine the percent of cholesterol released from the Fu5AH cells. Biological activity of the test samples was calculated and is expressed as percent of cholesterol efflux relative to a Reference Standard of Formula H described above at the same concentration as the lipoprotein complex in the test sample, which served as a positive experimental control. Results are shown below in Table 7, and demonstrate that the lipoprotein complexes tested have significant biological activity as measured in the cholesterol efflux assay.

TABLE 7

Biological Activity (by Induced Cholesterol Efflux) in the Fu5AH Cell-Based Assay

| Complex | SR-BI Mediated % Efflux 20 µg/ml | % of Reference Standard |
|---|---|---|
| ApoA-I/DPPG/Palmitoyl Sphingomyelin | 3.70 ± 0.09 | 92% |
| ApoA-I/DPPG/Egg Sphingomyelin | 3.61 ± 0.05 | 89% |
| ApoA-I/DPPG/Phytosphingomyelin | 2.24 ± 0.04 | 56% |

12. EXAMPLE 6: PHARMACODYNAMIC STUDY OF SINGLE, LOW DOSE ADMINISTRATION OF FORMULA B AND FORMULA H COMPLEXES IN RABBITS

Normal rabbits received a single injection of: (a) a 5 mg/kg dose of a preparation of Formula B (neutral lipoprotein complexes containing ApoA-I and SM in a 1:2.7 apolipoprotein: phospholipid weight ratio); (b) a 5 mg/kg dose of a preparation of Formula H (negatively charged lipoprotein complexes containing ApoA-I, SM, and DPPG in a 1:2.7 apolipoprotein: phospholipid weight ratio and a 97:3 SM:DPPG weight ratio); or (c) a control preparation, containing the diluent for the lipoprotein complex preparations. Four rabbits were tested with each of Formula B, Formula H and control.

Plasma levels of VLDL total cholesterol and triglycerides over time are shown in FIGS. 24 and 25. Plasma VLDL total cholesterol levels increased less and returned to baseline faster in the animals treated with Formula H (ApoA-I/DPPG/SM complexes) (b), than the levels in animals treated with Formula B (lipoprotein complexes of ApoA-I and SM). A similar effect was seen for triglyceride levels. This study showed that the transient elevation in these levels was of shorter duration with ApoA-I/DPPG/SM complexes complexes than with neutral lipoprotein complexes. This result is consistent with the results of a Phase I study of the lipoprotein complexes of Formula H in human subjects (described in Example 8 below).

13. EXAMPLE 7: COMPARATIVE PHARMACODYNAMIC STUDIES OF EGG SM AND SYNTHETIC PALMITOYL SM

The pharmacodynamic effect of Apolipoprotein A-I (ApoA-I)/egg SM and ApoA-I/synthetic palmitoylSM lipoprotein complexes intravenously injected into rabbits was studied. Following injection of the lipoprotein complexes, changes in plasma lipid and lipoprotein levels were measured.

Lipoprotein complexes of either ApoA-I/egg SM or ApoA-I/synthetic SM were administered to rabbits at doses of 5 mg/kg or 20 mg/kg by intravenous infusion into the ear vein, at a rate of 1 mL/min. 4 animals per group were studied. Plasma samples were taken before dosing, immediately following the end of the infusion, and 30 min, 45 min, 1 h, 2 h, 4 h, 6 h, 8 h, 10 h and 30 h after the initiation of the infusion. Plasma samples were then analyzed using commercial enzymatic kits for total cholesterol, unesterified cholesterol, phospholipids and total triglycerides. ApoA1 was assayed in plasma samples using commercial ELISA kits. The plasma samples were analyzed by GPC to determine total and unesterified cholesterol profiles. For the 5 mg/kg dose treatments, the results were quantified based on the percent of the total area under the curve for the chromatogram trace.

FIG. 26A-26D show the plasma levels of cholesterol, triglycerides, phospholipids and apoA-I over time in rabbits infused with 5 mg/kg and 20 mg/kg of either ApoA-I/egg SM or ApoA-I/synthetic SM. Rapid and significant cholesterol mobilization was observed within 30 minutes after initiation of infusions at both doses administered: Cholesterol mobilization peaked at 30 minutes after administration for the 5 mg/kg dose, and a large increase in cholesterol mobilization was observed at the 20 mg/kg dose. At each dose tested, both formulations had similar profiles for plasma triglycerides, plasma phospholipids and plasma recombinant human apoA-I.

FIG. 27A-27C show the plasma HDL-total cholesterol levels, plasma LDL-total cholesterol levels, and plasma VLDL-total cholesterol levels. The increase of HDL-total cholesterol for ApoA-I/egg SM and ApoA-I/synthetic SM was similar (FIG. 27A). There was little variation in plasma LDL-C and VLDL-C levels, and the levels were not substantially altered by injection of lipoprotein complexes of either formulation (FIG. 27B-27C).

The results of this study show that ApoA-I/egg SM and ApoA-I/synthetic SM lipoprotein complexes elicit similar responses in vivo.

14. EXAMPLE 8: PHASE I STUDY OF APOA-I/DPPG/SM COMPLEXES IN HEALTHY DYSLIDEMIC SUBJECTS

14.1. Materials and Methods

A Phase I clinical trial was conducted with lipoprotein complexes of Formula H as a randomized, double-blind, placebo controlled, cross-over, single rising-dose study in healthy volunteers with an LDL/HDL ratio greater than 3.0. The objectives of this Phase I study were to assess the safety, tolerability, pharmacokinetics and pharmacodynamics of a negatively charged lipoprotein complex when administered as a single dose. Escalating doses of 0.25, 0.75, 2.0, 5.0, 10.0, 15.0, 30.0 and 45.0 mg/kg were studied. Subjects received by infusion a sterile solution containing lipoprotein complexes of ApoA-I (prepared as described in Example 1), SM and DPPG (in protein: lipid weight ratio of 1:2.7 and lipid composition of 97% SM/3% DPPG (w/w)) that had been made by co-homogenization of the protein and lipid components. The sterile solution was a 10 mM phosphate buffered solution of pH 8.0 containing mannitol and sucrose (4% (w/w) sucrose, 2% (w/w) mannitol) in addition to the lipoprotein complexes.

14.2. Results

Below are summarized the clinical findings from this Phase I study.

Total Cholesterol:

Mean plasma total cholesterol concentrations at each time point are presented in Table 8 below:

TABLE 8

Mean Plasma Total Cholesterol Concentrations by Time Following Single IV Administration

| Dose | \<br\>Hours Postdose [Plasma Concentration (mg/dL)] | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 178.8 | 176.5 | 171.3 | 175.0 | 180.0 | 181.8 | 182.8 | 172.8 | 176.8 | 181.0 | 168.0 | 186.3 | 189.3 |
| 0.75 mg/kg | 199.5 | 193.5 | 192.3 | 193.8 | 210.5 | 200.3 | 196.5 | 190.5 | 189.8 | 184.0 | 189.8 | 205.0 | 196.3 |
| 2 mg/kg | 208.0 | 201.8 | 209.8 | 207.8 | 211.3 | 217.3 | 216.0 | 209.5 | 198.0 | 191.5 | 189.0 | 196.0 | 194.8 |
| 5 mg/kg | 180.8 | 175.5 | 178.5 | 185.5 | 191.5 | 192.5 | 181.5 | 187.0 | 190.8 | 191.8 | 181.3 | 189.8 | 194.3 |
| 10 mg/kg | 180.3 | 176.3 | 181.8 | 190.5 | 195.8 | 189.3 | 186.8 | 182.0 | 191.5 | 192.8 | 198.0 | 193.5 | 185.8 |
| 15 mg/kg | 183.5 | 187.0 | 197.0 | 207.3 | 214.8 | 217.8 | 197.0 | 185.5 | 194.8 | 189.8 | 200.5 | 188.8 | 186.0 |
| 30 mg/kg | 185.0 | 190.3 | 205.8 | 227.5 | 234.0 | 224.3 | 201.5 | 187.5 | 170.8 | 167.3 | 177.0 | 182.5 | 198.3 |
| 45 mg/kg | 208.5 | 208.3 | 220.5 | 244.3 | 269.0 | 278.5 | 262.3 | 273.8 | 233.3 | 231.8 | 228.0 | 213.5 | 223.8 |
| Placebo | 192.1 | 184.5 | 182.6 | 188.0 | 192.7 | 196.0 | 189.8 | 192.1 | 187.2 | 186.3 | 189.9 | 192.6 | 195.3 |

VLDL, LDL and HDL in Total Cholesterol:

Mean values for VLDL, LDL and HDL in total cholesterol are summarized by time point and dose in Tables 9-11 below:

TABLE 9

Mean VLDL in Total Cholesterol Following Single IV Administration

| Dose | Hours Postdose [Plasma Concentration (mg/dL)] | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 24.21 | 23.74 | 22.73 | 24.22 | 26.62 | 31.00 | 32.67 | 29.12 | 32.48 | 35.61 | 23.50 | 34.35 | 32.56 |
| 0.75 mg/kg | 31.05 | 29.29 | 29.14 | 32.38 | 39.74 | 41.67 | 40.93 | 36.12 | 36.15 | 36.69 | 31.86 | 38.40 | 34.33 |
| 2 mg/kg | 27.38 | 22.87 | 23.47 | 27.11 | 30.04 | 36.83 | 37.74 | 31.09 | 26.34 | 25.68 | 24.58 | 28.41 | 21.22 |
| 5 mg/kg | 23.04 | 19.65 | 21.02 | 25.01 | 31.10 | 34.34 | 29.85 | 28.88 | 25.02 | 25.14 | 18.80 | 23.64 | 17.97 |
| 10 mg/kg | 28.38 | 24.77 | 23.33 | 28.59 | 38.11 | 43.53 | 39.07 | 37.98 | 33.70 | 33.08 | 28.83 | 27.37 | 24.17 |
| 15 mg/kg | 21.74 | 19.67 | 19.14 | 23.04 | 32.01 | 42.13 | 40.74 | 34.65 | 31.76 | 29.44 | 27.43 | 22.41 | 25.02 |
| 30 mg/kg | 21.28 | 16.58 | 13.28 | 18.70 | 28.95 | 44.06 | 48.54 | 55.64 | 37.56 | 28.40 | 21.00 | 20.66 | 23.45 |
| 45 mg/kg | 37.83 | 32.12 | 30.69 | 28.23 | 38.68 | 57.31 | 64.26 | 81.80 | 69.79 | 60.82 | 47.92 | 37.99 | 42.00 |
| Placebo | 28.03 | 26.07 | 25.46 | 27.86 | 29.45 | 35.52 | 33.99 | 31.77 | 31.33 | 36.51 | 26.91 | 29.42 | 28.29 |

TABLE 10

Mean LDL in Total Cholesterol Following Single IV Administration

| Dose | Hours Postdose [Plasma Concentration (mg/dL)] | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 112.65 | 111.83 | 109.38 | 111.44 | 114.16 | 112.18 | 112.08 | 107.74 | 107.68 | 107.79 | 105.48 | 111.69 | 110.26 |
| 0.75 mg/kg | 129.52 | 126.39 | 125.37 | 124.40 | 131.92 | 121.88 | 120.06 | 118.66 | 117.25 | 110.64 | 117.03 | 125.19 | 122.05 |
| 2 mg/kg | 131.94 | 130.18 | 135.08 | 131.64 | 133.43 | 133.42 | 131.74 | 132.63 | 128.20 | 122.92 | 119.23 | 121.89 | 124.59 |
| 5 mg/kg | 110.67 | 108.14 | 107.32 | 111.83 | 113.90 | 113.99 | 109.25 | 114.09 | 121.08 | 121.28 | 113.18 | 115.33 | 123.03 |
| 10 mg/kg | 106.56 | 102.15 | 102.83 | 105.92 | 106.73 | 102.29 | 104.74 | 103.52 | 115.08 | 117.14 | 123.52 | 121.62 | 116.29 |
| 15 mg/kg | 116.42 | 113.70 | 114.80 | 118.08 | 120.51 | 119.67 | 108.28 | 106.08 | 117.27 | 116.84 | 122.43 | 120.18 | 114.27 |
| 30 mg/kg | 121.08 | 114.75 | 111.66 | 118.46 | 116.37 | 104.48 | 91.34 | 82.22 | 92.19 | 100.90 | 112.18 | 115.92 | 126.04 |
| 45 mg/kg | 127.94 | 124.70 | 126.10 | 132.06 | 136.32 | 133.79 | 125.62 | 126.61 | 115.32 | 124.94 | 133.93 | 130.10 | 136.17 |
| Placebo | 119.77 | 115.96 | 114.93 | 116.55 | 119.00 | 117.02 | 113.91 | 118.22 | 115.28 | 112.96 | 118.17 | 116.60 | 119.54 |

TABLE 11

Mean HDL in Total Cholesterol Following Single IV Administration

| Dose | Hours Postdose [Plasma Concentration (mg/dL)] | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 41.89 | 40.93 | 39.14 | 39.34 | 39.23 | 38.56 | 37.99 | 35.89 | 36.59 | 37.60 | 39.02 | 40.22 | 46.51 |
| 0.75 mg/kg | 38.93 | 37.81 | 37.74 | 36.98 | 38.83 | 36.70 | 35.51 | 35.71 | 36.36 | 36.67 | 40.87 | 41.41 | 39.86 |

TABLE 11-continued

Mean HDL in Total Cholesterol Following Single IV Administration

| Dose | \[Plasma Concentration (mg/dL)\] Hours Postdose | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 2 mg/kg | 48.68 | 48.70 | 51.20 | 49.00 | 47.78 | 47.00 | 46.52 | 45.78 | 43.46 | 42.90 | 45.19 | 45.70 | 48.93 |
| 5 mg/kg | 47.04 | 47.71 | 50.16 | 48.65 | 46.50 | 44.17 | 42.41 | 44.03 | 44.65 | 45.33 | 49.27 | 50.78 | 53.25 |
| 10 mg/kg | 45.31 | 49.32 | 55.59 | 55.98 | 50.91 | 43.43 | 42.94 | 40.50 | 42.72 | 42.53 | 45.65 | 44.51 | 45.29 |
| 15 mg/kg | 45.34 | 53.63 | 63.05 | 66.13 | 62.23 | 55.95 | 47.97 | 44.77 | 45.72 | 43.47 | 50.64 | 46.15 | 46.71 |
| 30 mg/kg | 42.64 | 58.91 | 80.81 | 90.34 | 88.67 | 75.72 | 61.62 | 49.64 | 41.01 | 37.95 | 43.82 | 45.93 | 48.76 |
| 45 mg/kg | 42.73 | 51.42 | 63.70 | 83.96 | 94.00 | 87.40 | 72.36 | 65.34 | 48.14 | 45.99 | 46.15 | 45.16 | 45.58 |
| Placebo | 44.26 | 42.47 | 42.16 | 43.62 | 44.28 | 43.43 | 41.91 | 42.07 | 40.61 | 40.06 | 44.85 | 46.57 | 47.48 |

Unesterified (Free) Cholesterol:

Mean plasma free (unesterified) cholesterol concentrations at each time point are presented in Table 12 below:

TABLE 12

Mean Plasma Free Cholesterol Concentrations by Time Following Single IV Administration

| Dose | \[Plasma Concentration (mg/dL)\] Hours Postdose | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 48.8 | 46.0 | 44.8 | 46.0 | 46.5 | 49.0 | 51.0 | 46.0 | 48.0 | 50.8 | 44.0 | 49.0 | 49.0 |
| 0.75 mg/kg | 54.0 | 52.8 | 51.8 | 54.0 | 58.3 | 56.5 | 55.8 | 52.8 | 51.0 | 50.5 | 51.0 | 56.5 | 52.0 |
| 2 mg/kg | 51.8 | 51.5 | 54.0 | 54.5 | 56.5 | 60.0 | 59.8 | 55.0 | 52.0 | 50.8 | 50.8 | 50.8 | 49.8 |
| 5 mg/kg | 46.5 | 45.8 | 48.5 | 52.3 | 55.5 | 56.8 | 53.0 | 52.5 | 49.5 | 49.8 | 45.0 | 47.3 | 48.0 |
| 10 mg/kg | 47.0 | 47.3 | 52.3 | 58.3 | 62.0 | 60.0 | 59.3 | 54.8 | 52.8 | 50.8 | 51.5 | 48.0 | 46.8 |
| 15 mg/kg | 46.5 | 50.5 | 57.8 | 67.3 | 74.0 | 75.0 | 69.0 | 58.8 | 55.8 | 51.8 | 51.5 | 48.0 | 49.0 |
| 30 mg/kg | 48.0 | 55.5 | 69.0 | 87.0 | 95.3 | 94.5 | 86.0 | 74.0 | 54.0 | 47.8 | 47.0 | 47.0 | 51.5 |
| 45 mg/kg | 54.3 | 57.5 | 66.5 | 87.3 | 110.0 | 122.0 | 119.5 | 124.0 | 92.3 | 79.5 | 61.5 | 57.0 | 59.8 |
| Placebo | 49.6 | 47.5 | 47.3 | 48.6 | 49.7 | 52.3 | 50.5 | 49.8 | 48.5 | 48.7 | 49.2 | 50.8 | 50.7 |

VLDL, LDL and HDL in Free Cholesterol:

Mean values for VLDL, LDL and HDL in free cholesterol are summarized by time point and dose in Tables 13-15 below:

TABLE 13

Mean VLDL in Free Cholesterol Following Single IV Administration

| Dose | \[Plasma Concentration (mg/dL)\] Hours Postdose | | | | | | | | | | | | |
|---|---|---|---|---|---|---|---|---|---|---|---|---|---|
| | 0 | 0.5 | 1 | 2 | 4 | 8 | 12 | 24 | 48 | 72 | 168 | 336 | 504 |
| 0.25 mg/kg | 10.78 | 10.19 | 9.88 | 10.42 | 11.08 | 13.69 | 15.43 | 12.22 | 14.57 | 16.84 | 10.81 | 15.05 | 14.17 |
| 0.75 mg/kg | 11.11 | 10.58 | 10.43 | 12.02 | 14.63 | 16.06 | 15.81 | 13.74 | 14.36 | 14.93 | 12.20 | 14.33 | 12.92 |
| 2 mg/kg | 9.15 | 8.24 | 8.59 | 10.08 | 11.47 | 14.56 | 14.48 | 11.13 | 10.04 | 10.04 | 9.74 | 10.75 | 7.54 |
| 5 mg/kg | 7.05 | 6.06 | 6.58 | 8.61 | 11.69 | 13.39 | 10.56 | 9.88 | 7.83 | 8.16 | 5.56 | 8.11 | 5.49 |
| 10 mg/kg | 10.24 | 8.66 | 8.71 | 11.29 | 16.31 | 19.18 | 16.38 | 14.88 | 12.50 | 12.02 | 9.94 | 9.13 | 8.46 |
| 15 mg/kg | 8.37 | 7.39 | 7.45 | 10.18 | 15.78 | 22.36 | 22.22 | 15.53 | 13.26 | 12.44 | 10.47 | 8.20 | 10.38 |
| 30 mg/kg | 6.93 | 5.19 | 4.52 | 7.23 | 13.88 | 23.42 | 28.04 | 29.43 | 15.23 | 10.82 | 7.82 | 7.19 | 8.67 |
| 45 mg/kg | 12.93 | 10.75 | 10.49 | 11.37 | 18.11 | 31.75 | 39.30 | 49.87 | 35.60 | 27.75 | 19.20 | 14.62 | 16.06 |
| Placebo | 10.07 | 9.48 | 9.39 | 10.19 | 10.86 | 13.78 | 13.18 | 11.66 | 11.87 | 13.04 | 9.99 | 11.53 | 10.99 |

TABLE 14

Mean LDL in Free Cholesterol Following Single IV Administration

Hours Postdose
[Plasma Concentration (mg/dL)]

| Dose | 0 | 0.5 | 1 | 2 | 4 | 8 | 12 | 24 | 48 | 72 | 168 | 336 | 504 |
|---|---|---|---|---|---|---|---|---|---|---|---|---|---|
| 0.25 mg/kg | 29.81 | 28.22 | 27.37 | 28.11 | 28.09 | 27.75 | 27.87 | 26.92 | 26.45 | 26.77 | 25.97 | 26.62 | 26.47 |
| 0.75 mg/kg | 35.40 | 34.45 | 33.57 | 34.57 | 35.95 | 33.29 | 32.73 | 32.20 | 30.10 | 28.61 | 30.89 | 34.30 | 31.50 |
| 2 mg/kg | 32.79 | 32.52 | 33.46 | 33.44 | 35.04 | 35.50 | 35.10 | 34.72 | 33.34 | 32.24 | 31.33 | 30.74 | 32.22 |
| 5 mg/kg | 29.12 | 27.62 | 27.55 | 30.07 | 32.23 | 32.72 | 32.09 | 32.71 | 32.24 | 31.97 | 29.05 | 28.55 | 31.61 |
| 10 mg/kg | 27.84 | 25.49 | 25.07 | 28.49 | 31.15 | 30.85 | 32.80 | 31.35 | 31.95 | 30.77 | 32.55 | 30.64 | 30.12 |
| 15 mg/kg | 28.85 | 26.58 | 26.15 | 30.35 | 34.87 | 36.44 | 33.71 | 33.11 | 33.07 | 30.62 | 30.42 | 30.75 | 29.15 |
| 30 mg/kg | 32.42 | 27.36 | 26.02 | 30.10 | 33.66 | 34.18 | 32.23 | 31.26 | 29.90 | 29.20 | 31.55 | 32.11 | 34.56 |
| 45 mg/kg | 33.10 | 31.36 | 32.31 | 35.69 | 42.10 | 46.54 | 47.40 | 52.93 | 44.68 | 41.67 | 33.72 | 34.22 | 35.45 |
| Placebo | 31.01 | 29.73 | 29.47 | 29.64 | 30.05 | 29.85 | 28.76 | 30.34 | 29.22 | 28.30 | 30.73 | 30.28 | 30.73 |

TABLE 15

Mean HDL in Free Cholesterol Following Single IV Administration

Hours Postdose
[Plasma Concentration (mg/dL)]

| Dose | 0 | 0.5 | 1 | 2 | 4 | 8 | 12 | 24 | 48 | 72 | 168 | 336 | 504 |
|---|---|---|---|---|---|---|---|---|---|---|---|---|---|
| 0.25 mg/kg | 8.16 | 7.59 | 7.50 | 7.47 | 7.33 | 7.56 | 7.70 | 6.86 | 6.97 | 7.14 | 7.21 | 7.33 | 8.36 |
| 0.75 mg/kg | 7.49 | 7.73 | 7.75 | 7.41 | 7.67 | 7.14 | 7.22 | 6.80 | 6.54 | 6.96 | 7.92 | 7.87 | 7.59 |
| 2 mg/kg | 9.82 | 10.74 | 11.95 | 10.97 | 9.99 | 9.93 | 10.17 | 9.16 | 8.62 | 8.47 | 9.68 | 9.26 | 9.99 |
| 5 mg/kg | 10.32 | 12.07 | 14.36 | 13.57 | 11.59 | 10.64 | 10.35 | 9.91 | 9.43 | 9.62 | 10.38 | 10.59 | 10.90 |
| 10 mg/kg | 8.92 | 13.10 | 18.47 | 18.47 | 14.54 | 9.96 | 10.07 | 8.52 | 8.30 | 7.96 | 9.01 | 8.23 | 8.17 |
| 15 mg/kg | 9.27 | 16.53 | 24.15 | 26.71 | 23.35 | 16.20 | 13.07 | 10.11 | 9.42 | 8.70 | 10.61 | 9.06 | 9.47 |
| 30 mg/kg | 8.65 | 22.95 | 38.46 | 49.67 | 47.70 | 36.89 | 25.73 | 13.31 | 8.87 | 7.73 | 7.64 | 7.70 | 8.27 |
| 45 mg/kg | 8.21 | 15.39 | 23.70 | 40.19 | 49.79 | 43.71 | 32.80 | 21.20 | 11.97 | 10.09 | 8.58 | 8.16 | 8.24 |
| Placebo | 8.49 | 8.30 | 8.39 | 8.76 | 8.75 | 8.71 | 8.53 | 7.82 | 7.41 | 7.38 | 8.51 | 8.94 | 8.94 |

Triglycerides:

Mean plasma triglyceride concentrations at each time point are presented in Table 16 below:

TABLE 16

Mean Plasma Triglyceride Concentrations by Time Following Single IV Administration Hours Postdose
[Plasma Concentration (mg/dL)]

| Dose | 0 | 0.5 | 1 | 2 | 4 | 8 | 12 | 24 | 48 | 72 | 168 | 336 | 504 |
|---|---|---|---|---|---|---|---|---|---|---|---|---|---|
| 0.25 mg/kg | 124.5 | 123.5 | 123.5 | 120.8 | 123.8 | 224.8 | 273.0 | 144.5 | 185.8 | 203.3 | 136.00 | 214.3 | 168.0 |
| 0.75 mg/kg | 125.5 | 127.3 | 131.5 | 133.5 | 138.0 | 191.8 | 205.0 | 148.8 | 163.3 | 184.0 | 177.5 | 180.8 | 180.8 |
| 2 mg/kg | 103.3 | 103.8 | 114.0 | 122.0 | 130.8 | 204.0 | 216.0 | 120.5 | 117.0 | 113.8 | 122.5 | 135.8 | 102.8 |
| 5 mg/kg | 90.0 | 84.0 | 90.3 | 108.5 | 127.0 | 194.0 | 132.0 | 105.5 | 89.0 | 93.0 | 88.5 | 122.8 | 70.0 |
| 10 mg/kg | 130.8 | 122.8 | 129.5 | 154.8 | 193.8 | 248.8 | 229.0 | 171.8 | 158.0 | 159.5 | 127.5 | 120.8 | 107.3 |
| 15 mg/kg | 109.3 | 113.5 | 129.0 | 168.3 | 236.8 | 382.3 | 364.5 | 180.5 | 170.8 | 157.3 | 124.8 | 88.8 | 132.0 |
| 30 mg/kg | 88.5 | 88.8 | 101.8 | 141.3 | 226.8 | 391.0 | 456.5 | 320.5 | 175.3 | 138.5 | 94.8 | 72.8 | 96.3 |
| 45 mg/kg | 156.5 | 159.0 | 169.0 | 212.0 | 328.3 | 592.8 | 745.3 | 705.8 | 491.5 | 408.5 | 236.0 | 181.3 | 216.5 |
| Placebo | 120.8 | 115.5 | 115.8 | 119.3 | 123.0 | 215.9 | 199.0 | 130.7 | 138.3 | 160.3 | 125.8 | 156.2 | 139.2 |

ApoA-I:

Change of subjects' baseline ApoA-I in mg/dL over time is shown in Table 17 below. The maximum changes in plasma ApoA-I are bolded for each dose.

TABLE 17

Mean Changes in Plasma ApoA-I by Time Following Single IV Administration

| Dose (mg/kg) | Hours Post Start of Infusion | | | | | | |
|---|---|---|---|---|---|---|---|
| | 0.5 | 1 | 2 | 4 | 8 | 12 | 24 |
| 0.25 | −1.8 | −3.9 | −1.5 | −1.1 | −1.8 | −1.5 | −5.4 |
| 0.75 | −0.9 | −3.8 | −2.5 | −1.9 | −0.7 | −5.2 | −3.1 |
| 2 | −2.3 | −3.8 | −2.1 | −0.8 | 0.1 | −3.7 | −2.4 |
| 5 | 0.5 | 6.8 | 8.1 | 5.3 | 2.6 | −2 | −0.6 |
| 10 | 8.6 | 17.8 | 17.8 | 13.9 | 7 | 5 | 0.3 |
| 15 | 16.3 | 32.5 | 30.9 | 27.4 | 21.3 | 10.3 | 8.5 |
| 30 | 36.1 | 71.8 | 68.3 | 61.8 | 45.8 | 24 | 15.4 |
| 45 | 23.3 | 48.6 | 93.8 | 93 | 71.3 | 39.2 | 14.9 |

Transaminase:

Mean values for liver alanine aminotransferase, or transaminase, levels, which are correlated with toxicity, are presented in Table 18 below. The normal range of alanine aminotransferase is 9 to 60 IU/L.

TABLE 18

Summary of Mean Values for Selected Alanine Aminotransferase by Treatment and Time Point

| Time Point | Placebo | Dose (mg/kg) | | | | | | |
|---|---|---|---|---|---|---|---|---|
| | | 0.25 | 0.75 | 2.0 | 5.0 | 10.0 | 15.0 | 30.0 | 45.0 |
| Baseline | 26.97 | 40.0 | 24.8 | 27.0 | 34.3 | 25.8 | 25.3 | 29.75 | 24.50 |
| 12 h | 25.84 | 40.8 | 21.0 | 25.0 | 33.5 | 26.5 | 25.3 | 35.25 | 33.25 |
| 24 h | 26.47 | 39.3 | 19.8 | 23.8 | 34.5 | 25.3 | 26.5 | 37.75 | 32.00 |
| 48 h | 26.16 | 39.5 | 21.8 | 22.3 | 35.8 | 23.5 | 29.0 | 36.25 | 28.50 |
| 72 h | 27.22 | 39.5 | 23.8 | 22.5 | 35.5 | 22.8 | 31.5 | 36.50 | 29.00 |
| 7 d | 27.97 | 40.3 | 25.3 | 24.8 | 33.5 | 20.0 | 43.3 | 35.75 | 27.00 |
| 14 d | 30.72 | 41.8 | 26.3 | 25.5 | 37.5 | 21.5 | 25.8 | 32.00 | 24.00 |
| 21 d | 29.13 | 49.7 | 25.0 | 27.0 | 32.3 | 22.3 | 34.3 | 28.50 | 23.25 |
| Placebo | | 0.25 | 0.75 | 2.0 | 5.0 | 10.0 | 15.0 | 30.0 | 45.0 |

Adverse Events:

A total of 7 (22%) subjects had adverse events. No subjects had adverse events considered by the investigator to be at least possibly related to study drug. There do not appear to be any dose-related trends in the occurrence of adverse events. No subjects had a serious adverse event, and no subject withdrew from the study due to an adverse events. Table 19 below provides a summary of adverse events by body system:

TABLE 19

Summary of Adverse Events by Body System [Number (%) of Subjects]

| Body System Adverse event | Placebo (N = 32) | Dose of Complex | | | | | | | |
|---|---|---|---|---|---|---|---|---|---|
| | | 0.25 mg/kg (N = 4) | 0.75 mg/kg (N = 4) | 2.0 mg/kg (N = 4) | 5.0 mg/kg (N = 4) | 10 mg/kg (N = 4) | 15 mg/kg (N = 4) | 30 mg/kg (N = 4) | 45 mg/kg (N = 4) |
| Gastrointestinal System | | | | | | | | | |
| Diarrhoea | 0 (0%) | 0 (0%) | 0 (0%) | 0 (0%) | 0 (0%) | 0 (0%) | 1 (25%) | 0 (0%) | 0 (0%) |
| Abdominal Pain/Cramping | 0 (0%) | 0 (0%) | 0 (0%) | 0 (0%) | 0 (0%) | 0 (0%) | 0 (0%) | 1 (25%) | 0 (0%) |
| Musculoskeletal System | | | | | | | | | |
| Toe Injury | 0 (0%) | 0 (0%) | 0 (0%) | 0 (0%) | 0 (0%) | 0 (0%) | 0 (0%) | 0 (0%) | 1 (25%) |
| Infections and Infestations | | | | | | | | | |
| Stye | 0 (0%) | 0 (0%) | 1 (25%) | 0 (0%) | 0 (0%) | 0 (0%) | 0 (0%) | 0 (0%) | 0 (0%) |
| Cold Symptoms | 1 (3%) | 0 (0%) | 0 (0%) | 0 (0%) | 0 (0%) | 0 (0%) | 0 (0%) | 0 (0%) | 0 (0%) |
| Nervous System | | | | | | | | | |
| Vasovagal Episode | 1 (3%) | 0 (0%) | 0 (0%) | 0 (0%) | 0 (0%) | 0 (0%) | 0 (0%) | 0 (0%) | 0 (0%) |
| Respiratory | | | | | | | | | |
| Cough | 1 (3%) | 0 (0%) | 0 (0%) | 0 (0%) | 0 (0%) | 0 (0%) | 0 (0%) | 0 (0%) | 0 (0%) |
| Sore Throat | 1 (3%) | 0 (0%) | 0 (0%) | 0 (0%) | 0 (0%) | 0 (0%) | 0 (0%) | 0 (0%) | 0 (0%) |

14.3. Conclusions

This Phase I study, which administered a preparation of a sterile solution comprising a negatively charged lipoprotein complex of Formula H in single IV doses of 0.25, 0.75 2.0, 5.0, 10.0, 15.0, 30.0 and 45.0 mg/kg, resulted in the following conclusions.

The preparation was well-tolerated at all doses in all subjects with an adverse event profile similar to that observed with placebo. The complex does not appear to affect clinical chemistry, hematology or coagulation parameters differently from placebo. No adverse effects on ECGs were observed. No antibodies to ApoA-I were detected following single dose administration.

Plasma concentrations of ApoA-I and sphingomyelin increased with dose: ApoA-I levels returned to baseline by 24 hours post-dose for doses up to 10 mg/kg and by 72 hours post-dose for doses above 10 mg/kg. Sphingomyelin levels returned to baseline by 24 hours post-dose for doses up to 5 mg/kg, by 72 hours post-dose for doses from 10 to 30 mg/kg, and by 7 days post-dose for subjects dosed with 45 mg/kg.

Cholesterol mobilization increased with increasing doses: Mobilization in the HDL fraction of free cholesterol was seen with doses as low as 2.0 mg/kg (mean 23% increase from baseline) and increased with dose. Triglyceride levels were transiently increased above levels seen with placebo at doses of 15 mg/kg and above.

In addition, administration of the complex did not significantly raise liver transaminase levels, and in all cases, the levels remained well within the normal range. This is in contrast to CSL-111, a reconstituted purified human ApoA-I from plasma complexed with soybean phosphtidylcholine, which has been seen to raise alanine amino-transferase levels up to more than 100-fold the upper normal limit in some patients, when administered at a dose of 80 mg/kg of patient weight. Tardif et al., 2007, JAMA 297:1675-1682.

Thus, the complexes of the disclosure can be administered at doses lower than those reported for other preparations that mimic HDL and still achieve clinically meaningful improvements in lipid parameters without detrimental side effects.

15. EXAMPLE 9: PHASE II CLINICAL STUDY OF APOA-I/SM/DPPG COMPLEXES IN THE TREATMENT OF SUBJECTS WITH ACUTE CORONARY SYNDROME

A clinical trial is conducted to further confirm the therapeutic benefit of low doses of negatively charged lipoprotein complexes of Formula H (ApoA-1, egg-sphingomyelin (egg-SM), and DPPG, in an apolipoprotein: phospholipid weight ratio of 1:2.7, with an egg-SM to DPPG weight ratio of 97:3) in the treatment of cardiovascular diseases. The ApoA-I is prepared by expression in CHO cells as described above in Examples 1, and the complexes are generated by the thermocycling methods of Example 4.

Subjects presenting with symptoms of ACS are eligible to be screened for this study. At the time of baseline catheterization, subjects need to have an adequate intravascular ultrasound (IVUS) evaluation of one "target" artery for IVUS which is not influenced by prior or present PCI, and the proximal 4 cm of the target artery should have a diameter stenosis between 0 and 50% by visual angiographic assessment, a reference diameter ≥2.5 mm and be free of filling defects suggestive of thrombus. Once the baseline IVUS has been evaluated by the IVUS Core Laboratory for overall quality, the presence of a suitable target vessel and the absence of technical factors which can preclude accurate reading of the IVUS images, the subject is randomized to receive an intravenous infusion, given over one hour, of placebo or one of three doses of the complexes (3, 6, or 12 mg/kg). Randomized subjects return at weekly intervals (i.e., every 7 to 11 days) for five additional infusions. End-of-treatment labs are drawn one week (5 to 9 days) after the last infusion. A follow-up IVUS is conducted approximately 3 weeks (14 to 35 days) after the last infusion. A follow-up visit occurs approximately 6 months (+/−2 weeks) after the last infusion to collect samples for Anti-ApoA1 antibody testing and to monitor for major adverse cardiac event (MACE) endpoints.

The primary endpoint is the nominal change in total plaque volume in a 30 mm segment of the target coronary artery assessed by three-dimensional IVUS. Other efficacy measurements include the percent change in plaque volume and the change in percent atheroma volume in the target 30 mm segment, the change in total vessel volume in the target 30 mm segment, as well as changes in plaque, lumen and total vessel volumes from baseline to follow-up in anatomically comparable 5 mm segments centered on the site with the smallest plaque burden at baseline, and the largest plaque burden at baseline on three-dimensional IVUS. The percent change in plaque volume is calculated as the nominal change divided by the baseline value, multiplied by 100. Percent atheroma (obstructive) volume is computed by dividing plaque volume by elastic external membrane (EEM) volume and then multiplying by 100.

16. SPECIFIC EMBODIMENTS, CITATION OF REFERENCES

Various aspects of the present disclosure are described in the embodiments set forth in the following numbered paragraphs.

1. A lipoprotein complex comprising an apolipoprotein fraction and a lipid fraction, wherein said lipid fraction consists essentially of 95 to 99 weight % neutral phospholipid and 1 to 5 weight % negatively charged phospholipid, wherein the apolipoprotein fraction-to-phospholipid fraction ratio is in the range of about 1:2.7 to about 1:3 by weight.

2. The lipoprotein complex of embodiment 1 in which the apolipoprotein is selected from preproapoliprotein, preproApoA-I, proApoA I, ApoA-I, preproApoA-II, proApoA II, ApoA II, preproApoA-IV, proApoA-IV, ApoA-IV, ApoA-V, preproApoE, proApoE, ApoE, preproApoA $I_{Milano}$, proApoA-$I_{Milano}$, ApoA-$I_{Milano}$, preproApoA-$I_{Paris}$, proApoA-$I_{Paris}$, and ApoA-$I_{Paris}$ and mixtures thereof.

3. The lipoprotein complex of embodiment 2 in which the apolipoprotein consists essentially of ApoA I having at least 90% or at least 95% sequence identity to a protein corresponding to amino acids 25 to 267 of SEQ ID NO:1.

4. The lipoprotein complex of embodiment 3 in which the apolipoprotein comprises a monomer, dimer and/or tetramer.

5. The lipoprotein complex of any one of embodiments 1 to 4 in which the apolipoprotein comprises an ApoA-I peptide mimetic.

6. The lipoprotein complex of any one of embodiments 1 to 5, wherein the apolipoprotein fraction-to-phospholipid fraction ratio is 1:2.7 by weight.

7. The lipoprotein complex of any one of embodiments 1 to 6, in which the lipid:apolipoprotein molar ratio ranges from about 1:105 to about 110, where the apolipoprotein value is expressed in ApoA-I equivalents.

8. The lipoprotein complex of embodiment 7, in which the lipid:apolipoprotein molar ratio is 1:108.

9. The lipoprotein complex any one of embodiments 1 to 8, wherein the neutral lipid is natural sphingomyelin or synthetic sphingomyelin.

10. The lipoprotein complex of embodiment 9 in which the sphingomyelin is egg-sphingomyelin.

11. The lipoprotein complex of embodiment 9 which is made from a sphingomyelin that is at least 95% pure.

12. The lipoprotein complex of any one of the embodiments 1 to 11, wherein said lipid fraction consists essentially of 96 to 98 weight % neutral phospholipid and 2 to 4 weight % negatively charged phospholipid.

13. The lipoprotein complex of embodiment 12, wherein said lipid fraction consists essentially of 97 weight % neutral phospholipid and 3 weight % negatively charged phospholipid.

14. The lipoprotein complex of embodiment 13, in which the negatively charged phospholipid comprises phosphatidylglycerol.

15. The lipoprotein complex of embodiment 14 in which the negatively charged phospholipid comprises or consists of a salt of 1,2-dipalmitoyl-sn-glycero-3-[phospho-rac-(1-glycerol)] (DPPG).

16. The lipoprotein complex of embodiment 15 in which the salt is a sodium, or potassium salt.

17. The lipoprotein complex of any one of the embodiments 1 to 16 in which the acyl chains of the neutral and/or negatively charged phospholipids are each, independently of one another, selected from a saturated or a mono-unsaturated hydrocarbon containing 12 to 26, 14 to 26, or 16 to 26 carbon atoms.

18. The lipoprotein complex of embodiment 17 in which each acyl chain of the neutral and/or negatively charged phospholipid are the same.

19. The lipoprotein complex of embodiment 17 in which each acyl chain of the neutral and/or negatively charged phospholipid is different.

20. The lipoprotein complex of embodiment 17 in which the acyl chains of the neutral and negatively charged phospholipid contain the same number of carbon atoms.

21. The lipoprotein complex of embodiment 17 in which the acyl chains of the neutral and negatively charged phospholipid have different degrees of saturation.

22. The lipoprotein complex of embodiment 17 in which the acyl chains of the neutral and negatively charged phospholipid contain 16 carbon atoms.

23. The population of lipoprotein complexes according to any one of embodiments 1 to 22.

24. A population of lipoprotein complexes, each comprising a lipid fraction and an apolipoprotein fraction consisting essentially of an apolipoprotein A-I ("ApoA-I"), wherein the population is characterized by one, two, three, four, five, six, seven, eight, nine or all ten of the following characteristics:
   (a) at least 80%, at least 85%, at least 90%, or at least 95% by weight over ApoA-I in said population is in mature form;
   (b) no more than 20%, no more than 15%, no more than 10% or no more than 5% by weight of ApoA-I in said population is in immature form;
   (c) the population contains no more than 100 picograms, no more than 50 picograms, no more than 25 picograms, no more than 10 picograms or no more than 5 picograms host cell DNA per milligram of ApoA-I;
   (d) the population contains no more than 500 nanograms, no more than 200 nanograms, no more than 100 nanograms, no more than 50 nanograms, or no more than 20 nanograms host cell protein per milligram of ApoA-I;
   (e) no more than 20%, no more than 15%, no more than 10% or no more than 5% by weight of ApoA-I in the population is in truncated form;
   (f) no more than 20%, no more than 15%, no more than 10%, no more than 5%, no more than 3%, no more than 2% or no more than 1% of each of methionine 112 and methionine 148 in said ApoA-I in said population is oxidized;
   (g) at least 80%, at least 85%, at least 90% or at least 90% of the lipoprotein complexes are in the form of particles of 4 nm to 15 nm or 6 nm to 15 nm in size as measured by gel permeation chromatography ("GPC") or dynamic light scattering ("DLS");
   (h) the population contains no more than 1 EU, no more than 0.5 EU, no more than 0.3 EU or no more than 0.1 EU of endotoxin per milligram of ApoA-I; and
   (i) no more than 10%, no more than 5%, no more than 4%, no more than 3%, no more than 2% or no more than 1% of the amino acids in the ApoA-I in said population is deamidated.

25. The population of embodiment 24 in which no more than 15%, or no more than 10%, no more than 5% or no more than 2% by weight of the lipid in the lipid fraction in said complexes is cholesterol.

26. The population of embodiment 25 which does not contain cholesterol.

27. The population of any one of embodiments 24 to 26 in which at least 85%, at least 90%, or at least 95% of the protein is mature ApoA-I protein.

28. The population of embodiment 27 in which less than 15%, less than 10%, or less than 10% of the protein is oxidized, deamidated, and/or truncated species.

29. The population of any one of embodiments 24 to 28 in which the lipoprotein complexes are at least 90%, at least 92.5%, at least 95%, at least 96%, at least 97% or at least 98% pure.

30. The population of any one of embodiments 24 to 29 in which the lipoprotein complexes are at least 80%, at least 85%, at least 90% or at least 95% homogeneous, as reflected by a single peak in gel permeation chromatography.

31. The population of embodiment 30 in which at least 80%, at least 85%, at least 90% or at least 95% of the lipoprotein complexes range 4 nm to 12 nm in size, 6 nm to 12 nm in size, or 8 nm to 12 nm in size, as measured by GPC or DLS.

32. The population of any one of embodiments 24 to 31 in which at least 95%, at least 96%, at least 97%, at least 98% or at least 99% of the protein is in complexes.

33. The population of any one of embodiments 24 to 32 which does not contain cholate.

34. The population of any one of embodiments 24 to 33 which does not contain any detergent.

35. The population of any one of embodiments 24 to 34 which contains less than 200 ppm, less 100 ppm or less than 50 ppm of non-aqueous solvent.

36. The population of any one of embodiments 24 to 35 wherein said ApoA-I is a human ApoA-I protein.

37. The population of any one of embodiments 24 to 36 wherein said ApoA-I is a recombinant ApoA-I.

38. The population of any one of embodiments 24 to 37 wherein the ApoA-I has an amino acid sequence with at least 90% or at least 95% sequence identity to a protein corresponding to amino acids 25 to 267 of SEQ ID NO:1.

39. The population of any one of embodiments 24 to 38 wherein said lipid fraction consists essentially of 95 to 99 weight % neutral phospholipid and 1 to 5 weight % negatively charged phospholipid.

40. The population embodiment 39 wherein said lipid fraction consists essentially of 96 to 98 weight % neutral phospholipid and 2 to 4 weight % negatively charged phospholipid.

41. The population of any one of embodiments 24 to 40, wherein said lipid fraction consists essentially of 97 weight % neutral phospholipid and 3 weight % negatively charged phospholipid.

42. The population of embodiment 41, wherein the neutral lipid is natural sphingomyelin or synthetic sphingomyelin, optionally wherein the lipid has a peroxide value of less than 5 meq O/kg, less than 4 meq O/kg, less than 3 meq O/kg, or less than 2 meq O/kg.

43. The population of embodiment 42 in which the sphingomyelin is egg-sphingomyelin.

44. The population of embodiment 42 which is made from a sphingomyelin that is at least 95% pure.

45. The population of of any one of embodiments 41 to 44, wherein the negatively charged phospholipid comprises phosphatidylglycerol.

46. The population of embodiment 45 in which the negatively charged phospholipid comprises or consists of a salt of 1,2-dipalmitoyl-sn-glycero-3-[phospho-rac-(1-glycerol)] (DPPG).

47. The population of embodiment 46 in which the salt is a sodium, or potassium salt.

48. The population of any one of embodiments 24 to 47 in which the acyl chains of the neutral and/or negatively charged phospholipids are each, independently of one another, selected from a saturated or a mono-unsaturated hydrocarbon containing 12 to 26, 14 to 26, or 16 to 26 carbon atoms.

49. The population of embodiment 48 in which each acyl chain of the neutral and/or negatively charged phospholipid are the same.

50. The population of embodiment 48 in which each acyl chain of the neutral and/or negatively charged phospholipid is different.

51. The population of embodiment 48 in which the acyl chains of the neutral and negatively charged phospholipid contain the same number of carbon atoms.

52. The population of embodiment 48 in which the acyl chains of the neutral and negatively charged phospholipid have different degrees of saturation.

53. The population of embodiment 48 in which the acyl chains of the neutral and negatively charged phospholipid contain 16 carbon atoms.

54. The population of any one of embodiments 24 to 41 which has an apolipoprotein fraction:lipid fraction molar ratio ranging from 1:80 to 120, from 1:85 to 1:110, or from 1:100 to 1:115, where the apolipoprotein value is expressed in ApoA-I equivalents.

55. The population of embodiment 54 which has an apolipoprotein fraction:lipid fraction molar ratio ranging from 1:80 to 1:90, from 1:90 to 1:100, from 1:100 to 1:110 or from 1:105 to 1:110, where the apolipoprotein value is expressed in ApoA-I equivalents.

56. The population of any one of embodiments 24 to 55 which has an apolipoprotein fraction-to-phospholipid fraction ratio ranging from 1:2 to about 1:3 by weight.

57. The population of any one of embodiments 24 to 40, wherein the apolipoprotein fraction-to-phospholipid fraction ratio ranges from 1:2.1 to 1:2.7 by weight.

58. The population of embodiment 57 wherein the apolipoprotein fraction-to-phospholipid fraction ratio is 1:2.7 by weight.

59. A pharmaceutical composition comprising or consisting essentially of a lipoprotein complex according to any one of embodiments 1 to 22 or a population of lipoprotein complexes according to any one of embodiments 23 to 58, and one or more pharmaceutically acceptable carriers, diluents and/or excipients.

60. A mammalian host cell engineered to express an ApoA-I protein, said ApoA-I protein comprising an amino acid sequence having at least 95% identity to positions 25 to 267 of SEQ ID NO:1.

61. The mammalian host cell of embodiment 60, wherein the protein is secreted into the medium when the host cell is cultured.

62. The mammalian host cell of embodiment 60 or embodiment 61, wherein the protein further comprises the signal sequence MKAAVLTLAVLFLTGSQA.

63. The mammalian host cell of any one of embodiments 60 to 62, wherein the protein further comprises the propeptide sequence RHFWQQ.

64. The mammalian host cell according to any one of embodiments 60 to 63, which is Chinese hamster ovary (CHO), CHO-S, CHO-K1, VERO, BHK, BHK 570, HeLa, COS-1, COS-7, MDCK cells, 293, 3T3, myeloma, PC12 and W138.

65. The mammalian host cell according to embodiment 64, which is a CHO cell. 66. The mammalian host cell according to embodiment 65, which is a CHO-S cell or a CHO-K1 cell.

67. The mammalian host cell according to any one of embodiments 60 to 66 which is capable of producing at least 0.5, 1, 2, 3, or 4 g/L of said ApoA-1 protein in culture.

68. The mammalian host cell according to embodiment 67, which is capable of producing up to 4, 5, 6, 7, 8, 9, 10, 12, 15 or 20 g/L of said ApoA-I protein in culture.

69. The mammalian host cell of embodiment 67 or embodiment 68, wherein the culture is a large scale culture.

70. The mammalian host cell of embodiment 69 wherein said large scale culture is at least 15 liters, at least 20 liters, at least 25 liters, or at least 30 liters.

71. The mammalian host cell of embodiment 70, wherein said large scale culture is about 50 liters, about 100 liters, about 200 liters or about 300 liters.

72. The mammalian host cell according to any one of embodiments 60 to 71, which comprises at least about 5 copies of a nucleotide sequence encoding said ApoA-I protein.

73. The mammalian host cell according to embodiment 72, wherein each nucleotide sequence is operably linked to a promoter.

74. The mammalian host cell according to embodiment 73, wherein the promoter is a cytomegalovirus promoter.

75. The mammalian host cell according to embodiment 74, wherein the promoter is an immediate early simian cytomegalovirus promoter.

76. The mammalian host cell according to any one of embodiments 60 to 75 which secretes a mature ApoA-I protein comprising or consisting of an amino amino sequence corresponding to amino acids 25 to 267 of SEQ ID NO:1.

77. A mammalian cell culture comprising a plurality of the mammalian host cell according to any one of embodiments 60 to 76.

78. The mammalian cell culture according to embodiment 77, which comprises at least about 0.5 g/L of mature ApoA-I protein comprising or consisting of an amino amino sequence corresponding to amino acids 25 to 267 of SEQ ID NO:1.

79. The mammalian cell culture according to embodiment 78, in which at least 80%, at least 85%, or at least 90% of said mature ApoA-I protein lacks a signal sequence.

80. The mammalian cell culture according to embodiment 78, in which at least 80%, at least 85%, or at least 90% of said mature ApoA-I protein lacks a signal sequence and a propeptide sequence.

81. The mammalian cell culture according to any one of embodiments 78 to 80, in which at least 80%, at least 85% or at least 90% of said mature ApoA-I protein is not truncated, oxidized or deamidated.

82. A method of producing mature, biologically active ApoA-1 protein, comprising culturing the mammalian host cell according any one of embodiments 60 to 76 under conditions in which the ApoA-I protein is expressed and secreted.

83. The method of embodiment 82, further comprising recovering from the supernatant of said cultured mammalian host cell said mature, biologically active ApoA-1 protein.

84. The method according to embodiment 82 or embodiment 83, further comprising purifying ApoA-I protein.

85. A pharmaceutical composition comprising a therapeutically effective amount of an ApoA-I protein obtained or obtainable by the method of embodiment 84.

86. The pharmaceutical composition of embodiment 85 in which the ApoA-I protein is complexed with lipid.

87. A method for minimizing oxidation products in a pharmaceutical composition comprising ApoA-I, comprising manufacturing said pharmaceutical composition under an inert gas.

88. The method of embodiment 87, wherein the inert gas is nitrogen, helium or argon.

89. The method of embodiment 87 or embodiment 88, wherein the pharmaceutical composition is a pharmaceutical composition of a lipoprotein complex comprising ApoA-I.

90. A method for preparing lipoprotein complexes, comprising:
 (a) cooling a starting suspension comprising a lipid component and a protein component from a temperature in a first temperature range to a temperature in a second temperature range,
 wherein said lipid component consists essentially of particles of lipids and wherein said protein component consists essentially of lipid-binding peptides and/or lipid-binding proteins;
 (b) heating the cooled suspension of (a) from a temperature in said second temperature range to a temperature in said first temperature range;
 (c) cooling said heated suspension of (b) from a temperature in said first temperature range to a temperature in said second temperature range; and
 (d) repeating steps (b) and (c) at least once,
 thereby forming lipoprotein complexes.

91. The method of embodiment 90, wherein step (c) comprises repeating steps (a) and (b) until at least 75%, at least 80%, at least 85%, at least 90%, at least 95%, at least 97%, at least 98%, or at least 99% of said lipid component and/or said protein component is in complexed form.

92. The method of embodiment 90 or embodiment 91, wherein step (c) comprises repeating steps (a) and (b) until lipoprotein complexes of least 75%, at least 80%, at least 85%, at least 90%, at least 95%, at least 97%, at least 98%, or at least 99% homogeneity are obtained.

93. The method of any one of embodiments 90 to 92, wherein step (d) comprises repeating steps (b) and (c) at least three, at least four, or at least five times.

94. The method of any one of embodiments 90 to 93, wherein step (c) comprises repeating steps (b) and (c) up to six, up to eight or up to ten times.

95. The method of any one of embodiments 90 to 94, wherein, following step (a), the suspension is maintained in the second temperature range for at least 1, at least 2, at least 3, at least 4 or at least 5 minutes prior to said heating step (b).

96. The method of any one of embodiments 90 to 95, wherein, following step (a), the suspension is maintained within the second temperature range for up to 6, up to 8, up to 10, up to 20 minutes, up to 30 minutes or up to 1 hour prior to said heating step (b).

97. The method of any one of embodiments 90 to 96, wherein, following step (b), the suspension is maintained within the first temperature range for at least 1, at least 2, at least 3, at least 4 or at least 5 minutes prior to said cooling step (c).

98. The method of any one of embodiments 90 to 97, wherein, following step (b), the suspension is maintained within the first temperature range for up to 6, up to 8, up to 10, up to 20 minutes, up to 30 minutes or up to 1 hour prior to said cooling step (c).

99. The method of any one of embodiments any one of embodiments 90 to 98, wherein the resulting lipoprotein complexes are not subject to centrifugation.

100. The method of any one of embodiments 90 to 99, wherein the lipid component and the protein component represent the majority of lipids and proteins and peptides, respectively, in said starting suspension of step (a).

101. The method of any one of embodiments 90 to 100, wherein the lipid component represents at least 60%, at least 70%, at least 80% or at least 90% of lipids in said starting suspension of step (a).

102. The method of any one of embodiments 90 to 101, wherein the protein component represents at least 60%, at least 70%, at least 80% or at least 90% of proteins and peptides in said starting suspension of step (a).

103. The method of any one of embodiments 90 to 102, wherein up to 5%, up to 10%, up to 15% or up to 20% of lipids in said suspension are pre-complexed to the protein component in the starting suspension of step (a).

104. The method of any one of embodiments 90 to 103, wherein said first temperature range includes temperatures no less than 10 degrees below and no more than 15, no more than 10, or no more than 5 degrees above the transition temperature of said protein component.

105. The method of any one of embodiments 90 to 104, wherein said second temperature range includes temperatures no less than 5 or no less than 10 degrees below and no more than 5 degrees above the transition temperature of said lipid component.

106. The method of any one of embodiments 90 to 105, wherein said first temperature ranges spans no more than 1° C., 2° C., 3° C., 4° C., 5° C., 7° C. or 10° C.

107. The method of any one of embodiments 90 to 106, wherein said second temperature ranges spans no more than 1° C., 2° C., 3° C., 4° C., 5° C., 7° C. or 10° C.

108. The method of any one of embodiments 90 to 107 further comprising the step of forming said starting suspension.

109. The method of embodiment 108, wherein forming said suspension comprises the step of combining a suspension of lipid particles and a solution of said lipid-binding peptides and/or lipid-binding proteins, each preheated at a temperature in said first range.

110. The method of embodiment 108, wherein forming said suspension comprises the step of mixing a population of lipid particles and said lipid-binding peptides and/or lipid-binding proteins pre-complexed with lipid, each preheated at a temperature in said first range.

111. The method of embodiment 110, wherein lipid pre-complexed with lipid-binding peptides and/or lipid-binding proteins is no more than 5%, no more than 10%, no more than 15%, or no more than 20% of the total lipid in said starting suspension.

112. The method of any one embodiments 109 to 111, wherein the solution of lipids is a solution of homogenized lipids.

113. The method of embodiment 112, further comprising prior to said combining step the step of forming a solution of homogenized lipids using high pressure homogenization.

114. The method of embodiment 113, wherein said high pressure homogenization is at a pressure of over 1500 bars, over 1800 bars, or over 2000 bars.

115. The method of embodiment 114, wherein said high pressure homogenization is performed at a pressure of 1900 to 2500 bars.

116. The method of any one of embodiments 90 to 115, in which the lipid component consists essentially of lipid particles, said lipid particles being:
  (i) at least 45 nm, at least 50 nm, at least 55 nm or at least 60 nm in size, as measured by DLS; and
  (ii) up to 65 nm, up to 70 nm, up to 75 nm, up to 80 nm in size, up to 100 nm, up to 120 nm, up to 150 nm, up to 200 nm, up to 250 nm, up to 300 nm, up to 500 nm in size as measured by DLS.

117. The method of embodiment 116, said the lipid particles being up to 65 nm, up to 70 nm, up to 75 nm, or up to 80 nm in size as measured by DLS.

118. The method of embodiment 116, said the lipid particles being up to 100 nm, up to 120 nm, up to 150 nm, up to 200 nm, up to 250 nm, up to 300 nm, up to 500 nm in size as measured by DLS.

119. The method of any one of embodiments 90 to 116, wherein steps (b) and (c) are repeated until lipoprotein complexes of 4 nm to 15 nm, 5 nm to 15 nm, 6 nm to 15 nm, or 8 nm to 15 nm are obtained.

120. The method of any one of embodiments 90 to 116, wherein steps (b) and (c) are repeated until lipoprotein complexes of 5 nm to 12 nm, 6 nm to 12 nm in size, or 8 nm to 12 nm are obtained.

121. The method of any one of embodiments 90 to 120, in which one, more than one or all steps are carried out under an inert gas.

122. The method of embodiment 121, wherein the inert gas is nitrogen.

123. The method of any one of embodiments 90 to 122, wherein said protein component comprises or consists of lipid-binding proteins.

124. The method of embodiment 123, wherein said lipid-binding proteins are ApoA-1, ApoA-II, ApoA-IV, ApoC-I, ApoC-II, ApoC-III, ApoE or mixtures thereof.

125. The method of any one of embodiments 90 to 122, wherein said protein component comprises or consists of lipid-binding peptides.

126. The method of embodiment 125, wherein said lipid binding peptides are analogues of ApoA-I, ApoA-II, ApoA-IV, ApoC-I, ApoC-II, ApoC-III, ApoE or mixtures thereof.

127. The method of any one of embodiments 90 to 126, wherein said lipid component comprises or consists of natural lipids, synthetic lipids, or a mixture thereof.

128. The method of embodiment 127, wherein said lipid component comprises or consists of ether phospholipids, short chain phospholipids, cholesterol, cholesterol derivatives, phosphatidylcholines, phosphatidylethanolamines, phosphatidylserines, phosphatidylinositols, sphingolipids, phosphatidylglycerols, gangliosides, and/or cerebrosides.

129. The method of embodiment 128, wherein said lipid component comprises or consists of egg phosphatidylcholine, soybean phosphatidylcholine, dipalmitoylphosphatidylcholine, dimyristoylphosphatidylcholine, distearoylphosphatidylcholine, 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine, dioleophosphatidylethanolamine, dilauroylphosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, sphingomyelin, dipalmitoylsphingomyelin, distearoylsphingomyelin, dipalmitoylphosphatidylglyercol salt, acid, galactocerebroside, dilaurylphosphatidylcholine, (1,3)-D-mannosyl(1,3)diglyceride, aminophenylglycoside, and/or 3-cholesteryl-6'-(glycosylthio)hexyl ether glycolipids.

130. The method of any one of embodiments 90 to 126, wherein said lipid component comprises neutral lipids.

131. The method of embodiment 130, wherein said lipid component is predominantly neutral lipids.

132. The method of embodiment 130 or embodiment 131, wherein said neutral lipids comprise sphingomyelins.

133. The method of embodiment 132, wherein said neutral lipids are predominantly sphingomyelins.

134. The method of embodiment 132 or embodiment 133 in which the sphingomyelins comprise or consist of D-erythrose-sphingomyelin and/or D-erythrose dihydrosphingomyelin.

135. The method of any one of embodiments 130 to 135, wherein said starting suspension further comprises negatively charged phospholipids.

136. The method of embodiment 135, wherein said negatively charged phospholipids comprise or consist of phosphatidylglycerols.

137. The method of embodiment 136, wherein said phosphatidylglycerols have C16:0 acyl chains.

138. The method of embodiment 136 or embodiment 137, wherein said phosphatidylglycerols comprise or consist of a salt of 1,2-dihexadecanoyl-sn-glycero-3-phospho-(1'-rac-glycerol).

139. The method of embodiment 138, wherein the salt is a sodium salt.

140. The method of any one of embodiments 90 to 139, wherein lipid:protein molar ratio in said starting suspension is from about 2:1 to about 200:1.

141. The method of embodiment 140 in which the lipid:protein molar ratio in said starting suspension is from about 10:1 to about 125:1.

142. The method of embodiment 140 in which the lipid:protein molar ratio in said starting suspension is from about 10:1 to about 150:1.

143. The method of embodiment 140 in which the lipid:protein molar ratio in said starting suspension is from about 75:1 to 125:1.

144. The method of any one of embodiments 90 to 143, wherein the starting suspension contains negatively charged lipid, neutral lipid and lipid-binding peptides in a molar ratio ranging from 2-6 (negatively charged lipid): 90-120 (neutral lipid): 1 (lipid-binding peptide, lipid binding protein or mixtures thereof).

145. The method of any one of embodiments 90 to 144, wherein said first temperature range is 55° C. to 60° C.

146. The method of any one of embodiments 90 to 145, wherein said second temperature range is between 35° C. and 40° C.

147. The method of any one of embodiments 90 to 146, which further comprises the step of lyophilizing the resulting lipoprotein complexes.

148. The method of embodiment 147, further comprising the step of adding an isotonicity agent prior to lyophilization.

149. A pharmaceutical composition comprising a population of lipoprotein complexes, wherein said lipoprotein complexes are:
  (a) 4 nm to 15 nm in size or 6 nm to 15 nm in size, or between 5 and 12 nm in size, or between 8 and 10 nm in size, as measured by GPC or DLS; and
  (b) at least 75%, at least 80%, at least 85%, at least 90%, at least 95%, at least 97%, at least 98%, at or at least 99% homogeneous, as reflected by a single peak in gel permeation chromatography.

150. A method for making a pharmaceutical composition, comprising:
  (a) preparing a population of lipoprotein complexes according to the method of any one of embodiments 90 to 146; and
  (b) combining said population of lipoprotein complexes with one or more pharmaceutically acceptable excipients.

151. The method of embodiment 150, wherein the pharmaceutical composition is prepared under an inert gas.

152. The method of embodiment 151, wherein the inert gas is nitrogen, helium or argon.

153. The method of any one of embodiments 150 to 152, further comprising the step of lyophilizing the pharmaceutical composition.

154. The method of any one of embodiments 150 to 152, further comprising the step of aliquoting the pharmaceutical composition into individual unit doses.

155. The method of embodiment 154, further comprising the step of lyophilizing the individual unit doses.

156. A method for making a pharmaceutical composition, comprising reconstituting a lyophilized preparation of lipoprotein complexes according to the method of embodiment 147 or made by the method of embodiment 153 or embodiment 155.

157. The method of embodiment 156, further comprising combining the reconstituted lipoprotein complexes with one or more pharmaceutically acceptable excipients.

158. The method of embodiment 156 or embodiment 157, further comprising the step of aliquoting the pharmaceutical composition into individual unit doses.

159. A liquid pharmaceutical composition made by the method of embodiment 150 or embodiment 156.

160. A lyophilized pharmaceutical composition made by the method of embodiment 153.

161. A liquid unit dosage form made by the method of embodiment 158.

162. A liquid unit dosage form comprising a therapeutically effective amount of the pharmaceutical composition of embodiment 149.

163. A dry unit dosage form made by the method of embodiment 155.

164. A method for treating a dyslipidemic disorder, comprising administering to a subject in need thereof a therapeutically effective amount of
  (a) a lipoprotein complex according to any one of embodiments 1 to 22;
  (b) a population of lipoprotein complexes according to any one of embodiments 23 to 58;
  (c) a pharmaceutical composition according to any one of embodiments 59, 149, and 159;
  (d) a therapeutically effective amount of lipoprotein complexes made by the method of any one of embodiments 90 to 148;
  (e) a unit dosage form according to embodiment 161 or embodiment 162;
  (f) a lipoprotein complex that does not result in liver enzyme elevation following a single administration of up to 45 mg/kg to a healthy volunteer;
  (g) a lipoprotein complex that does not result in liver enzyme elevation following two, three, four, five or six administrations to a human subject;
  (h) a lipoprotein complex that does not result in liver enzyme elevation following a single administration to a human subject in a dose of 1 mg/kg to 20 mg/kg;
  (i) a lipoprotein complex that does not result in liver enzyme elevation following two, three, four, five or six administrations to a human subject, each administration in a dose of 1 mg/kg to 20 mg/kg;
  (j) a lipoprotein complex that does not result in more than two-fold triglyceride increase following a single administration of up to 20 mg/kg to a healthy volunteer;
  (k) a lipoprotein complex that does not result in more than two-fold triglyceride increase following two, three, four, five or six administrations to a human subject;
  (l) a lipoprotein complex that does not result in more than two-fold triglyceride increase following a single administration to a human subject in a dose of 1 mg/kg to 20 mg/kg; or
  (m) a lipoprotein complex that does not result in more than two-fold triglyceride increase following two, three, four, five or six administrations to a human subject, each administration in a dose of 1 mg/kg to 20 mg/kg.

165. The method of embodiment 164, further comprising repeating said administration.

166. The method of embodiment 165, wherein the administration is repeated at an interval of 6 days to 12 days.

167. The method of embodiment 166, wherein the administration is weekly.

168. The method of any one of embodiments 165 to 167, wherein the administration occurs over a period of one month, five weeks, six weeks, two months, three months, six months, one year, 2 years, 3 years, or longer.

169. The method of any one of embodiments 165 to 167, wherein the administration occurs once, twice, three times, four times, five times, six times, seven times, eight times, nine times, ten times, eleven times, or twelve times.

170. The method of any one of embodiments 164 to 169 wherein the administration is intravenous.

171. The method of embodiment 170 wherein the administration is by infusion.

172. The method of embodiment 171, wherein the infusion occurs over a period of one to four hours.

173. The method of embodiment 171, wherein the infusion occurs over a period of up to 24 hours.

174. The method of any one of embodiments 170 to 173 wherein the amount of the lipoprotein complex ranges from about 0.25 mg/kg ApoA-I equivalents to about 30 mg/kg ApoA-I equivalents per administration.

175. The method of embodiment 174 wherein the amount of the lipoprotein complex ranges from about 1 mg/kg ApoA-I equivalents to about 15 mg/kg ApoA-1 equivalents per administration.

176. The method of embodiment 175 wherein the amount of the lipoprotein complex ranges from about 2 mg/kg ApoA-I equivalents to about 12 mg/kg ApoA-I equivalents per administration.

177. The method of embodiment 176 in which the amount of lipoprotein complex is about 3 mg/kg ApoA-I equivalents per administration.

178. The method of embodiment 176 in which the amount of lipoprotein complex is about 6 mg/kg ApoA-I equivalents per administration.

179. The method of embodiment 176 in which the amount of lipoprotein complex is about 12 mg/kg ApoA-I equivalents per administration.

180. A method for treating a dyslipidemic disorder, comprising:
(a) administering to a subject with an initial dose of 1 mg kg to 12 mg/kg of:
(i) a lipoprotein complex according to any one of embodiments 1 to 22;
(ii) a population of lipoprotein complexes according to any one of embodiments 23 to 58;
(iii) a pharmaceutical composition according to any one of embodiments 59, 149, and 159;
(iv) a therapeutically effective amount of lipoprotein complexes made by the method of any one of embodiments 90 to 148;
(v) a unit dosage form according to embodiment 161 or embodiment 162;
(vi) a lipoprotein complex that does not result in liver enzyme elevation following a single administration of up to 45 mg/kg to a healthy volunteer;
(vii) a lipoprotein complex that does not result in liver enzyme elevation following two, three, four, five or six administrations to a human subject;
(viii) a lipoprotein complex that does not result in liver enzyme elevation following a single administration to a human subject in a dose of 1 mg/kg to 20 mg/kg;
(ix) a lipoprotein complex that does not result in liver enzyme elevation following two, three, four, five or six administrations to a human subject, each administration in a dose of 1 mg/kg to 20 mg/kg;
(x) a lipoprotein complex that does not result in more than two-fold triglyceride increase following a single administration of up to 20 mg/kg to a healthy volunteer;
(xi) a lipoprotein complex that does not result in more than two-fold triglyceride increase following two, three, four, five or six administrations to a human subject;
(xii) a lipoprotein complex that does not result in more than two-fold triglyceride increase following a single administration to a human subject in a dose of 1 mg/kg to 20 mg/kg; or
(xiii) a lipoprotein complex that does not result in more than two-fold triglyceride increase following two, three, four, five or six administrations to a human subject, each administration in a dose of 1 mg/kg to 20 mg/kg;
(b) determining whether the subject's triglyceride, VLDL-cholesterol and/or VLDL-triglyceride is elevated to more than two fold 4, 8, 12, 24, 48, 72, 168, 336 or 504 hours after said administration; and
(c) if the subject's triglyceride, VLDL-cholesterol and/or VLDL-triglyceride is elevated to more than two fold of the pre-dosing levels, repeating said administration but at a lower dose, and if the subject's triglyceride, VLDL-cholesterol and/or VLDL-triglyceride is not elevated to more than two fold of the pre-dosing levels, then repeating said administration at an equivalent or greater dose.

181. The method of any one of embodiments 165 to 180, wherein said subject has or is susceptible to hyperlipidemia or cardiovascular.

182. The method of embodiment 181 wherein the patient is has or is susceptible to hyperlipidemia and said hyperlipidemia is hypercholesterolemia.

183. The method of embodiment 181 wherein the patient is has or is susceptible to cardiovascular disease and wherein the cardiovascular disease is atherosclerosis, stroke, myocardial infarction, acute coronary syndrome, angina pectoris, intermittent claudication, critical limb ischemia, atrial valve sclerosis or restenosis.

184. The method of any one of embodiments 165 to 183 further comprising adjunctively administering a bile-acid resin, niacin, an anti-inflammatory agent, a statin, a fibrate, a CETP inhibitor, a platrelt aggregation inhibitor, an anticoagulant, an agonist of PCSK9 and/or an inhibitor of cholesterol absorption.

185. The method of embodiment 181, further comprising administering a statin selected from atorvastatin, rosuvastatin, pravastatin or lovastatin.

186. The method of embodiment 181, further comprising administering the fibrate fenofibrate.

187. The method of embodiment 181, further comprising administering the cholesterol absorption inhibitor zetia.

188. The method of embodiment 181, further comprising administering a CETP inhibitor selected from anacetrapib and dalcetrapib.

189. The method of embodiment 181, further comprising administering an antibody agonist of PCSK9 or a ligand agonist of PCSK9.

190. The method of embodiment 181, further comprising administering the cholesterol absorption inhibitor clopidogrel bisulfate.

191. The method of embodiment 181, further comprising administering the anticoagulant warfarin.

192. The method of embodiment 181, further comprising administering the anti-inflammatory agent aspirin.

193. A composition comprising one, two or three homogeneous populations of lipoprotein complexes.

194. The composition of embodiment 193, wherein the lipoprotein complexes in at least one of the homogeneous populations have the characteristics of a complex according to any one of embodiments 1 to 22.

195. The composition of embodiment 193 or embodiment 194, wherein at least one, two or three of said populations have the characteristics of a population according to any one of embodiments 23 to 58.

All cited references are incorporated herein by reference in their entirety and for all purposes to the same extent as if each individual publication, patent or patent application was specifically and individually indicated to be incorporated herein by reference in its entirety for all purposes.

Many modifications and variations of this invention can be made without departing from its spirit and scope, as will be apparent to those skilled in the art. The specific embodiments described are offered by way of example only, and the invention is to be limited only by the terms of the appended claims along with the full scope of equivalents to which such claims are entitled.

What is claimed is:

1. A population of lipoprotein complexes, each comprising
   (a) a lipid fraction consisting of a sphingomyelin and, optionally, 1,2-dipalmitoyl-sn-glycero-3-[phospho-rac-(1-glycerol)](DPPG); and
   (b) an apolipoprotein fraction consisting essentially of an Apolipoprotein A-I ("ApoA-I");
   wherein
      (i) at least 95% by weight of the apolipoprotein in the population is in complexed form;
      (ii) at least 95% by weight of the lipid in the population is in complexed form;
      (iii) at least 95% of the population is in a single peak in a gel permeation chromatogram;
      (iv) the population has an apolipoprotein fraction-to-phospholipid fraction ratio of 1:2.7 by weight; and
      (v) the weight ratio of the sphingomyelin to DPPG, when present, is 97:3.

2. The population of claim 1, further characterized by at least one of the following characteristics:
   (a) at least 95% of the lipoprotein complexes are in the form of particles of 4 nm to 15 nm in size as measured by dynamic light scattering ("DLS");
   (b) at least 95% by weight of ApoA-I in said population is in mature form;
   (c) no more than 5% by weight of ApoA-I in said population is in immature form; and
   (d) no more than 10% by weight of ApoA-I in the population is in truncated form.

3. The population of claim 1, further characterized by at least one of the following characteristics:
   (a) no more than 5% of each of methionine 112 and methionine 148 in said ApoA-I in said population is oxidized;
   (b) no more than 4% of the amino acids of the ApoA-I in said population is deamidated;
   (c) the population contains no more than 1 EU of endotoxin per milligram of ApoA-I;
   (d) the population contains no more than 25 picograms host cell DNA per milligram of ApoA-I; and
   (e) the population contains no more than 100 nanograms host cell protein per milligram of ApoA-I.

4. The population of claim 1 wherein said ApoA-I is a human ApoA-I protein.

5. The population of claim 1 wherein said ApoA-I is a recombinant ApoA-I.

6. The population of claim 1, wherein said lipid fraction consists of 97 weight % sphingomyelin and 3 weight % DPPG.

7. The population of claim 6 in which the sphingomyelin is egg-sphingomyelin.

8. The population of claim 6, wherein the lipid has a peroxide value of less than 5 meq 0/kg.

9. The population of claim 1, wherein the amino acid sequence of said ApoA-I consists of amino acids 25 to 267 of SEQ ID NO: 1.

10. The population of claim 9, wherein said lipid fraction consists of 97 weight % sphingomyelin and 3 weight % DPPG.

11. The population of claim 10 in which the sphingomyelin is egg-sphingomyelin.

12. The population of claim 1, wherein said lipid fraction consists of sphingomyelin.

13. The population of claim 9, wherein said lipid fraction consists of sphingomyelin.

14. A pharmaceutical composition comprising the population of claim 1 and one or more pharmaceutically acceptable carriers, diluents, and/or excipients.

15. The pharmaceutical composition of claim 14, comprising lipoprotein complexes having 2 ApoA-I molecules per lipoprotein complex.

16. The pharmaceutical composition of claim 15, comprising a lipoprotein complexes having 3 or 4 ApoA-I molecules or ApoA-I equivalents per lipoprotein complex.

17. A pharmaceutical composition which consists essentially of the population of claim 1 and one or more pharmaceutically acceptable carriers, diluents and/or excipients.

18. A unit dosage form comprising a therapeutically effective amount of a pharmaceutical composition of claim 17.

19. A pharmaceutical composition comprising the population of claim 9 and one or more pharmaceutically acceptable carriers, diluents, and/or excipients.

20. A pharmaceutical composition comprising the population of claim 10 and one or more pharmaceutically acceptable carriers, diluents, and/or excipients.

21. A pharmaceutical composition comprising the population of claim 11 and one or more pharmaceutically acceptable carriers, diluents, and/or excipients.

22. A pharmaceutical composition comprising the population of claim 12 and one or more pharmaceutically acceptable carriers, diluents, and/or excipients.

23. A pharmaceutical composition comprising the population of claim 13 and one or more pharmaceutically acceptable carriers, diluents, and/or excipients.

24. A method for treating a dyslipidemic disorder, comprising administering to a subject in need thereof a therapeutically effective amount of a population of lipoprotein complexes according to claim 1.

25. A method for treating a dyslipidemic disorder, comprising:
(a) administering to a subject an initial dose of 1 mg/kg to 12 mg/kg of a population of lipoprotein complexes according to claim 1;
(b) determining whether the subject's triglyceride, VLDL-cholesterol and/or VLDL-triglyceride is elevated to more than two fold 4, 8, 12, 24, 48, 72, 168, 336 or 504 hours after said administration; and
(c) if the subject's triglyceride, VLDL-cholesterol and/or VLDL-triglyceride is elevated to more than two fold of the pre-dosing levels, repeating said administration but at a lower dose, and if the subject's triglyceride, VLDL-cholesterol and/or VLDL-triglyceride is not elevated to more than two fold of the pre-dosing levels, then repeating said administration at an equivalent or greater dose.

* * * * *

SEQUENCE LISTING

<160> NUMBER OF SEQ ID NOS: 4

<210> SEQ ID NO 1
<211> LENGTH: 267
<212> TYPE: PRT
<213> ORGANISM: Homo sapiens

<400> SEQUENCE: 1

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 2
<211> LENGTH: 18
<212> TYPE: PRT
<213> ORGANISM: Homo sapiens
<220> FEATURE:
<221> NAME/KEY: SIGNAL
<222> LOCATION: (1)..(18)

<400> SEQUENCE: 2

```
Met Lys Ala Ala Val Leu Thr Leu Ala Val Leu Phe Leu Thr Gly Ser
1               5                   10                  15

Gln Ala
```

<210> SEQ ID NO 3

```
<211> LENGTH: 6
<212> TYPE: PRT
<213> ORGANISM: Homo sapiens
<220> FEATURE:
<221> NAME/KEY: PROPEP
<222> LOCATION: (1)..(6)

<400> SEQUENCE: 3

Arg His Phe Trp Gln Gln
1               5

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence:  Synthetic
      polypeptide
<220> FEATURE:
<221> NAME/KEY: MOD_RES
<222> LOCATION: (22)..(22)
<223> OTHER INFORMATION: Isonipecotic acid

<400> SEQUENCE: 4

Lys Leu Lys Gln Lys Leu Ala Glu Leu Leu Glu Asn Leu Leu Glu Arg
1               5                   10                  15

Phe Leu Asp Leu Val Xaa
            20
```